United States Patent
Schiltz et al.

(10) Patent No.: US 12,311,029 B2
(45) Date of Patent: May 27, 2025

(54) PROTEOLYSIS-TARGETING CHIMERIC MOLECULES (PROTACs) THAT INDUCE DEGRADATION OF INDOLEAMINE 2,3-DIOXYGENASE (IDO) PROTEIN

(71) Applicant: Northwestern University, Evanston, IL (US)

(72) Inventors: Gary E. Schiltz, Naperville, IL (US); Derek A. Wainwright, Brookfield, IL (US)

(73) Assignee: Northwestern University, Evanston, IL (US)

( * ) Notice: Subject to any disclaimer, the term of this patent is extended or adjusted under 35 U.S.C. 154(b) by 37 days.

(21) Appl. No.: 18/492,746

(22) Filed: Oct. 23, 2023

(65) Prior Publication Data

US 2024/0165248 A1 May 23, 2024

Related U.S. Application Data

(62) Division of application No. 17/305,311, filed on Jul. 2, 2021, now Pat. No. 11,839,659.

(60) Provisional application No. 63/047,913, filed on Jul. 2, 2020.

(51) Int. Cl.
 A61K 47/64 (2017.01)
 A61K 47/54 (2017.01)
 C07K 16/28 (2006.01)

(52) U.S. Cl.
 CPC ............ A61K 47/64 (2017.08); A61K 47/545 (2017.08); C07K 16/2818 (2013.01)

(58) Field of Classification Search
 CPC .................................................... A61K 47/64
 See application file for complete search history.

(56) References Cited

U.S. PATENT DOCUMENTS

| | | |
|---|---|---|
| 2004/0234623 A1 | 11/2004 | Munn et al. |
| 2009/0081155 A1 | 3/2009 | Munn et al. |
| 2010/0055111 A1 | 3/2010 | Sharma et al. |
| 2010/0311804 A1 | 12/2010 | Munn et al. |
| 2011/0136796 A1 | 6/2011 | Mautino et al. |
| 2013/0142815 A1 | 6/2013 | Ganapathy |
| 2014/0377307 A1 | 12/2014 | Munn et al. |
| 2015/0352206 A1 | 12/2015 | Gajewski et al. |
| 2016/0022619 A1 | 1/2016 | Balog et al. |
| 2016/0046596 A1 | 2/2016 | Banerjee et al. |
| 2016/0060237 A1 | 3/2016 | Balog et al. |
| 2016/0060266 A1 | 3/2016 | Kumar et al. |
| 2016/0137595 A1 | 5/2016 | Markwalder et al. |
| 2016/0143870 A1 | 5/2016 | Markwalder et al. |
| 2016/0200674 A1 | 7/2016 | Markwalder et al. |
| 2016/0289171 A1 | 10/2016 | Balog et al. |
| 2016/0361298 A1 | 12/2016 | Novick et al. |
| 2016/0362412 A1 | 12/2016 | Mautino et al. |
| 2016/0367564 A1 | 12/2016 | Cowley et al. |
| 2017/0009271 A1 | 1/2017 | Hunter et al. |
| 2017/0037125 A1 | 2/2017 | Leopold et al. |
| 2017/0095473 A1 | 4/2017 | Molineaux et al. |
| 2017/0107178 A1 | 4/2017 | Cowley et al. |
| 2017/0129911 A1 | 5/2017 | Lippard et al. |
| 2017/0182156 A1 | 6/2017 | Khleif |
| 2017/0231999 A1 | 8/2017 | Balog et al. |
| 2017/0260188 A1 | 9/2017 | Kumar et al. |
| 2017/0267668 A1 | 9/2017 | Cowley et al. |
| 2017/0319527 A1 | 11/2017 | Ganapathy et al. |
| 2018/0030026 A1 | 2/2018 | Banerjee et al. |
| 2018/0037553 A1 | 2/2018 | Cowley et al. |
| 2018/0072660 A1 | 3/2018 | Balog et al. |
| 2018/0072716 A1 | 3/2018 | Wang et al. |
| 2018/0079712 A1 | 3/2018 | Balog et al. |
| 2018/0085465 A1 | 3/2018 | Bradner et al. |
| 2018/0134684 A1 | 5/2018 | Bradner et al. |
| 2018/0186785 A1 | 7/2018 | Crews et al. |
| 2018/0186787 A1 | 7/2018 | Cowley et al. |
| 2018/0271861 A1 | 9/2018 | Tokunaga et al. |
| 2018/0312497 A1 | 11/2018 | Baradi et al. |
| 2018/0327419 A1 | 11/2018 | Bradner et al. |
| 2018/0333492 A1 | 11/2018 | Gajewski et al. |
| 2018/0353483 A1 | 12/2018 | Yeleswaram et al. |
| 2018/0354908 A1 | 12/2018 | Cowley et al. |
| 2019/0002402 A1 | 1/2019 | Balog et al. |
| 2019/0016703 A1 | 1/2019 | Gray et al. |
| 2019/0022157 A1 | 1/2019 | Coffin |
| 2019/0031665 A1 | 1/2019 | Gurjar et al. |
| 2019/0040025 A1 | 2/2019 | Wu et al. |
| 2019/0071415 A1 | 3/2019 | Bradner et al. |
| 2019/0076539 A1 | 3/2019 | Phillips et al. |

(Continued)

OTHER PUBLICATIONS

Zhai et al., "Immunosuppresive IDO in Cancer: Mechanisms of Action, Animal Models, and Targeting Strategies," Front Immunol. Jun. 16, 2020;11:1185.

An et al., "Small-molecule PROTACs: An emerging and promising approach for the development of targeted therapy drugs," EBioMedicine. Oct. 2018; 36: 553-562.

Gu et al., "PROTACs: An Emerging Targeting Technique for Protein Degradation in Drug Discovery," Bioessays. Apr. 2018; 40(4):e1700247.

Tinworth, Christopher P., Hannah Lithgow, and Ian Churcher. "Small molecule-mediated protein knockdown as a new approach to drug discovery." MedChemComm 7.12 (2016): 2206-2216.

(Continued)

*Primary Examiner* — Nizal S Chandrakumar

(74) *Attorney, Agent, or Firm* — Quarles & Brady LLP

(57) ABSTRACT

Disclosed are proteolysis-targeting chimeric molecules (PROTACs) that induce degradation of IDO protein. The disclosed PROTACs typically include a first targeting moiety that binds to IDO (Miro). The first targeting moiety typically is linked via a bond or a linker (L) to a second targeting moiety that binds to an E3 ubiquitin ligase ($M_{E3}$). As such, the disclosed PROTACS may be described as having a formula $M_{IDO}$-L-$M_{E3}$ or $M_{E3}$-L-$M_{IDO}$.

17 Claims, 132 Drawing Sheets

(56) References Cited

U.S. PATENT DOCUMENTS

| | | |
|---|---|---|
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0106417 A1 | 4/2019 | Gray et al. |
| 2019/0119215 A1 | 4/2019 | Shan et al. |
| 2019/0119216 A1 | 4/2019 | Cherney et al. |
| 2019/0135758 A1 | 5/2019 | Cherney et al. |
| 2019/0144416 A1 | 5/2019 | Williams et al. |
| 2019/0144417 A1 | 5/2019 | Williams et al. |
| 2019/0151295 A1 | 5/2019 | Crew et al. |
| 2019/0151457 A1 | 5/2019 | Bradner et al. |
| 2019/0152932 A1 | 5/2019 | Wang et al. |
| 2019/0194190 A1 | 6/2019 | Yang et al. |
| 2019/0225618 A1 | 7/2019 | Mautino et al. |
| 2019/0231776 A1 | 8/2019 | Molineaux et al. |
| 2019/0247527 A1 | 8/2019 | Li et al. |
| 2019/0262502 A1 | 8/2019 | Garcia-Gareta et al. |
| 2019/0263798 A1 | 8/2019 | Harling et al. |
| 2019/0270812 A1 | 9/2019 | Leopold et al. |
| 2019/0275161 A1 | 9/2019 | Hheightman et al. |
| 2019/0284184 A1 | 9/2019 | Wang et al. |
| 2019/0292150 A1 | 9/2019 | Jeon et al. |
| 2019/0352307 A1 | 11/2019 | Yu et al. |
| 2019/0367465 A1 | 12/2019 | Jiang et al. |
| 2020/0022966 A1 | 1/2020 | Tang et al. |
| 2020/0024273 A1 | 1/2020 | Wang et al. |
| 2020/0069646 A1 | 3/2020 | Balog et al. |
| 2020/0069695 A1 | 3/2020 | Balog et al. |
| 2020/0085817 A1 | 3/2020 | Jaenisch et al. |
| 2020/0093932 A1 | 3/2020 | Friedman et al. |
| 2020/0095231 A1 | 3/2020 | Balog et al. |
| 2020/0102298 A1 | 4/2020 | Gray et al. |
| 2020/0140456 A1 | 5/2020 | Phillips et al. |
| 2020/0172492 A1 | 6/2020 | Cowley et al. |
| 2020/0179347 A1 | 6/2020 | Yeleswaram et al. |

OTHER PUBLICATIONS

Hu, Mingxing, et al. "Discovery of the first potent proteolysis targeting chimera (PROTAC) degrader of indoleamine 2, 3-dioxygenase 1." Acta Pharmaceutica Sinica B 10.10 (2020): 1943-1953.

Cherney, Emily C., et al. "Discovery and preclinical evaluation of BMS-986242, a potent, selective inhibitor of indoleamine-2, 3-dioxygenase 1." ACS Medicinal Chemistry Letters 12.2 (2021): 288-294.

Sundaresan, Vidyasankar, and Ravinder Abrol. "Towards a general model for protein-substrate stereoselectivity." Protein science 11.6 (2002): 1330-1339.

Venkatesh, Srini, and Robert A. Lipper. "Role of the development scientist in compound lead selection and optimization." Journal of pharmaceutical sciences 89.2 (2000): 145-154.

J. G. Cannon, Chapter Nineteen in Burger's Medicinal Chemistry and Drug Discovery, Fifth Edition, vol. I: Principles and Practice, Wiley-Interscience 1995, pp. 783-802, 784.

Meyers, Joshua, et al. "Privileged structures and polypharmacology within and between protein families." ACS Medicinal Chemistry Letters 9.12 (2018): 1199-1204.

Top-10 IDO1-degrading PROTACs at 10uM

| PROTAC | %IDO1 remaining | % IDO1 degraded |
|---|---|---|
| NU223612 | 6 | 94 |
| NU223807 | 6 | 94 |
| NU223603 | 6 | 94 |
| NU223851 | 9 | 91 |
| NU223805 | 10 | 90 |
| NU223817 | 10 | 90 |
| NU223152 | 12 | 88 |
| NU223617 | 12 | 88 |
| NU223151 | 14 | 86 |
| NU223806 | 14 | 86 |

Figure 9

NU618 (BMS parental) compound blocks NU612 induced IDO1 degradation

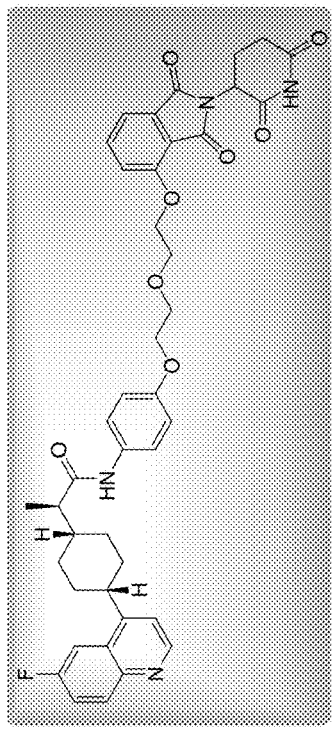
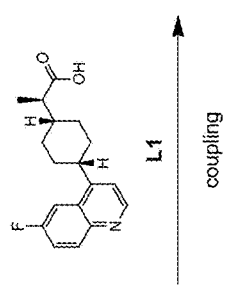
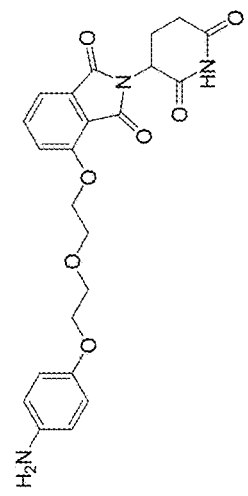
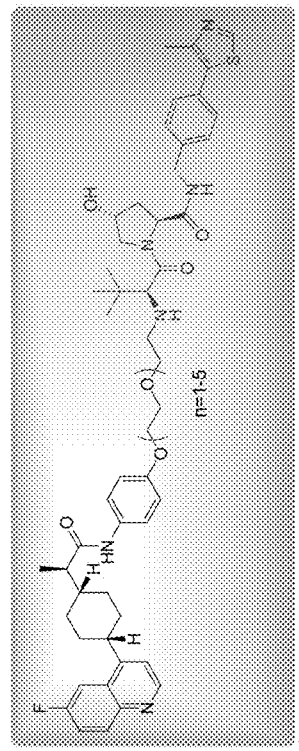
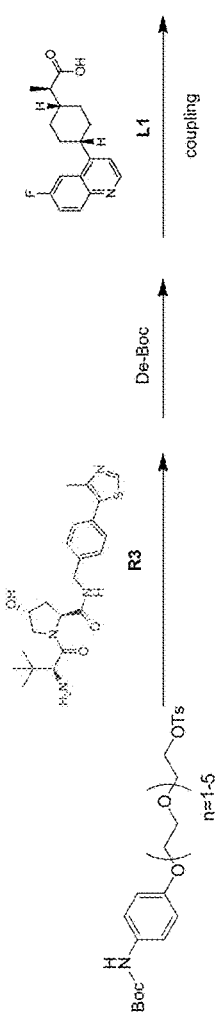
Figure 38
Figure 39

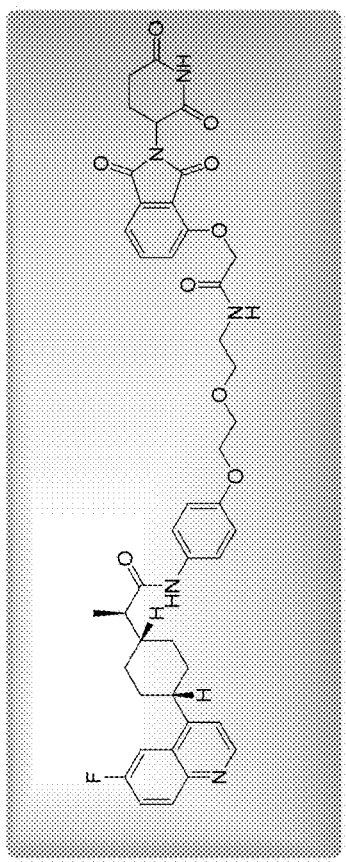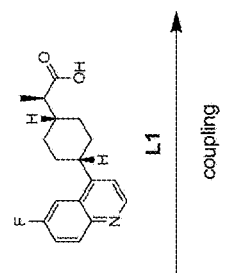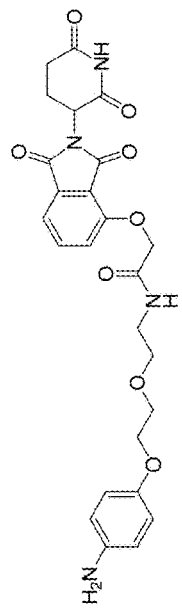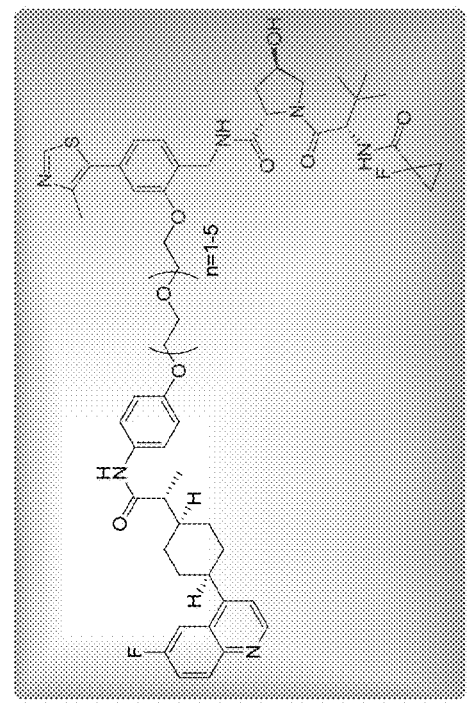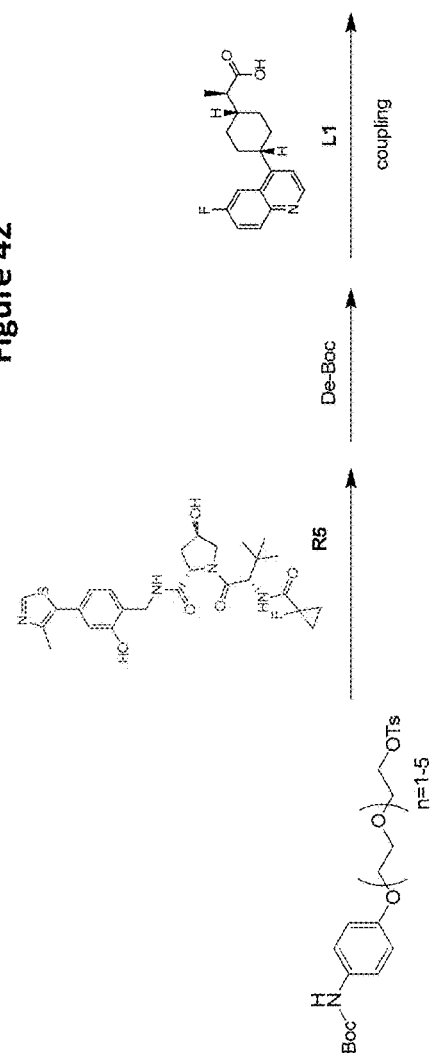
Figure 42
Figure 43

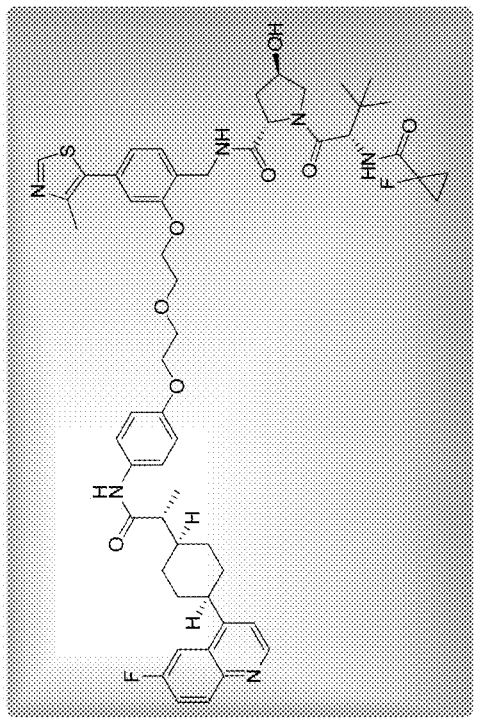
Figure 44
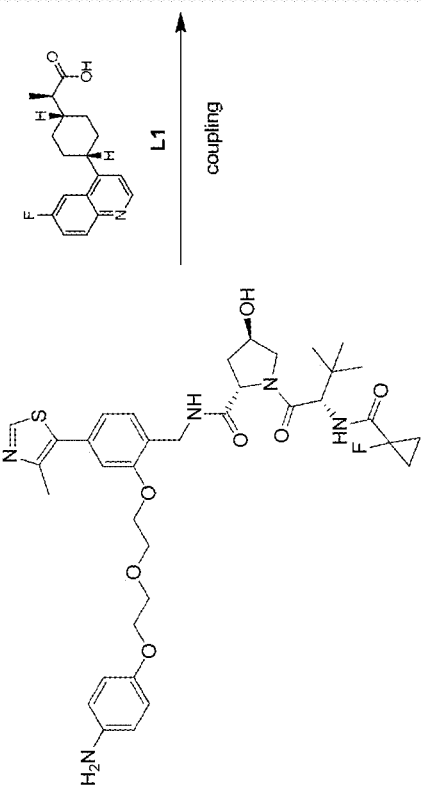
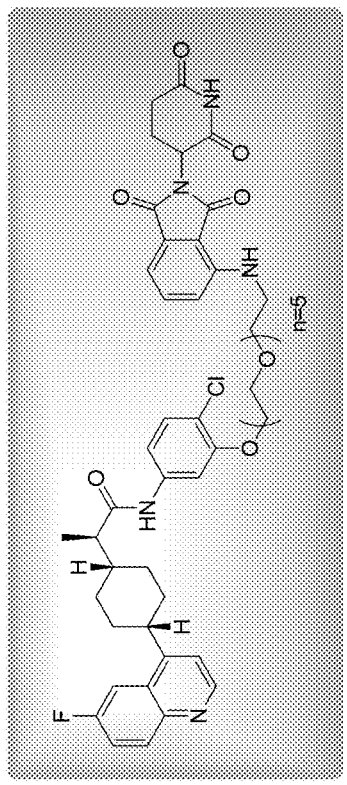
Figure 45
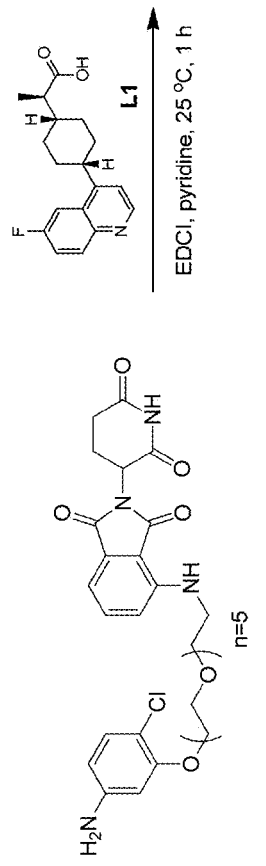

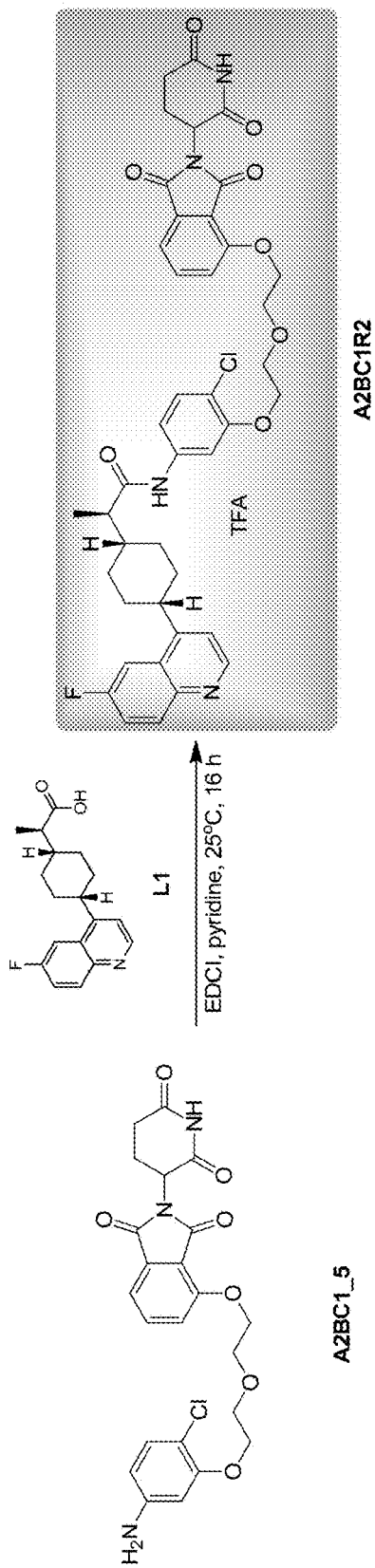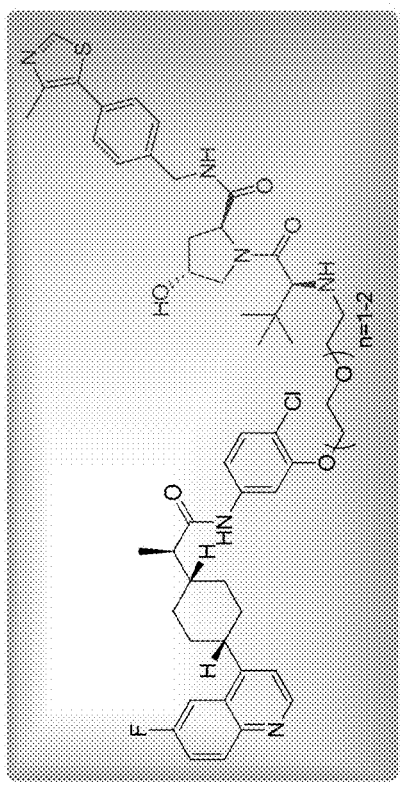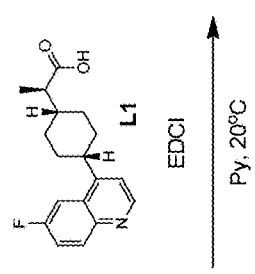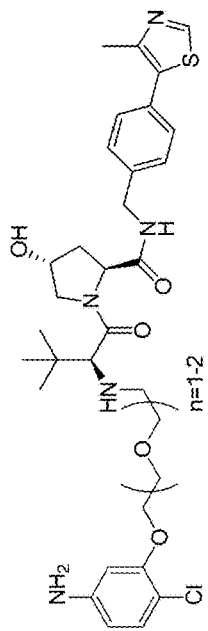
Figure 46
Figure 47

Figure 50

| Molecule Name (Synonym) | Structure |
|---|---|
| NUCC-0223599 (A1BC1R1) | 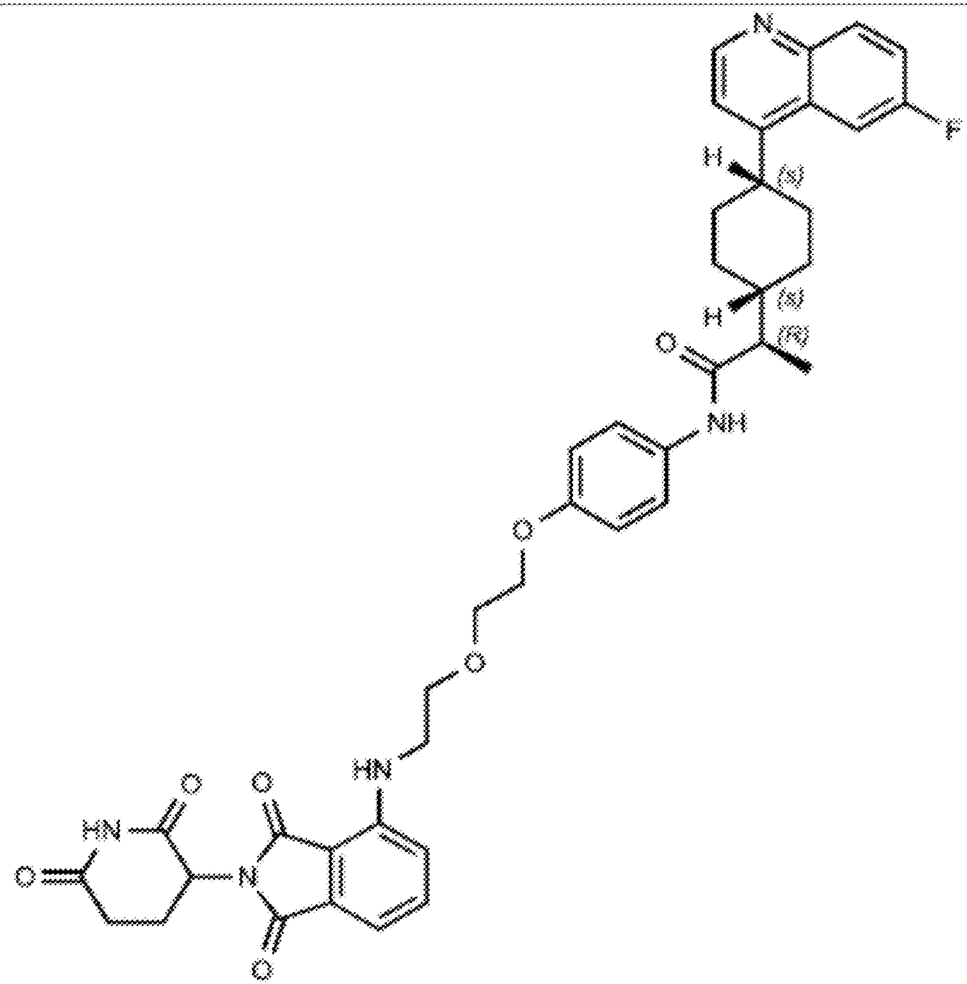 |

NUCC-0223600
(A1BC1R2)

NUCC-0223601 (A1BC1R4)

NUCC-0223602 (A1BC2R1)

NUCC-0223603 (A1BC2R2)

NUCC-0223604 (A1BC2R4)

NUCC-0223605 (A1BD1R1)

NUCC-0223606 (A1BD1R2)

NUCC-0223607 (A1BD1R4)

NUCC-0223608 (A1BD2R4)

NUCC-0223609 (A1BF1R2)

NUCC-0223610 (A1BF1R1)

NUCC-0223611 (A1BF1R4)

NUCC-0223612 (A1BF2R1)

NUCC-0223613 (A1BF2R2)

NUCC-0223614 (A2BD1R2)

NUCC-0223615 (A2BD2R2)

NUCC-0223616 (A2BC1R2)

| | |
|---|---|
| NUCC-0223617 (A2BC2R2) |  |
| NUCC-0223618 (L1-M1, Linfodostat, TMOL_T4532) |  |

NUCC-0223619 (L1-M2)

NUCC-0223792 (A1BF2R4)

NUCC-0223793 (A2BC1R1)

NUCC-0223794 (A2BC1R4)

NUCC-0223795 (A2BC2R1)

NUCC-
0223796
(A2BC2R4)

NUCC-
0223797
(A2BD1R4)

NUCC-0223798 (A2BD2R4)

NUCC-0223799 (A1BC1R3)

NUCC-0223800 (A1BC2R3)

NUCC-0223801 (A1BC1R5)

NUCC-0223802 (A1BC2R5)

NUCC-0223803 (A1BD1R5)

NUCC-0223804 (A1BD2R5)

NUCC-0223805 (A1BE1R1)

NUCC-0223806 (A1BE1R4)

NUCC-0223807 (A1BE2R1)

NUCC-0223808 (A1BE2R2)

NUCC-0223809 (A2BC1R3)

NUCC-0223810 (A2BC2R3)

NUCC-0223811 (A2BC1R5)

NUCC-0223812 (A2BC2R5)

NUCC-0223813 (A2BD1R1)

NUCC-0223814 (A2BD2R1)

NUCC-0223815 (A2BD1R5)

NUCC-0223816 (A2BD2R5)

NUCC-0223817 (A2BD3R5)

NUCC-0223850 (A1BE1R5)

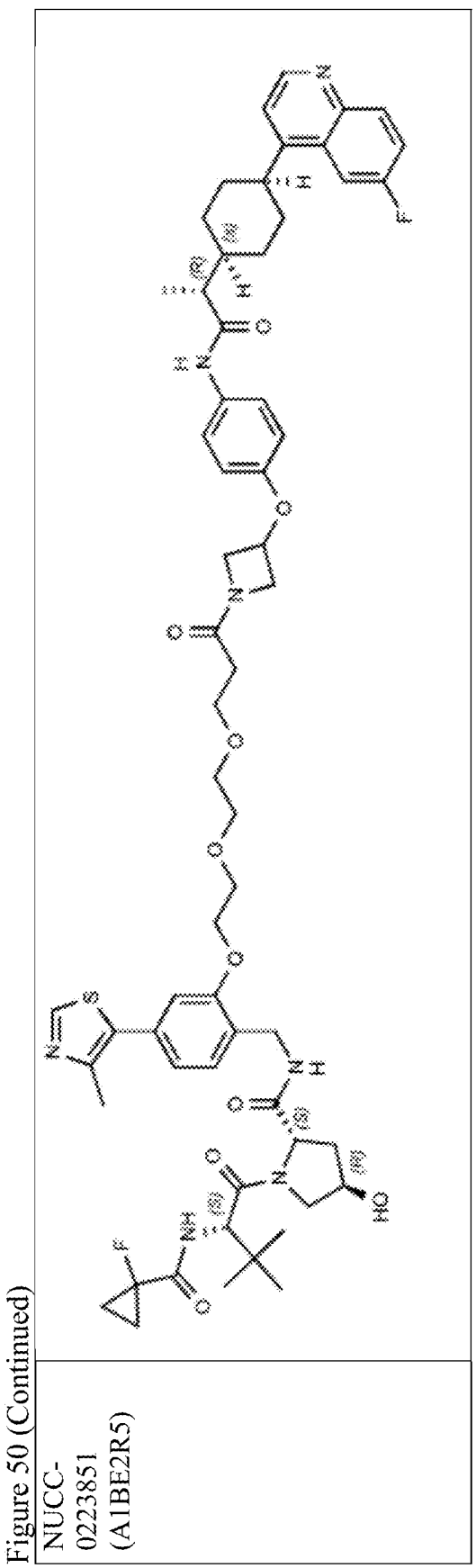
Figure 50 (Continued) NUCC-0223851 (A1BE2R5)

NUCC-0223852 (A1BF1R5)

NUCC-0223853
(A1BF2R5)

NUCC-0223854 (A2BD1R3)

NUCC-0223855 (A2BD2R3)

NUCC-0223856 (A2BD3R3)

NUCC-0223857 (A2BD3R2)
NUCC-0223858 (A1BE2R4)

NUCC-0226134 (A1BC3R3)

NUCC-0226139 (A1BE4R4)

NUCC-0226140 (A2BC3R1)

NUCC-0226141 (A2BC3R2)

NUCC-0226142 (A2BC3R3)

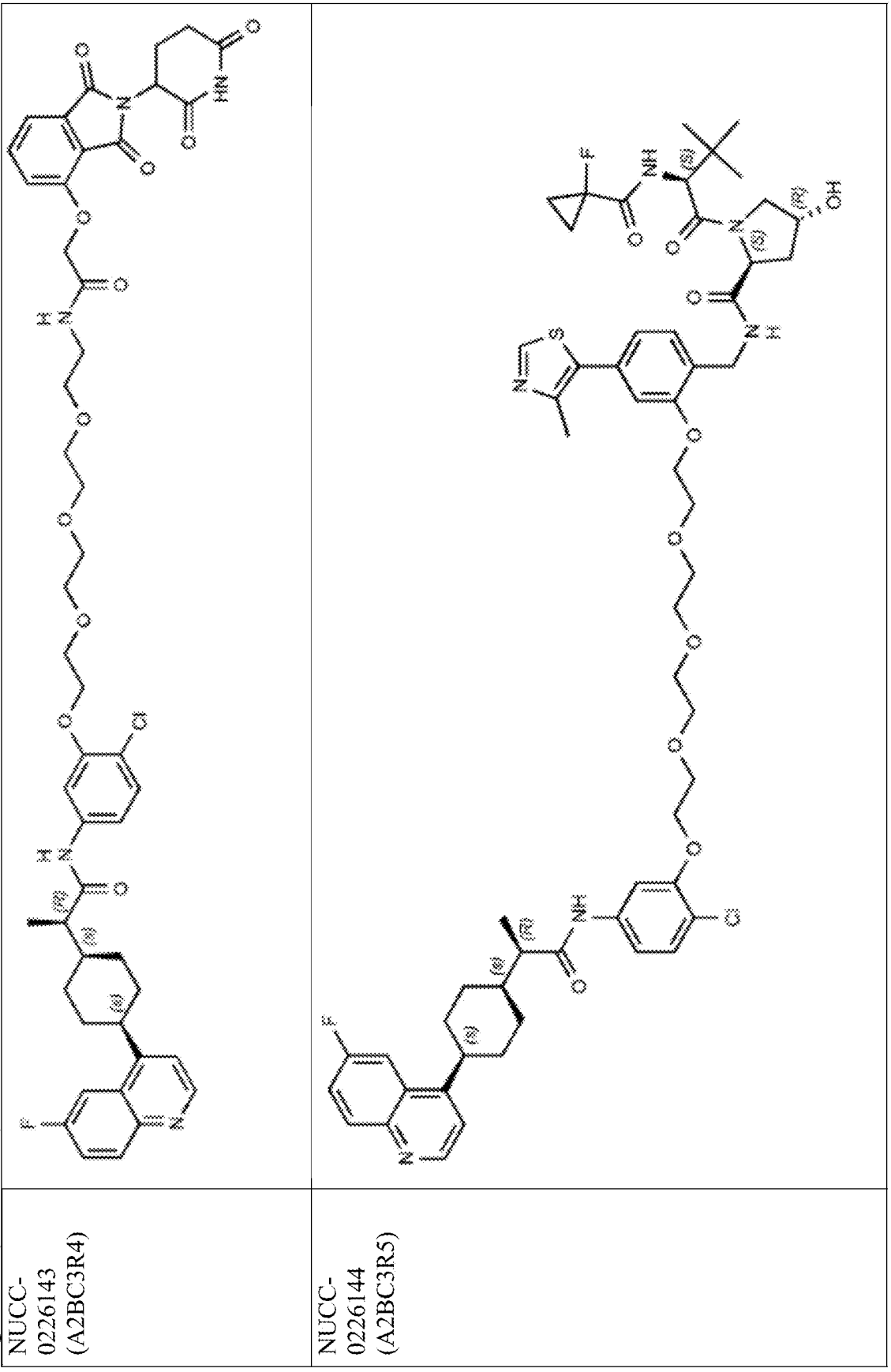

NUCC-0226145 (A2BC5R1)

NUCC-0226146 (A2BC5R2)

NUCC-0226147 (A2BC5R3)

NUCC-0226148 (A2BC5R4)

NUCC-0226149 (A2BC5R5)

NUCC-0226150 (A1BD3R5)

NUCC-0226151 A1BE1R2)

NUCC-0226152 (A1BF1R3)

NUCC-0226153 (A1BF2R3)

NUCC-0226154 (A1BF3R3)

NUCC-0226157 (A2BD3R4)
NUCC-0226178 (A1BD1R3)

NUCC-0226179
A1BD2R3)

NUCC-0226180 (A1BD3R1)

NUCC-0226181 (A1BC4R1)

| NUCC-0226182 (A1BC4R2) |  |
| NUCC-0226183 (A1BC4R3) |  |

| | |
|---|---|
| NUCC-0226184 (A1BC4R4) |  |
| NUCC-0226185 (A1BC4R5) |  |

NUCC-0226186 (A1BC5R1)

NUCC-0226187 (A1BC5R2)

| NUCC-0226188 (A1BC5R3) |  |
| NUCC-0226189 (A1BC5R4) |  |

NUCC-0226190 (A1BC5R5)

NUCC-0226191 (A1BF3R2)

NUCC-0226192 (A1BF3R5)

NUCC-0226193 (A1BF4R2)
NUCC-0226194 (A1BF4R5)

NUCC-0226197 (A2BC4R3)
NUCC-0226198 (A2BC4R4)

NUCC-0226199 (A2BC4R5)

PROTEOLYSIS-TARGETING CHIMERIC MOLECULES (PROTACs) THAT INDUCE DEGRADATION OF INDOLEAMINE 2,3-DIOXYGENASE (IDO) PROTEIN

CROSS-REFERENCE TO RELATED PATENT APPLICATIONS

The present application is a divisional of U.S. application Ser. No. 17/305,311, filed Jul. 2, 2021, which is based on, and claims the benefit of priority under 35 U.S.C. § 119(e) to U.S. Provisional Application No. 63/047,913, filed on Jul. 2, 2020. The contents of these applications are incorporated herein by reference in their entirety.

BACKGROUND

The field of the invention relates to proteolysis-targeting chimeric molecules (PROTACs) that induce degradation of indoleamine 2,3-dioxygenase (IDO) protein. In particular, the field of the invention relates to PROTACs that target IDS for degradation which may be utilized for the treatment of diseases and disorders associated with IDO activity such as cell proliferation diseases and disorders including cancers The indoleamine 2,3-dioxygenase (IDO) protein plays a crucial role in the progression of cancers. (See Zhai et al., Immunosuppresive IDO in Cancer: Mechanisms of Action, Animal Models, and Targeting Strategies," Front Immunol. 2020 Jun. 16; 11:1185, the content of which is incorporated herein by reference in its entirety). For example, the median survival of primary glioblastoma multiforme (GBM) patients following aggressive surgical intervention, radiotherapy, chemotherapy, and tumor treating fields (TTF) is only ~14-16 months; IDO protein plays a critical immunosuppressive role in the progression of GBM which is independent of IDO's enzyme activity. Enzymatic inhibition of IDO failed in a phase 3 ECHO-301/KEYNOTE-252 clinical trial suggesting a futility of IDO enzyme inhibitor treatment in patients with cancer. Although the mechanism for IDO's contribution to progression of GBM is not understood and remains as an active area of investigation, a more effective IDO neutralizing pharmacologic is required for abolishing IDO's immunosuppressive effect(s).

To address this need, the present inventors developed small molecule targeted degraders of IDO, termed IDO-proteolysis targeted chimeras (PROTACs). Proteolysis-targeting chimeric molecules (PROTACs) are an emerging technology that may be utilized to target previously "undruggable" targets, such as transcription factors and non-enzymatic proteins. (See, e.g., An et al., "Small-molecule PROTACs: An emerging and promising approach for the development of targeted therapy drugs," EBioMedicine. 2018 October; 36: 553-562; and Gu et al., "PROTACs: An Emerging Targeting Technique for Protein Degradation in Drug Discovery," Bioessays. 2018 April; 40(4):e1700247, the contents of which are incorporated herein by reference in their entireties). PROTACs are chimeric molecules that may be characterized as "hetero-bifunctional" in that PROTACs include a ligand for recruiting an E3 ubiquitin ligase, a linker, and another ligand to bind with the protein targeted for degradation. Designed as such, PROTACs "hijack" the E3 ubiquitin ligase to the protein which is targeted for protein degradation via ubiquitination, even if the targeted protein is not a physiological substrate for degradation via the ubiquitin-proteasome system. Here, we disclose PROTACs that induce degradation of IDO protein.

The inventors' compounds bind with high affinity to IDO and recruit an E3 ubiquitin ligase that initiates polyubiquitination of IDO and causes its degradation by the proteasome. The IDO-PROTACs thereby abolish all immunosuppressive effects of IDO, including its enzymatic- and non-enzymatic dependent functions. The IDO-PROTACs have been initially validated in human glioblastoma cell lines, but are applicable to all forms of cancer and non-cancerous cells that also express IDO under pathologic circumstances.

SUMMARY

Disclosed are proteolysis-targeting chimeric molecules (PROTACs) that induce degradation of idoleamine 2,3-dioxygenase (IDO) protein. The disclosed PROTACs comprise a moiety that binds to IDO covalently attached to a moiety that binds to a ubiquitin ligase. The disclosed PROTACs typically include a first targeting moiety that binds to IDO ($M_{IDO}$) which may be derived from an inhibitor of IDO that binds to IDO. Suitable first targeting moieties may include a substituted quinoline that binds to IDO such as a 4-cyclohexyl substituted quinoline. The first targeting moiety may be covalently attached via a bond or a linker (L) to a second targeting moiety that binds to a ubiquitin ligase such as an E3 ubiquitin ligase ($M_{E3}$). As such, the disclosed PROTACS may be described as having a formula $M_{IDO}$-L-$M_{E3}$ or $M_{E3}$-L-$M_{IDO}$.

The disclosed PROTACs target the E3 ubiquitin ligase moiety to IDO which subsequently is ubiquitinated and targeted for degradation. The disclosed PROTACs may be utilized for the treatment of diseases and disorders associated with IDO such as cell proliferation diseases and disorders including cancer.

The disclosed PROTACs typically include a first targeting moiety that binds to IDO ($M_{IDO}$) which may be derived from a substituted quinoline that binds to IDO. Suitable substituted quinolines that bind to IDO may include, but are not limited to 4-cyclohexyl substituted quinolones. In some embodiments, the targeting moiety for IDO ($M_{IDO}$) may be derived from a substituted quinoline having a formula which may include, but is not limited to formula I:

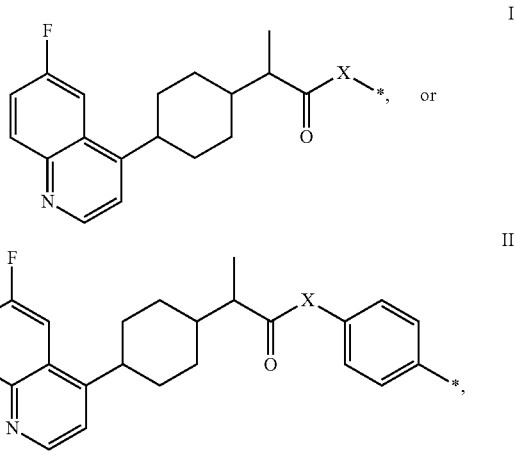

wherein
X is O or NH.

The IDO targeting moiety of the disclosed PROTACs ($M_{IDO}$) typically is linked via a bond or a linker (L) to a second targeting moiety that binds to an E3 ubiquitin ligase ($M_{E3}$). The IDO targeting moiety may comprise a radical form of a compound of a formula I, for example wherein the IDO moiety is attached to the linker via a form of X, or of formula I.

Suitable linkers for the disclosed PROTACs may include, but are not limited to linkers comprising a polyethylene glycol moiety. Other suitable linkers for the disclose PROTACS may include an alkylalkyne moiety, and/or an aminoalkyl alkyne moiety.

The E3 ubiquitin ligase targeting moiety of the disclosed PROTACs (ME3) typically binds and/or targets the PROTACs to an E3 ubiquitin ligase. Suitable E3 ubiquitin ligases may include, but are not limited to, Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

The E3 ubiquitin ligase targeting moiety of the disclosed PROTACs (ME3) typically is derived from a compound that binds to an E3 ubiquitin ligase, for example, as a ligand for an E3 ubiquitin ligase. Suitable ligands may include, but are not limited to, ligands derived from thalidomide, pomalidomide, lenalidomide, VHL ligand 1 (VHL-1), VHL ligand 2 (VHL-2), VH032, VL-269, LCL161, hydroxyproline-based ligands, and HIF-1α-derived (R)-hydroxyproline, including radicalized forms.

The disclosed PROTACs may exhibit one or more biological activities. The disclosed PROTACs may inhibit the growth of cells that express IDO (preferably by at a concentration of less than about 100 µM, 50 µM, 10 µM, 1 µM, 0.1 µM, 0.05 µM, 0.01 µM, 0.005 µM, 0.001 µM, or less). The disclosed PROTACs may not inhibit the growth of cells that do not express IDO (preferably at a concentration of greater than about 0.001 µM, 0.005 µM, 0.01 µM, 0.5 µM, 0.1 µM, 1.0 µM, 10 µM, and 100 µM or higher).

Also disclosed are pharmaceutical compositions comprising the disclosed PROTACs and a suitable pharmaceutical carrier, excipient, or diluent. The disclosed pharmaceutical compositions may comprise an effective amount of the PROTACs for inhibiting the growth of cancer cells when administered to a subject in need thereof.

Also disclosed are methods for treating cell proliferation diseases and disorders such as cancer. The methods may include administering the disclosed PROTACs s or pharmaceutical compositions comprising the disclosed PROTACs to a subject in need thereof, for example, to a subject having cancer. The disclosed PROTACs or pharmaceutical compositions comprising the disclosed PROTACs may be administered with additional therapeutic agents such as immunotherapy agents (e.g., anti-PD1 antibodies and/or anti-PD-L1 antibodies), optionally in combination with the disclosed PROTACs, in order to treat cell proliferative diseases and disorders. Cell proliferative diseases and disorders treated by the disclosed methods may include, but are not limited to, cancers selected from the group consisting of glioblastoma muliforme (GBM), multiple myeloma, leukemia, non-small cell lung cancer, colon cancer, cancer of the central nervous system, melanoma, ovarian cancer, renal cancer, uterine cancer, prostate cancer, pancreatic cancer, and breast cancer.

BRIEF DESCRIPTION OF THE FIGURES

FIG. 9. Top-10 IDO1-degrading PROTACs at 10 uM.

FIG. 38 shows the general procedure for preparation of A1BC1R2 (NUCC-0223600).

FIG. 39 shows the synthetic scheme for the synthesis of A1BC1-3R3, take A1BC1R3 as an example.

FIG. 42 shows the general procedure for preparation of A1BC1R4 (NUCC-0223601)—Notebook Page: ET32240-251.

FIG. 43 shows the synthetic scheme for the synthesis of A1BC1~3R5, take A1BC1R5 as an example.

FIG. 44 shows the general procedure for preparation of A1BC1R5 (NUCC-0223801)—Notebook Page: ET32240-403.

FIG. 45 shows the general procedure for preparation of Compound A2BC5R1 (NUCC-0226145) Notebook Page: ET32240-853.

FIG. 46 shows the general procedure for preparation of A2BC1R2 (NUCC-0223616)—Notebook Page: ET32240-240.

FIG. 47 shows the general procedure for preparation of Compound A2BC1R3 (NUCC-0223809)—Notebook Page: ET32240-535.

DETAILED DESCRIPTION

Figure 1:
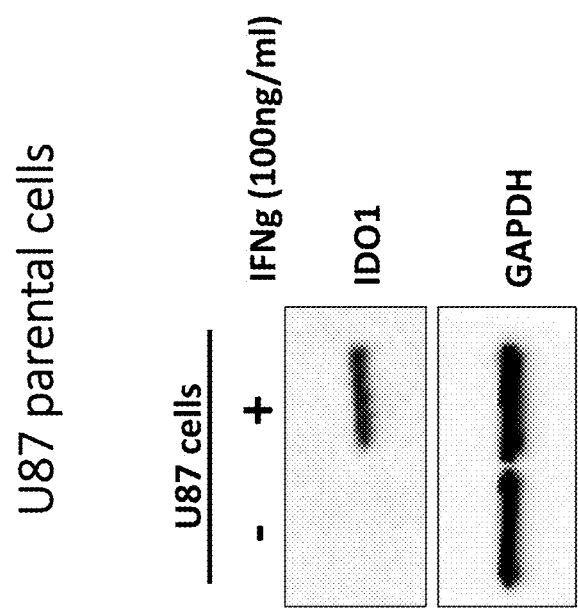
FIG. 1. Induction of IDO1 expression in U87 parental cells by INFg.
Figure 2:
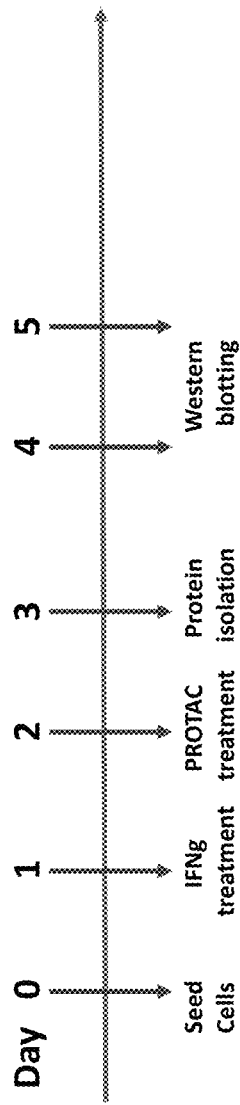
FIG. 2. Screening method for PROTAC-induced degradation of IDO1 using INFg-treated U87 parental cells.
Figure 3:
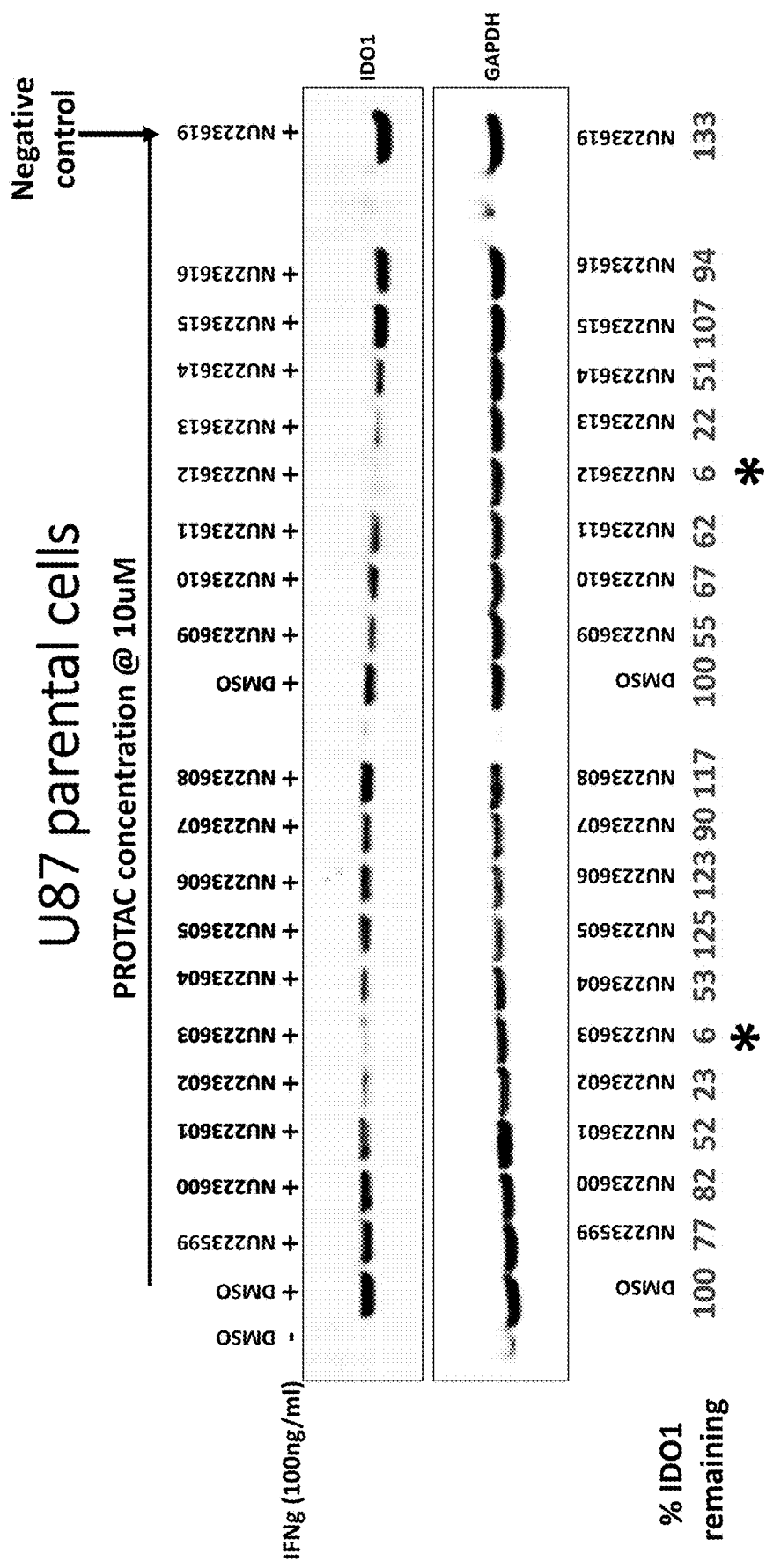
FIG. 3. Results of screening method for PROTAC-induced degradation of IDO1 using INFg-treated U87 parental cells.
Figure 4:
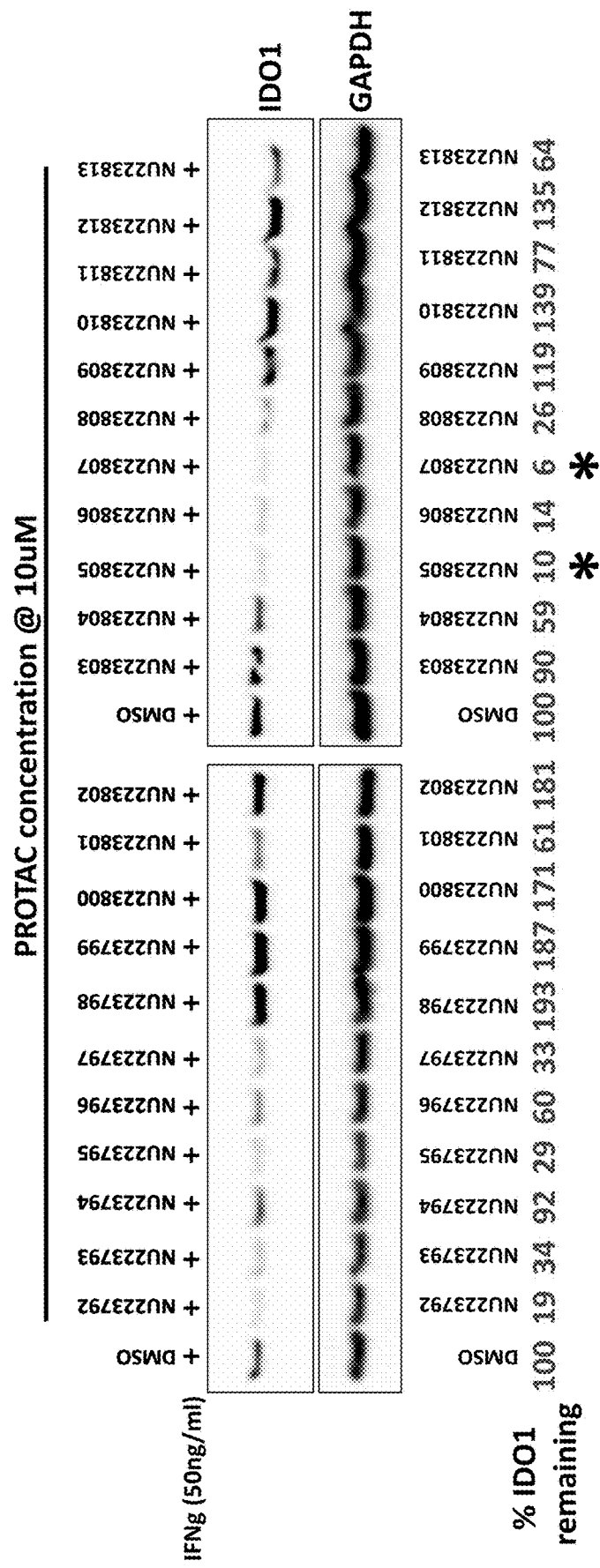
FIG. 4. Results of screening method for PROTAC-induced degradation of IDO1 using INFg-treated U87 parental cells.
Figure 5:
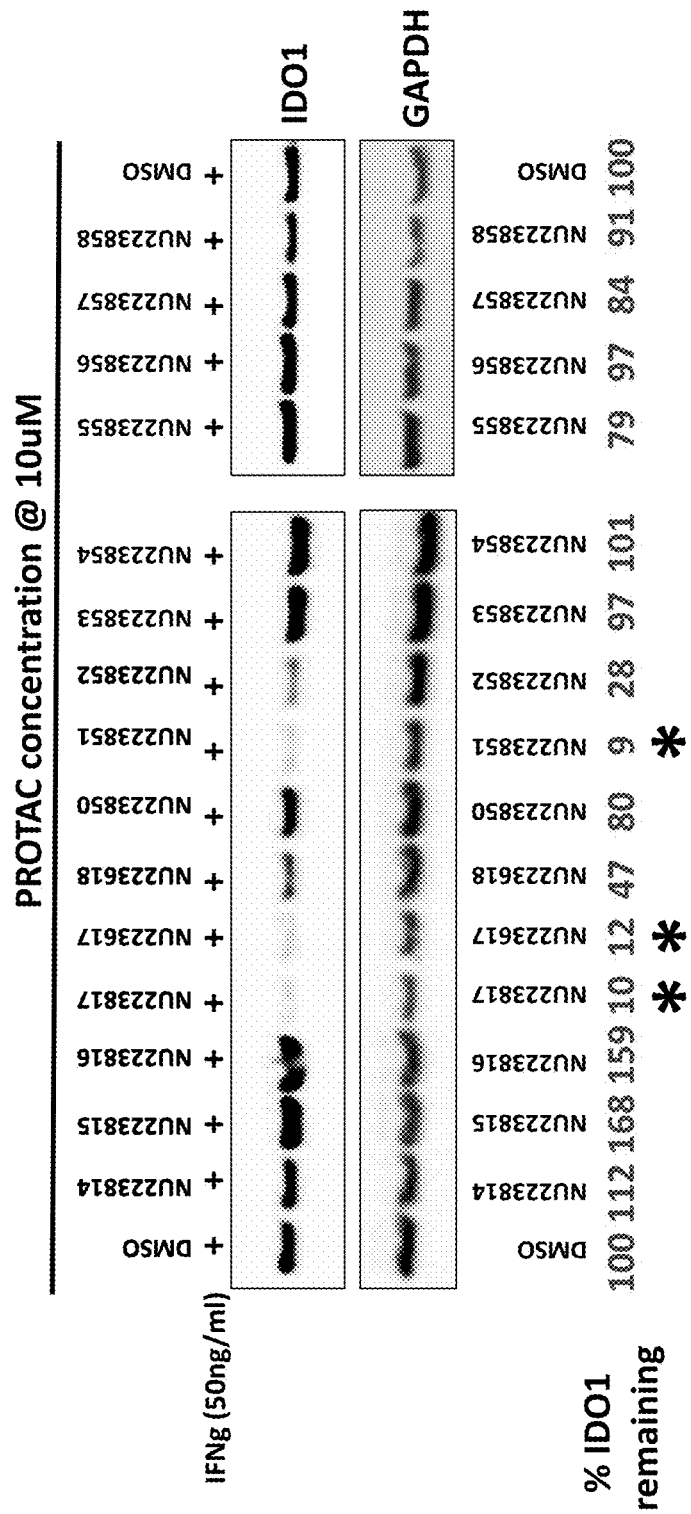
FIG. 5. Results of screening method for PROTAC-induced degradation of IDO1 using INFg-treated U87 parental cells.
Figure 6:
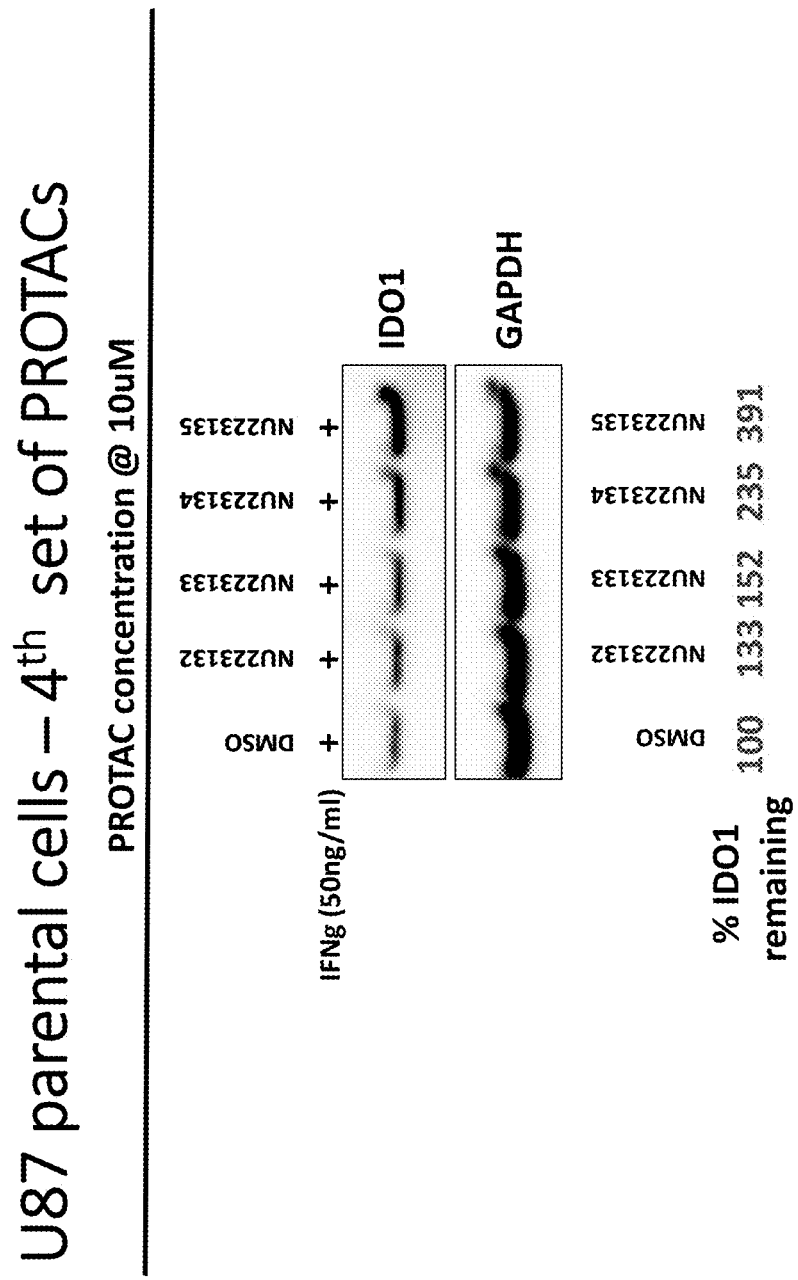
FIG. 6. Results of screening method for PROTAC-induced degradation of IDO1 using INFg-treated U87 parental cells.
Figure 7:
FIG. 7. Results of screening method for PROTAC-induced degradation of IDO1 using INFg-treated U87 parental cells.
Figure 8:
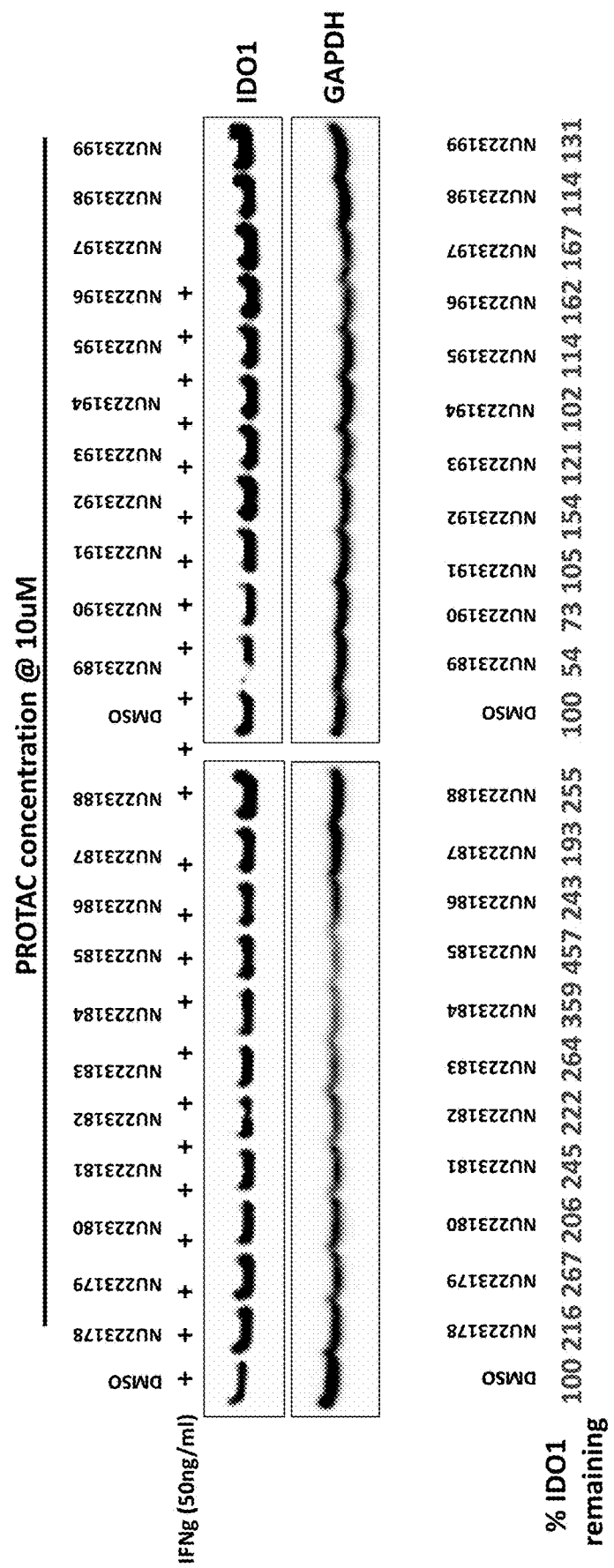
FIG. 8. Results of screening method for PROTAC-induced degradation of IDO1 using INFg-treated U87 parental cells.
Figure 10:
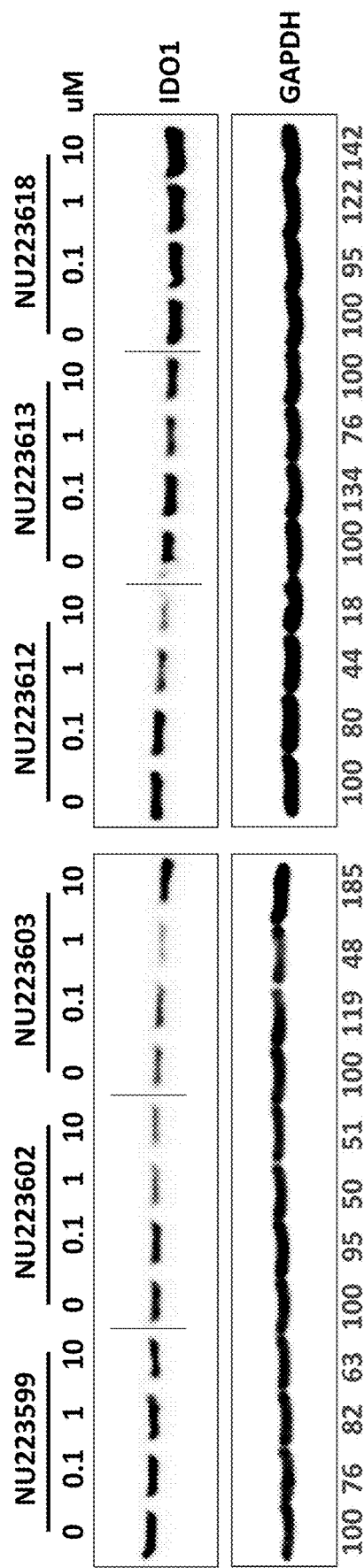
FIG. 10. Testing multiple doses of PROTAC compounds.
Figure 11:
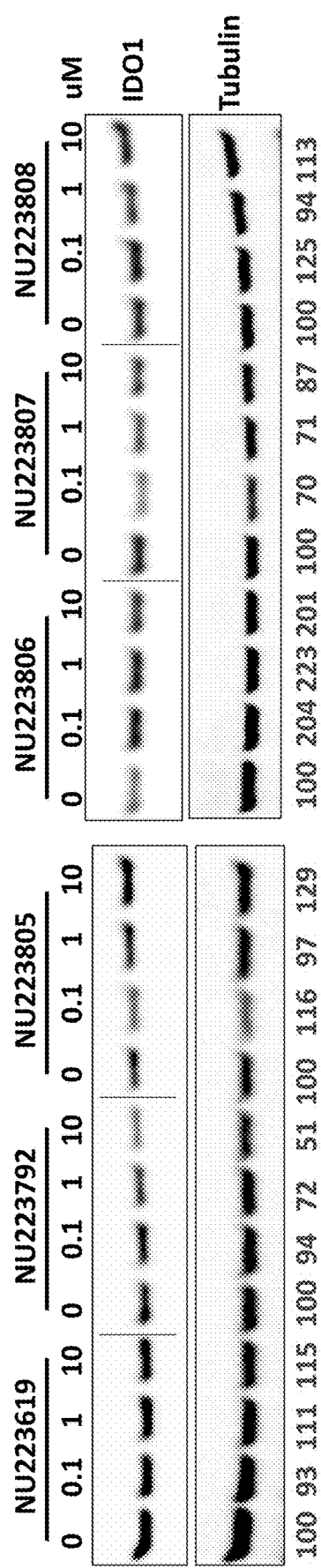
FIG. 11. Testing multiple doses of PROTAC compounds.
Figure 12:
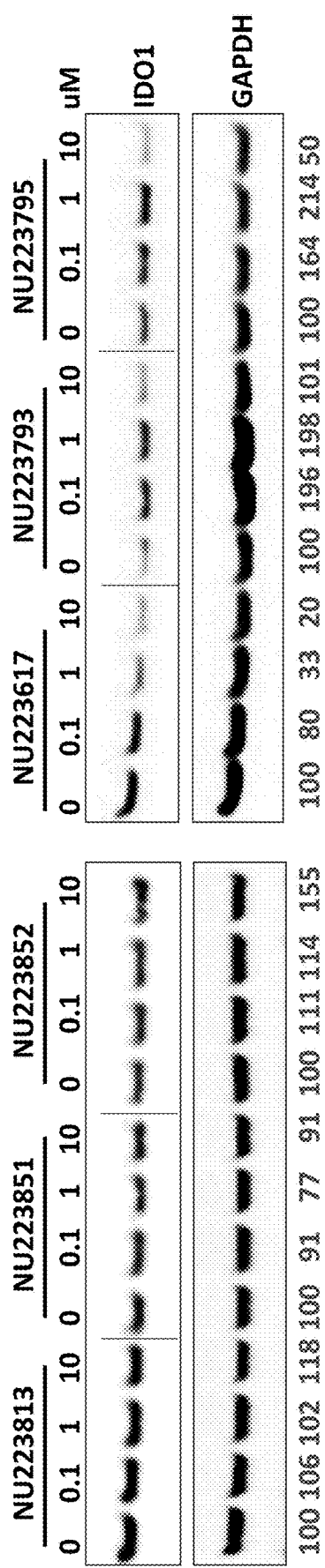
FIG. 12. Testing multiple doses of PROTAC compounds.
Figure 13:
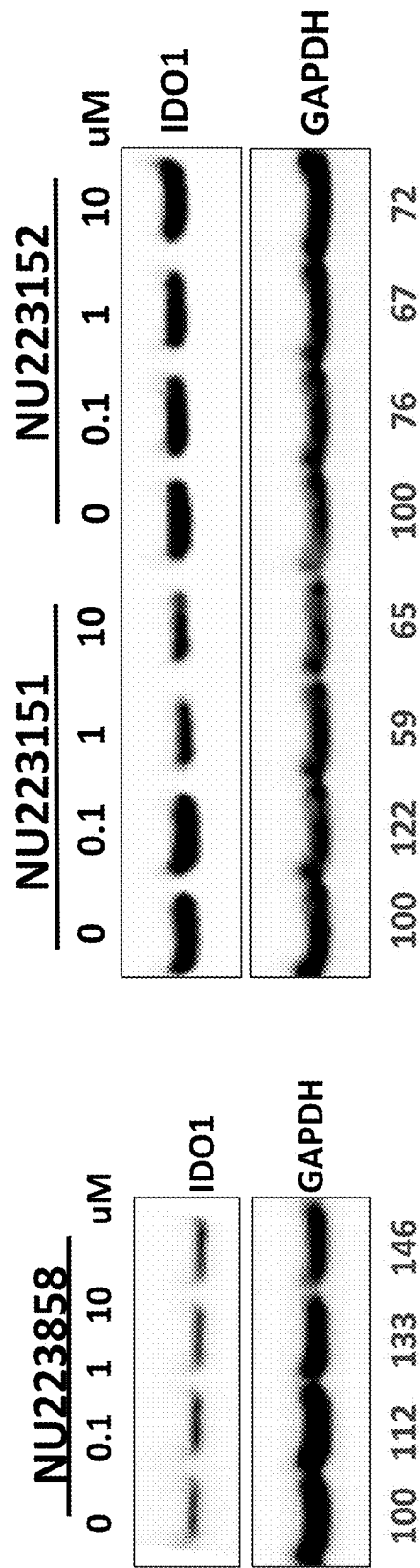
FIG. 13. Testing multiple doses of PROTAC compounds.
Figure 14:
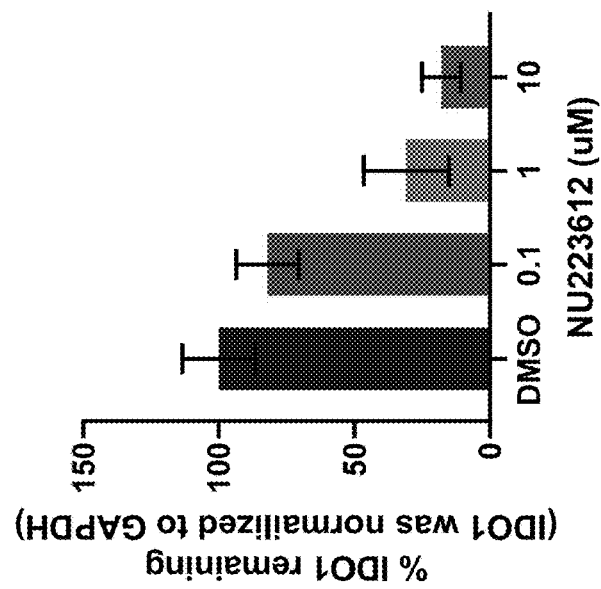
FIG. 14. Testing NU22361 at 0, 0.1, 1, and 10 uM.
Figure 14:
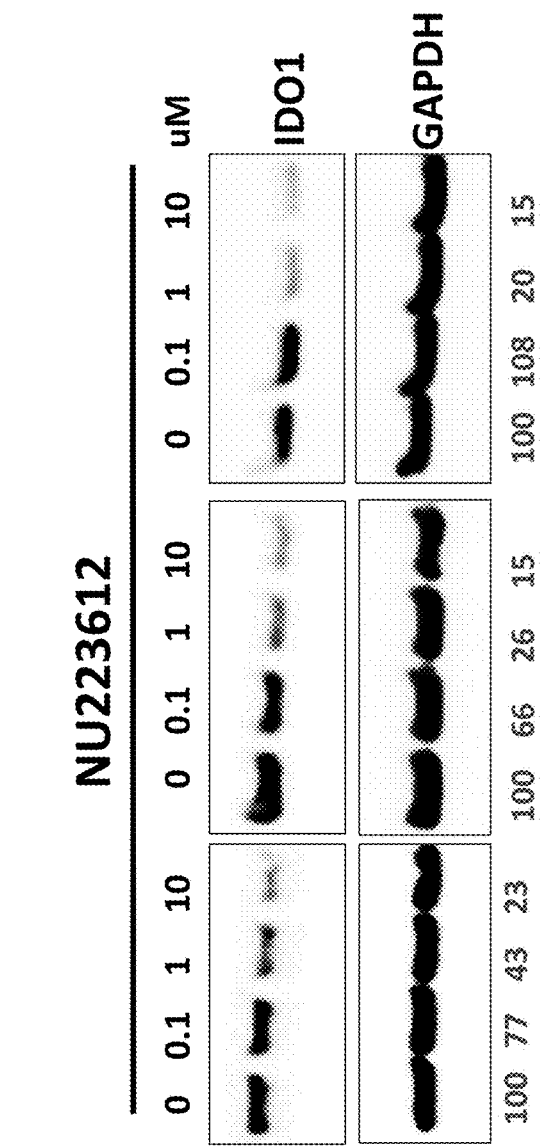
Figure 15:
FIG. 15. Time course of NU223612 treatment on IDO1 degradation.
Figure 16:
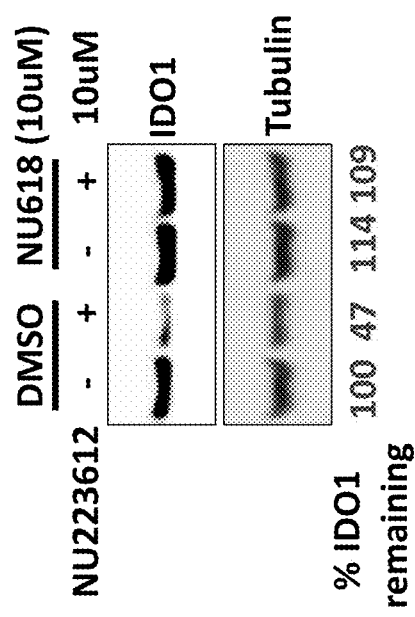
FIG. 16. NU618 (BMS parental) compound blocks NU612 induced IDO1 degradation.
Figure 17:
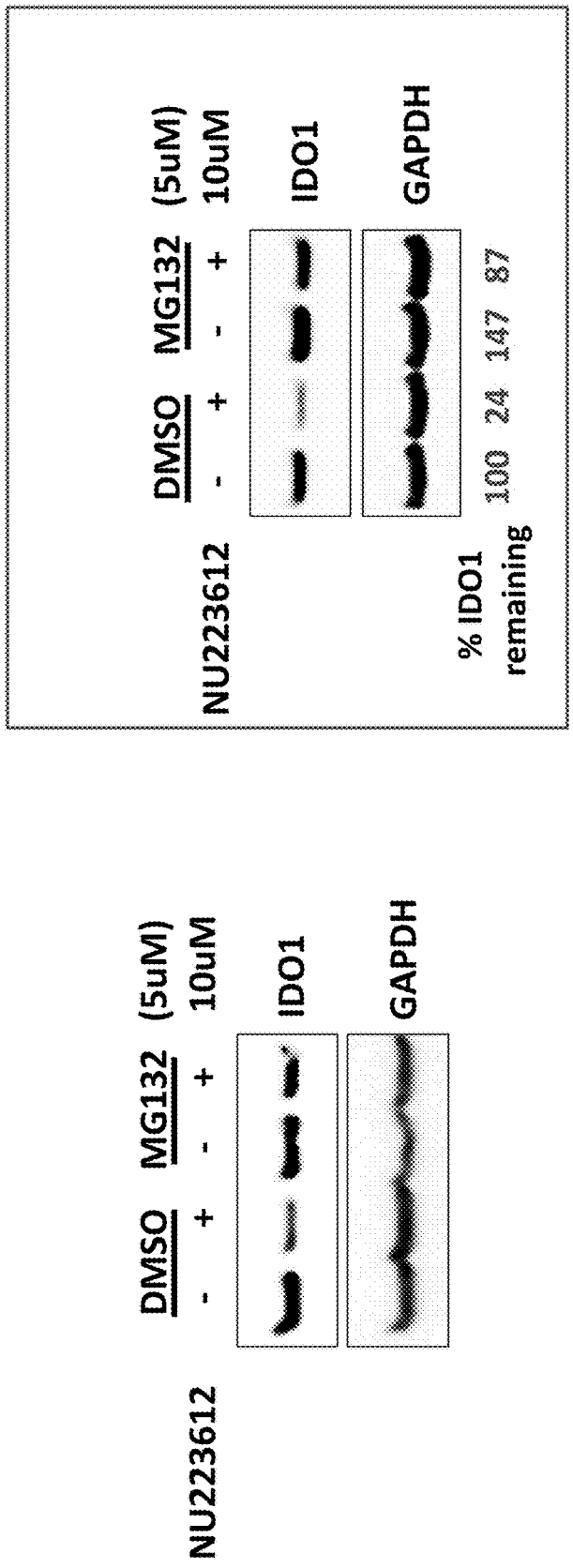
FIG. 17. MG132 (proteasome inhibitor) blocks NU223612 induced IDO1 degradation.
Figure 18:
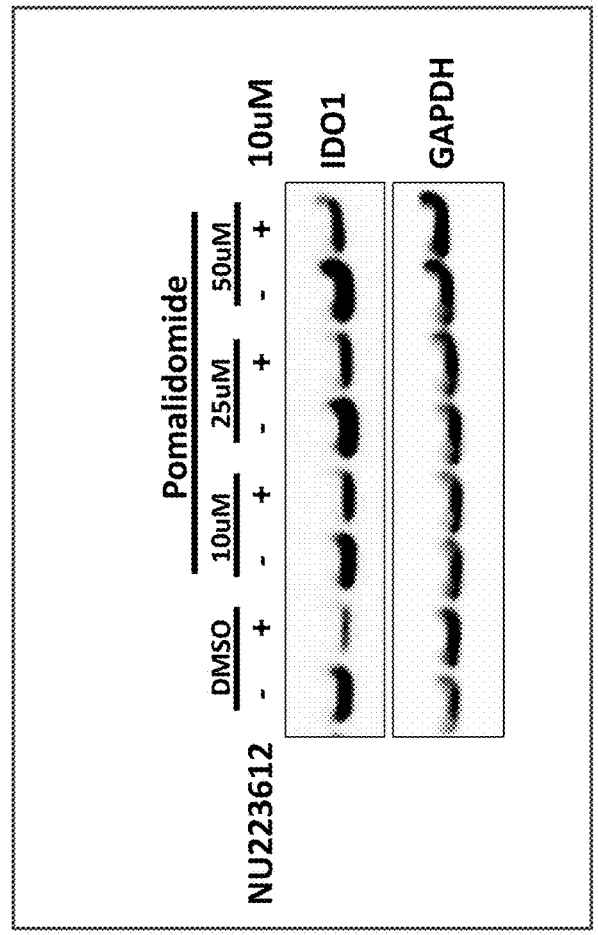
FIG. 18. CRBN ligand blocks NU223612 induced IDO1 degradation.
Figure 19:
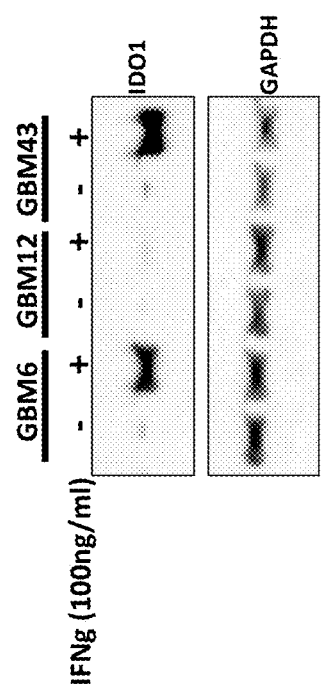
FIG. 19. Tests in additional cell lines.
Figure 20:
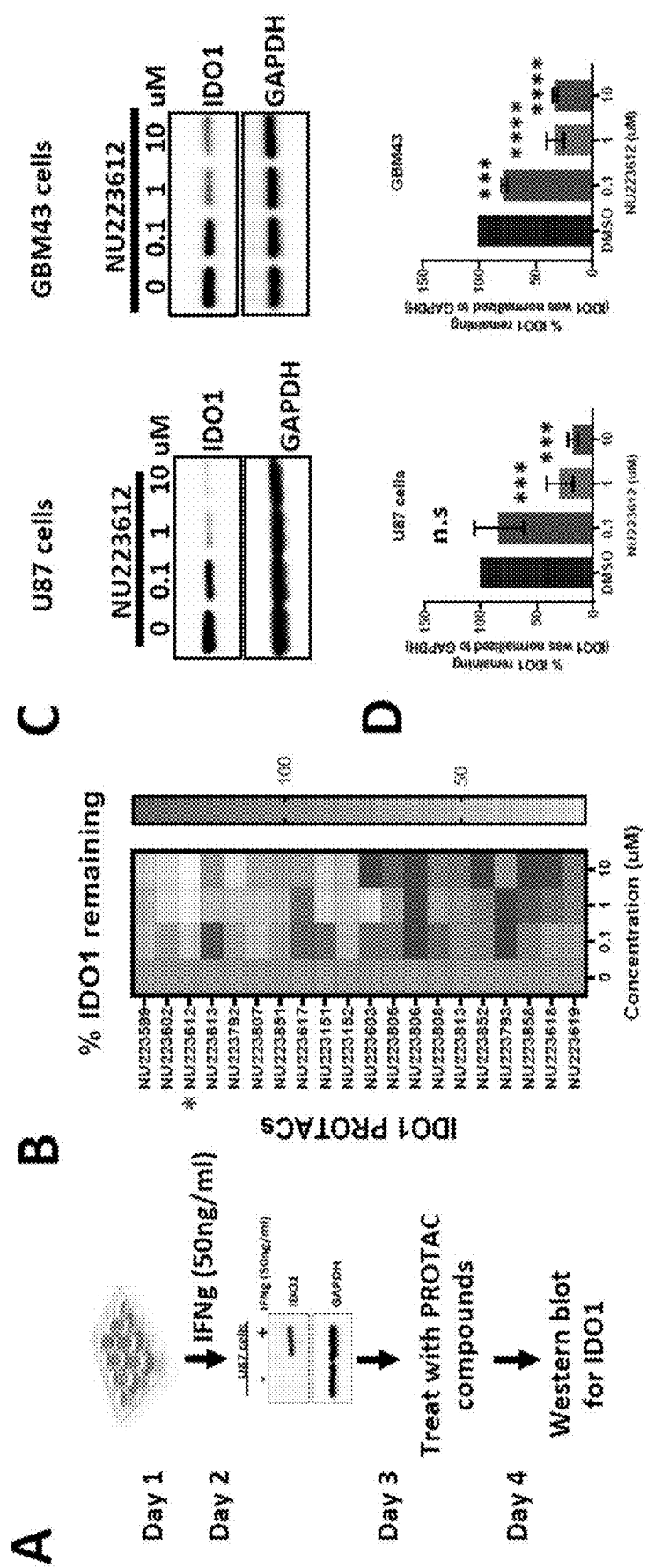
FIG. 20. Discovery of lead IDO-PROTAC to induce IDO1 degradation in cancer cells. A. Schema for screening IDO-PROTAC compounds in U87 cells. B. Heat map analysis to screen highly potent IDO-PROTACs. Percent IFNg-induced IDO1 levels (normalized to untreated samples) were calculated in U87 cells after treating with IDO-PROTAC compounds at 0, 0.1, 1, and 10 uM concentration for 24 hours. C. IDO-PROTAC (NU223612) induced IDO1 degradation in U87 and GBM43 cells using western blot analysis. IDO1 was induced in U87 and GBM43 cells with IFNg (50 ng/ml) for 24 hours followed by treatment with IDO-PROTAC for 24 hours before protein samples were prepared for western blotting analysis. D. Percent normalized IDO1 protein levels in U87 and GBM43 cells (from panel C) after treating with lead IDO-PROTAC (NU223612) for 24 hours. E & F. Testing moderate and poor IDO-PROTAC compounds on IDO1 protein levels in U87 cells. G & H. Testing mutant version of IDO-PROTAC (NU226211) and parental compound (NU223618) on IDO1 protein levels in U87 and GBM43 cells after treating for 24 hours. Structures of IDO-PROTAC (I), mutant IDO-PROTAC (J), and parental compound (K).
Figure 20:
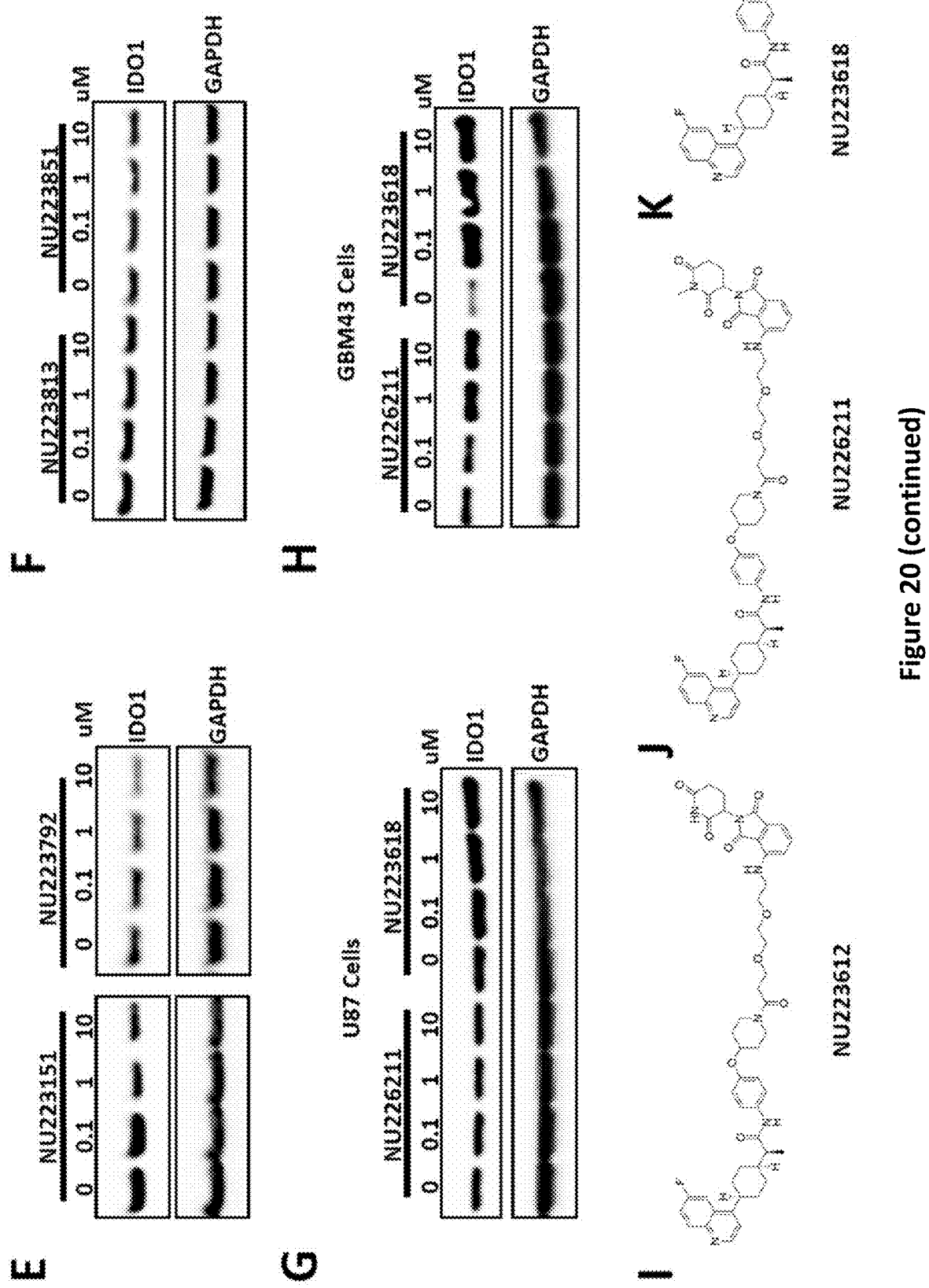
Figure 21:
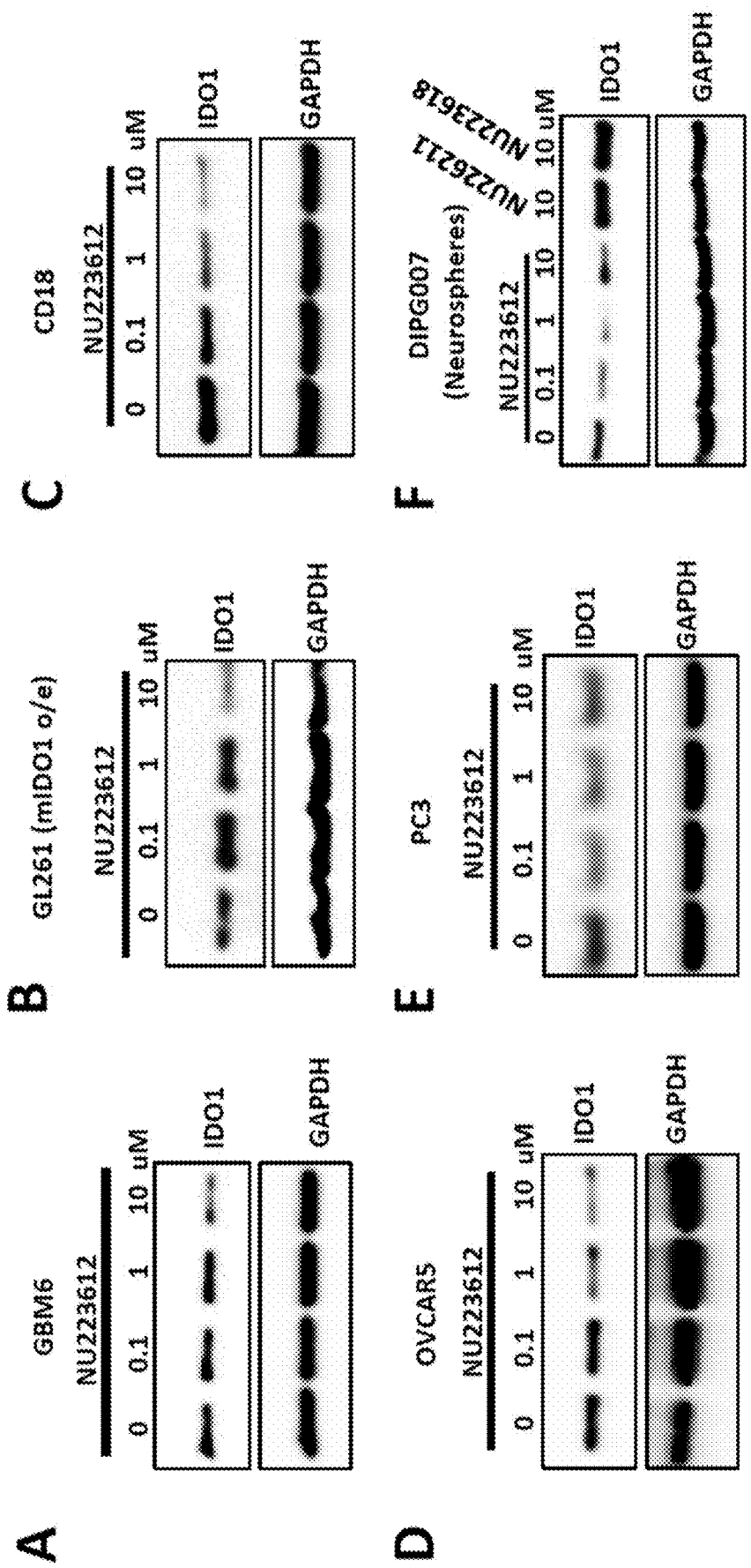
FIG. 21. Validation of IDO-PROTAC induced IDO degradation. Western blotting analysis to determine the effect of IDO-PROTAC on IFNg-induced IDO1 levels in GBM6 cells (A), mouse GBM cells (GL261) over expressing mouse IDO1 (B), pancreatic cancer (CD18) cells (C), ovarian (OVCAR5) cells (D), prostate cancer (PC3) cells (E), and pediatric GBM cells (DIPG007 grown as neurospheres (F). Western blotting analysis to determine the effect of IDO-PROTAC on IFNg-induced IDO1 levels in PBMCs from GBM patient (G), and non-GBM patient (H). Western blotting analysis to determine the effect of IDO-PROTAC on PBMCs-induced IDO1 levels in U87 cells in a co-culture system (I). J. Western blotting analysis to determine the effect of IDO-PROTAC on IFNg-induced subcellular IDO1 levels in U87 cells.
Figure 21:
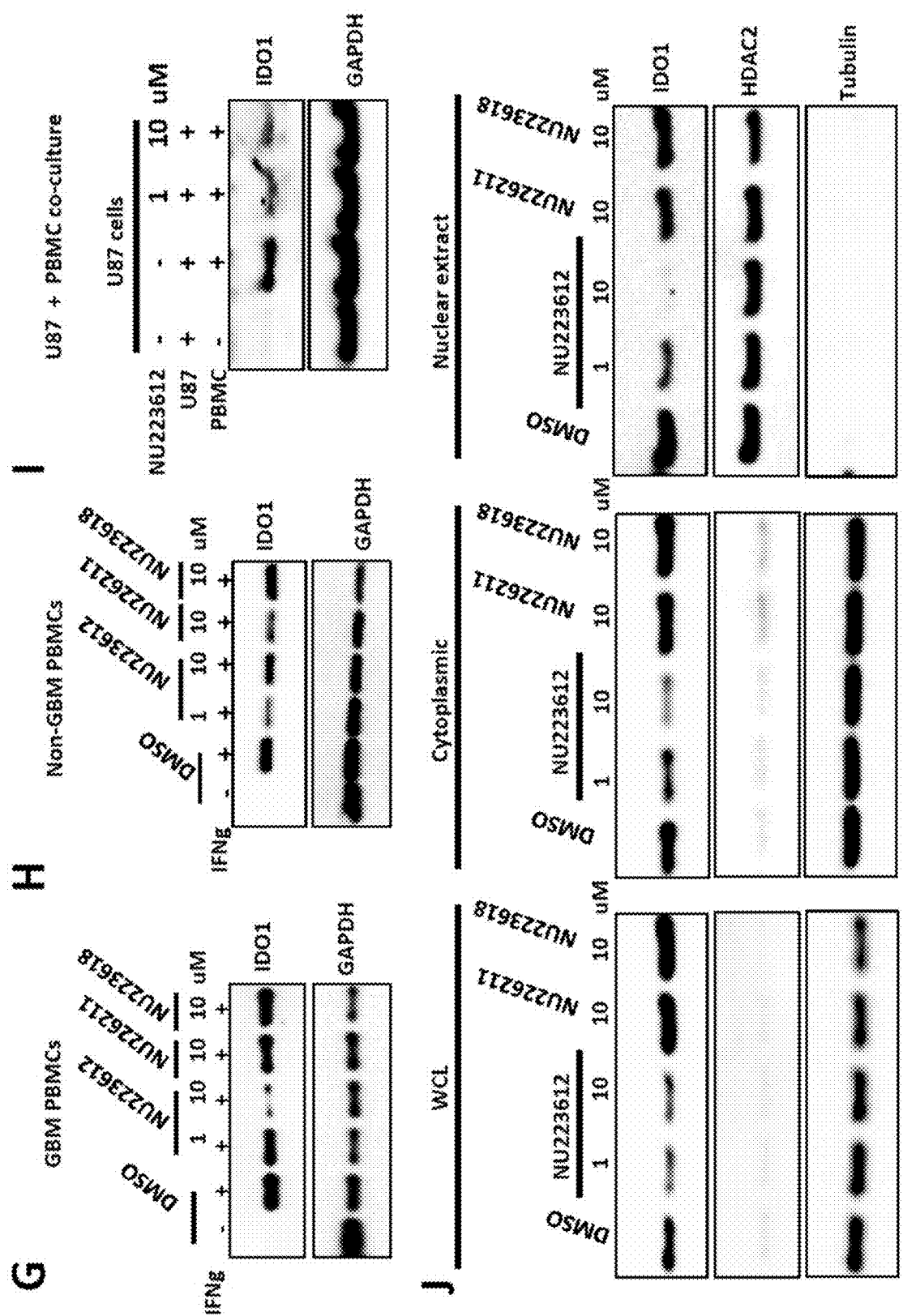
Figure 22:
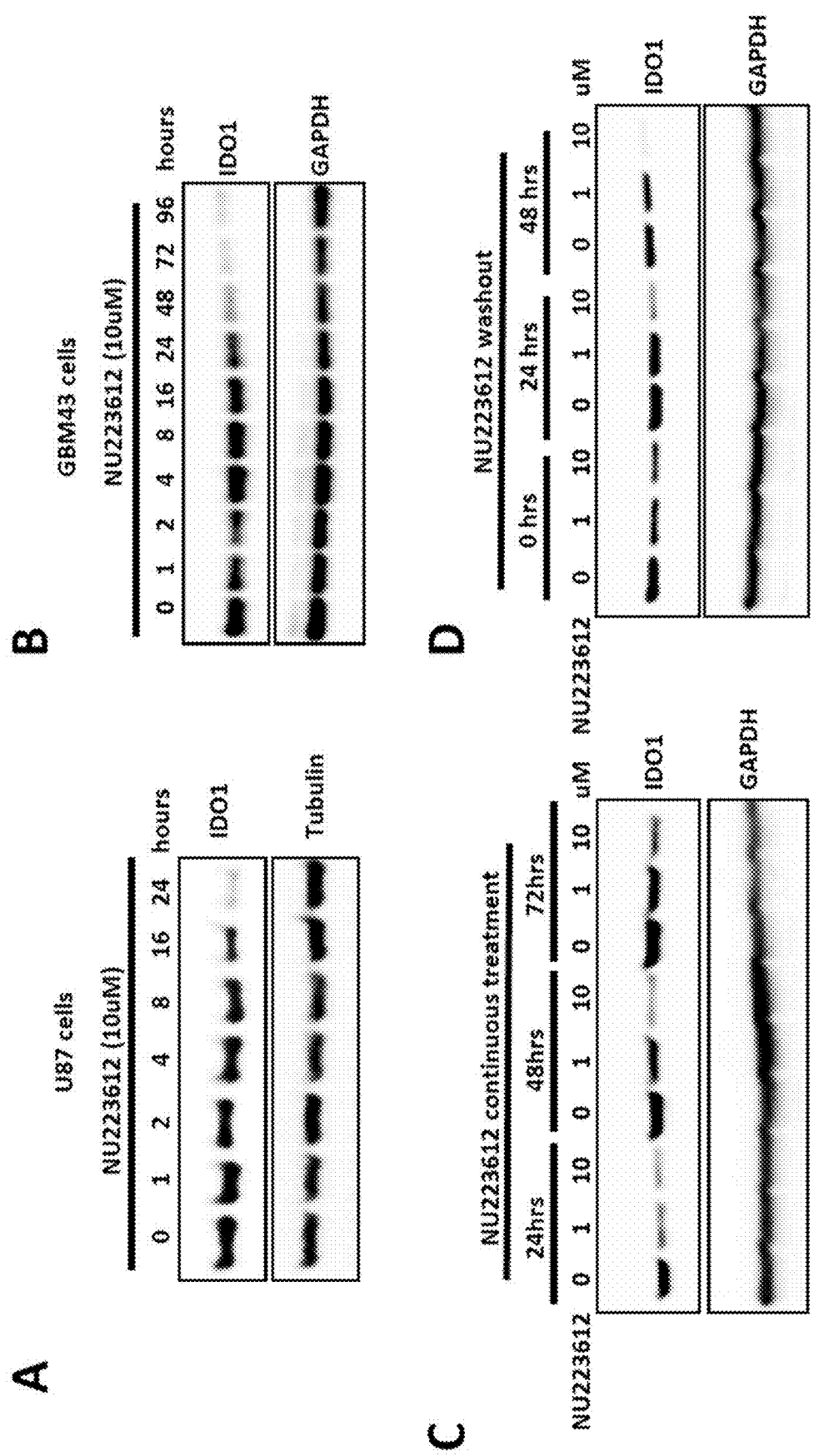
FIG. 22. IDO-PROTAC mediated IDO1 degradation. A & B. Western blot analysis of IDO1 and GAPDH to determine quickly IDO-PROTAC induces IDO1 protein degradation in U87 and GBM43 cells respectively. C. Western blot analysis IDO1 to determine the effect of a single continuous treatment of IDO-PROTAC on IDO1 protein levels at multiple time points in U87 cells. D. Similar to panel C, U87 cells were treated with IDO-PROTAC for 24 hours and cells were cultured without IDO-PROTAC for up to 48 hours. Protein samples were tested in western blot analysis to determine protein levels of IDO1 upon withdrawal of IDO-PROTAC. E. U87 cells were treated with an extended dose range of IDO-PROTAC for 24 hours and protein samples were analyzed through western blot. F. Representative curve of percent IFNg-induced IDO1 levels (normalized to untreated samples) were calculated in U87 cells (from panel E) to determine KD50 that produces 50% of IDO1 degradation. G. GBM43 cells were treated with an extended dose range of IDO-PROTAC for 24 hours and protein samples were analyzed through western blot. H. Representative curve of percent IFNg-induced IDO1 levels (normalized to untreated samples) were calculated in GBM43 cells (from panel H) to determine D50 that produces 50% of IDO1 degradation.
Figure 22:
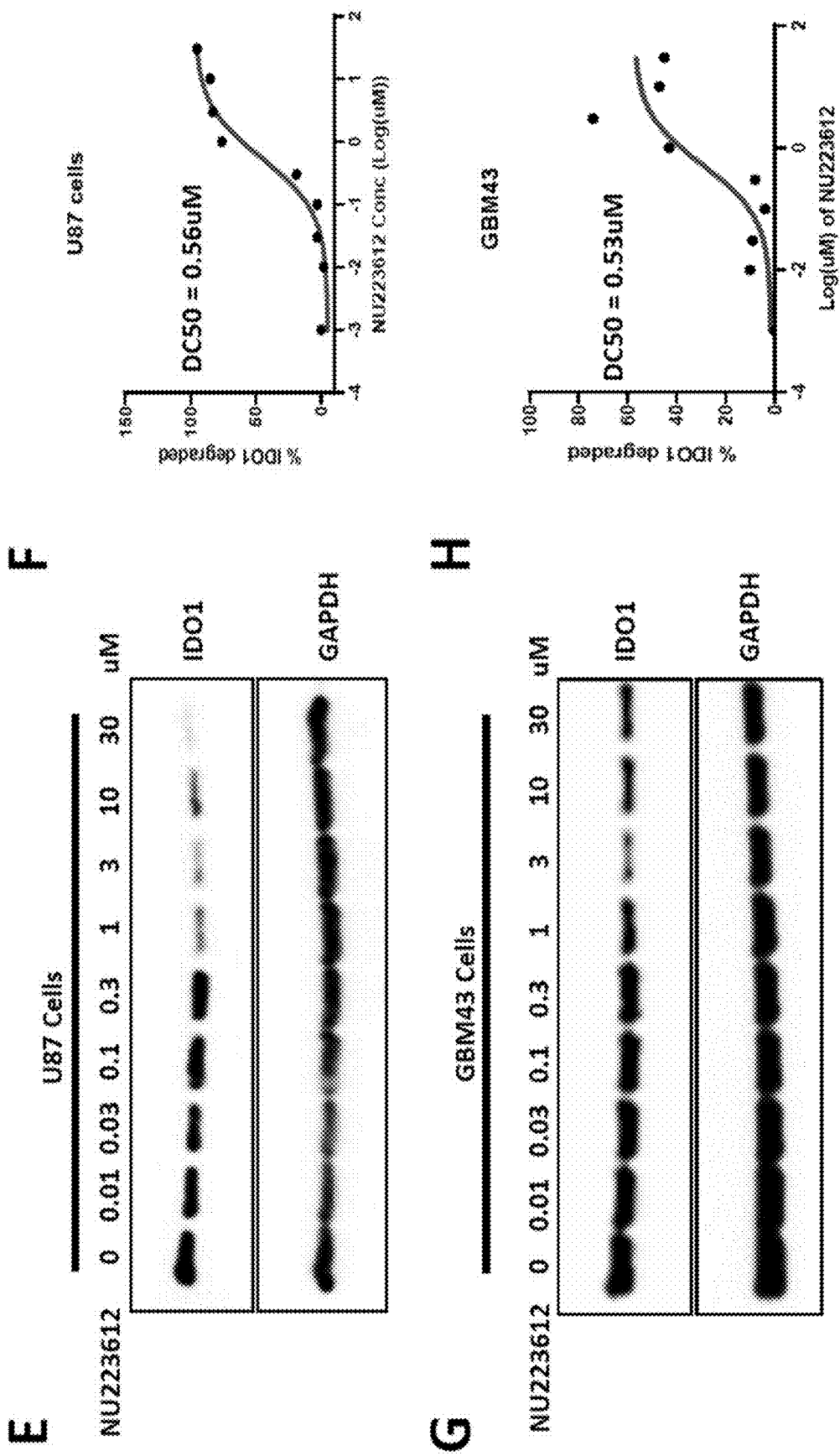
Figure 23:
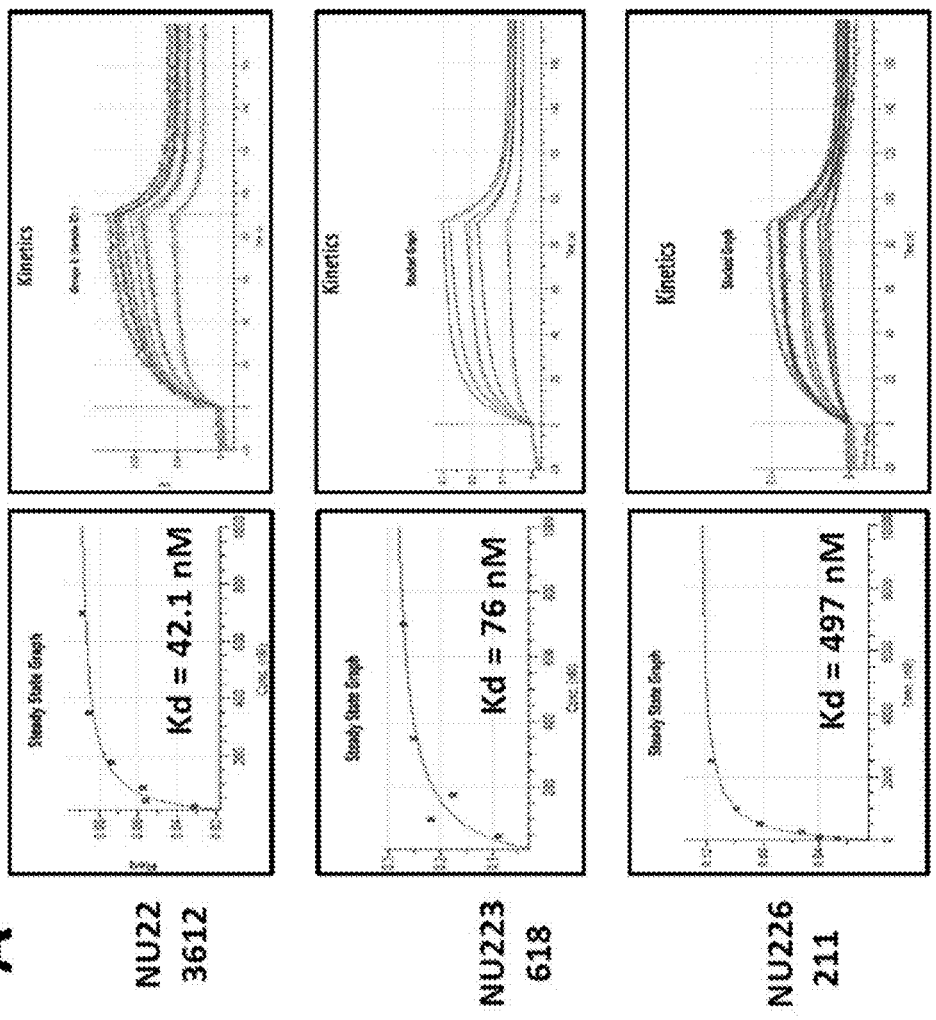
FIG. 23. Mechanistic understanding of IDO-PROTAC-induced IDO1 degradation. A. Representative biolayer interferometry sensorgrams to determine the affinity (Kd) and binary complex formation between IDO1 protein and IDO-PROTAC, IDO1-inhibitor, or mutant-IDO-PROTAC. B. Surface plasmon resonance (SPR) assays to determine ternary complex formation between IDO-PROTAC, IDO1 protein and E3-ligase. C. Western blotting analysis to determine IDO1 ubiquitination in immunoprecipitated samples isolated from U87 cells (IDO1 flag over expressing cells) after treating with IDO-PROTAC, mutant IDO-PROTAC or parental compound. D. Western blotting analysis of IDO1 and GAPDH to determine the effect of parental competitive IDO1-inhibitor (NU223628)(D), non-competitive IDO-inhibitor (E), E-3-ligase ligand (pomalidomide) (F), E1 ligase inhibitor (ML4924) (G), and proteosome inhibitor (MG132) (H) on IDO-PROTAC induced IDO1 degradation. B. NU223618 (parental compound) competes with IDO-PROTAC and blocks IDO1 degradation. C. Proteosome pathway inhibitor (MG132) blocks IDO-PROTAC-induced IDO1 degradation. D. E3-ligase ligand (Pomalidomide) blocks IDO-PROTAC-induced IDO1 degradation Validation of IDO-PRTAC. E. E1-ligase inhibitor (MLN4924) blocks IDO-PROTAC-induced IDO1 degradation in U87 cells.
Figure 23:
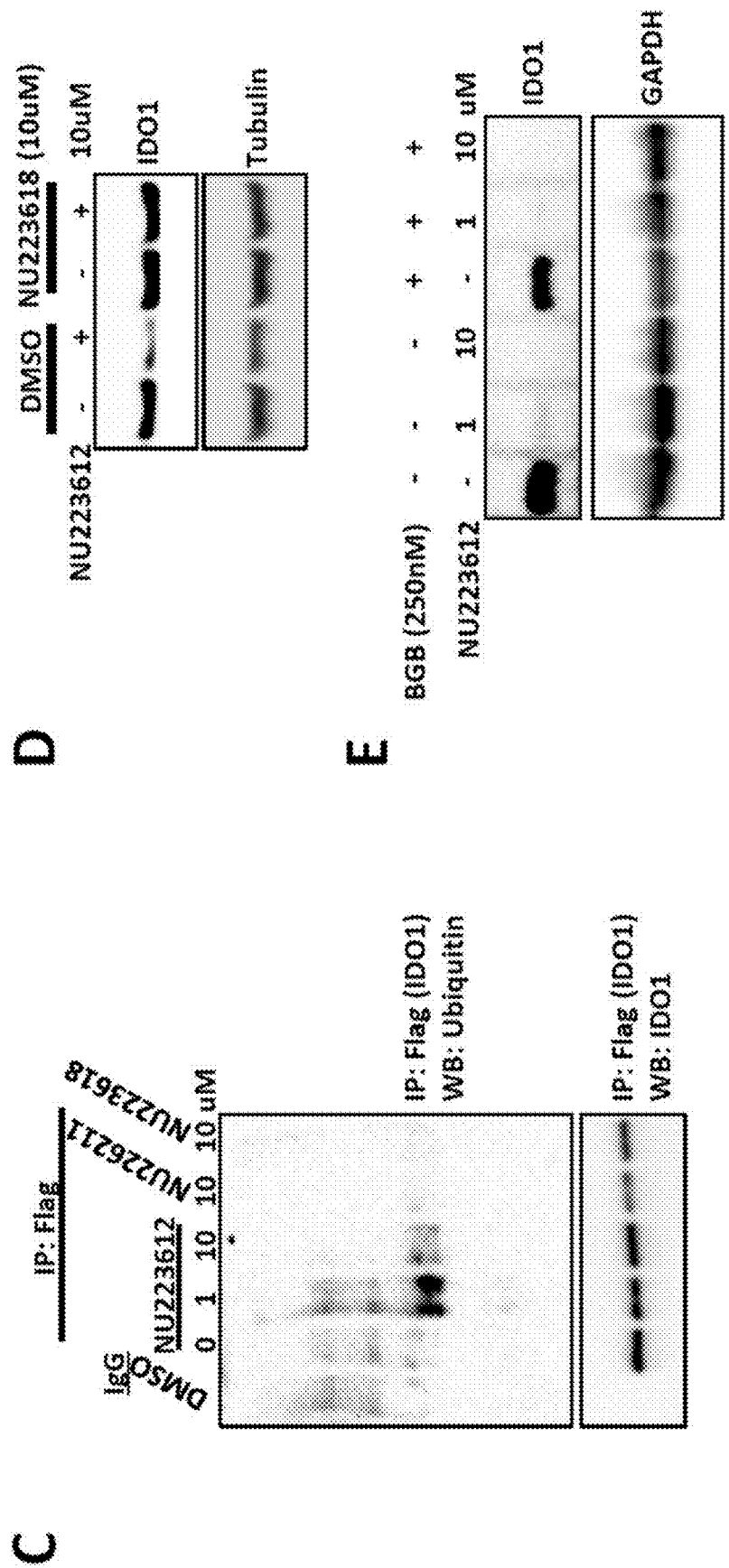
Figure 23:
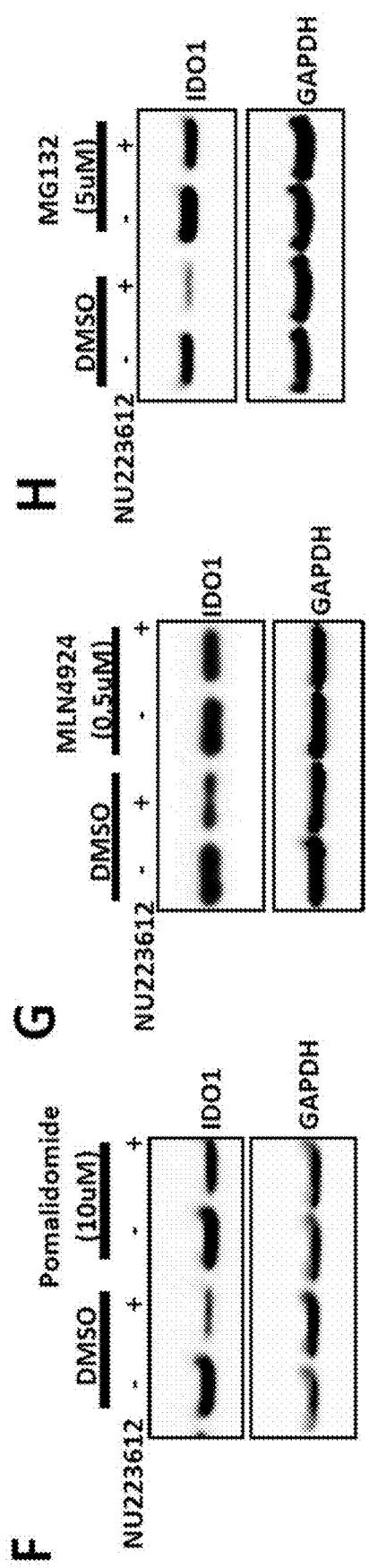
Figure 24:
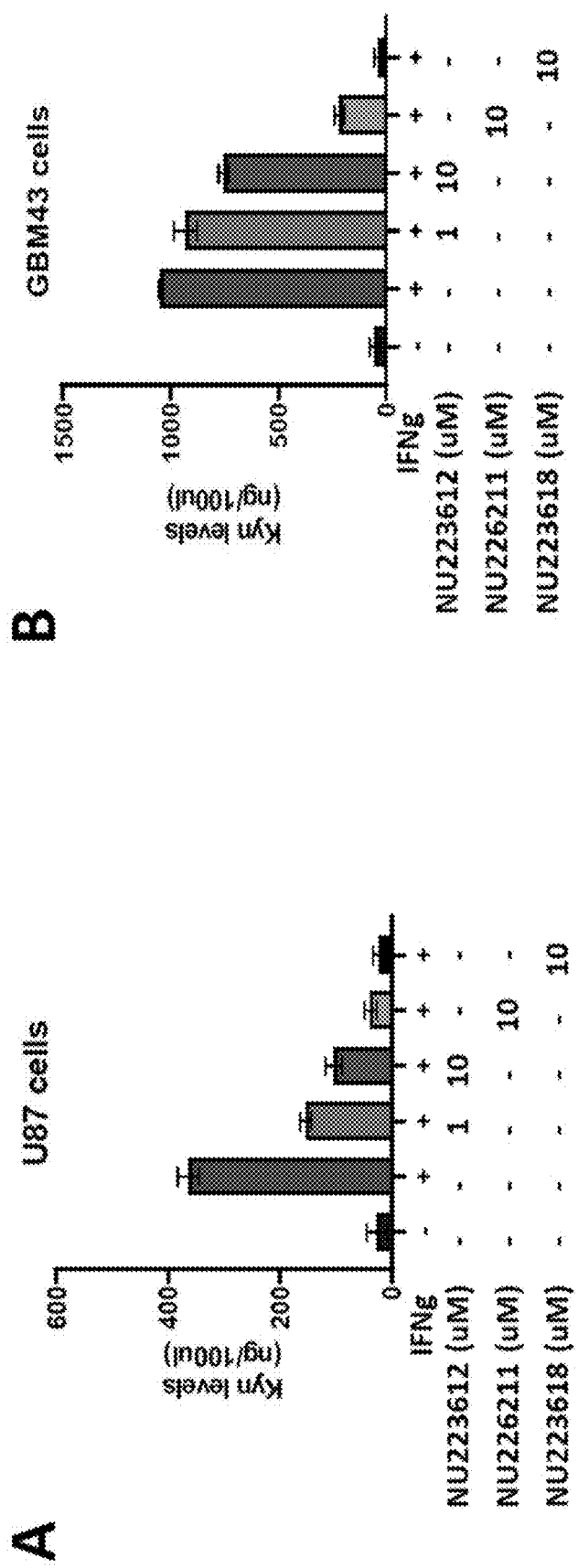
FIG. 24. IDO-PROTAC inhibits both enzyme-dependent and enzyme-independent functions of IDO1 in GBM cells. A & B. Effect of IDO-PROTAC, mutant IDO-PROTAC, and IDO-inhibitor on kynurenine production in U87 & GBM43 cells respective cells. Cells were treated with IDO-PROTAC, mutant IDO-PROTAC, or IDO-inhibitor in the presence of INFg (50 ng/ml) for 24 hours and cell culture supernatants were collected to measure IFNg-induced kynurenine levels using a modified Erlich method. Cells cultured in the absence of IFNg serves as a control group. C. Western blotting analysis to determine the effect of IDO-PROTAC and IDO-inhibitor on IDO1 protein levels, phospho-NFkB (p65) levels, total-NFkB (p65) levels and GAPDH levels in U87 cells. IDO1 protein was induced with IFNg for 24 hours in U87 cells followed by treatment with IDO-PROTAC and IDO-inhibitor for 24 hours at multiple concentrations. D. Western blotting analysis to determine the effect of IDO-PROTAC, mutant IDO-PROTAC, and IDO-inhibitor on IDO1 protein levels, phospho-NFkB (p65) levels, total-NFkB (p65) levels and GAPDH levels in a breast cancer cell line, MDA MB 231. E. Western blotting analysis to determine the effect of IDO-PROTAC on the levels of IDO1 protein, phospho-NFkB (p65), total-NFkB (p65) and GAPDH in U87 IDO1 overexpressing (flag-tagged) cells. Cells were treated with DMSO or IDO-PROTAC (10 uM) for 24 hours prior to protein extraction. U87 parental cells serves as a control group for basal phosphorylation of NFkB. F. Western blotting analysis to determine the effect of IDO-PROTAC on cytoplasmic and nuclear levels of IDO1 protein, phospho-NFkB (p65), total-NFkB (p65), HDAC2 (Nuclear marker) and tubulin (cytoplasmic marker) in U87 cells. Cells were treated with DMSO or IDO-PROTAC (10 uM) for 24 hours prior to protein extraction.
Figure 24:
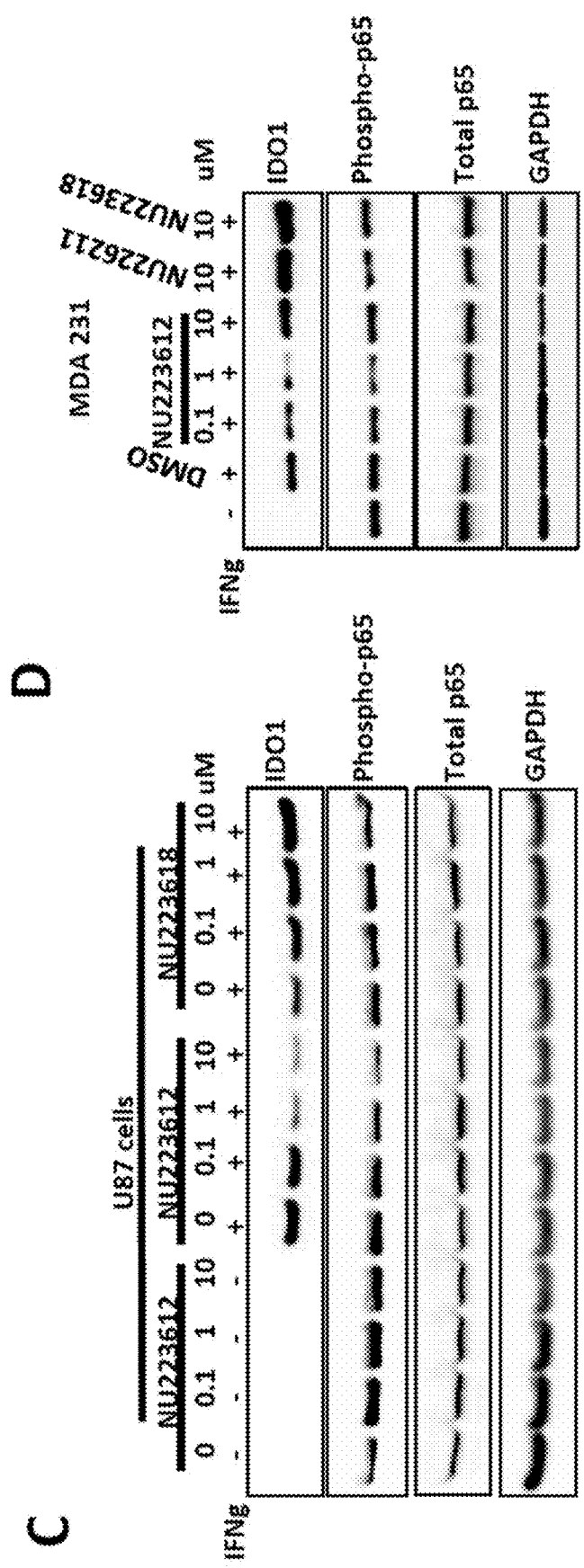
Figure 24:
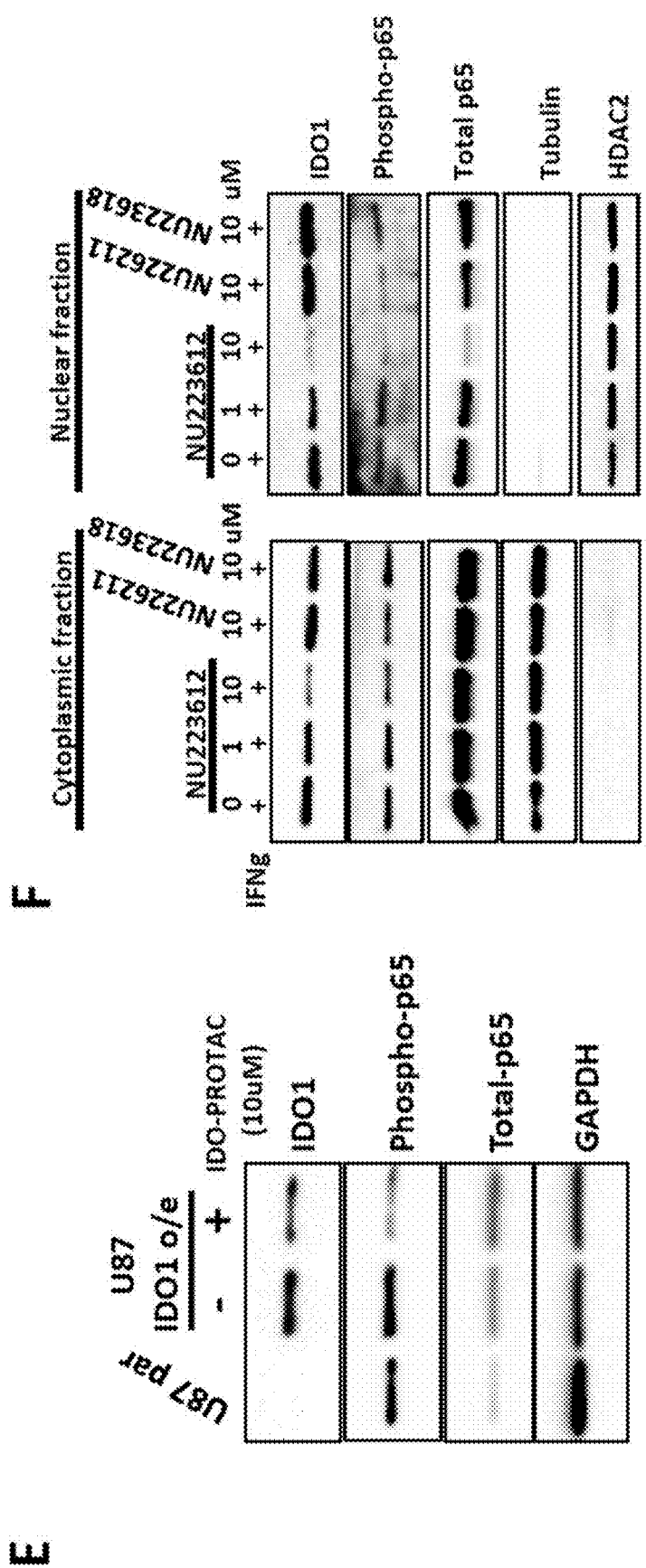
Figure 25:
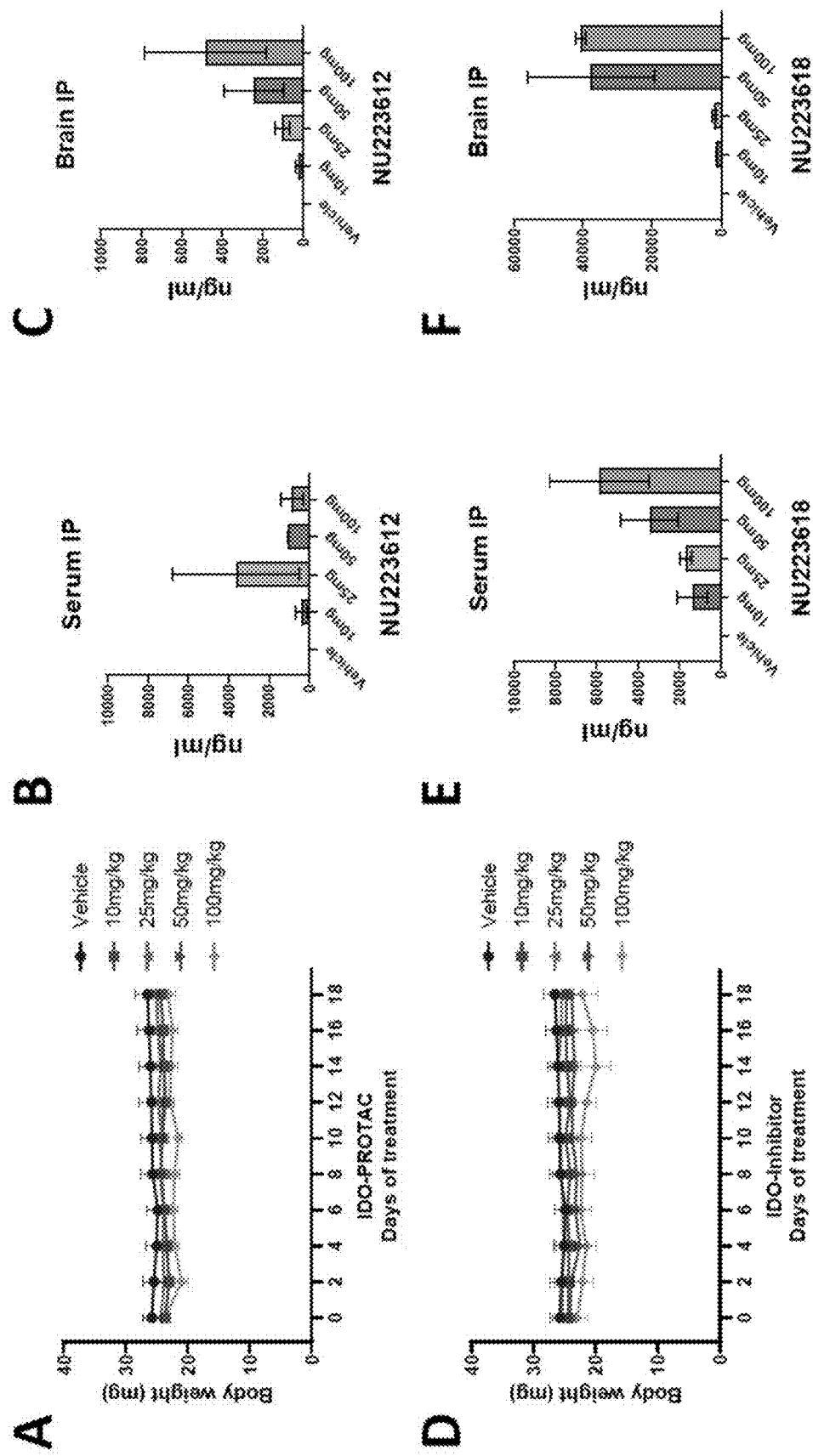
FIG. 25. In vivo activity of IDO-PROTAC. A & B. C57BL/6 mice were treated with IDO-PROTAC (A) or IDO-inhibitor (B) i.p. for 3 weeks once per day. Mouse body weight was measured every 2-3 days (mean±SEM; n=3). C & D. Serum levels of IDO-PROTAC (C) and IDO-inhibitor (D) in C57BL/6 mice. C57BL/6 mice were treated with IDO-PROTAC or IDO-inhibitor i.p. for 3 weeks once per day (from panel A & B). After 3 weeks of treatment serum samples were prepared from these mice and subjected for mass spectrometry analysis of IDO-PROTAC and IDO-inhibitor. E & F. Brain accumulation of IDO-PROTAC (E) and IDO-inhibitor (F) in C57BL/6 mice. C57BL/6 mice were treated with IDO-PROTAC or IDO-inhibitor i.p. for 3 weeks once per day (from panel A & B). After 3 weeks of treatment brain tissue samples were prepared from these mice and subjected for mass spectrometry analysis of IDO-PROTAC and IDO-inhibitor. G & H. Pharmaco kinetics (PK) of IDO-PROTAC in C57BL/6 mice. Mice were treated with IDO-PROTAC at 25 mg/kg i.p. and serum and brain samples were collected for mass spectrometry analysis of IDO-PROTAC. I. Half life, AUC, and CMax of IDO-PROTAC in serum and brain samples. J. Western blotting analysis of IDO1 and GAPDH in tumor lysates. Nude mice/C57BL/6 were engrafted with IDO1 overexpressing GBM cells intracranially. Three weeks after engraftment, mice were treated with IDO-PROTAC (25 mg/kg) and tumor samples were prepared at 0, 4, 8, 16, and 24 hours for western blotting analysis.
Figure 25:
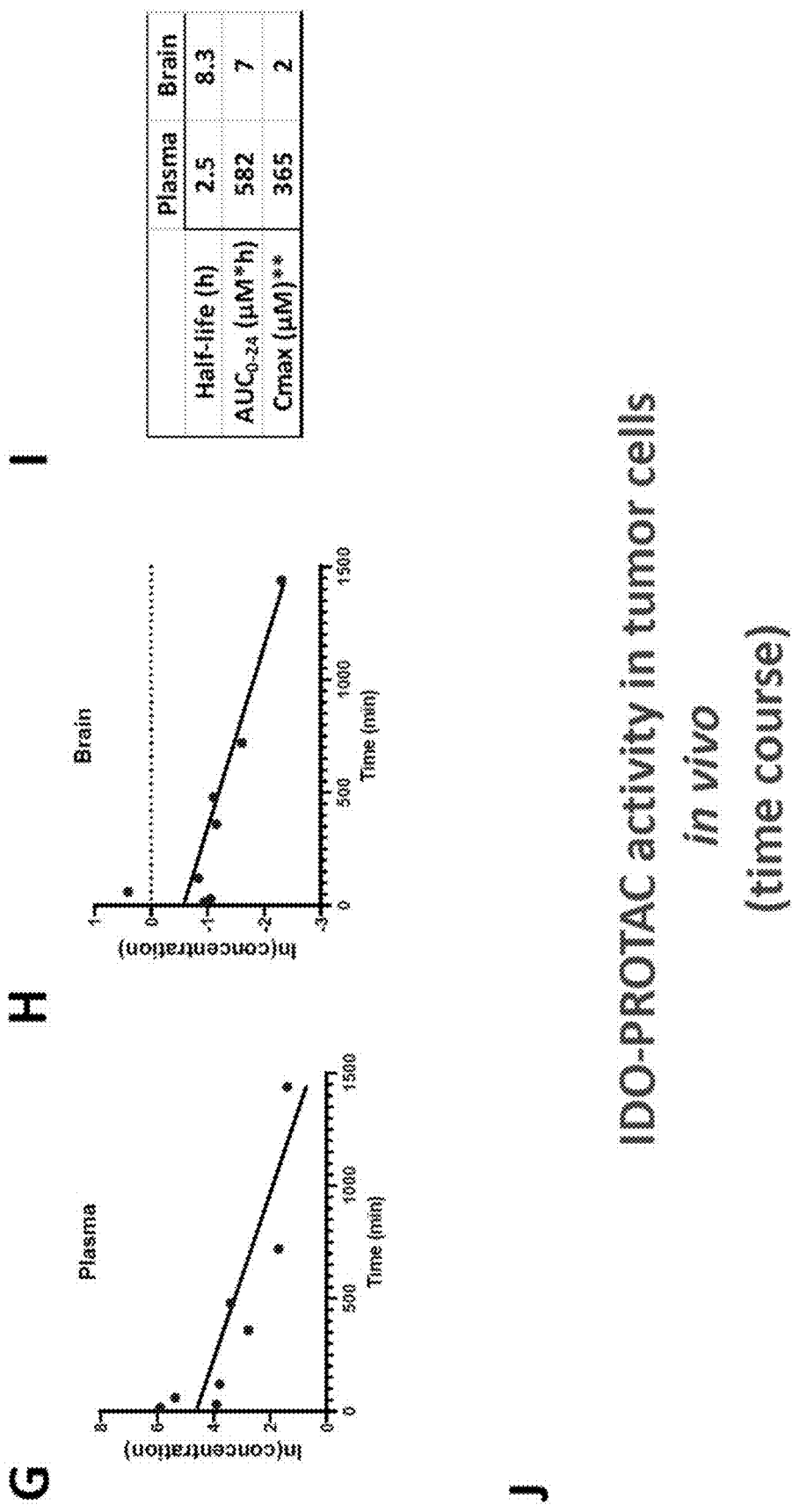
Figure 26:
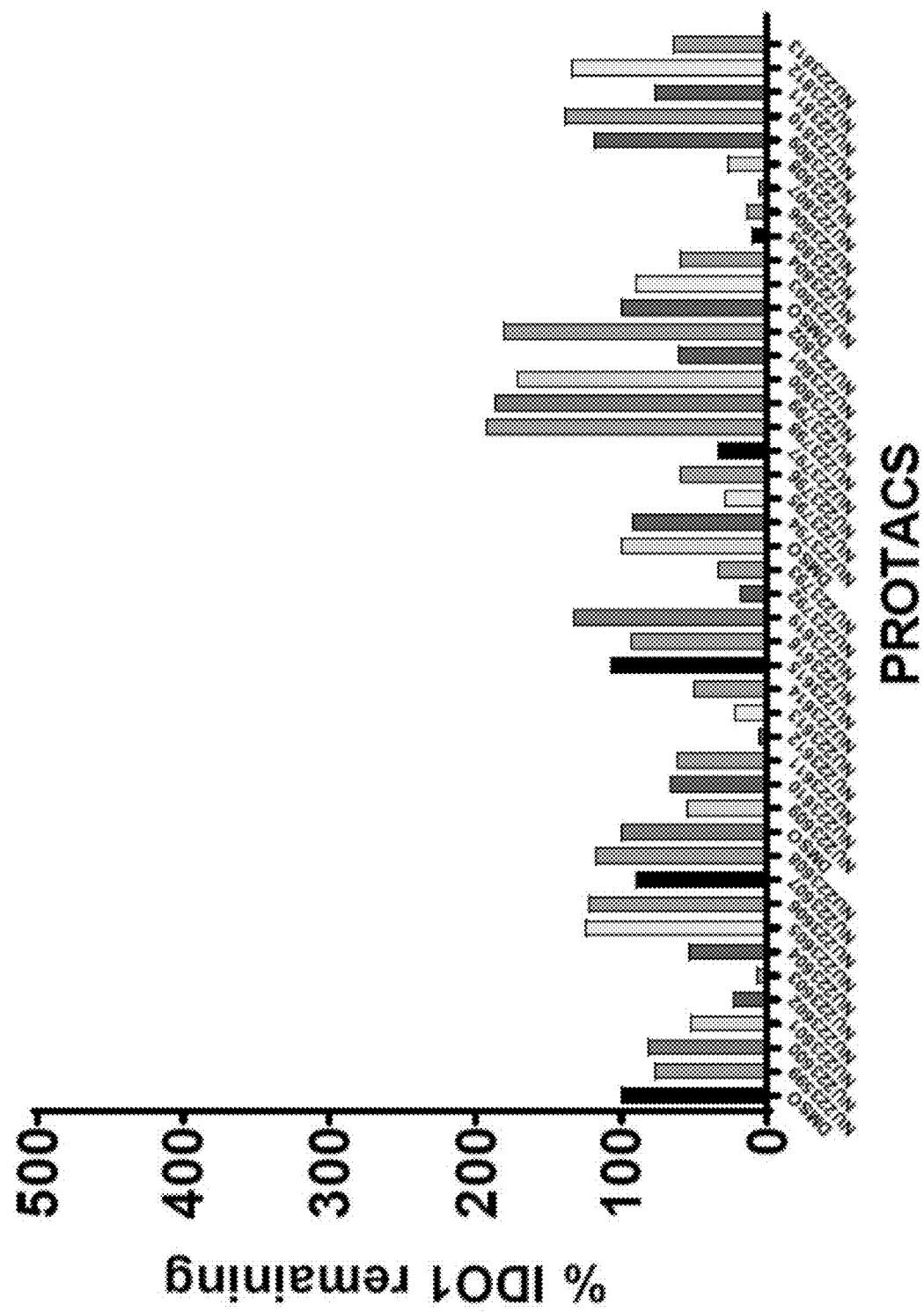
FIG. 26. Representative graphs to screen highly potent IDO-PROTACs. Percent IFNg-induced IDO1 levels (normalized to untreated samples) were calculated in U87 cells after treating with IDO-PROTAC compounds at 10 uM concentration for 24 hours.
Figure 26:
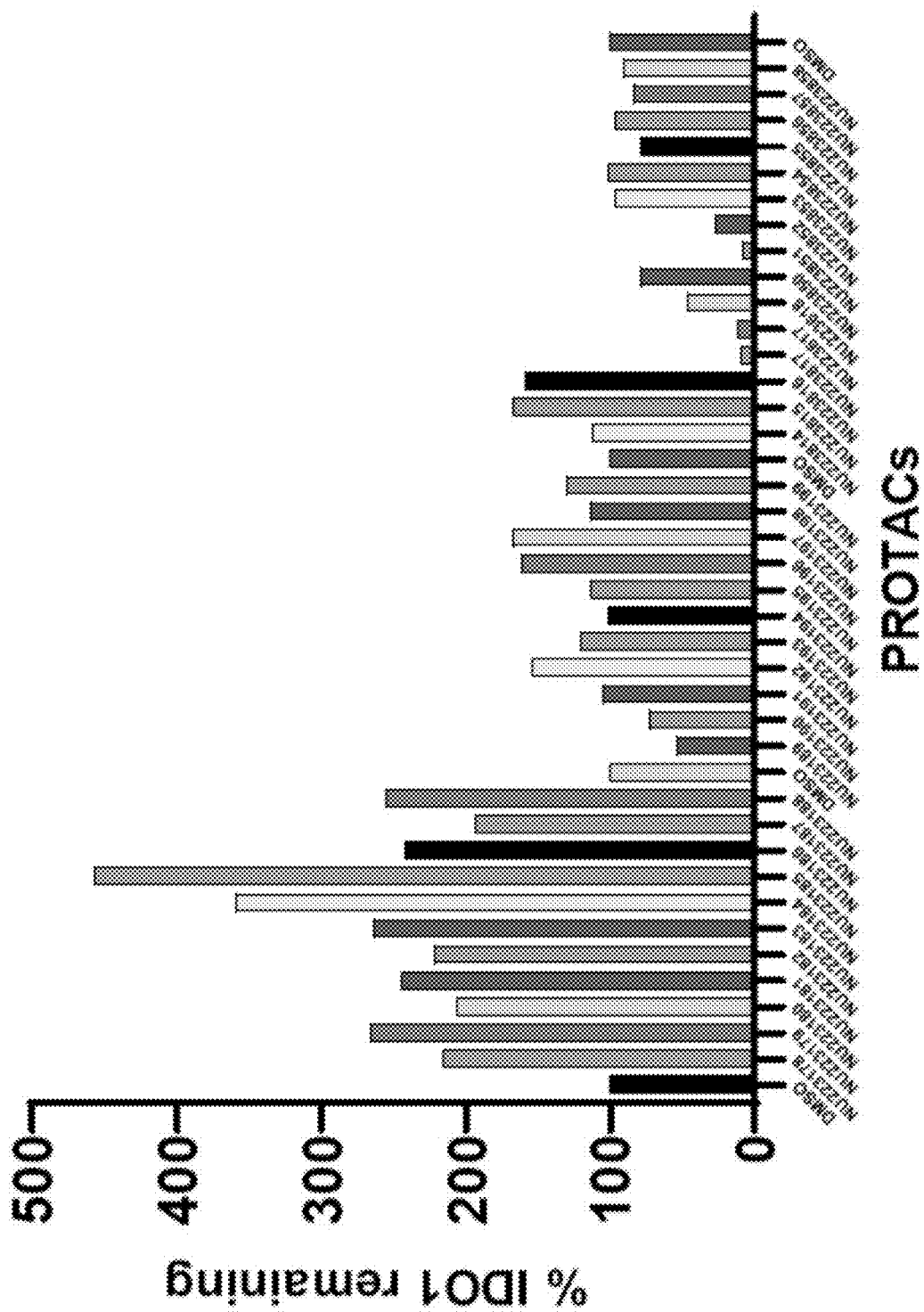
Figure 26:
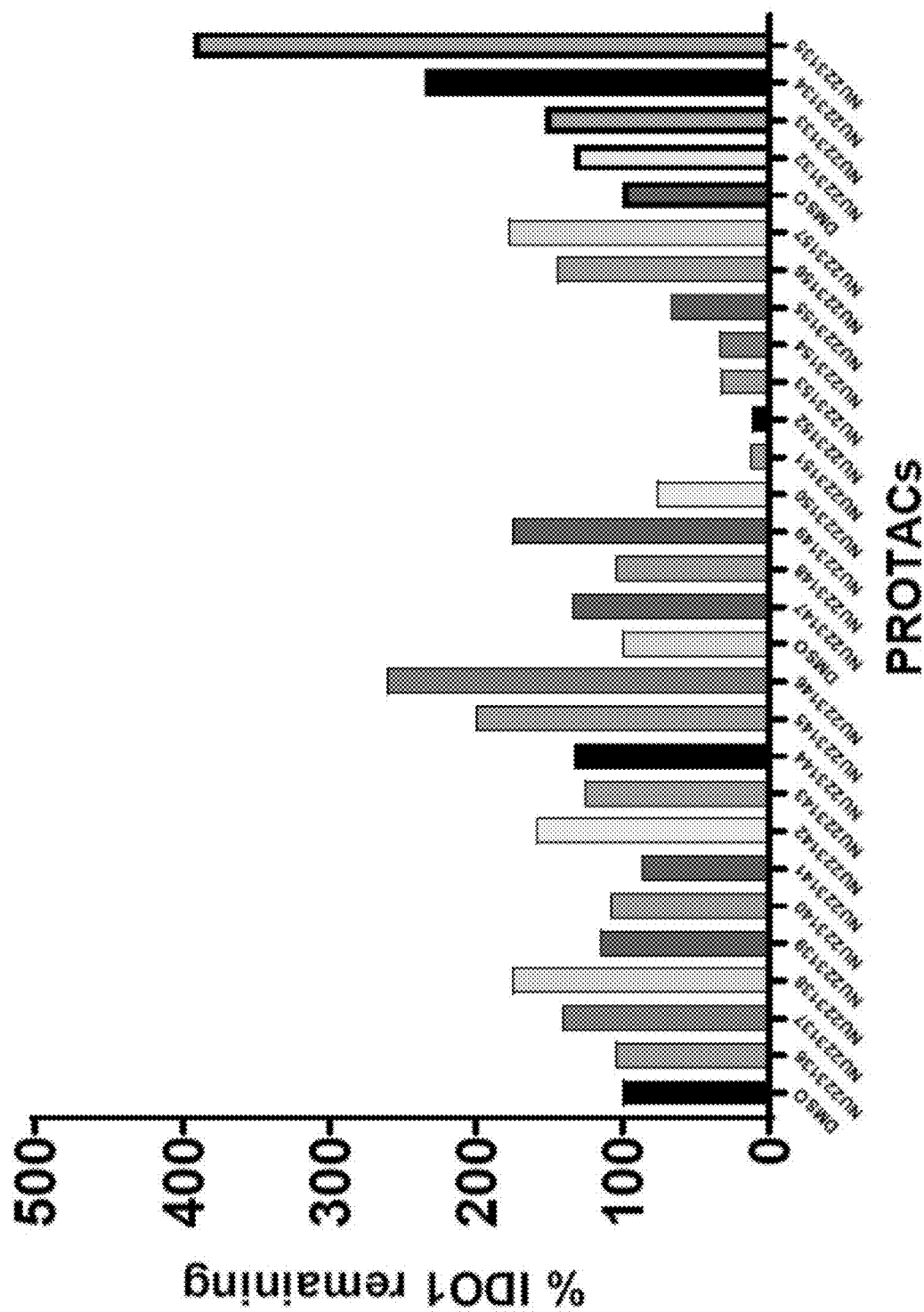
Figure 27:
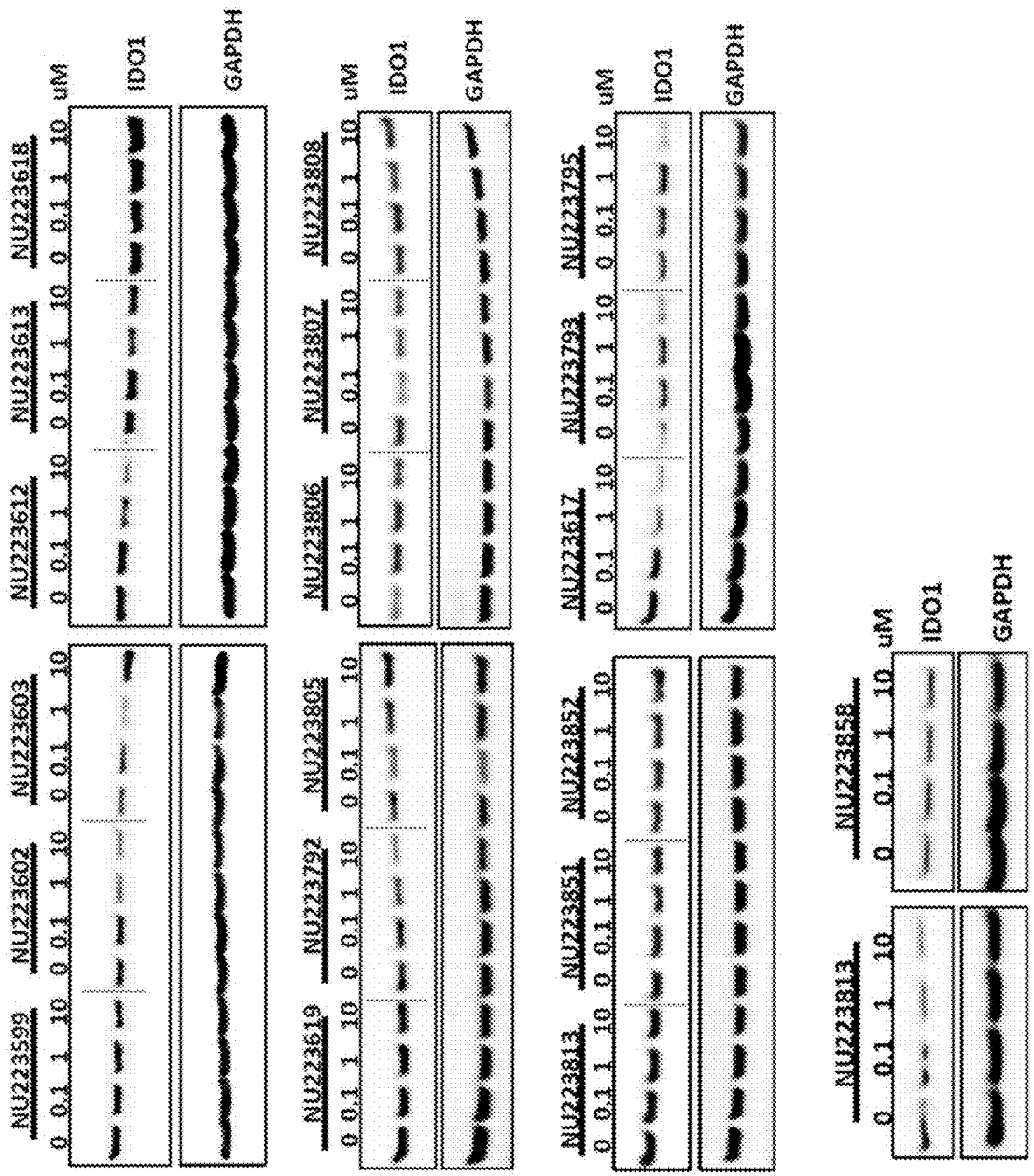
FIG. 27. Representative western blots to identify a lead IDO-PROTAC in U87 cells. IDO1 protein was induced in U87 cells with IFNg (50 ng/ml) for 24 hours followed by treatment with IDO-PROTAC at 0, 0.1, 1, and 10 uM for 24 hours before protein samples were prepared for western blotting analysis of IDO1 and GAPDH.
Figure 28:
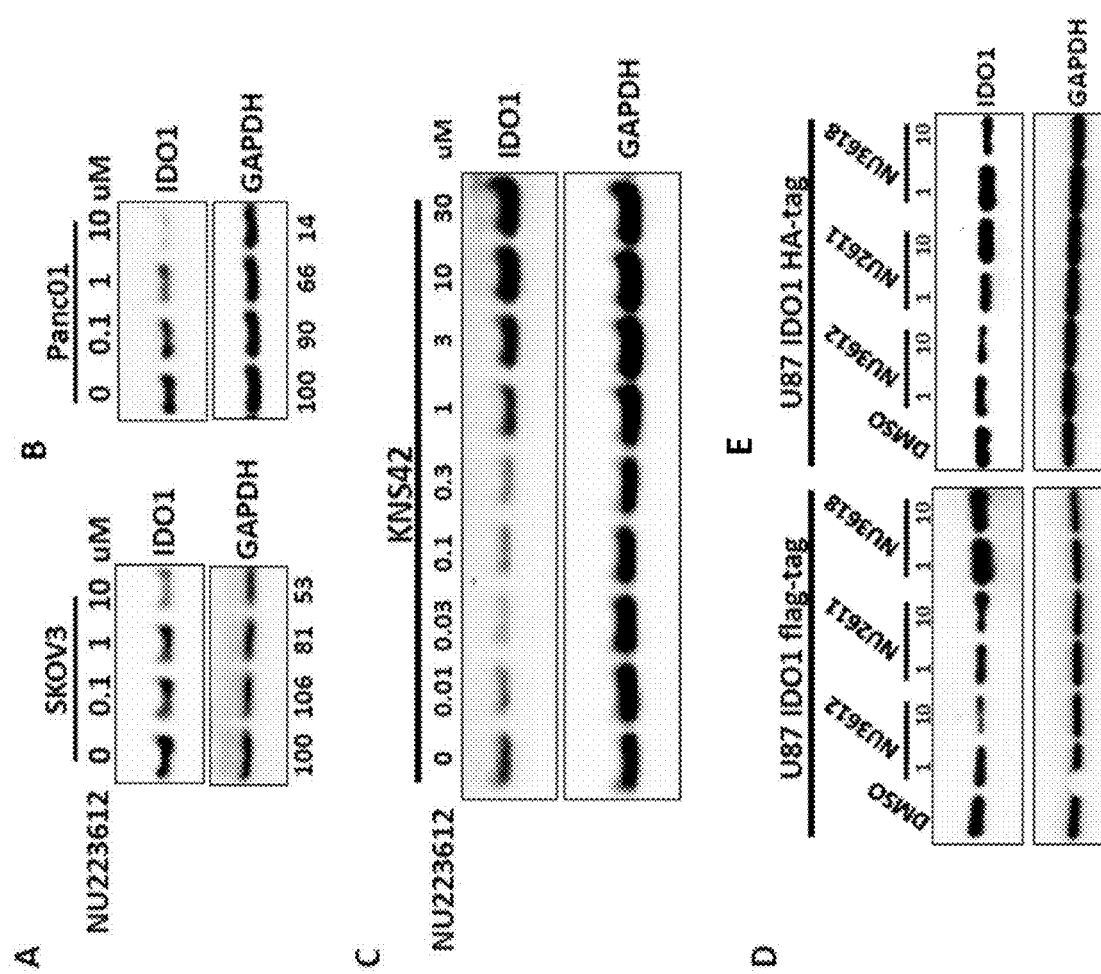
FIGS. 28. A & B. IDO1 protein was induced in SKOV3 and Panc01 cells with IFNg (50 ng/ml) for 24 hours followed by treatment with IDO-PROTAC at 0, 0.1, 1, and 10 uM for 24 hours before protein samples were prepared for western blotting analysis of IDO1 and GAPDH. C. KNS42 cells treated with IDO-PROTAC for 24 hours and protein samples were analyzed for IDO1 and GAPDH using western blotting analysis. D & E. U87 cells stably expressing either flag-tagged or HA-tagged IDO1 were treated with IDO- PROTAC, mutant IDO-PROTAC, or IDO-inhibitor for 24 hours and analyzed for IDO1 and GAPDH using western blotting analysis.
Figure 29:
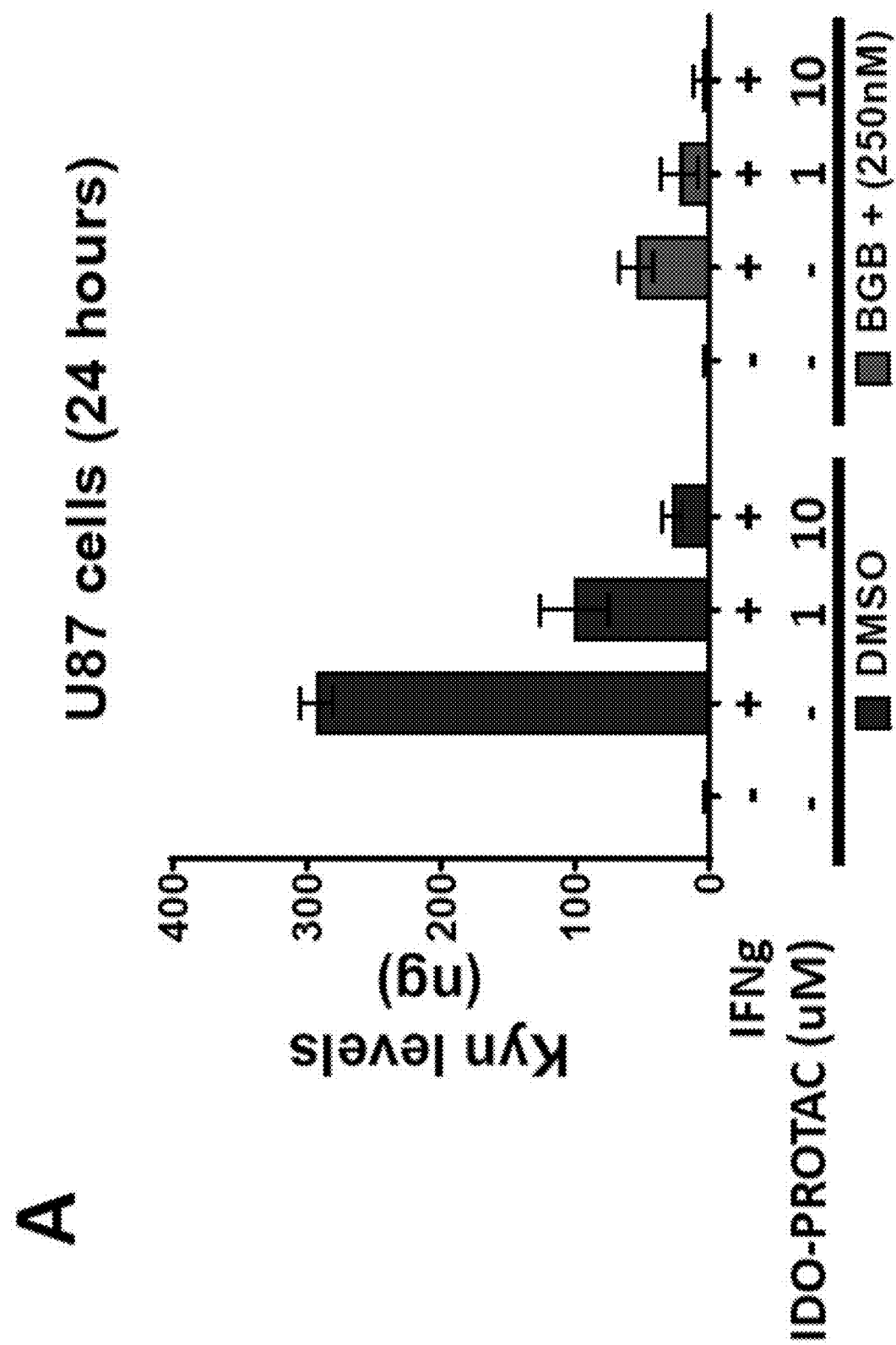
FIG. 29. A. U87 cells were treated with INFg (50 ng/ml) and IDO-PROTAC in the absence and presence of a non-competitive IDO-inhibitor (BGB-5704) and cell culture supernatants were collected to measure IFNg-induced kynurenine levels using a modified Ehrlich method. Cells cultured in the absence of IFNg serves as a control group. B-D. Kynurenine production in OVCAR5, PC3, and CD18 cells treated with IDO-PROTAC in the presence of IFNg.
Figure 29:
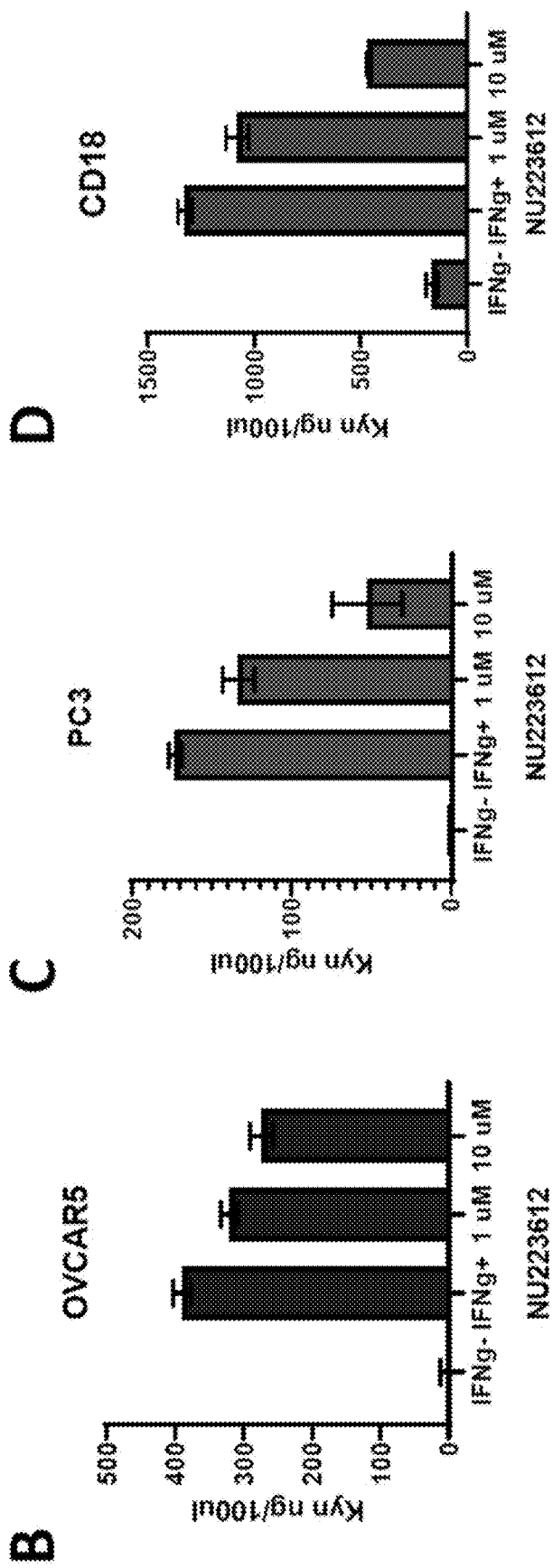
Figure 30:
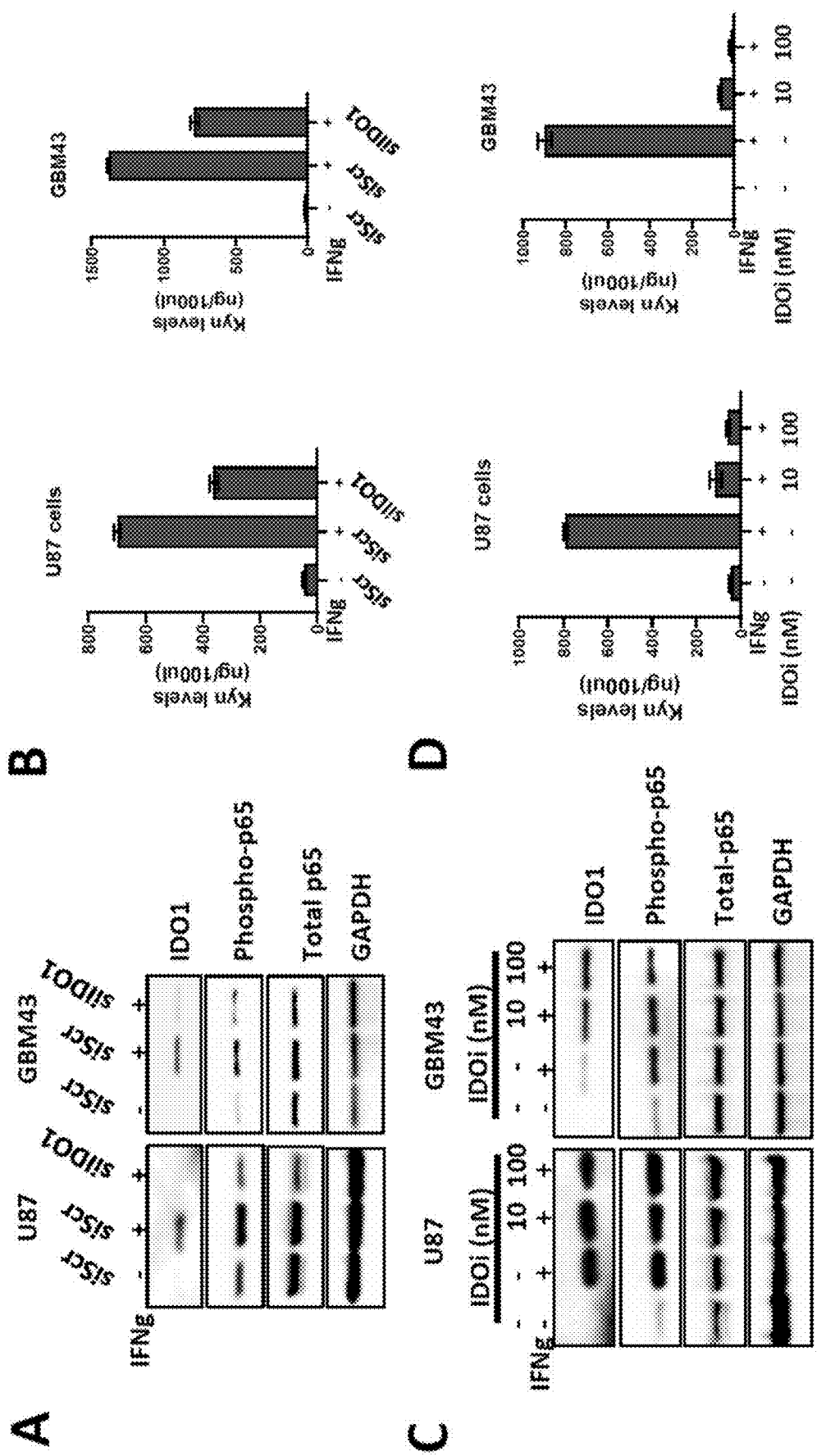
FIG. 30. A. Western blotting analysis of IDO1, phospho-p65, total p65, and GAPDH in U87 and GBM43 cells after knocking down of IDO1 for 24 hours. After 24 hours, cells were treated with IFNg to induce IDO1 expression for another 24 hours before protein samples were isolated for western blotting. B. Supernatants from panel A were analyzed for kynurenine levels using modified Ehrlich method. C. Western blotting analysis of IDO1, phospho-p65, total p65, and GAPDH in U87 and GBM43 cells after treating with IDO1 enzyme inhibitor for 24 hours in the presence of IFNg (to induce IDO1 expression). D. Supernatants from panel C were analyzed for kynurenine levels using modified Ehrlich method.
Figure 31:
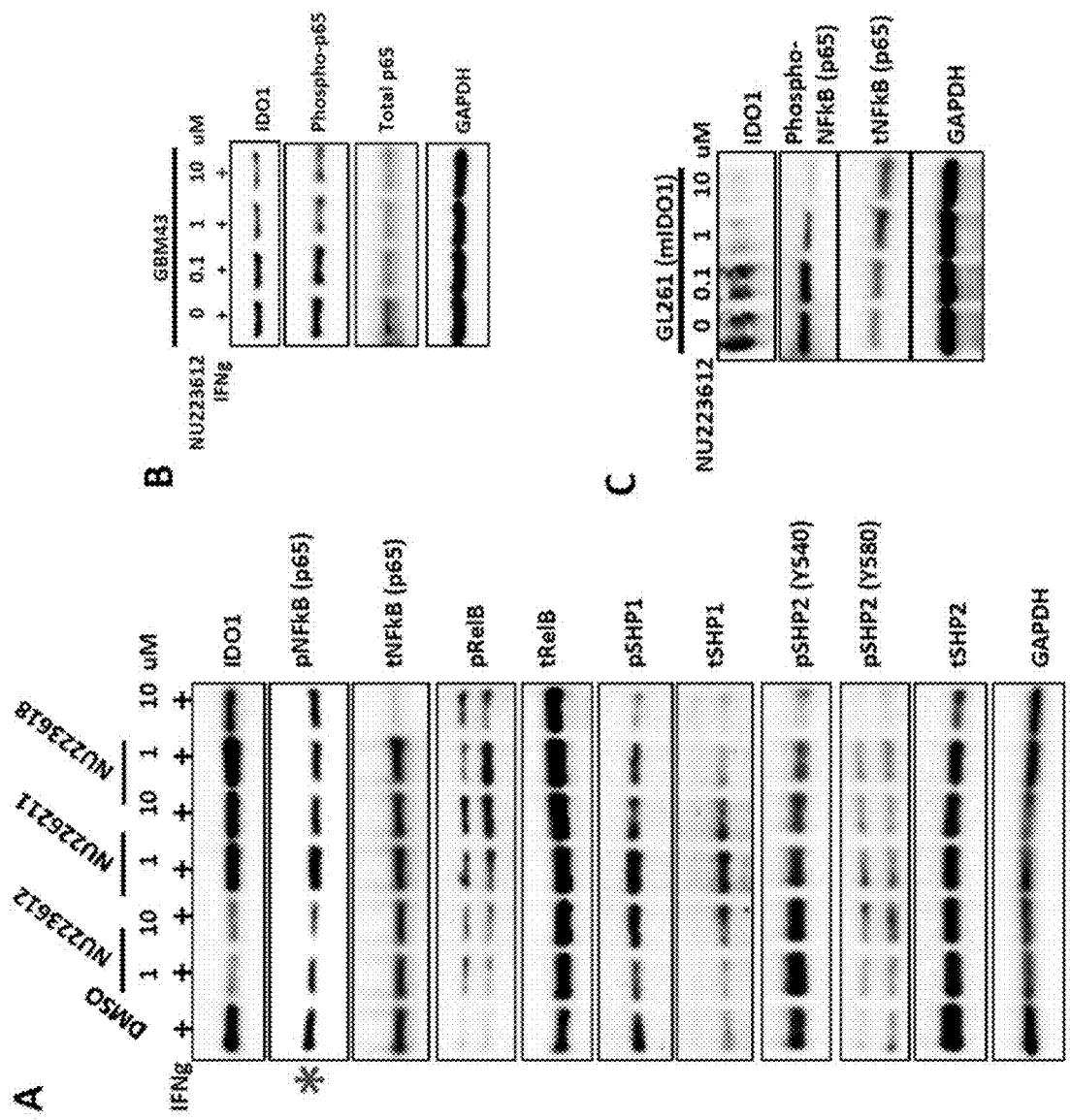
FIG. 31. A. Western blotting analysis of IDO1, GAPDH, and GAPDH and key NFkB pathway signaling molecules in U87 cells after treating with IDO-PROTAC, mutant-IDO-PROTAC and IDO1 enzyme inhibitor for 24 hours. Prior to prepare protein samples, U87 cells were treated with IFNg to induce IDO1 expression. B. Western blotting analysis of IDO1, phospho-p65, total p65, and GAPDH in GBM43 cells after treating with IDO-PROTAC for 24 hours in the presence of IFNg (to induce IDO1 expression). C. Western blotting analysis of IDO1, phospho-p65, total p65, and GAPDH in GL261 cells stably overexpressing mouse IDO1.
Figure 32:
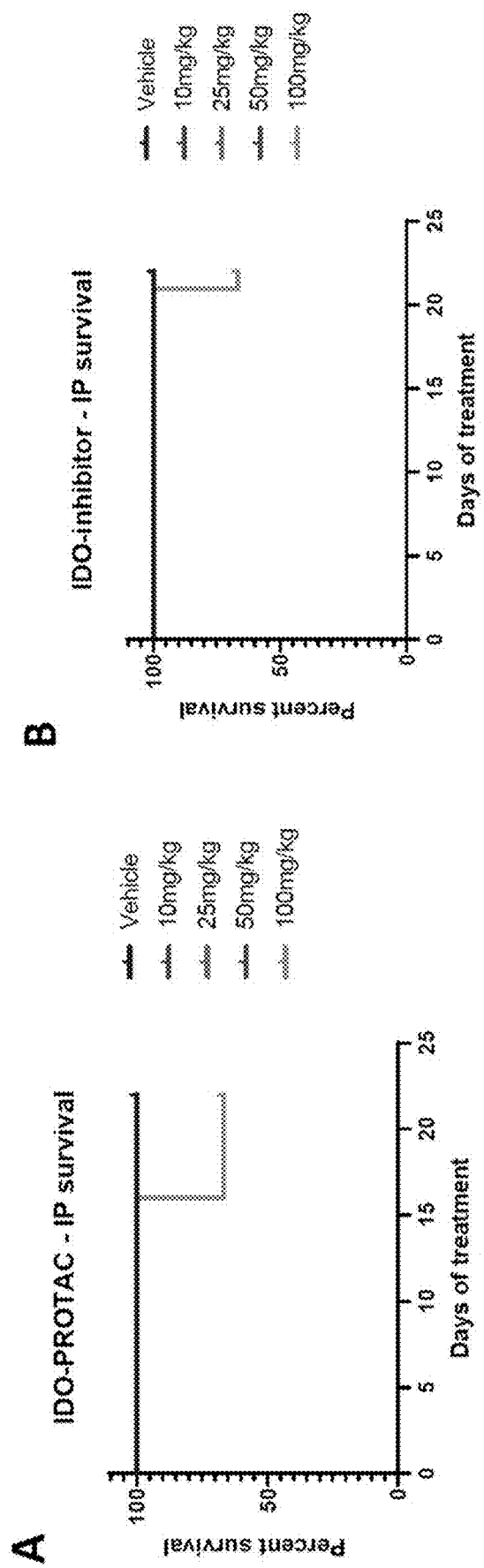
FIG. 32. Kaplan-Meir survival curves of wild type C57BL/6 mice treated with IDO-PROTAC or IDO enzyme inhibitor for 3 weeks.
Figure 33:
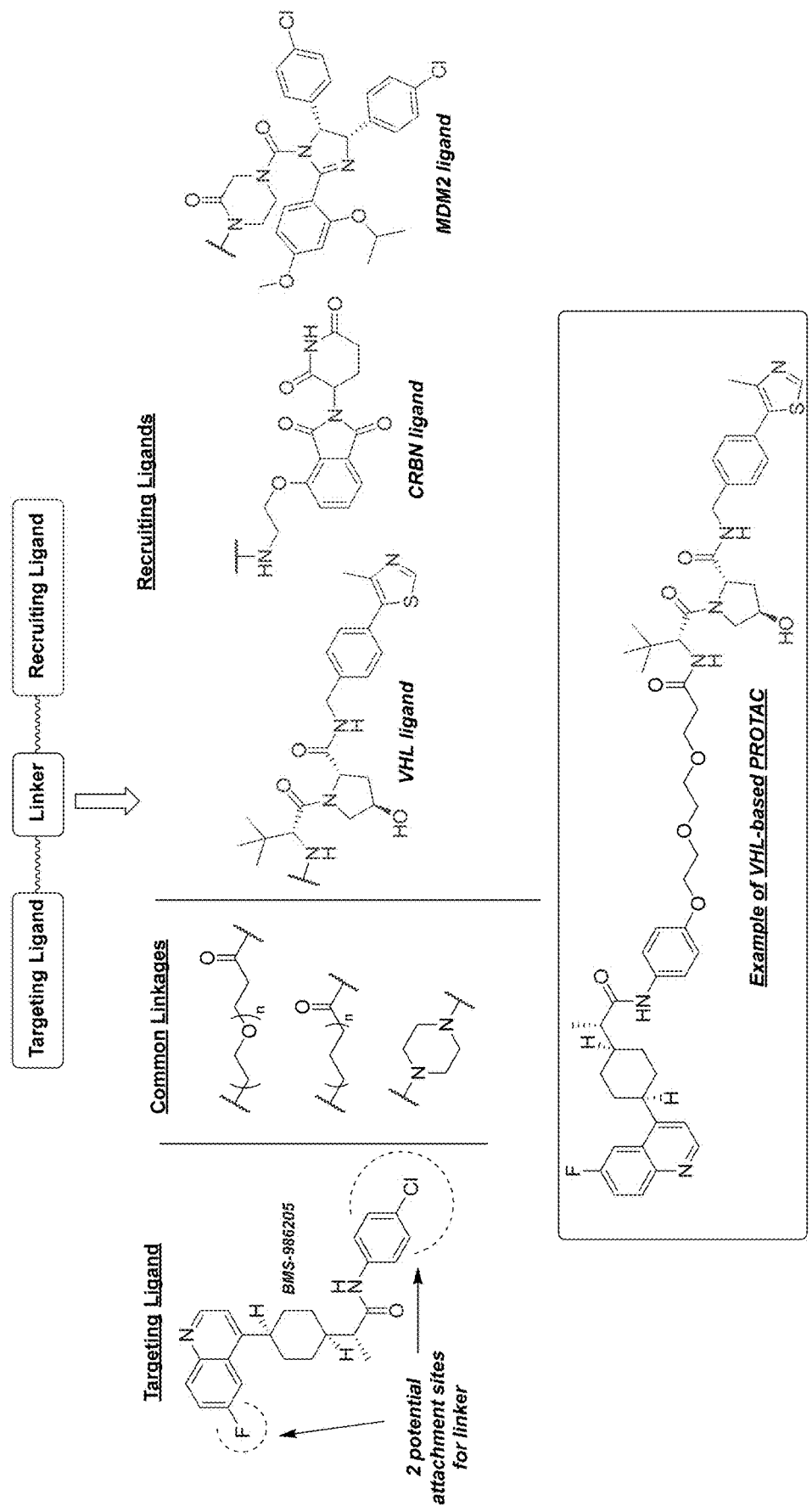
FIG. 33. Exemplary strategy for preparing IDO-PROTAC.
Figure 34:
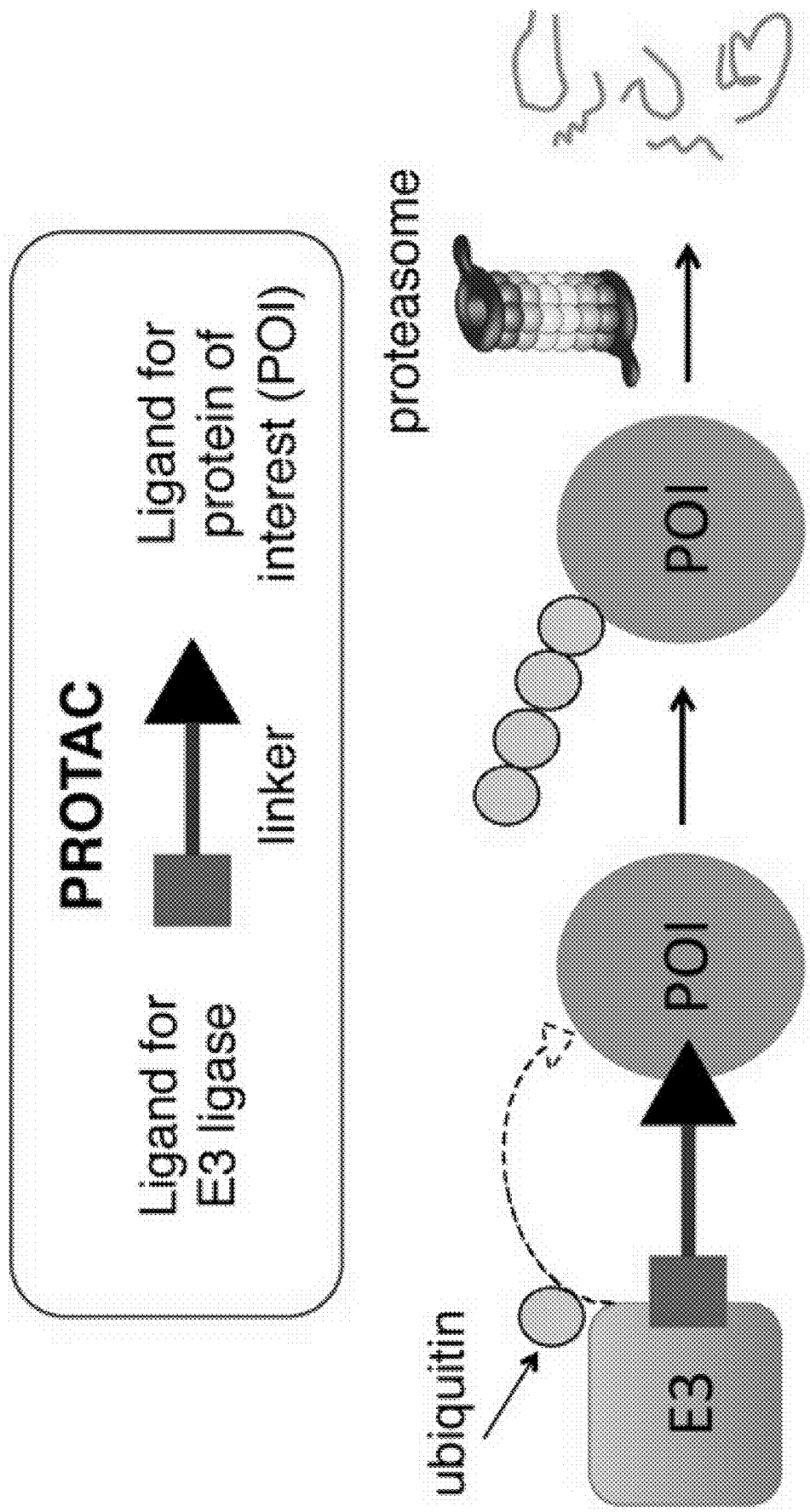
FIG. 34. Illustration of IDO-PROTAC mechanisms of action.
Figure 35:
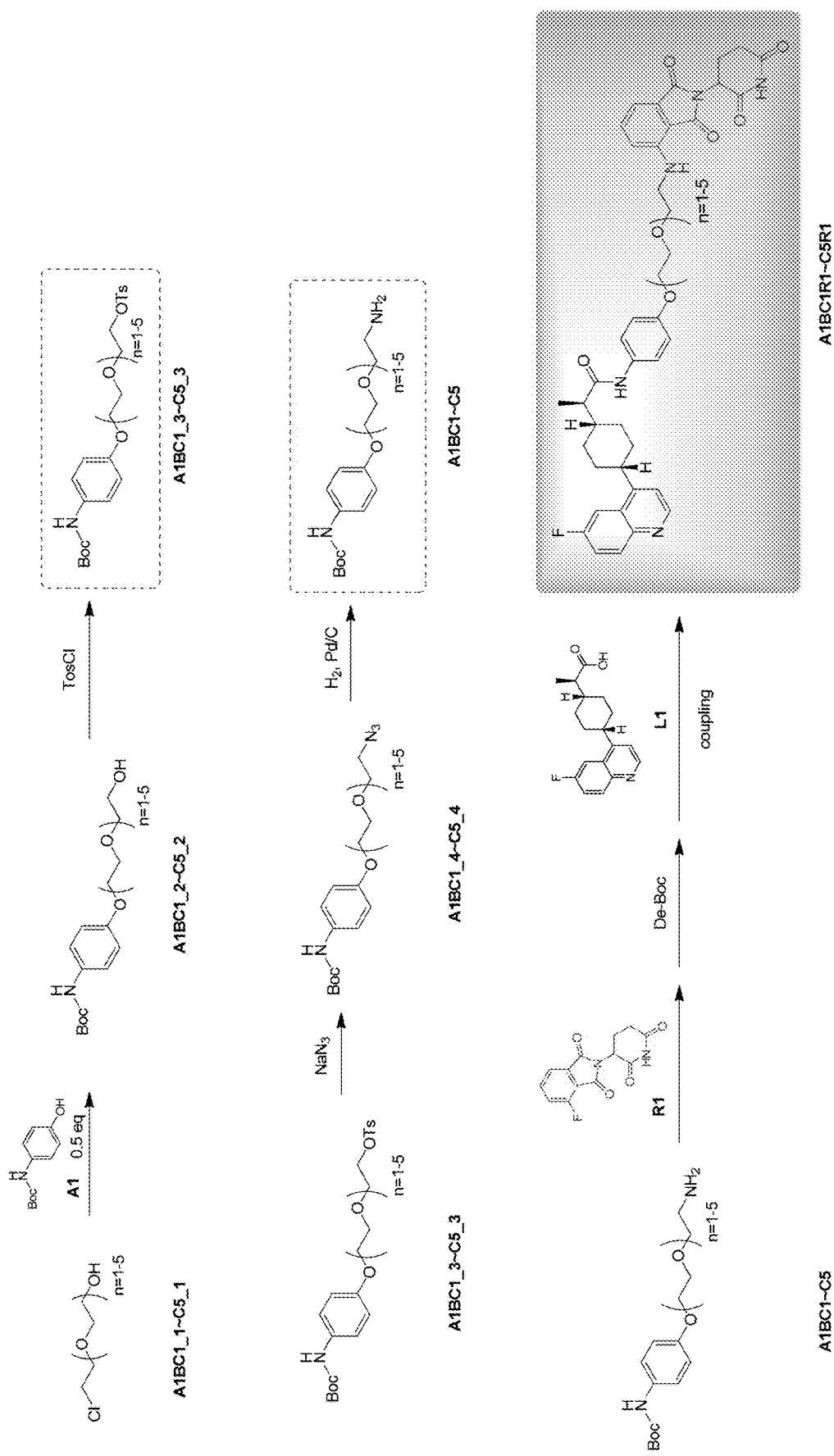
FIG. 35 shows the synthetic scheme for the synthesis of A1BC1R1-C5R1, take A1BC1R1 as an example.
Figure 36:
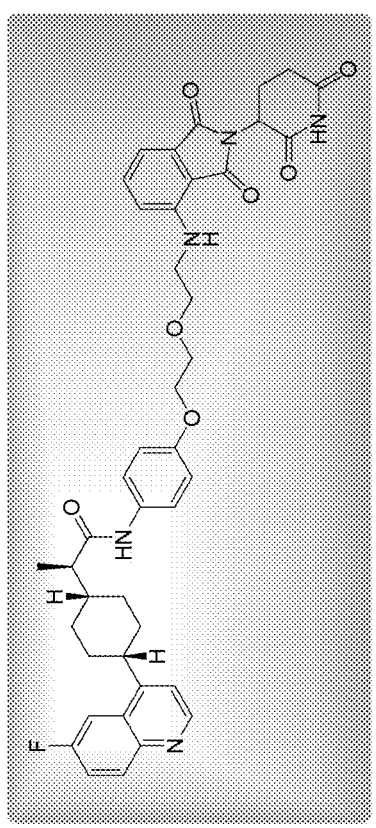
FIG. 36 shows the general procedure for preparation of compound A1BC1R1 (NUCC-0223599).
Figure 36:
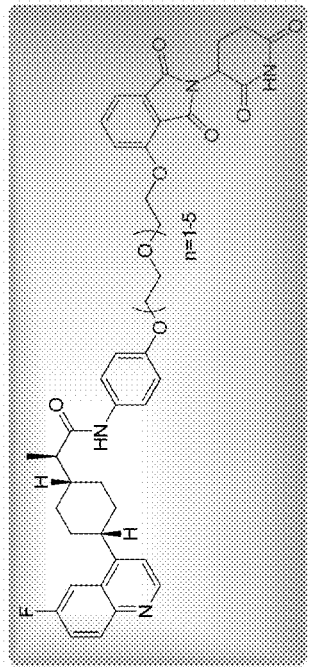
Figure 37:
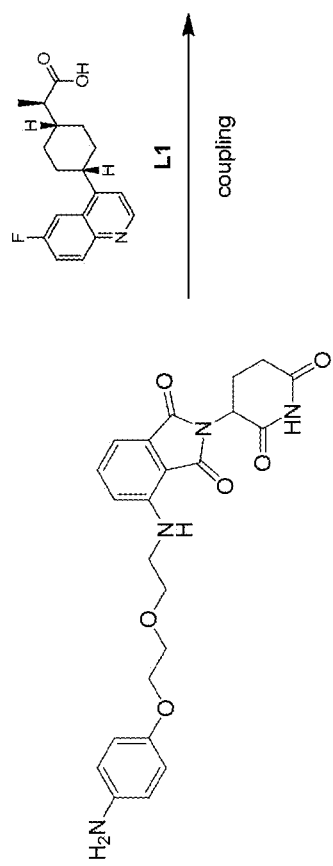
FIG. 37 shows the synthetic scheme for the synthesis of A1BC1-3R2, take A1BC1R2 as an example.
Figure 37:
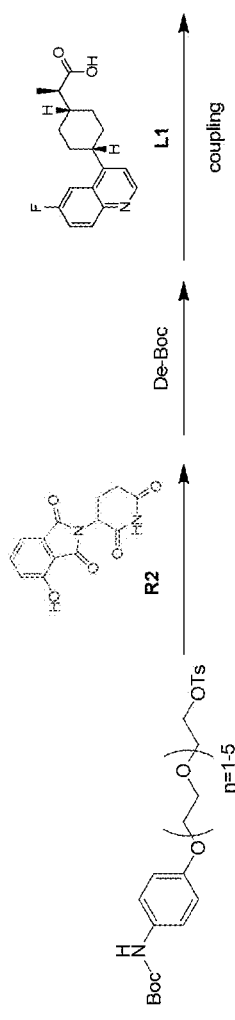
Figure 40:
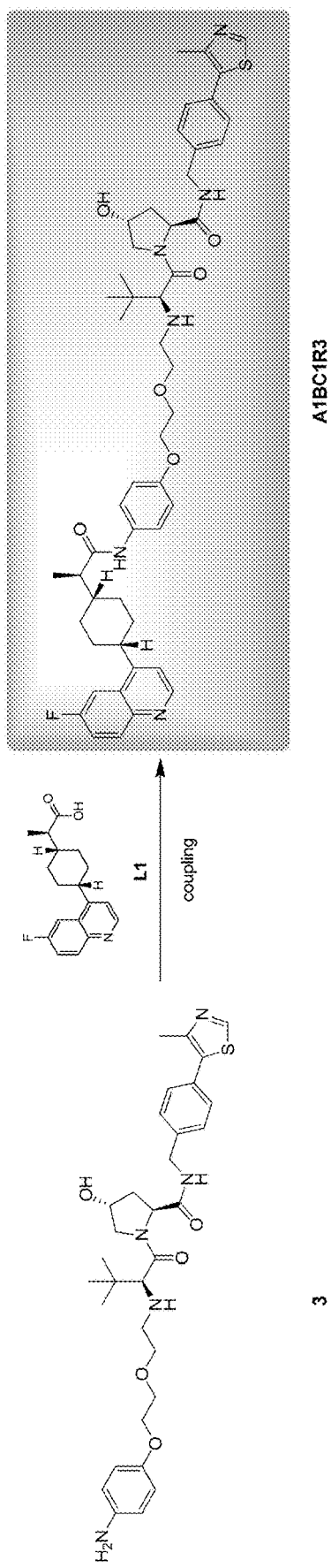
FIG. 40 shows the general procedure for preparation of A1BC1R3 (NUCC-0223799)—Notebook Page: ET32240-341.
Figure 41:
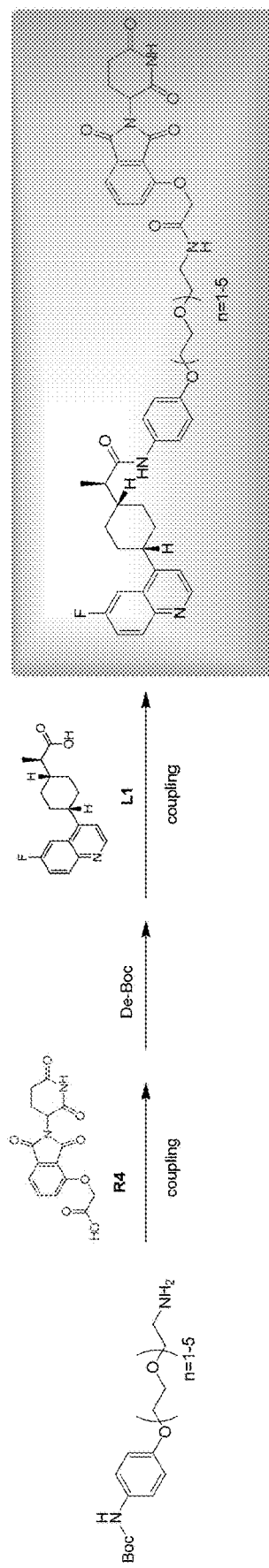
FIG. 41 shows the synthetic scheme for the synthesis of A1BC1-3R4, take A1BC1R4 as an example.
Figure 48:
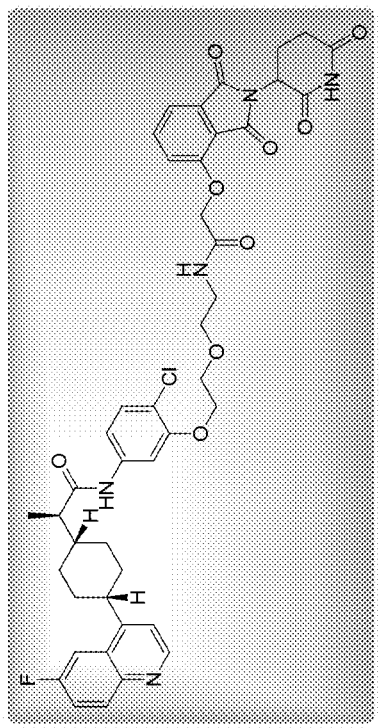
FIG. 48 shows the general procedure for preparation of A2BC1R4 (NUCC-0223794)—Notebook Page: ET32240-298.
Figure 48:
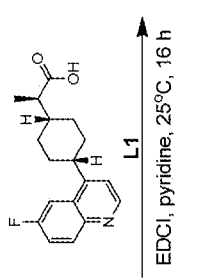
Figure 48:
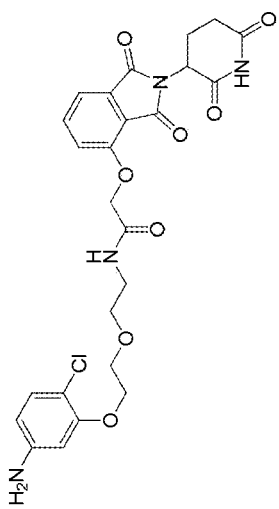
Figure 49:
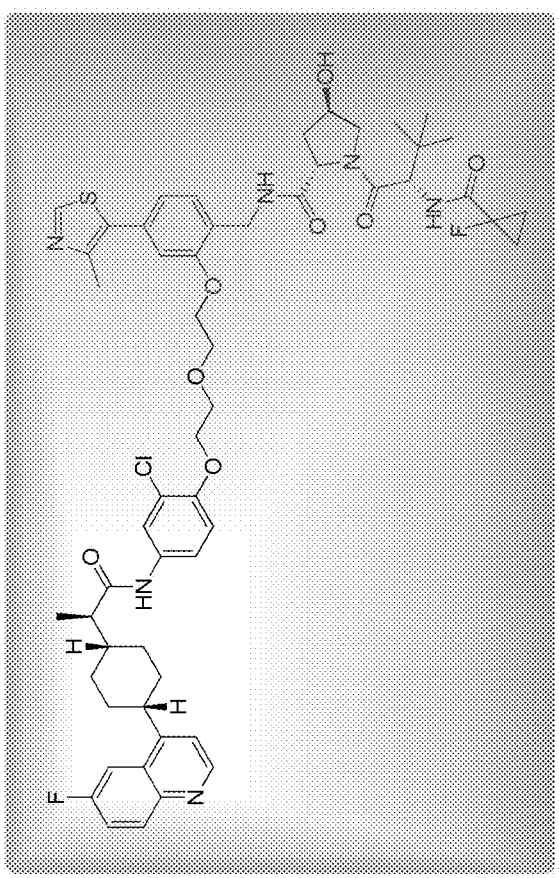
FIG. 49 shows the general procedure for preparation of Compound A2BC1R5 (NUCC-0223811)—Notebook Page: ET32240-539.
Figure 49:
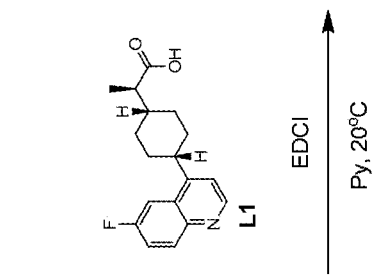
Figure 49:
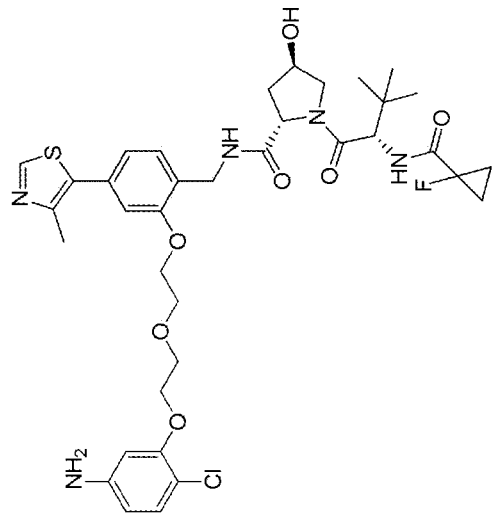

The present invention is described herein using several definitions, as set forth below and throughout the application.

Unless otherwise specified or indicated by context, the terms "a", "an", and "the" mean "one or more." For example, "a compound" and "a substituent" and a "moiety" and a "PROTAC" should be interpreted to mean "one or more compounds" and "one or more substituents" and "one or more moieties" and "one or more PROTACs", respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment.

A "subject in need of treatment" may include a subject having a disease, disorder, or condition that is responsive to therapy with a proteolytic-targeted chimeric molecule (PROTAC), which his targeted to IDO for degradation of IDO. For example, a "subject in need of treatment" may include a subject having a cell proliferative disease, disorder, or condition such as cancer (e.g., cancers such as glioblastoma multiforme (GBM), multiple myeloma, leukemia, non-small cell lung cancer, colon cancer, cancer of the central nervous system, melanoma, ovarian cancer, renal cancer, prostate cancer, colorectal cancer, uterine cancer, pancreatic cancer, and breast cancer). A "subject in need of treatment" may include a subject having a cell proliferative disease, disorder, or condition such as cancer that is associated with IDO activity and/or that may be treated by administering an effective amount of an agent that modulates IDO activity.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "modulate" means decreasing or inhibiting activity and/or increasing or augmenting activity. For example, modulating IDO activity may mean increasing or augmenting IDO activity and/or decreasing or inhibiting IDO activity. The proteolytic-targeted chimeric molecules (PROTACs) disclosed herein may be administered to modulate IDO activity.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched $C_1$-$C_6$ alkyl group). Exemplary alkylene groups include, but are not limited to —$CH_2$—, —$CH_2CH_2$—, —$CH_2CH_2CH_2$—, —$CH(CH_3)CH_2$—, —$CH_2CH(CH_3)CH_2$—, —$CH(CH_2CH_3)CH_2$—, and the like.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido (or amidocarboxyl), carboxylic acid, —C(O) alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds and molecules (e.g., PROTACs) of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds and molecules may be designated by the symbols "R" or "S," or "+" or "−" depending on the configuration of substituents around the stereogenic carbon atom and or the optical rotation observed. The present invention encompasses various stereo isomers of these compounds and molecules and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds and molecules, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

The formulae of the compounds and molecules disclosed herein should be interpreted as encompassing all possible stereoisomers, enantiomers, or epimers of the compounds and molecules unless the formulae indicates a specific stereoisomer, enantiomer, or epimer. The formulae of the compounds and molecules disclosed herein should be interpreted as encompassing salts, esters, amides, or solvates thereof of the compounds and molecules.

Proteolytic-Targeting Chimeric Molecules (PROTACs) that Induce Degradation of Indoleamine 2,3-Dioxygenase (IDO) Protein Disclosed herein are proteolytic-targeted chimeric molecules (PROTACs) that induce degradation of IDO protein. In some embodiments, the disclosed molecules may be described as having a having a formula: $M_{IDO}$-L-$M_{E3}$ or alternatively $M_{E3}$-L-$M_{IDO}$, wherein $M_{IDO}$ is a moiety that binds to IDO, L is a bond or a linker covalently attaching $M_{IDO}$ and ME3, and $M_{E3}$ is a moiety that binds to an E3 ubiquitin ligase. Compounds that bind and/or inhibit IDO are disclosed in the prior art and may include, but are not limited to compounds disclosed in U.S. Publication Nos. 2020/0179347; 2020/0172492; 2020/0095231; 2020/0093932; 2020/0069695; 2020/0069646; 2020/0024273; 2019/0367465; 2019/0352307; 2019/0292150; 2019/0284184; 2019/0270812; 2019/0247527; 2019/0231776; 2019/0225618; 2019/0152932; 2019/0144417; 2019/0144416; 2019/0135758; 2019/0119216; 2019/0119215; 2019/0040025; 2019/0031665; 2019/0022157; 2019/0002402; 2018/0354908; 2018/0353483; 2018/0333492; 2018/0312497; 2018/0271861; 2018/0186787; 2018/0079712; 2018/0072716; 2018/0072660; 2018/0037553; 2018/0030026; 2017/0319527; 2017/0267668; 2017/0260188; 2017/0231999; 2017/0182156; 2017/0129911; 2017/0107178; 2017/0095473; 2017/0037125; 2017/0009271; 2016/0367564; 2016/0362412; 2016/0361298; 2016/0289171; 2016/0200674; 2016/0143870; 2016/0137595; 2016/0060266; 2016/0060237; 2016/0046596; 2016/0022619; 2015/0352206; 2014/0377307; 2013/0142815; 2011/0136796; 2010/0311804; 2010/0055111; 2009/0081155; and 2004/0234623, the contents of which are incorporated herein by reference in their entireties.

In some embodiments of the disclosed PROTACs, $M_{IDO}$ has a formula derived from a compound having formula I or II (e.g. a radicalized or functionalized form thereof):

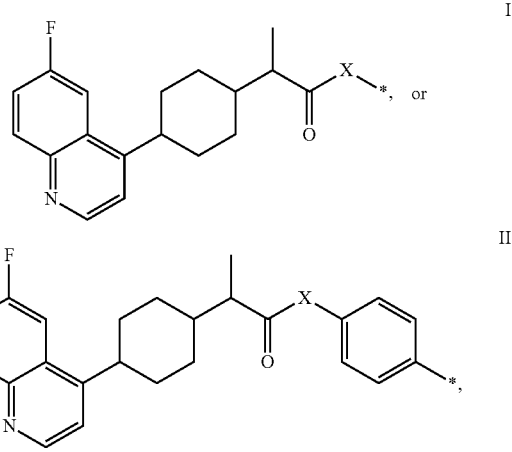

wherein

X is O or NH.

The disclosed PROTACs may include a bond or a linker (L) that conjugates the IDO binding moiety ($M_{IDO}$) and the E3 ubiquitin ligase binding moiety (ME3). The PROTAC linker connects the functional moieties of a PROTAC, a target protein binder and an E3 ligase recruiter. Linkers used in the development of PROTACs include polyethylene glycol (PEG) linkers, Alkyl-Chain linkers, and Alkyl/ether linkers. Other PROTAC linkers may include those linkers described in one or more of U.S. Publication Nos. 2020/0140456; 2020/0102298; 2020/0085817; 2020/0022966; 2019/0275161; 2019/0263798; 2019/0262502; 2019/0194190; 2019/0151457; 2019/0151295; 2019/0106417; 2019/0076542; 2019/0076541; 2019/0076540; 2019/0076539; 2019/0071415; 2019/0016703; 2018/0327419; 2018/0186785; 2018/0134684; and 2018/0085465; the contents of which are incorporated herein by reference in their entireties.

In some embodiments, the disclosed PROTACs comprise a linker (L) which comprises a polyethylene glycol moiety, an alkylalkyne moiety, and/or an aminoalkyl alkyne moiety that links the IDO binding moiety ($M_{IDO}$) and the E3 ubiquitin ligase binding moiety ($M_{E3}$).

In some embodiments, the disclose PROTACs comprise a linker (L) which comprises a formula selected from *—(CH$_2$)$_m$—(CH$_2$CH$_2$O)$_n$—*, *—CH$_2$—C(O)—NH—(CH$_2$)$_m$—(CH$_2$CH$_2$O)$_n$—*, *—(CH$_2$CH$_2$O)$_m$—(CH$_2$)$_n$—C(O)—*, *—CH$_2$—C(O)—NH—(CH$_2$CH$_2$O)$_m$—(CH$_2$)$_n$—C(O)—*, *—CH$_2$—C(O)—NH—(CH$_2$)$_m$—(CH$_2$CH$_2$O)$_m$—*, *—(CH$_2$CH$_2$O)$_m$—(CH$_2$)$_n$—C(O)—*, wherein m and n may be the same or different and m and n are >0-20 and optionally less than 18, 16, 14, 12, 10, 8, 6, 4 or 2.

In some embodiments, the disclosed PROTACs comprise a linker (L) which comprises a formula selected from:

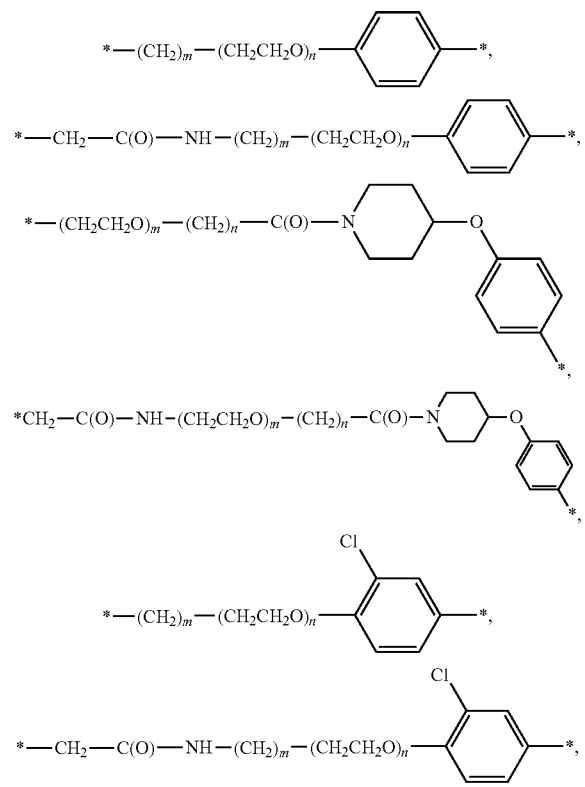

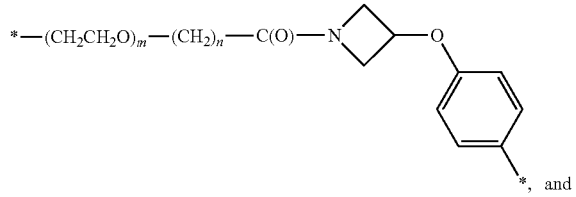

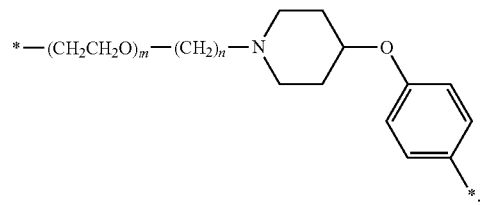

wherein m and n may be the same or different and m and n are >0-20 and optionally less than 18, 16, 14, 12, 10, 8, 6, 4 or 2.

The disclosed PROTACs typically include a moiety that binds to an E3 ubiquitin ligase ($M_{E3}$), for example, as a ligand for the E3 ubiquitin ligase ($M_{E3}$). Ligands for E3 ubiquitin ligases for use in preparing PROTACs are known in the art. (See, e.g., An et al., "Small-molecule PROTACs: An emerging and promising approach for the development of targeted therapy drugs," EBioMedicine. 2018 October; 36: 553-562; and Gu et al., "PROTACs: An Emerging Targeting Technique for Protein Degradation in Drug Discovery," Bioessays. 2018 April; 40(4):e1700247, the contents of which are incorporated herein by reference in their entireties).

In some embodiments of the disclosed PROTACs, $M_{E3}$ is a moiety that binds to an E3 ubiquitin ligase selected from Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

In other embodiments of the disclosed PROTACs, $M_{E3}$ is a moiety derived from thalidomide, pomalidomide, lenalidomide, iberdomide, (S,R,S)-AHPC-Me hydrochloride, (S,R,S)-AHPC-Me dihydrochloride, cereblon modulator 1, thalidomide-propargyl, (S,R,S)-AHPC-propargyl, (S,R,S)-AHPC hydrochloride, CC-885, thalidomide-O—COOH, lenalidomide hemihydrate, thalidomide fluoride, thalidomide-OH, lenalidomide-Br, thalidomide D4, lenalidomide hydrochloride, (S,R,S)-AHPC-Me, cIAP1 ligand 1, TD-106, E3 ligase Ligand 8, E3 ligase Ligand 9, E3 ligase Ligand 10, E3 ligase Ligand 13, E3 ligase Ligand 14, E3 ligase Ligand 18, BC-1215, VHL ligand 1 (VHL-1), VHL ligand 2 (VHL-2), VHL Ligand 8 (VHL-8), VH032, VH032-cyclopropane-F, VH032 thiol, VH-298, VL-269, VL-285, LCL161, hydroxyproline-based ligands, HIF-1α-derived (R)-hydroxyproline, Nutlin carboxylic acid, (4R,5S)-Nutlin carboxylic acid, (S,R,S)-AHPC-Boc, AR antagonist 1, NV03, (S,R,S)-AHPC TFA, (S,R,S)-AHPC, β-Naphthoflavone-CH2-Br, β-Naphthoflavone-CH2-OH, Bestatin-amido-Me, MV-1-NH-Me, (S,S,S)-AHPC hydrochloride, and cIAP1 ligand 2.

In further embodiments of the disclosed PROTACs, $M_{E3}$ has a formula selected from:
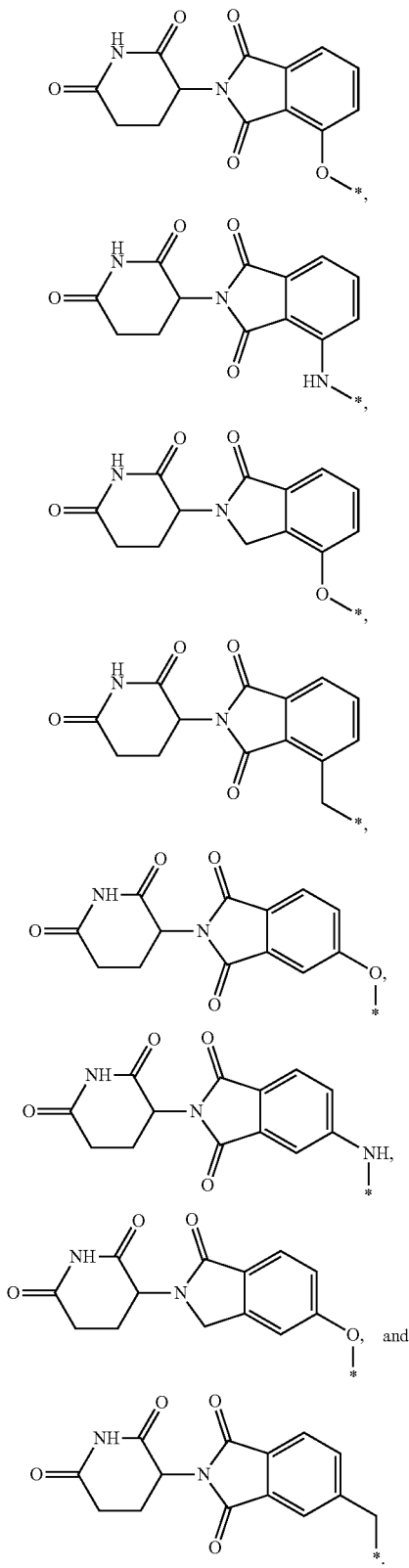
In alternative embodiments of the disclosed PROTACs, $M_{E3}$ has a formula selected from:
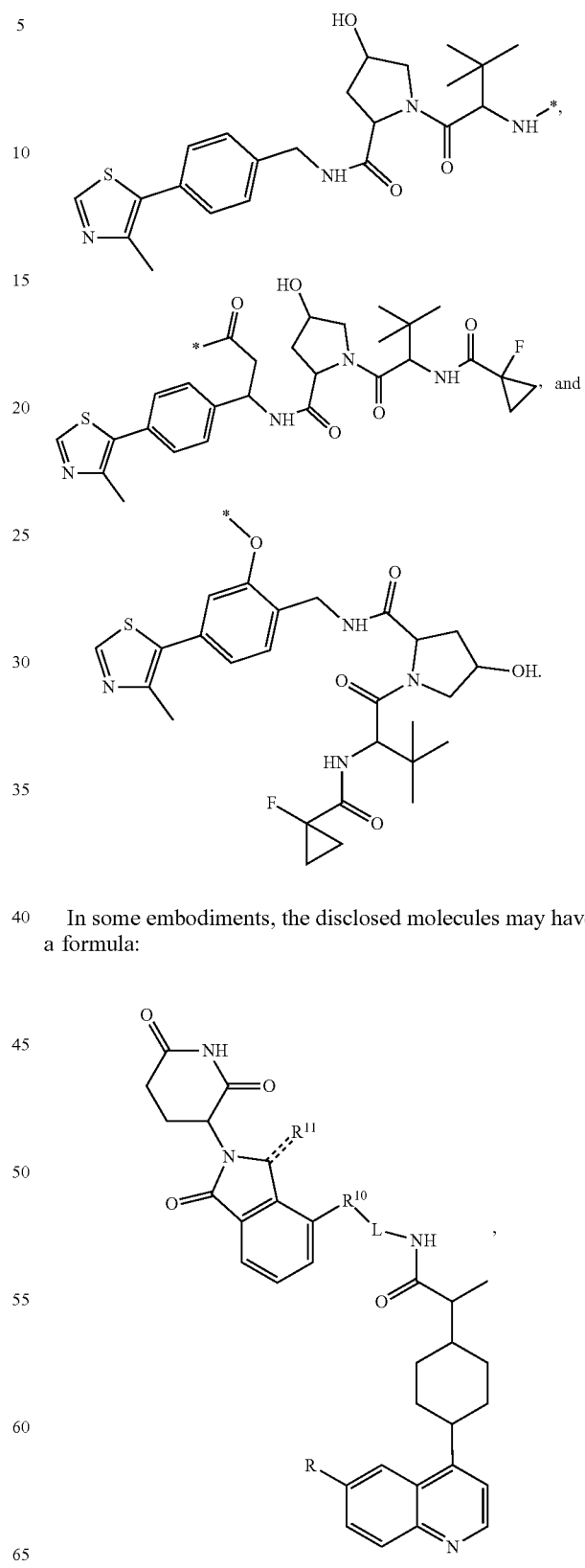
In some embodiments, the disclosed molecules may have a formula:

wherein $R^{10}$ is O or NH;

$R^1$ is absent or present and when present $R^{11}$ is O.

In other embodiments, the disclosed molecules may have a formula:

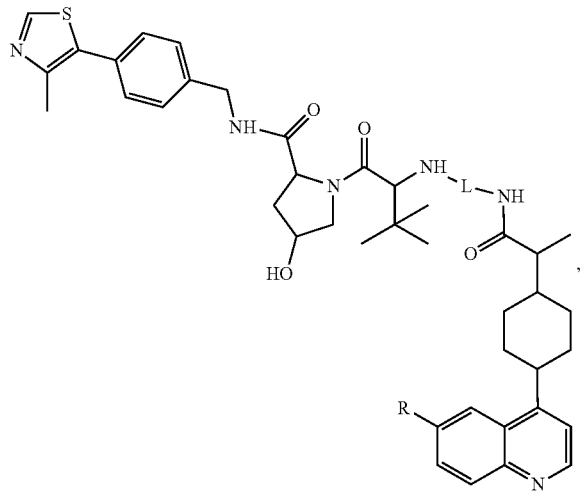

In other embodiments, the disclosed molecules may have a formula:

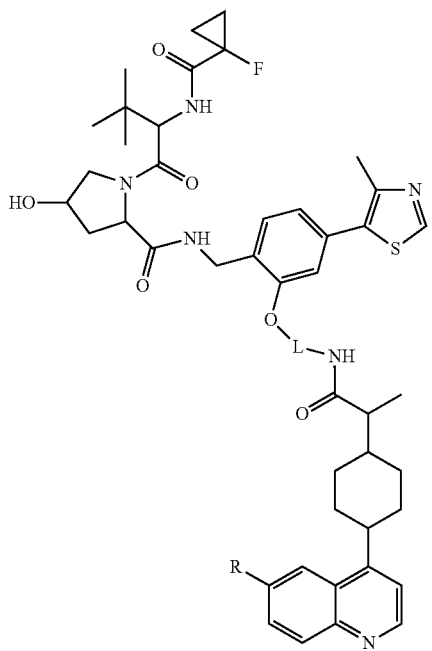

The disclosed PROTACs may be formulated as pharmaceutical compositions. In some embodiments, pharmaceutical compositions as contemplated herein include a PROTAC as disclosed herein, for example, in an effective amount for treating a disease or disorder associated with IDO, and a suitable pharmaceutical carrier, excipient, or diluent.

The disclosed PROTACs and/or pharmaceutical compositions comprising the disclosed PROTACs may be administered to subjects in need thereof, for example, to treat and/or prevent a disease or disorder associated with expression of IDO. Suitable diseases or disorders associated with expression of IDO may include cell proliferative diseases or disorders such as cancer. Suitable cancers treated and/or prevented in the disclosed methods may include, but are not limited to, glioblastoma multiforme (GBM), colorectal cancer, multiple myeloma, leukemia, non-small cell lung cancer, colon cancer, cancer of the central nervous system, melanoma, ovarian cancer, renal cancer, prostate cancer, pancreatic cancer, and breast cancer.

17. The method of any of claims 14-16, further comprising administering an anti-PD1 agent to the subject (e.g., an anti-PD1 antibody), before, concurrently with, or after administering the composition of claim 13.

18. The method of any of claims 14-16, further comprising administering an anti-PD-L1 agent to the subject (e.g., an anti-PD-L1 antibody), before, concurrently with, or after administering the composition of claim 13.

Use of the Disclosed Proteolytic-Targeted Chimeric Molecules (PROTACs) for Inhibiting IDO Activity The disclosed proteolytic-targeted chimeric molecules (PROTACs) may exhibit one or more biological activities. The disclosed PROTACs may inhibit the growth of cells that express IDO (preferably by at least 50%, 60%, 70%, 80%, 90%, 95%, 96%, 97%, 98%, or 99% at a concentration of less than about 100 µM, 50 µM, 10 µM, 1 µM, 0.1 µM, 0.05 µM, 0.01 µM, 0.005 µM, 0.001 µM, or less). The disclosed PROTACs may not inhibit the growth of cells that do not express IDO (preferably by not more than 50%, 40%, 30%, 20%, 10%, 5%, 4%, 3%, 2% or less at a concentration of greater than about 0.001 µM, 0.005 µM, 0.01 µM, 0.5 µM, 0.1 µM, 1.0 µM, 10 µM, and 100 µM or higher). Concentration ranges also are contemplated herein, for example, a concentration range bounded by end-point concentrations selected from 0.001 µM, 0.005 µM, 0.01 µM, 0.5 µM, 0.1 µM, 1.0 µM, 10 µM, and 100 µM. Preferably, the disclosed PROTACs may not produce significant DNA damage (e.g., in an rH2AX staining assay at a concentration greater than about 0.001 µM, 0.005 µM, 0.01 µM, 0.1 µM, 1.0 µM, 10 µM, 100 µM, or higher).

The disclosed PROTACs may be effective in inhibiting cell proliferation of cancer cells, including cancer cells that express IDO and whose proliferation is inhibiting by inhibiting the biological activity of IDO. The disclosed PROTACs may be effective in inhibiting cell proliferation of one or more types of cancer cells including: multiple myeloma cells, such as MM.1S cells; leukemia cells, such as CCRF-CEM, HL-60(TB), MOLT-4, RPMI-8226 and SR; non-small lung cancer cells, such as A549/ATCC, EKVX, HOP-62, HOP-92, NCI-H226, NCI-H23, NCI-H322M, NCI-H460 and NCI-H522; colon cancer cells, such as COLO 205, HCC-2998, HCT-116, HCT-15, HT29, KM12 and SW-620; CNS: SF-268, SF-295, SF-539, SNB-19, SNB-75 and U251; melanoma cancer cells, such as LOX IMVI, MALME-3M, M14, MDA-MB-435, SK-MEL-2, SK-MEL-28, SK-MEL-5, UACC-257 and UACC-62; ovarian cancer cells, such as IGR-OV1, OVCAR-3, OVCAR-4, OVCAR-5, OVCAR-8, NCI/ADR-RES and SK-OV-3; renal cancer cells, such as 786-0, A498, ACHN, CAKI-1, RXF 393, SN12C, TK-10 and UO-31; prostate cancer cells, such as DU-145 and PC-3; pancreatic cancer cells, such as PANC-1, AsPC-1, KP-3, BxPC-3, TCC-PAN2, and MIA PaCa-2. AsPC-1, BxPC-3 and MIA PaCa-2; and breast cancer cells, such as MCF7, MDA-MB-231/ATCC, MDA-MB-468, HS 578T, BT-549 and T-47D.

Cell proliferation and inhibition thereof by the presently disclosed PROTACs may be assessed by cell viability methods disclosed in the art including colorimetric assays that utilize dyes such as MTT, XTT, and MTS to assess cell viability. Preferably, the disclosed PROTACs have an $IC_{50}$ of less than about 10 µM, 5 µM, 1 µM, 0.5 µM, 0.01 µM, 0.005 µM, 0.001 µM or lower in the selected assay.

The disclosed compounds and molecules (e.g., PROTACs) may be formulated as anti-cancer therapeutics, including hematologic malignancies, breast, lung, pancreas and prostate malignancies. The disclosed compounds and molecules also may be formulated as anti-inflammation therapeutics.

The compounds and molecules (e.g., PROTACs) utilized in the methods disclosed herein may be formulated as pharmaceutical compositions that include: (a) a therapeutically effective amount of one or more compounds and molecules as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µM).

The disclosed compounds and molecules and pharmaceutical compositions comprising the disclosed compounds and molecules may be administered in methods of treating a subject in need thereof. For example, in the methods of treatment a subject in need thereof may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, pancreatic cancer, and breast cancer).

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds and molecules may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds and molecules for achieving therapy in the disclosed methods of treatment may include dose levels falling within ranges having as end-points any of these disclosed dose levels (e.g., 500-2000 ng/kg body weight of the subject).

The compounds and molecules utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds and molecules utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds and molecules utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil® 200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds and molecules such as phenol, or quaternary compounds and molecules such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds and molecules utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules. In some embodiments, the compounds and molecules are formulated as a composition for administration orally (e.g., in a solvent such as 5% DMSO in oil such as vegetable oil).

The compounds and molecules utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds and molecules may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Additional Therapeutic Agents

The disclosed PROTACs may be administered with additional therapeutic agents. In some embodiments, the disclosed PROTACs are administered with additional immunotherapeutic agents in order to treat cancers, such as GBM.

In some embodiments, the disclosed PROTACs may be administered to a subject in need thereof in a treatment method comprising administering the disclosed PROTACs to the subject and further comprising administering an anti-PD1 agent to the subject (e.g., an anti-PD1 antibody), before, concurrently with, or after administering the disclosed PROTACs. In some embodiments, the disclosed PROTACs may be administered to a subject in need thereof in a treatment method comprising administering the disclosed PROTACs to the subject and further comprising administering an anti-PD-L1 agent to the subject (e.g., an anti-PD-L1 antibody), before, concurrently with, or after administering the disclosed PROTACs.

EXAMPLES

The following examples are illustrative and should not be interpreted to limit the scope of the claimed subject matter.

Example 1—Synthesis of Compounds that Induce Degradation of Indoleamine 2,3 Deoxygenase (IDO) Protein The compounds disclosed herein may be synthesized using the following exemplary synthetic schemes and also in FIGS. 35-49.

Experimental for Largest Scale Run:

General Procedure for Preparation of Compound 2

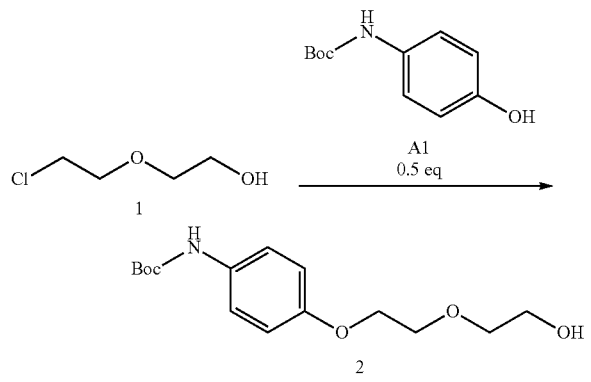

To a solution of A1 (2 g, 9.56 mmol) and Compound 1 (2.38 g, 19.12 mmol, 2.02 mL) in ACN (20 mL) was added K$_2$CO$_3$ (3.96 g, 28.67 mmol) and KI (158.67 mg, 955.83 umol) at 20° C. The mixture was stirred for 12 hr at 80° C. LCMS showed the starting material was consumed and the desired MS was detected. The reaction solution was concentrated under reduced pressure to give a residue which was diluted with water (50 mL), extracted with ethyl acetate (3×30 mL), washed with saturated brine (50 mL), dried over anhydrous sodium sulfate, concentrated under reduced pressure. The residue was purified by column chromatography (SiO$_2$, Petroleum ether/Ethyl acetate=1/0 to 1/1). Compound 2 (2.8 g, 9.42 mmol, 98.52% yield) was obtained as white solid. $^1$H NMR (400 MHz, DMSO-d$_6$) δ 9.12 (br s, 1H), 7.33 (br d, J=8.44 Hz, 2H), 6.83 (d, J=9.05 Hz, 2H), 4.61 (t, J=5.32 Hz, 1H), 3.92-4.10 (m, 2H), 3.67-3.74 (m, 2H), 3.43-3.54 (m, 4H), 1.46 (s, 9H)

General Procedure for Preparation of Compound 3

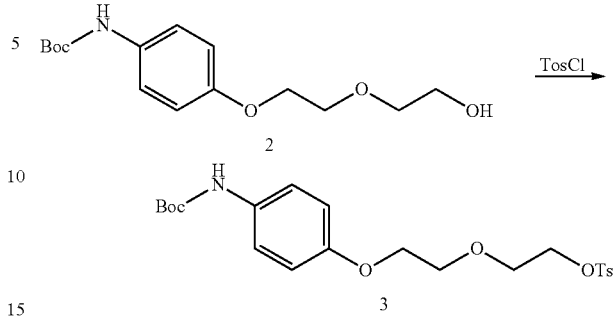

To a solution of Compound 2 (2.80 g, 9.42 mmol, 1 eq), DMAP (230.08 mg, 1.88 mmol, 0.2 eq) and TEA (1.91 g, 18.83 mmol, 2.62 mL, 2 eq) in DCM (50 mL) was added 4-methylbenzenesulfonyl chloride (2.69 g, 14.12 mmol, 1.5 eq) at 0° C. The mixture was stirred for 12 hr at 80° C. LCMS showed the starting material was consumed and the desired MS was detected. The reaction solution was diluted with water (50 mL), extracted with ethyl acetate (3×30 mL), washed with saturated brine (50 mL), dried over anhydrous sodium sulfate, concentrated under reduced pressure. The residue was purified by column chromatography (SiO2, Petroleum ether/Ethyl acetate=1/0 to 1/1). Compound 3 (3.7 g, 8.19 mmol, 87.02% yield) was obtained as light yellow oil. $^1$H NMR (400 MHz, DMSO-d$_6$) δ 9.14 (br s, 1H), 7.77 (d, J=8.16 Hz, 2H), 7.43 (d, J=7.94 Hz, 2H), 7.33 (br d, J=8.60 Hz, 2H), 6.81 (d, J=9.04 Hz, 2H), 4.09-4.17 (m, 2H), 3.90-3.97 (m, 2H), 3.58-3.68 (m, 4H), 2.38 (s, 3H), 1.46 (s, 9H)

General Procedure for Preparation of Compound 4

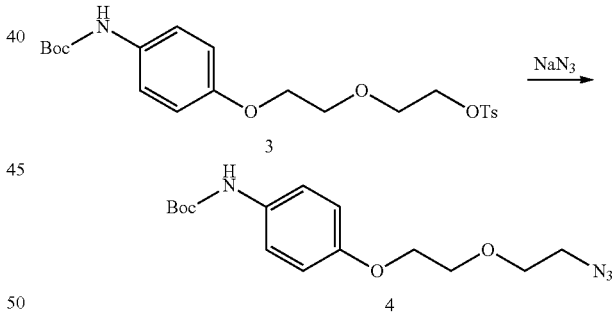

To a solution of Compound 3 (2 g, 4.43 mmol, 1 eq) in DMF (25 mL) was added NaN3 (719.88 mg, 11.07 mmol, 2.5 eq) at 20° C. The mixture was stirred for 3 hr at 60° C. TLC showed the starting material was consumed and one major new spot with lower polarity was detected. The reaction solution was poured into water (50 mL), extracted with ethyl acetate (3×30 mL), washed with saturated brine (50 mL), dried over anhydrous sodium sulfate, concentrated under reduced pressure. The crude product was used for the next step directly. Compound 4 (1.4 g, 4.34 mmol, 98.05% yield) was obtained as colorless oil. $^1$H NMR (400 MHz, DMSO-d$_6$) δ 9.12 (br s, 1H), 7.33 (br d, J=8.44 Hz, 2H), 6.83 (d, J=9.05 Hz, 2H), 3.98-4.07 (m, 2H), 3.98-4.07 (m, 1H), 3.72-3.79 (m, 2H), 3.60-3.69 (m, 2H), 3.42 (t, J=4.89 Hz, 2H), 1.46 (s, 9H)

General Procedure for Preparation of Compound 5

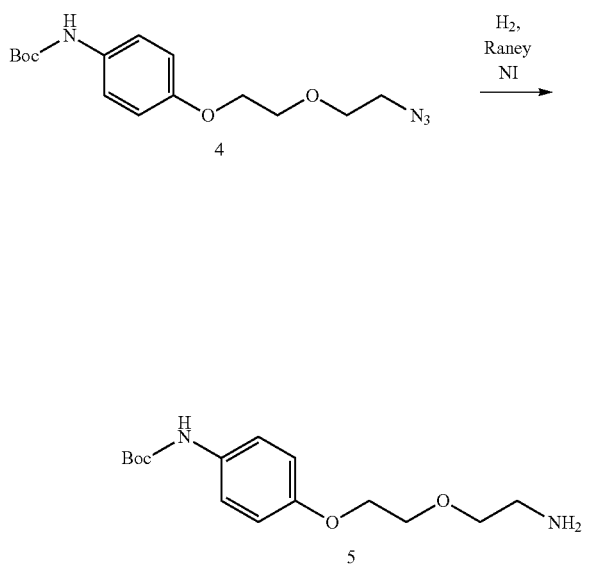

General Procedure for Preparation of Compound 6

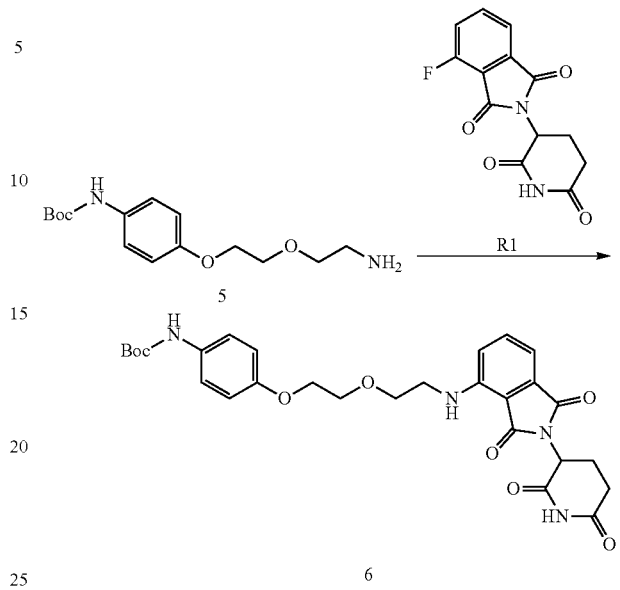

To a solution of Compound 4 (1.3 g, 4.03 mmol, 1 eq) in EtOH (100 mL) was added Ni (2.37 g, 40.33 mmol, 10 eq) at 20° C. The mixture was stirred for 1 hr at 20° C. under $H_2$ (8.15 mg, 4.03 mmol, 1 eq) at 15 psi. LCMS showed the starting material was consumed and the desired MS was detected. The reaction solution was filtered through a pad of celite. The filtrate was concentrated under reduced pressure to give a residue. The residue was used for the next step directly. Compound 5 (1 g, 3.37 mmol, 83.67% yield) was obtained as colorless oil. $^1$H NMR (400 MHz, DMSO-$d_6$) δ 9.10 (br s, 1H), 7.33 (br d, J=8.68 Hz, 2H), 6.77-6.90 (m, 2H), 3.97-4.08 (m, 2H), 3.63-3.74 (m, 2H), 3.36-3.44 (m, 2H), 2.73 (s, 1H), 2.62-2.69 (m, 2H), 1.35-1.55 (m, 9H)

To a solution of Compound 5 (300 mg, 1.01 mmol, 1 eq) and R1 (279.61 mg, 1.01 mmol, 1 eq) in DMF (3 mL) was added DIEA (523.31 mg, 4.05 mmol, 705.27 uL, 4 eq) at 20° C. The mixture was stirred for 2 hr at 100° C. LCMS showed the starting material was consumed and the desired MS was detected. The reaction solution was poured into water (20 mL), extracted with ethyl acetate (3×20 mL), washed with saturated brine (20 mL), dried over anhydrous sodium sulfate, concentrated under reduced pressure. The residue was purified by column chromatography (SiO2, Petroleum ether/THF=1/0 to 1/1). Compound 6 (250 mg, 452.43 umol, 44.69% yield) was obtained as yellow solid.

General Procedure for Preparation of Compound 7—Notebook Page: ET32240-162

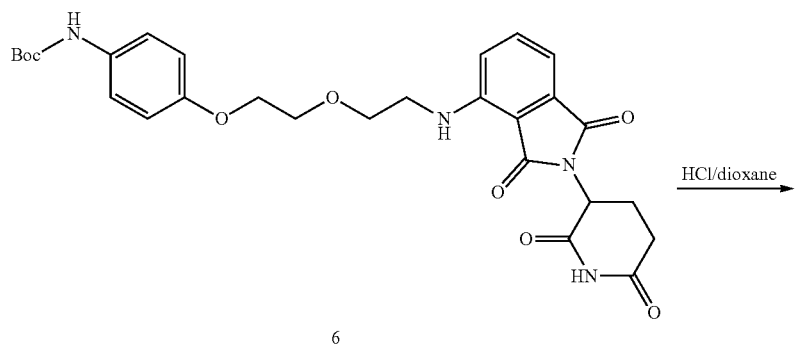

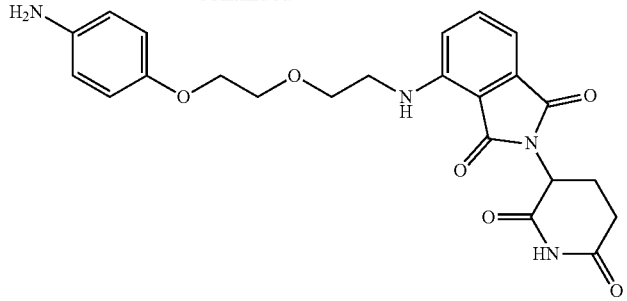

7

A solution of Compound 6 (230 mg, 416.23 umol, 1 eq) in 4 N HCl/dioxane (416.23 umol, 10 mL, 1.00 eq) was stirred at 20° C. for 1 hr. LCMS showed all the starting material was consumed and the desired MS was detected. The reaction mixture was concentrated under reduced pressure directly at 30° C. The residue was used for the next directly without further purification. Compound 7 (200 mg, 409.06 umol, 98.28% yield, HCl) was obtained as a light yellow solid.

To a solution of L1 (61.64 mg, 204.53 umol, 1 eq) in DMF (1.5 mL) was added DIEA (79.30 mg, 613.60 umol, 106.88 uL, 3 eq) and HATU (77.77 mg, 204.53 umol, 1 eq) at 0° C. The reaction was stirred at 0° C. for 30 min. The Compound 7 (100 mg, 204.53 umol, 1 eq, HCl) was added to the mixture. And the reaction was stirred at 0° C. for 30 min and then stirred at 20° C. for 5 hrs. LCMS showed the starting material was consumed completely and the desired MS was detected. The mixture was filtered directly. The filtrate was purified by pre_HPLC and lyophilized. (column: Nano-micro Kromasil C18 100*40 mm 10 um; mobile phase: [water(0.1% TFA)-ACN]; B %: 5%-44%, 8 min) NUCC-0223599 (65.4 mg, 76.96 umol, 37.63% yield, 100% purity, TFA) was obtained as yellow solid.
NUCC-0223599:
$^1$H NMR (400 MHz, DMSO-$d_6$) δ 11.08 (s, 1H), 9.81 (s, 1H), 8.98 (d, J=4.89 Hz, 11H), 8.04-8.22 (m, 2H), 7.77 (dt, J=2.69, 8.68 Hz, 1H), 7.70 (d, J=4.77 Hz, 1H), 7.57 (dd, J=7.09, 8.56 Hz, 1H), 7.50 (d, J=9.05 Hz, 2H), 7.15 (d, J=8.68 Hz, 1H), 7.04 (d, J=6.97 Hz, 1H), 6.87 (dd, J=1.22, 9.05 Hz, 2H), 6.64 (br s, 1H), 5.05 (dd, J=5.38, 12.72 Hz, 11H), 5.01-5.09 (m, 1H), 4.02-4.09 (m, 2H), 3.78 (br s, 2H), 3.69-3.70 (m, 2H), 3.50 (br s, 2H), 3.45 (br s, 1H), 2.77-2.96 (m, 2H), 2.53-2.64 (m, 2H), 1.58-2.10 (m, 10H), 1.13 (d, J=6.72 Hz, 3H)
$^{19}$F NMR (376 MHz, DMSO-$d_6$) δ −74.61 (s, 1F)
LCMS: $t_R$=2.309 min, 100% purity, m/z=736.4 (M+H)$^+$
A1BC2R1 (NUCC-0223602):
$^1$H NMR (400 MHz, DMSO-d6) δ ppm 11.08 (s, 1H) 9.94 (s, 1H) 9.16 (d, J=5.26 Hz, 1H) 8.25-8.38 (m, 2H) 7.90-8.05 (m, 2H) 7.47-7.64 (m, 3H) 7.13 (d, J=8.56 Hz, 1H) 7.02 (d, J=6.97 Hz, 1H) 6.85 (d, J=9.05 Hz, 2H) 6.61 (br s, 1H) 5.04 (dd, J=12.78, 5.32 Hz, 1H) 3.96-4.04 (m, 2H) 3.70-3.72 (m, 2H) 3.61-3.64 (m, 2H) 3.59 (s, 4H) 3.47 (br d, J=5.01 Hz, 2H) 2.79-2.97 (m, 2H) 2.52-2.61 (m, 2H) 2.40-2.47 (m, 1H) 1.59-2.07 (m, 10H) 1.12 (d, J=6.60 Hz, 3H)
LCMS: $t_R$=2.331 min, 100% purity, m/z=780.3 (M+H)$^+$
A1BC3R1 (NUCC-0226132):
$^1$H NMR (400 MHz, DMSO-$d_6$) δ 11.08 (s, 1H), 9.81 (s, 1H), 9.01 (d, J=4.85 Hz, 1H), 8.03-8.26 (m, 2H), 7.67-7.89 (m, 2H), 7.39-7.59 (m, 3H), 7.10 (d, J=8.60 Hz, 1H), 7.01 (d, J=6.84 Hz, 11H), 6.84 (d, J=9.04 Hz, 2H), 6.58 (br s, 11H), 5.03 (dd, J=5.40, 12.90 Hz, 11H), 3.97-4.01 (m, 2H), 3.68 (br s, 2H), 3.60 (br d, J=5.51 Hz, 2H), 3.52 (br d, J=3.53 Hz, 10H), 3.43 (br s, 2H), 2.75-2.93 (m, 2H), 2.56 (br d, J=16.54 Hz, 2H), 1.48-2.08 (m, 10H), 1.11 (d, J=6.62 Hz, 3H)
$^{19}$F NMR (376 MHz, DMSO-$d_6$) δ −69.21 (s, 1F), −71.10 (s, 1F), −74.80 (s, 1F)
LCMS: $t_R$=2.295 min, 100% purity, m/z=824.4 (M+H)$^+$
A1BC4R1 (NUCC-0226181):
$^1$H NMR (ET32240-992-P1A, 400 MHz, DMSO-$d_6$400 MHz, DMSO-$d_6$) δ 1.12 (br d, J=6.60 Hz, 3H), 1.42-2.07 (m, 12H), 2.58 (br d, J=16.51 Hz, 2H), 2.78-2.93 (m, 2H), 3.45 (br s, 3H), 3.49 (s, 3H), 3.51-3.53 (m, 3H), 3.53-3.57 (m, 5H), 3.60 (br t, J=5.32 Hz, 3H), 3.68-3.70 (m, 2H), 4.00-4.03 (m, 1H), 5.05 (dd, J=12.90, 5.32 Hz, 11H), 6.59 (br s, 11H), 6.87 (d, J=9.05 Hz, 2H), 7.03 (d, J=7.09 Hz, 1H), 7.12 (d, J=8.56 Hz, 1H), 7.47-7.60 (m, 3H), 7.65-7.70 (m, 1H), 7.76 (td, J=8.68, 2.69 Hz, 1H), 8.05-8.18 (m, 1H), 8.05-8.18 (m, 2H), 8.96 (d, J=4.77 Hz, 11H), 9.83 (s, 11H), 11.10 (s, 11H)
LCMS: $t_R$=2.353 min, 93.2% purity, m/z=868.2 (M+H)$^+$
A1BC5R1 (NUCC-0226186):
$^1$H NMR (ET32240-965-P1C, 400 MHz, CDCl$_3$) δ 1.25 (br s, 3H), 1.69-2.19 (m, 10H), 2.57-2.92 (m, 4H), 3.40 (br s, 3H), 3.55-3.74 (m, 18H), 3.79 (br s, 2H), 4.05 (br s, 2H), 4.82 (br d, J=4.63 Hz, 1H), 6.74-7.14 (m, 4H), 7.24 (br s, 2H), 7.42 (br s, 3H), 7.69-8.05 (m, 4H), 8.23-8.63 (m, 3H), 9.07 (br s, 1H)
LCMS: RT=2.315 min, 100.0% purity, m/z=9123 (M+H)$^+$ Experimental for Largest Scale Run:
General Procedure for Preparation of Compound 2

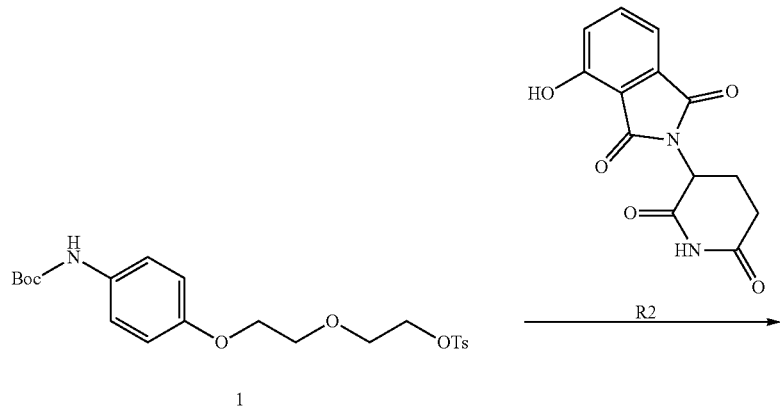

1

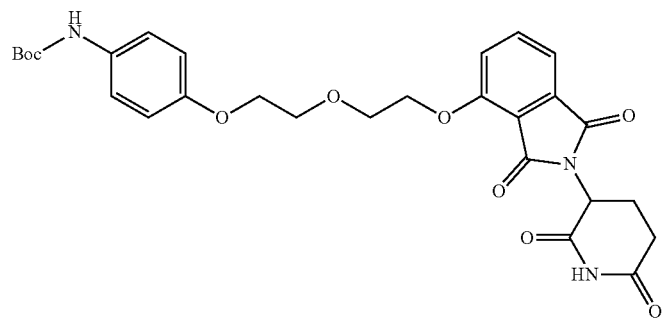

2

To a solution of Compound 1 (300 mg, 664.40 umol, 1 eq) in DMF (4 mL) was added $K_2CO_3$ (137.74 mg, 996.61 umol, 1.5 eq) and R2 (182.20 mg, 664.40 umol, 1 eq). The mixture was stirred at 40° C. for 12 hr. LCMS showed a little of starting material was remaining and the desired MS was detected. The mixture was poured into water (20 mL) and extracted with ethyl acetate (3×10 mL), dried over anhydrous sodium sulfate, concentrated under reduced pressure. The resulting residue was purified by column chromatography (SiO2, Petroleum ether/Ethyl acetate=1/0 to Y/1). Compound 2 (200 mg, 361.30 umol, 54.38% yield) was obtained as a white solid. $^1$H NMR (400 MHz, DMSO-d6) δ 11.10 (s, 1H), 9.11 (br s, 1H), 7.80 (dd, J=7.50, 8.38 Hz, 1H), 7.53 (d, J=8.60 Hz, 1H), 7.45 (d, J=7.06 Hz, 1H), 7.31 (br d, J=8.60 Hz, 2H), 6.73-6.89 (m, 2H), 5.02-5.39 (m, 1H), 4.26-4.44 (m, 2H), 3.99-4.08 (m, 2H), 3.77-3.93 (m, 4H), 2.80-2.88 (m, 1H), 2.51-2.64 (m, 2H), 1.99-2.06 (m, 1H), 1.45 (s, 9H)

General Procedure for Preparation of Compound 3

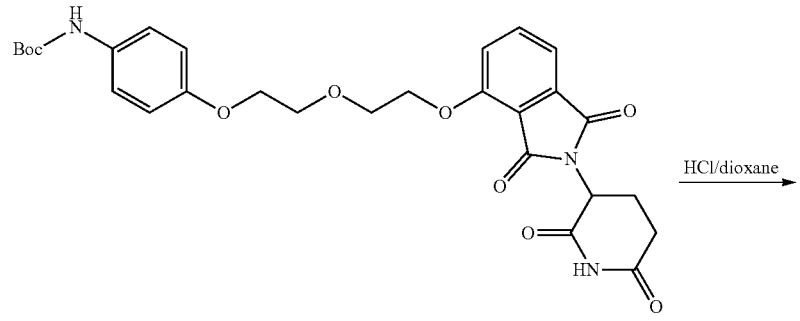

2

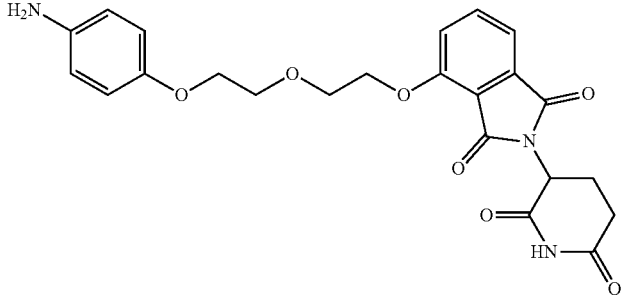

A solution of Compound 2 (120 mg, 216.78 umol, 1 eq) in 4 N HCl/dioxane (216.78 umol, 2 mL, 1.00 eq) was stirred at 20° C. for 1 hr. LCMS showed all the starting material was consumed and the desired MS was detected. The reaction mixture was concentrated under reduced pressure directly at 20° C. The residue was used for the next directly without further purification. Compound 3 (100 mg, 204.12 umol, 94.16% yield, HCl) was obtained as a light yellow solid.

To a solution of L1 (36.91 mg, 122.47 umol, 1 eq) in DMF (1 mL) was added DIEA (47.49 mg, 367.42 umol, 64.00 uL, 3 eq) and HATU (46.57 mg, 122.47 umol, 1 eq) at 0° C. The reaction was stirred at 0° C. for 30 min. The Compound 3 (60 mg, 122.47 umol, 1 eq, HCl) was added to the mixture. And the reaction was stirred at 0° C. for 30 min and then stirred at 20° C. for 5 hrs. LCMS showed the starting material was consumed completely and the desired MS was detected. The mixture was filtered directly. The filtrate was purified by pre-HPLC and lyophilized. (column: Phenomenex Luna C18 150*30 mm*5 um; mobile phase: [water (0.1% TFA)-ACN]; B %: 30%-60%, 10 min) A1BC1R2 (NUCC-0223600) (17.8 mg, 20.92 umol, 17.08% yield, 100% purity, TFA) was obtained as yellow solid.

A1BC1R2 (NUCC-0223600):

$^1$H NMR (400 MHz, DMSO-d$_6$) δ 11.08 (s, 1H), 9.80 (s, 1H), 9.00 (d, J=4.89 Hz, 1H), 8.06-8.25 (m, 2H), 7.66-7.89 (m, 3H), 7.41-7.59 (m, 4H), 6.87 (d, J=8.93 Hz, 2H), 5.08 (dd, J=5.44, 12.65 Hz, 1H), 4.31-4.45 (m, 2H), 3.99-4.16 (m, 2H), 3.77-3.97 (m, 4H), 3.51-3.52 (m, 1H), 2.76-2.95 (m, 2H), 2.54-2.65 (m, 2H), 1.58-2.10 (m, 10H), 1.13 (d, J=6.72 Hz, 3H)

$^{19}$F NMR (377 MHz, DMSO-d$_6$) δ −69.34--69.06 (m, 1F), −71.21--70.97 (m, 1F), −74.71 (s, 1F)

LCMS: $t_R$=2.214 min, 100% purity, m/z=737.4 (M+H)$^+$

A1BC2R2 (NUCC-0223603):

$^1$H NMR (400 MHz, DMSO-d$_6$) δ 11.08 (s, 1H), 9.80 (s, 1H), 9.02 (d, J=4.89 Hz, 1H), 8.09-8.23 (m, 2H), 7.71-7.85 (m, 3H), 7.48-7.57 (m, 3H), 7.45 (d, J=7.21 Hz, 1H), 6.86 (d, J=9.05 Hz, 2H), 5.08 (dd, J=5.38, 12.84 Hz, 1H), 4.31-4.38 (m, 2H), 3.98-4.06 (m, 2H), 3.80-3.85 (m, 2H), 3.70-3.75 (m, 2H), 3.65-3.69 (m, 2H), 3.58-3.63 (m, 2H), 3.50 (br t, J=10.76 Hz, 1H), 2.78-2.96 (m, 2H), 2.52-2.62 (m, 2H), 1.60-2.07 (m, 10H), 1.13 (d, J=6.60 Hz, 3H)

$^{19}$F NMR (377 MHz, DMSO-d$_6$) δ −69.22 (s, 1F), −71.10 (s, 1F), −74.78 (s, 1F)

LCMS: $t_R$=2.219 min, 100% purity, m/z=781.3 (M+H)$^+$

A1BC3R2 (NUCC-0226133):

$^1$H NMR (400 MHz, DMSO-d$_6$) δ 11.10 (br s, 11H), 9.81 (s, 11H), 8.86 (d, J=4.63 Hz, 11H), 8.09 (dd, J=5.95, 9.26 Hz, 11H), 7.97 (dd, J=2.65, 11.03 Hz, 11H), 7.79 (dd, J=7.50, 8.38 Hz, 1H), 7.66 (dt, J=2.76, 8.65 Hz, 1H), 7.39-7.59 (m, 5H), 6.86 (d, J=9.04 Hz, 2H), 5.08 (dd, J=5.29, 12.79 Hz, 1H), 4.26-4.39 (m, 2H), 3.94-4.07 (m, 2H), 3.76-3.82 (m, 2H), 3.67-3.74 (m, 2H), 3.61-3.66 (m, 2H), 3.50-3.58 (m, 6H), 3.38-3.43 (m, 1H), 2.74-2.95 (m, 2H), 2.51-2.62 (m, 2H), 1.48-2.16 (m, 10H), 1.12 (d, J=6.62 Hz, 3H)

LCMS: $t_R$=2.209 min, 95.6% purity, m/z=825.3 (M+H)$^+$

A1BC4R2 (NUCC-0226182):

$^1$H NMR (400 MHz, DMSO-d$_6$) δ 1.13 (br d, J=6.60 Hz, 3H), 1.52-2.11 (m, 11H), 2.73-3.02 (m, 3H), 3.43-3.60 (m, 10H), 3.64 (br dd, J=5.69, 3.73 Hz, 2H), 3.67-3.74 (m, 2H), 3.77-3.85 (m, 2H), 3.96-4.06 (m, 3H), 4.31-4.39 (m, 3H), 5.04-5.14 (m, 11H), 6.82-6.99 (m, 2H), 7.38-7.65 (m, 4H), 7.68-7.93 (m, 3H), 8.10-8.33 (m, 2H), 9.03 (br d, J=4.52 Hz, 1H), 9.81 (s, 11H), 11.05-11.19 (m, 11H)

LCMS: $t_R$=2.260 min, 99.3% purity, m/z=869.1 (M+H)$^+$
A1BC5R2 (NUCC-0226187):
LCMS: RT=3.006 min, 97.4% purity, m/z=911.4 (M−H)$^+$
Experimental for Largest Scale Run:
General Procedure for Preparation of Compound 2—Notebook Page: ET32240-321

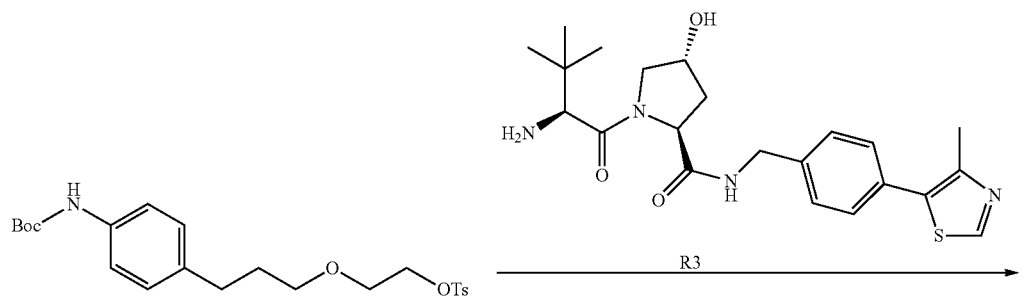

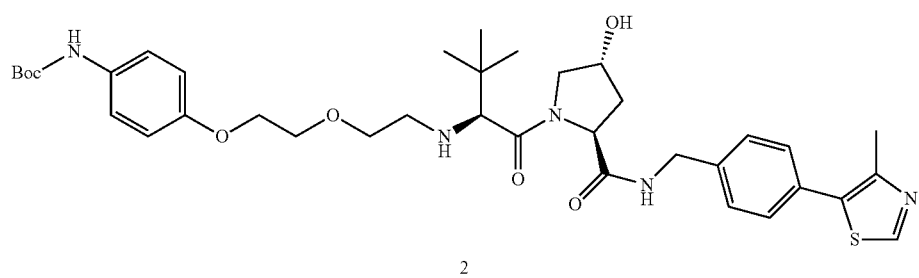

To a solution of R3 (100 mg, 232.25 umol, 1 eq) and Compound 1 (125.84 mg, 278.71 umol, 1.2 eq) in DMSO (1.5 mL) was added DIEA (60.03 mg, 464.51 umol, 80.91 uL, 2 eq) and KI (192.77 mg, 1.16 mmol, 5 eq).The mixture was stirred at 80° C. for 12 hr. LCMS showed the starting material was consumed and the desired product was detected. The reaction mixture was poured into water (3 mL), filtered and concentrated under reduced pressure. The residue was used for the next step directly. Compound 2 (150 mg, 211.30 umol, 90.98% yield) was obtained as a white solid.
General Procedure for Preparation of Compound 3—Notebook Page: ET32240-337

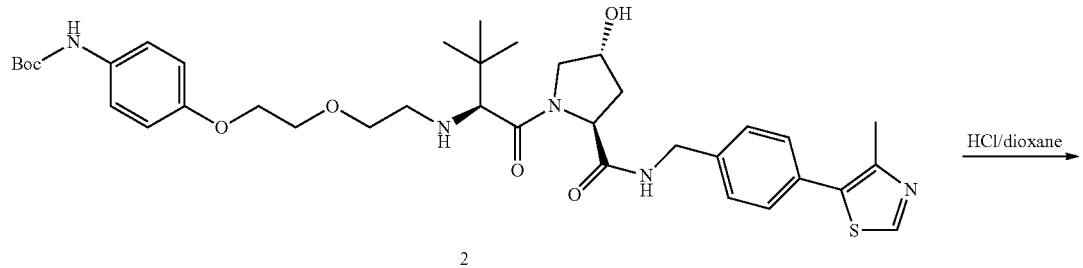

-continued

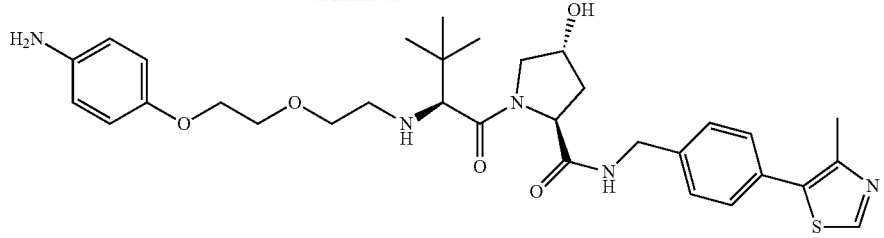

3

A solution of Compound 3 (130 mg, 183.13 umol, 1 eq) in 4 N HCl/dioxane (183.13 umol, 2 mL, 1 eq) was stirred for 1 hr at 20° C. LCMS showed the starting material was consumed and the desired MS was detected. The reaction solution was concentrated under reduced pressure at 30° C. The residue was used for the next step without further purification. Compound 2 (110 mg, 170.22 umol, 92.95% yield, HCl) was obtained as white solid.

To a solution of L1 (24.71 mg, 82.00 umol, 1 eq) in DMF (1 mL) was added DIEA (31.79 mg, 245.99 umol, 42.85 uL, 3 eq) and HATU (31.18 mg, 82.00 umol, 1 eq) at 0° C. The reaction was stirred at 0° C. for 30 min. The Compound 3 (50 mg, 82.00 umol, 1 eq, HCl) was added to the mixture. And the reaction was stirred at 0° C. for 30 min and then stirred at 20° C. for 5 hrs. LCMS showed the starting material was consumed completely and the desired MS was detected. The mixture was filtered directly. The filtrate was purified by pre-HPLC and lyophilized. (column: Nano-micro Kromasil C18 100*40 mm 10 um; mobile phase: [water(0.1% TFA)-ACN]; B %: 25%-48%, 8 min) A1BC1R3 (NUCC-0223799) (21 mg, 20.85 umol, 25.43% yield, 100% purity, TFA) was obtained as white solid.

A1BC1R3 (NUCC-0223799):

$^1$H NMR (400 MHz, DMSO-$d_6$) δ 9.84 (s, 1H), 8.98 (s, 1H), 8.91 (d, J=4.65 Hz, 1H), 8.67-8.85 (m, 2H), 8.27 (br s, 1H), 8.12 (dd, J=5.75, 9.17 Hz, 1H), 8.03 (dd, J=2.63, 10.94 Hz, 1H), 7.72 (dt, J=2.69, 8.68 Hz, 1H), 7.63 (d, J=4.77 Hz, 1H), 7.53 (d, J=8.93 Hz, 2H), 7.39 (s, 4H), 6.89 (d, J=9.05 Hz, 2H), 4.59 (t, J=8.44 Hz, 1H), 4.44 (dd, J=6.54, 15.83 Hz, 1H), 4.30 (br s, 1H), 4.23 (br dd, J=5.44, 15.71 Hz, 2H), 4.10 (br s, 2H), 3.79 (br d, J=4.16 Hz, 4H), 3.35-3.52 (m, 3H), 3.10 (br s, 1H), 2.95 (br s, 1H), 2.78-2.89 (m, 1H), 2.43 (s, 3H), 2.14 (br dd, J=7.89, 12.78 Hz, 1H), 1.47-2.04 (m, 10H), 1.12 (d, J=6.60 Hz, 3H), 1.05 (s, 9H)

$^{19}$F NMR (376 MHz, DMSO-$d_6$) δ −74.31 (s, 1F), −112.34 (br s, 1F)

LCMS: $t_R$=2.100 min, 100% purity, m/z=893.4 (M+H)$^+$

A1BC2R3 (NUCC-0223800):

$^1$H NMR (400 MHz, DMSO-$d_6$) δ 9.84 (s, 1H), 8.98 (s, 1H), 8.93 (d, J=4.65 Hz, 1H), 8.72 (br t, J=5.93 Hz, 2H), 8.26 (br s, 11H), 8.13 (dd, J=5.81, 9.23 Hz, 1H), 8.04 (dd, J=2.45, 10.88 Hz, 1H), 7.73 (dt, J=2.69, 8.68 Hz, 1H), 7.64 (d, J=4.77 Hz, 11H), 7.52 (d, J=8.93 Hz, 2H), 7.33-7.43 (m, 4H), 6.87 (d, J=8.93 Hz, 2H), 4.60 (t, J=8.31 Hz, 1H), 4.44 (br dd, J=6.48, 15.77 Hz, 1H), 4.35 (br s, 1H), 4.24 (br d, J=5.50 Hz, 1H), 4.20 (br d, J=5.26 Hz, 1H), 4.05 (br s, 1H), 3.80 (br d, J=11.13 Hz, 1H), 3.69-3.76 (m, 4H), 3.57-3.65 (m, 4H), 3.37-3.56 (m, 3H), 3.09 (br d, J=13.08 Hz, 1H), 2.88-3.01 (m, 1H), 2.78-2.88 (m, 1H), 2.44 (s, 3H), 1.45-2.21 (m, 11H), 1.12 (d, J=6.48 Hz, 3H), 0.97-1.09 (m, 9H)

$^{19}$F NMR (377 MHz, DMSO-$d_6$) δ −74.32 (s, 1F), −112.18 (br s, 1F)

LCMS: $t_R$=2.131 min, 92.4% purity, m/z=469.4 (M/2+H)$^+$

A1BC3R3 (NUCC-0226134):

$^1$H NMR (400 MHz, DMSO-$d_6$) δ 9.81 (s, 1H), 8.90-9.00 (m, 1H), 8.86 (d, J=4.41 Hz, 11H), 8.55 (t, J=5.95 Hz, 11H), 8.09 (dd, J=5.95, 9.26 Hz, 1H), 7.97 (dd, J=2.65, 11.03 Hz, 1H), 7.66 (dt, J=2.87, 8.71 Hz, 1H), 7.46-7.58 (m, 3H), 7.31-7.45 (m, 4H), 6.86 (d, J=9.04 Hz, 2H), 4.93-5.07 (m, 1H), 4.47-4.62 (m, 1H), 4.16-4.44 (m, 3H), 3.96-4.08 (m, 2H), 3.66-3.74 (m, 2H), 3.44-3.65 (m, 10H), 3.39-3.43 (m, 2H), 3.31 (br s, 2H), 3.07 (s, 11H), 2.75-2.90 (m, 1H), 2.56-2.69 (m, 1H), 2.42-2.45 (m, 3H), 1.54-2.21 (m, 12H), 1.11 (d, J=6.62 Hz, 3H), 0.76-1.01 (m, 9H)

LCMS: $t_R$=2.123 min, 100% purity, m/z=491.5 (M/2+H)$^+$

A1BC4R3 (NUCC-0226183):

$^1$H NMR (400 MHz, DMSO-$d_6$) δ 1.06 (s, 9H), 1.11 (s, 1H), 1.13 (s, 2H), 1.11-1.13 (m, 1H), 1.52 (d, J=7.06 Hz, 1H), 1.64 (br d, J=10.36 Hz, 3H), 1.70-1.77 (m, 2H), 1.83-2.03 (m, 5H), 2.10-2.20 (m, 1H), 2.44 (s, 3H), 2.78-2.86 (m, 1H), 2.88-2.96 (m, 1H), 3.07 (br s, 1H), 3.53 (s, 6H), 3.56 (br s, 5H), 3.68-3.72 (m, 6H), 4.00-4.05 (m, 2H), 4.17-4.27 (m, 3H), 4.37 (br s, 1H), 4.45 (br dd, J=15.77, 6.50 Hz, 1H), 4.59 (br t, J=8.38 Hz, 1H), 6.87 (br d, J=9.04 Hz, 2H), 7.39 (s, 4H), 7.51 (d, J=9.04 Hz, 2H), 7.67 (d, J=4.63 Hz, 1H), 7.72-7.79 (m, 11H), 8.08 (dd, J=10.80, 2.21 Hz, 1H), 8.15 (dd, J=9.04, 5.73 Hz, 1H), 8.23 (br s, 1H), 8.73 (br t, J=5.84 Hz, 2H), 8.95 (d, J=4.63 Hz, 1H), 8.99 (s, 1H), 9.83 (s, 1H)

LCMS: $t_R$=1.928 min, 95.7% purity, m/z=513.3 (M/2+H)$^+$

A1BC5R3 (NUCC-0226188):

$^1$H NMR: 400 MHz, DMSO-$d_6$ δ=0.95-1.23 (m, 1H), 0.97-1.20 (m, 1H), 1.05-1.15 (m, 11H), 1.13 (d, J=6.60 Hz, 1H), 1.56-2.03 (m, 111H), 2.16 (br dd, J=12.65, 7.76 Hz, 1H), 2.31-2.35 (m, 1H), 2.44 (s, 3H), 2.47-2.54 (m, 123H), 2.66-2.69 (m, 1H), 2.78-2.98 (m, 2H), 3.02-3.14 (m, 1H), 3.43 (br t, J=11.55 Hz, 1H), 3.48-3.62 (m, 18H), 3.67-3.74 (m, 4H), 3.80 (br d, J=11.00 Hz, 1H), 3.99-4.06 (m, 2H), 4.24 (br dd, J=15.96, 5.20 Hz, 3H), 4.35-4.50 (m, 4H), 4.60 (br t, J=8.31 Hz, 2H), 6.88 (d, J=9.05 Hz, 2H), 7.40 (s, 4H), 7.52 (d, J=8.93 Hz, 2H), 7.61 (d, J=4.65 Hz, 11H), 7.71 (td, J=8.71, 2.63 Hz, 11H), 8.02 (dd, J=10.94, 2.63 Hz, 11H), 8.12 (dd, J=9.11, 5.81 Hz, 1H), 8.16-8.32 (m, 11H), 8.65-8.83 (m, 1H), 8.73 (br t, J=5.75 Hz, 1H), 8.91 (d, J=4.65 Hz, 1H), 8.99 (s, 1H), 9.83 (s, 11H)

LCMS (ESI+): m/z=535.2 (M/2+H)+, RT: 2.184 min. 98.4% purity.

Experimental for Largest Scale Run:
General Procedure for Preparation of Compound 2—Notebook Page: ET32240-208

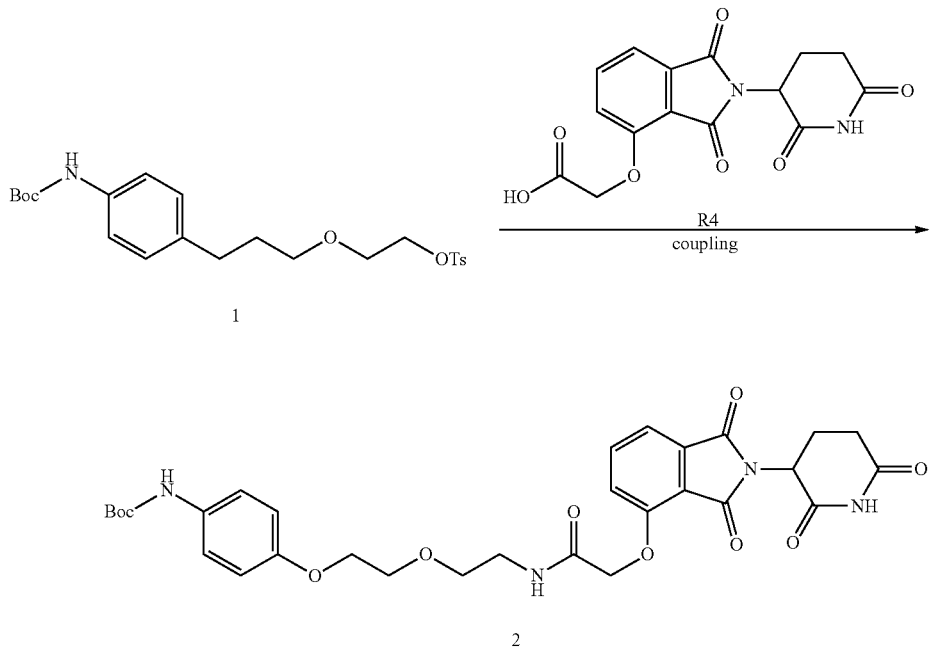

To a solution of Compound 1 (196.23 mg, 662.12 umol, 1.1 eq) and R⁴ (200 mg, 601.93 umol, 1 eq) in DMF (4 mL) was added DIEA (388.97 mg, 3.01 mmol, 524.21 uL, 5 eq) and $T_3P$ (1.15 g, 1.81 mmol, 1.07 mL, 50% purity, 3 eq) drop-wise at 0° C. The mixture was stirred for 2 hr at 20° C. LCMS showed the starting material was consumed and the desired MS was detected. The mixture was poured into water (20 mL), extracted with ethyl acetate (3×20 mL), washed with brine (20 mL), dried over sodium sulfate, filtered and the filtrate was concentrated under reduced pressure. The resulting residue was purified by column chromatography (SiO2, Petroleum ether/Ethyl acetate=1/1 to 0/1). Compound 2 (300 mg, 491.31 umol, 81.62% yield) was obtained as yellow solid. $^1$H NMR (400 MHz, DMSO-$d_6$) δ 11.11 (s, 1H), 9.09 (br s, 1H), 8.03 (br t, J=5.56 Hz, 1H), 7.79 (dd, J=7.40, 8.38 Hz, 1H), 7.49 (d, J=7.21 Hz, 1H), 7.39 (d, J=8.44 Hz, 1H), 7.32 (br d, J=8.56 Hz, 2H), 6.82 (d, J=9.05 Hz, 2H), 5.11 (dd, J=5.38, 12.96 Hz, 1H), 4.78 (s, 2H), 3.97-4.10 (m, 2H), 3.67-3.76 (m, 2H), 3.54 (t, J=5.69 Hz, 2H), 3.33-3.39 (m, 2H), 2.81-2.90 (m, 1H), 2.53-2.64 (m, 2H), 1.96-2.10 (m, 1H), 1.46 (s, 9H)

General Procedure for Preparation of Compound 3—Notebook Page: ET32240-232

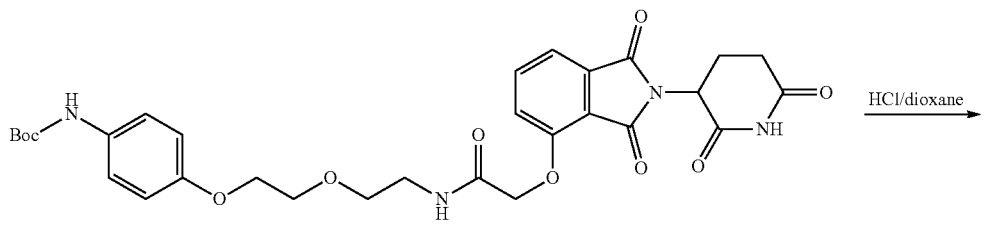

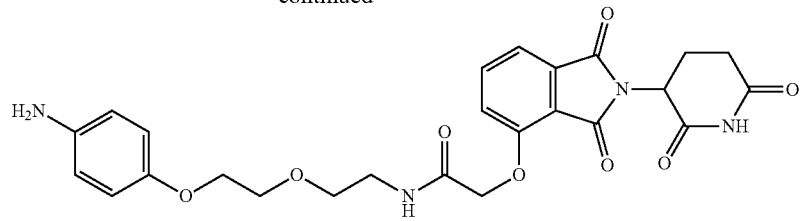

3

A solution of Compound 2 (100 mg, 163.77 umol, 1 eq) in 4 N HCl/dioxane (4.89 mg, 1.5 mL) was stirred for 1 hr at 20° C. LCMS showed the starting material was consumed and the desired MS was detected. The reaction solution was concentrated under reduced pressure at 30° C. The residue was used for the next step without further purification. Compound 3 (85 mg, 155.41 umol, 94.89% yield, HCl) was obtained as yellow solid.

To a solution of L1 (33.06 mg, 109.70 umol, 1 eq) in DMF (1 mL) was added DIEA (42.53 mg, 329.09 umol, 57.32 uL, 3 eq) and HATU (41.71 mg, 109.70 umol, 1 eq) at 0° C. The reaction was stirred at 0° C. for 30 min. The Compound 3 (60 mg, 109.70 umol, 1 eq, HCl) was added to the mixture. And the reaction was stirred at 0° C. for 30 min and then stirred at 20° C. for 5 hrs. LCMS showed the starting material was consumed completely and the desired MS was detected. The mixture was filtered directly. The filtrate was purified by pre_HPLC and lyophilized. (column: Phenomenex Luna C18 150*30 mm*5 um; mobile phase: [water (0.1% TFA)-ACN]; B %: 30%-60%, 10 min) A1BC1R4 (NUCC-0223601) (50 mg, 55.07 umol, 50.21% yield, TFA) was obtained as white solid.
A1BC1R4 (NUCC-0223601):

$^1$H NMR (400 MHz, DMSO-d$_6$) δ 11.12 (s, 1H), 9.80 (s, 1H), 9.14 (d, J=5.14 Hz, 1H), 8.17-8.33 (m, 2H), 8.04 (t, J=5.62 Hz, 1H), 7.85-7.97 (m, 2H), 7.78 (dd, J=7.40, 8.38 Hz, 1H), 7.45-7.54 (m, 3H), 7.38 (d, J=8.56 Hz, 1H), 6.87 (d, J=9.05 Hz, 2H), 5.11 (dd, J=5.32, 12.90 Hz, 1H), 4.78 (s, 2H), 3.99-4.08 (m, 2H), 3.70-3.77 (m, 2H), 3.49-3.64 (m, 3H), 3.35 (q, J=5.58 Hz, 2H), 2.78-2.97 (m, 2H), 2.53-2.65 (m, 2H), 1.54-2.11 (m, 10H), 1.14 (d, J=6.60 Hz, 3H)

$^{19}$F NMR (377 MHz, DMSO-d$_6$) δ −69.20 (s, 1F), −71.08 (br s, 1F), −74.98 (s, 1F)

LCMS: t$_R$=2.113 min, 100% purity, m/z=794.3 (M+H)$^+$
A1BC2R4 (NUCC-0223604):

$^1$H NMR (400 MHz, DMSO-d6) δ ppm 11.12 (s, 1H) 9.98 (s, 1H) 9.17 (d, J=5.26 Hz, 1H) 8.26-8.40 (m, 2H) 7.89-8.06 (m, 3H) 7.74-7.84 (m, 1H) 7.45-7.58 (m, 3H) 7.38 (d, J=8.56 Hz, 1H) 6.86 (d, J=9.05 Hz, 2H) 5.11 (dd, J=12.84, 5.38 Hz, 1H) 4.78 (s, 2H) 3.98-4.05 (m, 2H) 3.70 (br s, 2H) 3.57 (br d, J=2.69 Hz, 2H) 3.53-3.55 (m, 2H) 3.45-3.48 (m, 2H) 3.31 (q, J=5.58 Hz, 2H) 2.81-2.98 (m, 2H) 2.52-2.63 (m, 2H) 2.39-2.48 (m, 1H) 1.60-2.10 (m, 10H) 1.12 (d, J=6.60 Hz, 3H)

LCMS: t$_R$=2.127 min, 96.6% purity, m/z=838.4 (M+H)$^+$
A1BC3R4 (NUCC-0226135):

$^1$H NMR (400 MHz, DMSO-d$_6$) δ 11.13 (s, 1H), 9.85 (s, 1H), 9.06 (d, J=4.85 Hz, 1H), 8.13-8.24 (m, 2H), 8.02 (t, J=5.62 Hz, 1H), 7.74-7.91 (m, 3H), 7.45-7.55 (m, 3H), 7.38 (d, J=8.38 Hz, 1H), 6.87 (d, J=9.04 Hz, 2H), 5.10-5.14 (m, 1H), 4.78 (s, 2H), 3.95-4.06 (m, 2H), 3.64-3.75 (m, 2H), 3.41-3.60 (m, 11H), 3.31 (q, J=5.44 Hz, 2H), 2.75-2.97 (m, 2H), 2.51-2.64 (m, 2H), 1.57-2.13 (m, 10H), 1.12 (d, J=6.62 Hz, 3H)

$^{19}$F NMR (376 MHz, DMSO-d$_6$) δ −69.20 (s, 1F), −71.09 (s, 1F), −74.75 (s, 1F), −110.66 (br s, 1F)

LCMS: t$_R$=2.147 min, 100% purity, m/z=882.3 (M+H)$^+$
A1BC4R4 (NUCC-0226184):

$^1$H NMR (ET32240-987-PLA2, 400 MHz, DMSO-d$_6$) δ 1.12 (br d, J=6.60 Hz, 3H), 1.57-2.08 (m, 12H), 2.59 (br d, J=16.99 Hz, 2H), 2.78-2.95 (m, 2H), 3.30 (q, J=5.42 Hz, 2H), 3.41-3.56 (m, 13H), 3.63-3.65 (m, 1H), 3.63-3.64 (m, 2H), 3.95-4.09 (m, 2H), 4.78 (s, 2H), 5.11 (dd, J=12.90, 5.32 Hz, 1H), 6.87 (d, J=9.05 Hz, 2H), 7.38 (d, J=8.56 Hz, 1H), 7.46-7.54 (m, 3H), 7.72 (br d, J=4.77 Hz, 1H), 7.76-7.83 (m, 2H), 8.00 (br t, J=5.38 Hz, 1H), 8.09-8.20 (m, 2H), 8.99 (d, J=4.77 Hz, 1H), 9.82 (s, 1H), 11.12 (s, 1H)

LCMS: t$_R$=2.160 min, 100% purity, m/z=463.8 (M/2+H)$^+$
A1BC5R4 (NUCC-0226189):

$^1$H NMR (400 MHz, DMSO-d$_6$) δ 1.13 (d, J=6.60 Hz, 3H), 1.57-2.09 (m, 12H), 2.55-2.64 (m, 1H), 2.78-2.95 (m, 2H), 3.30 (q, J=5.50 Hz, 2H), 3.48 (br s, 6H), 3.50-3.54 (m, 7H), 3.55-3.59 (m, 2H), 3.66-3.74 (m, 2H), 3.99-4.07 (m, 2H), 4.78 (s, 2H), 4.84-5.05 (m, 1H), 4.96 (br s, 3H), 5.11 (br dd, J=12.90, 5.32 Hz, 1H), 6.87 (d, J=9.05 Hz, 2H), 7.39 (d, J=8.56 Hz, 1H), 7.46-7.54 (m, 3H), 7.77-7.90 (m, 3H), 7.99 (br t, J=5.50 Hz, 1H), 8.17-8.24 (m, 2H), 9.07 (d, J=5.01 Hz, 11H), 9.80 (s, 1H), 11.11 (s, 1H)

LCMS (ESI+): m/z=485.8 (M+H)+, RT: 2.182 min. 90.8 purity

Experimental for Largest Scale Run:
General Procedure for Preparation of Compound 2—Notebook Page: ET32240-375.

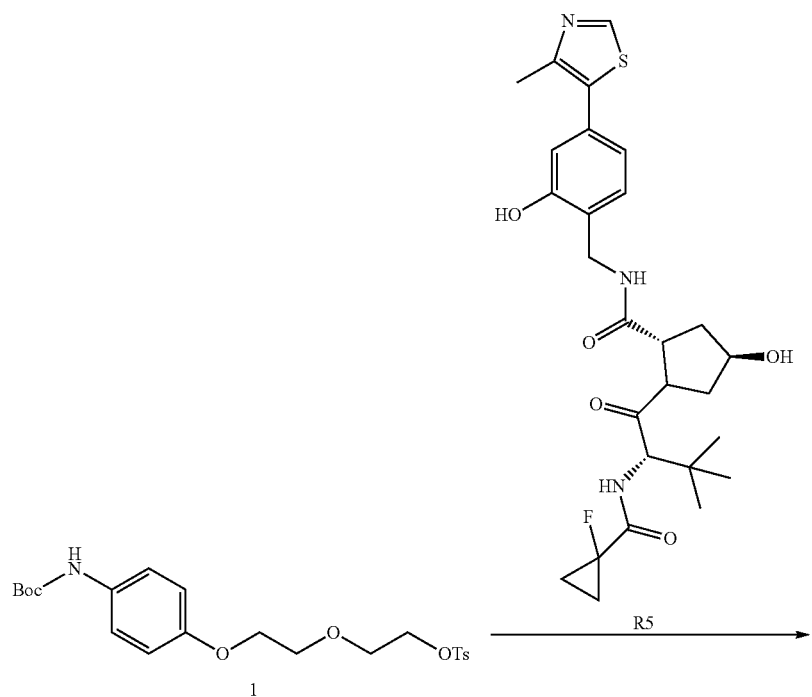
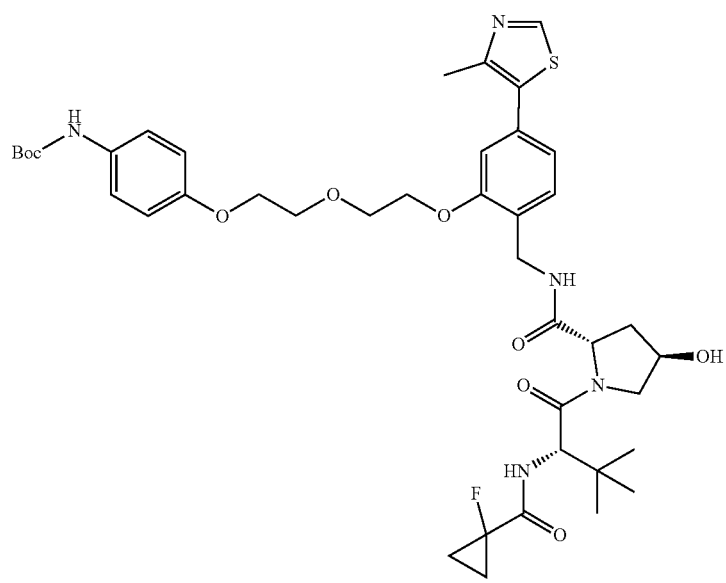

To a solution of R5 (100 mg, 187.75 umol, 1 eq) in DMF (1.5 mL) was added K₂CO₃ (51.90 mg, 375.50 umol, 2 eq), KI (155.83 mg, 938.74 umol, 5 eq) and Compound 1 (93.25 mg, 206.52 umol, 1.1 eq). The mixture was stirred at 80° C. for 2 hr. LCMS showed the starting material was consumed completed. The reaction mixture was poured into water (20 mL), and then filtered. The filtered cake was concentrated under reduced pressure. The residue was used for the next step directly without further purification. Compound 2 (120 mg, 147.79 umol, 78.72% yield) was obtained as light yellow solid.

General Procedure for Preparation of Compound 3—Notebook Page: ET32240-395

The residue was used for the next step without further purification. Compound 3 (110 mg, 147.00 umol, 99.46% yield, HCl) was obtained as light yellow solid.

To a solution of L1 (40 mg, 132.73 umol, 1 eq) in DMF (2 mL) was added DIEA (51.46 mg, 398.20 umol, 69.36 uL, 3 eq) and HATU (50.47 mg, 132.73 umol, 1 eq) at 0° C. The reaction was stirred at 0° C. for 30 min. The Compound 3 (99.33 mg, 132.73 umol, 1 eq, HCl) was added to the mixture. And the reaction was stirred at 0° C. for 30 min and then stirred at 20° C. for 5 hrs. LCMS showed the starting material was consumed completely and the desired MS was detected. The mixture was filtered directly. The filtrate was purified by pre-HPLC and lyophilized. (column: Nano-

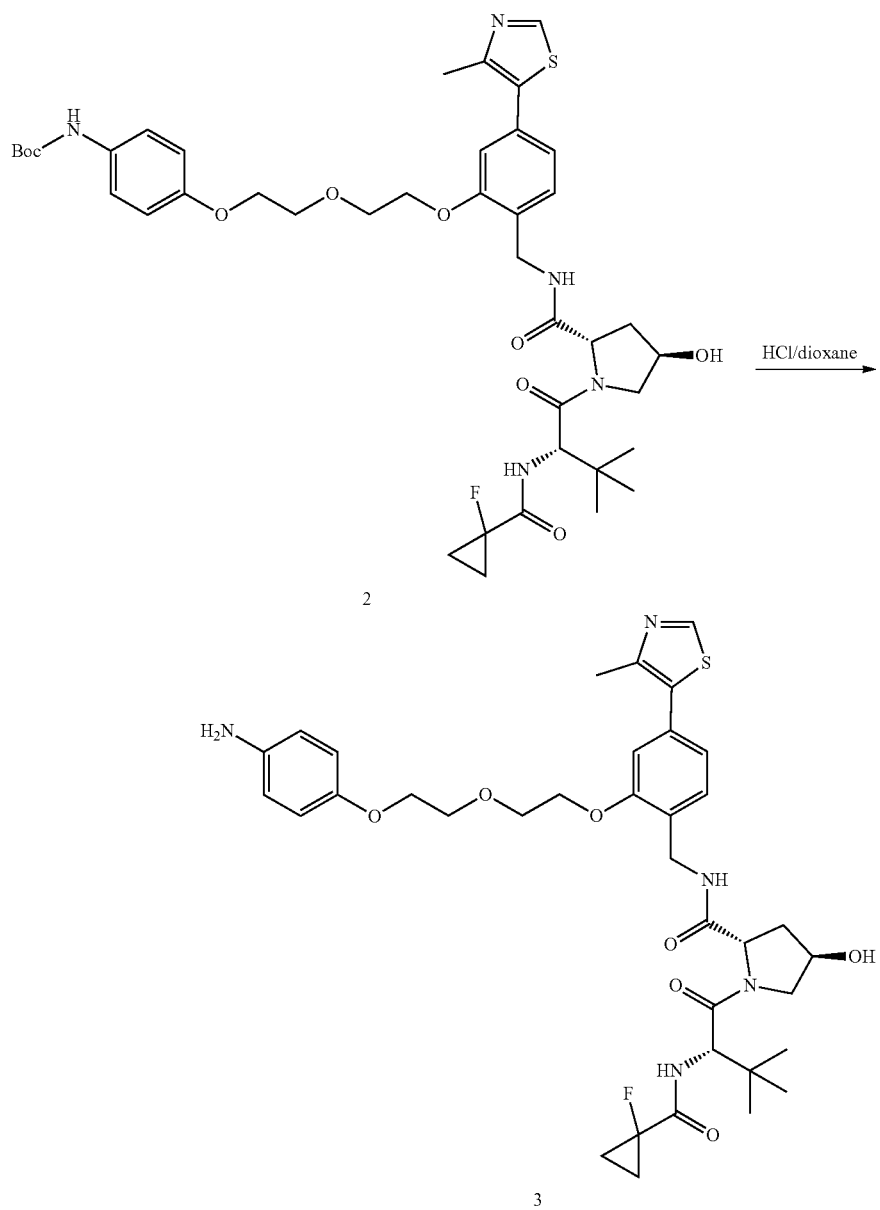

A solution of Compound 2 (120 mg, 147.79 umol, 1 eq) in 4 N HCl/dioxane (147.79 umol, 1 mL, 1 eq) was stirred for 1 hr at 20° C. LCMS showed the starting material was consumed and the desired MS was detected. The reaction solution was concentrated under reduced pressure at 30° C.

micro Kromasil C18 100*40 mm 10 um; mobile phase: [water(0.1% TFA)-ACN]; B %: 25%-55%, 8 min) A1BC1R5 (NUCC-0223801) (32.8 mg, 29.57 umol, 22.28% yield, 100% purity, TFA) was obtained as light yellow solid. ¹H NMR (400 MHz, DMSO-d₆) δ 9.89 (s, 1H), 9.12 (d, J=5.01 Hz, 1H), 9.04-9.10 (m, 1H), 8.49-8.72 (m, 1H), 8.21-8.33 (m, 2H), 7.92 (dt, J=2.57, 8.68 Hz, 1H), 7.86 (d, J=4.89 Hz, 1H), 7.52-7.65 (m, 2H), 7.43-7.51 (m, 1H), 7.37 (br d, J=9.05 Hz, 1H), 7.09-7.20 (m, 1H), 7.06 (d, J=7.58 Hz, 1H), 6.96 (d, J=8.93 Hz, 2H), 4.69 (br s, 1H), 4.61 (br s, 1H), 4.43 (br s, 1H), 4.38 (br d, J=5.99 Hz, 1H), 4.27-4.34 (m, 3H), 4.12-4.20 (m, 2H), 3.93 (td, J=4.51, 9.20 Hz, 4H), 3.66-3.77 (m, 2H), 3.54-3.65 (m, 1H), 2.86-3.00 (m, 1H), 2.56 (s, 1H), 2.54 (s, 3H), 1.62-2.28 (m, 10H), 1.38-1.50 (m, 2H), 1.30 (br dd, J=2.38, 8.13 Hz, 2H), 1.22 (d, J=6.60 Hz, 3H), 1.04 (s, 10H)

$^{19}$F NMR (377 MHz, DMSO-$d_6$) δ −74.83 (s, 1F), −110.98 (br s, 1F), −196.21 (s, 1F)

LCMS: $t_R$=2.404 min, 100% purity, m/z=995.5 (M/2+H)$^+$

A1BC2R5 (NUCC-0223802):

$^1$H NMR (400 MHz, DMSO-$d_6$) δ 9.81 (s, 1H), 9.06 (d, J=5.01 Hz, 1H), 8.94-9.01 (m, 1H), 8.41-8.59 (m, 1H), 8.13-8.26 (m, 2H), 7.76-7.91 (m, 2H), 7.34-7.55 (m, 3H), 7.23-7.32 (m, 1H), 7.04 (s, 1H), 6.96 (br d, J=7.70 Hz, 1H), 6.86 (d, J=8.93 Hz, 2H), 4.59 (br d, J=9.17 Hz, 1H), 4.51 (t, J=8.25 Hz, 1H), 4.27-4.37 (m, 2H), 4.12-4.25 (m, 3H), 3.97-4.07 (m, 2H), 3.76-3.84 (m, 2H), 3.69-3.75 (m, 2H), 3.45-3.68 (m, 7H), 2.78-2.90 (m, 1H), 2.47 (s, 1H), 2.45 (s, 3H), 1.57-2.15 (m, 10H), 1.30-1.40 (m, 2H), 1.17-1.24 (m, 2H), 1.13 (d, J=6.60 Hz, 3H), 0.95 (s, 10H)

$^{19}$F NMR (377 MHz, DMSO-$d_6$) δ −74.87 (s, 1F), −110.62 (br s, 1F), −198.51--194.10 (m, 1F)

LCMS: $t_R$=2.405 min, 100% purity, m/z=520.4 (M/2+H)$^+$

A1BC3R5 (NUCC-0226136):

$^1$H NMR (400 MHz, DMSO-$d_6$) δ 9.84 (s, 1H), 9.09 (d, J=5.07 Hz, 1H), 8.98 (s, 1H), 8.46-8.56 (m, 1H), 8.18-8.29 (m, 2H), 7.80-7.95 (m, 2H), 7.51 (d, J=9.04 Hz, 2H), 7.40 (d, J=7.72 Hz, 1H), 7.15-7.32 (m, 1H), 6.92-7.07 (m, 2H), 6.86 (d, J=9.04 Hz, 2H), 4.59 (d, J=9.26 Hz, 1H), 4.51 (t, J=8.16 Hz, 1H), 4.25-4.38 (m, 2H), 4.10-4.25 (m, 3H), 3.96-4.06 (m, 2H), 3.74-3.82 (m, 2H), 3.49-3.73 (m, 13H), 2.78-2.91 (m, 1H), 2.45 (s, 3H), 1.56-2.16 (m, 11H), 1.28-1.45 (m, 2H), 1.16-1.27 (m, 2H), 1.12 (d, J=6.62 Hz, 3H), 0.95 (s, 9H)

$^{19}$F NMR (376 MHz, DMSO-$d_6$) δ −74.88 (s, 1F), −110.31 (br s, 1F), −198.13--194.50 (m, 1F)

LCMS: $t_R$=2.170 min, 100% purity, m/z=1083.4 (M+H)$^+$

A1BC4R5 (NUCC-0226185):

$^1$H NMR (ET32240-911-P1H3 400 MHz, DMSO-d6) δ 0.95 (s, 9H), 1.12 (d, J=6.62 Hz, 3H), 1.17-1.25 (m, 2H), 1.31-1.36 (m, 1H), 1.36-1.41 (m, 1H), 1.64 (br s, 3H), 1.70-1.79 (m, 2H), 1.80-2.03 (m, 5H), 2.05-2.14 (m, 1H), 2.45 (s, 3H), 2.77-2.91 (m, 1H), 3.46-3.53 (m, 8H), 3.53-3.57 (m, 4H), 3.57-3.65 (m, 4H), 3.67-3.72 (m, 2H), 3.74-3.81 (m, 2H), 3.98-4.05 (m, 2H), 4.15-4.24 (m, 3H), 4.27-4.36 (m, 2H), 4.51 (t, J=8.16 Hz, 1H), 4.59 (d, J=9.04 Hz, 1H), 6.86 (d, J=9.04 Hz, 2H), 6.96 (d, J=7.72 Hz, 1H), 7.03 (s, 1H), 7.28 (dd, J=9.15, 2.54 Hz, 1H), 7.40 (d, J=7.72 Hz, 11H), 7.50 (d, J=8.82 Hz, 2H), 7.72-7.85 (m, 2H), 8.12-8.21 (m, 2H), 8.48 (t, J=5.84 Hz, 1H), 8.98 (s, 1H), 9.02 (d, J=4.85 Hz, 1H), 9.81 (s, 1H)

LCMS: $t_R$=2.363 min, 97.8% purity, m/z=564.5 (M/2+H)$^+$

A1BC5R5 (NUCC-0226190):

$^1$H NMR (ET32240-972-P1A, 400 MHz, CDCl$_3$) δ 0.99 (s, 9H), 1.18-1.38 (m, 8H), 1.70-1.97 (m, 7H), 2.10-2.38 (m, 4H), 2.54 (br s, 3H), 2.88-3.14 (m, 1H), 3.44 (br s, 1H), 3.52-3.99 (m, 22H), 4.05 (br s, 2H), 4.11-4.29 (m, 2H), 4.34-4.75 (m, 5H), 6.64-7.17 (m, 5H), 7.29-7.45 (m, 2H), 7.55-7.69 (m, 1H), 7.75 (br t, J=7.61 Hz, 1H), 7.71-7.81 (m, 1H), 7.89 (br d, J=8.16 Hz, 1H), 8.12-8.49 (m, 1H), 8.73-8.84 (m, 1H), 8.86-9.22 (m, 3H)

LCMS: RT=2.450 min, 100% purity, m/z=586.5 (M/2+H)$^+$

Synthetic Scheme:

Scheme 1: Synthesis of A1BC1~C5R1, Take A2BC5R1 as an example.

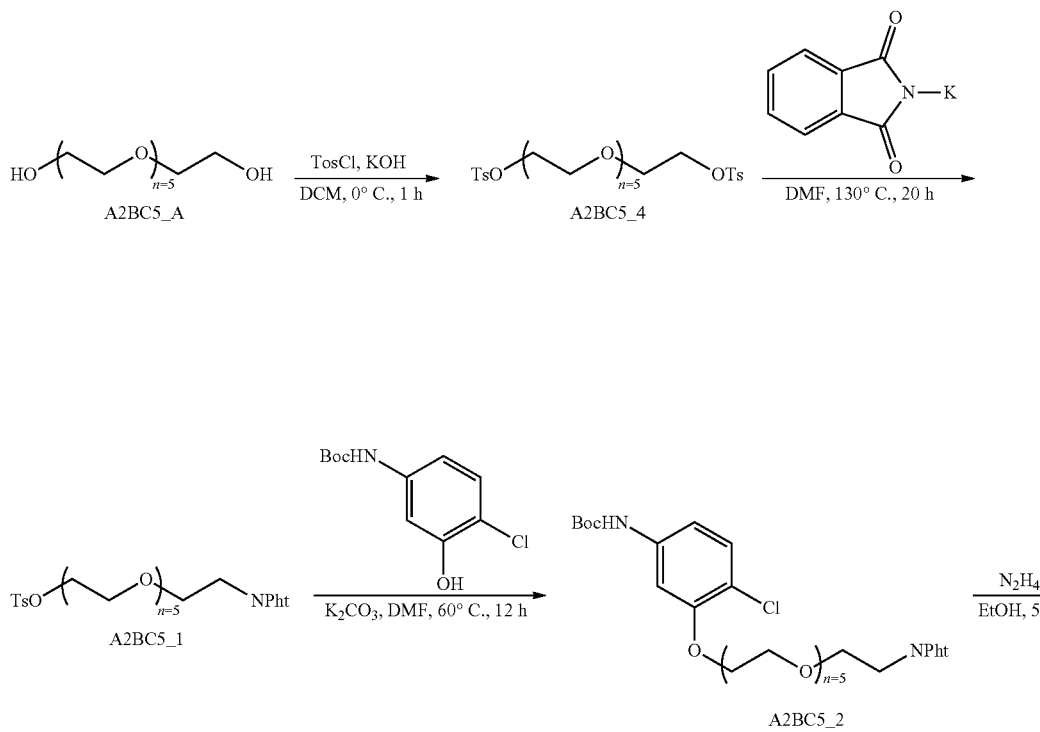

-continued

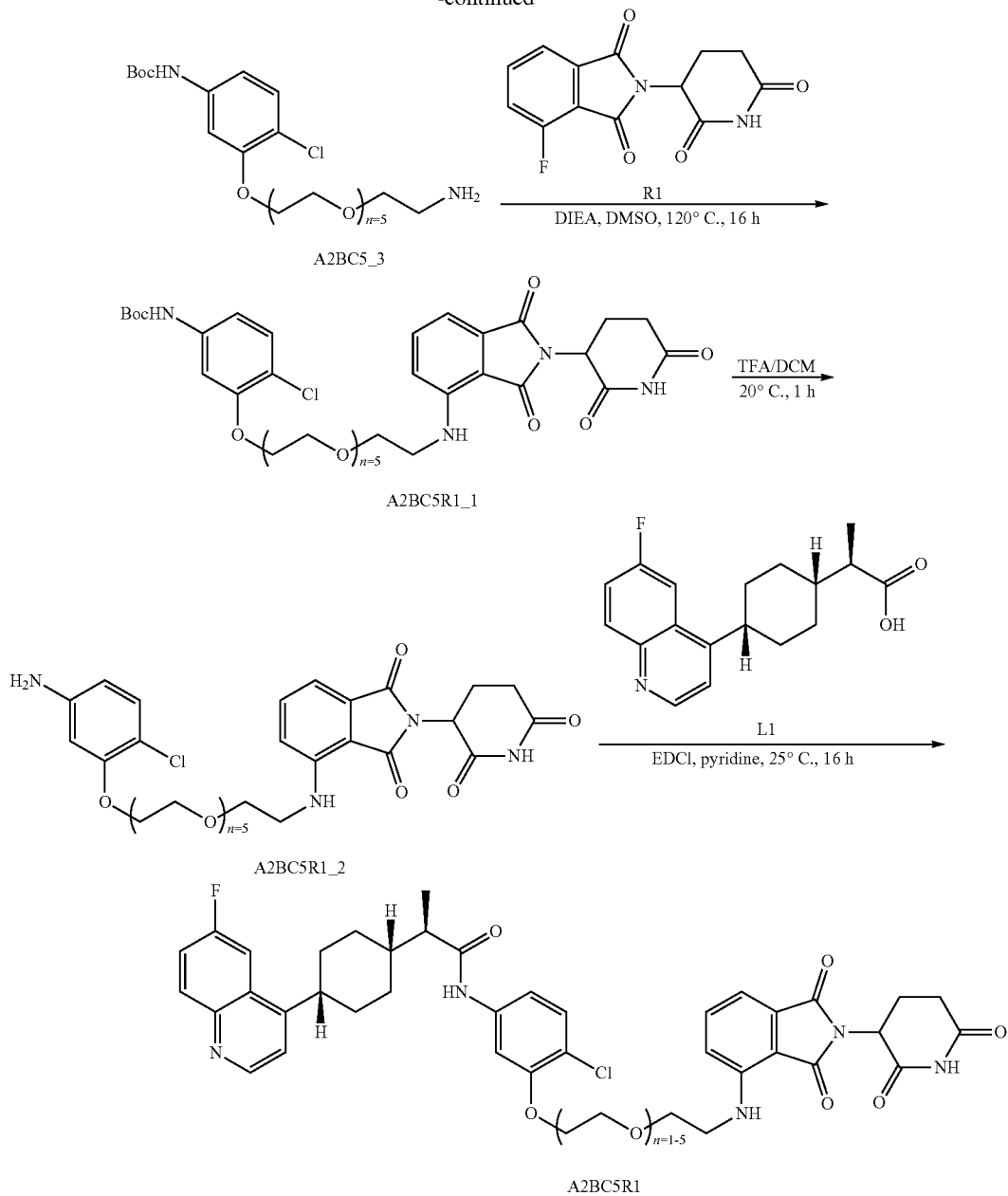

Experimental for Largest Scale Run:

Synthetic Scheme 3: Synthesis of A2BC5R1 (NUCC-0226145) as an Example.

General Procedure for Preparation of Compound A2BC5-4
Notebook Page: ET32240-709.

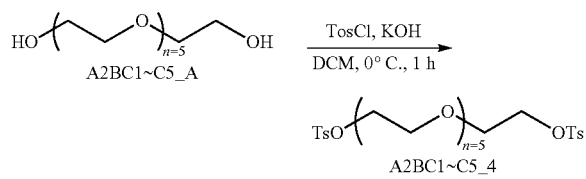

To a solution of Compound A2BC1-C5_A (10 g, 35.42 mmol, 1 eq), 4-methylbenzenesulfonyl chloride (13.51 g, 70.84 mmol, 2 eq) in dichloromethane (70 mL) was added potassium hydroxide (15.90 g, 283.36 mmol, 8 eq). The mixture was stirred at 0° C. for 1 hr. LCMS (ET32240-709-P1R1) showed A2BC1-C5_A was consumed completely and one main peak with desired m/z was detected. The reaction mixture was quenched with water and extracted with dichloromethane (40 mL×3). The combined organic layers were washed with brine (20 mL×2), dried over sodium sulfate, filtered and concentrated under reduced pressure to give crude product, which was used for next step without further purification. Compound A2BC1-5_4 (18.9 g, 28.35 mmol, 80.04% yield, 88.6% purity) was obtained as colorless solid, structure checking by HNMR.

¹H NMR (ET32240-9709-P1, 400 MHz, chloroform-d)

δ ppm 2.43 (s, 6H) 3.56 (s, 7H) 3.59-3.62 (m, 7H) 3.66 (dd, J=8.88, 4.25 Hz, 6H) 4.12-4.17 (m, 4H) 7.33 (d, J=8.13 Hz, 4H) 7.78 (d, J=8.38 Hz, 4H)

General Procedure for Preparation of Compound A2BC5-1 Notebook Page: ET32240-719

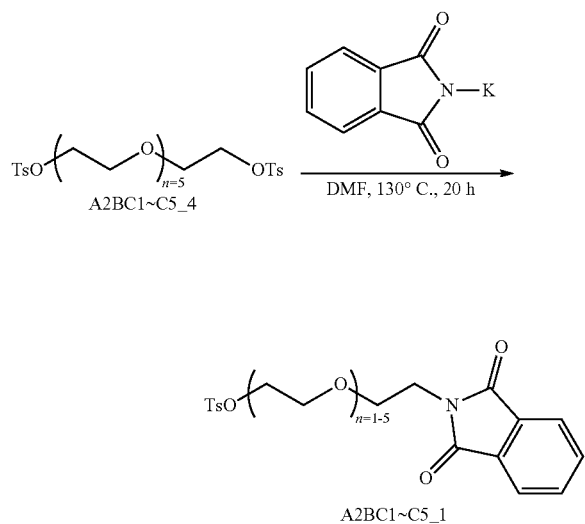

To a solution of Compound A2BC5-4 (9 g, 15.24 mmol, 1 eq) in DMF (90 mL) was added (1, 3-dioxoisoindolin-2-yl) potassium (2.82 g, 15.24 mmol, 1 eq). The mixture was stirred at 25° C. for 2 hr. LCMS showed the starting material was consumed completely and desired m/z was detected. The reaction mixture was filtered. The filtrate was purified by pre-HPLC (0.05% HCl) to give product. Compound A2BC5-1 (10 g, 17.68 mmol, 58.02% yield) was obtained as a colorless oil.

General Procedure for Preparation of Compound A2BC5_2 Notebook Page: ET32240-778

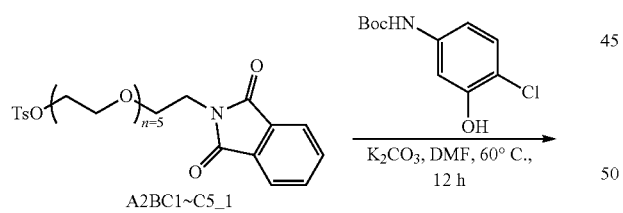

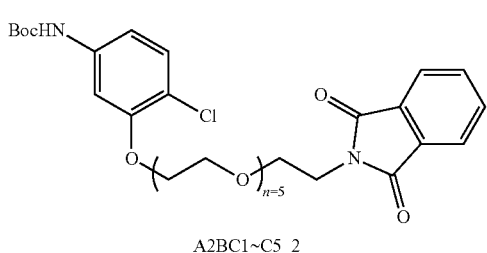

A mixture of Compound A2BC5-2 (1.5 g, 6.16 mmol, 1 eq) in N, N-dimethylformamide (10 mL) was added potassium carbonate (1.28 g, 9.23 mmol, 1.5 eq). The mixture was stirred at 80° C. for 12 hr. LCMS showed starting material was consumed completely and one main peak with desired m/z was detected. The reaction was filtered and collected liquid. The mixture was added water and extracted with ethyl acetate (15 mL×3), the combined organic was washed with brine and dried by sodium sulfate, then was concentrated into under reduce pressure to give residue. The residue was purified by column chromatography (SiO2, Petroleum ether/Ethyl acetate=10/1 to 5/1) to give product. Compound A2BC5-2 (3 g, 4.60 mmol, 74.74% yield, 97.7% purity) was obtained as a colorless oil.

¹H NMR (ET32240-778-PL 400 MHz, chloroform-d)

S ppm 1.48 (s, 9H) 3.56 (s, 5H) 3.59-3.67 (m, 7H) 3.68-3.78 (m, 4H) 3.68-3.78 (m, 1H) 3.83-3.91 (m, 4H) 4.17 (br t, J=4.69 Hz, 2H) 4.40 (br s, 2H) 6.78 (dd, J=8.57, 1.81 Hz, 1H) 6.92 (s, 1H) 7.17 (d, J=8.50 Hz, 1H) 7.23 (br s, 1H) 7.69 (dd, J=5.32, 3.06 Hz, 2H) 7.81 (dd, J=5.19, 3.06 Hz, 2H)

General procedure for preparation of Compound A2BC5-3 Notebook Page: ET32240-806.

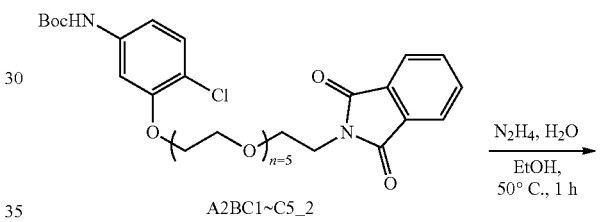

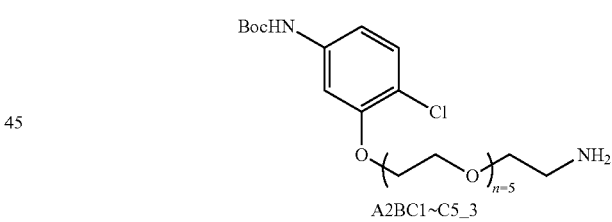

A mixture of Compound A2BC5-2 (3 g, 4.71 mmol, 1 eq) and hydrazine hydrate (831.95 mg, 14.13 mmol, 807.72 uL, 85% purity, 3 eq) in ethyl alcohol (50 mL) was stirred at 80° C. for 1 hr. LCMS (ET32240-806-P1R1) indicated Compound A2BC5-2 was consumed and the desired m/z was found. The reaction mixture was cooled to 20° C. and concentrated in reduced pressure at 45° C. The residue was partitioned between with ethyl acetate (50 mL) and water (50 mL). The organic phase was washed with brine (15 mL), dried with anhydrous sodium sulfate, filtered and concentrated in vacuum to give Compound A2BC5-3 (2.3 g, 4.43 mmol, 94.03% yield, 97.6% purity) as a colorless oil was obtained.

General Procedure for Preparation of Compound A2BC5R1_1 Notebook Page: ET32240-812.

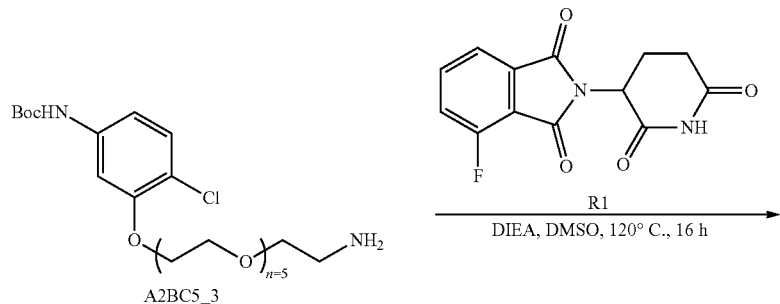

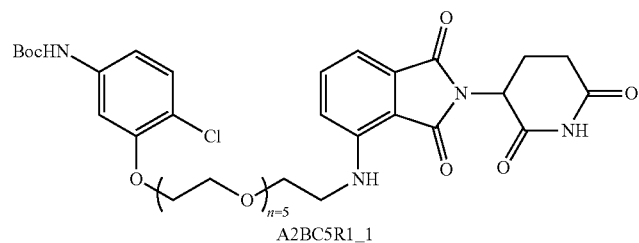

To a solution of R1 (200 mg, 724.06 umol, 1 eq) (550.67 mg, 1.09 mmol, 1.5 eq) and Compound A2BC5-3 in dimethylsulfoxide (1 mL) was added Diisopropylethylamine (748.64 mg, 5.79 mmol, 1.01 mL, 8 eq). The mixture was stirred at 100° C. for 12 hr. LC-MS showed $R^1$ was consumed completely and one main peak with desired m/z was detected. The mixture was filtered. The filtrate was purified by pre-HPLC (0.04% HCl) to give product. Compound A2BC5R1_1 (210 mg, 266.34 umol, 36.78% yield, 96.8% purity) was obtained as yellow solid.

General Procedure for Preparation of Compound A2BC5R1_2 Notebook Page: ET32240-846.

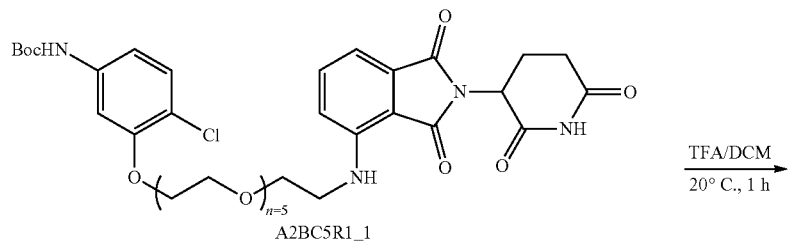

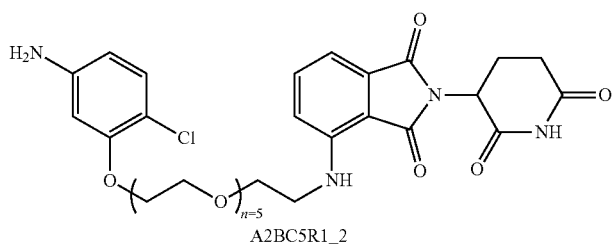

The mixture of Compound A2BC5R1_1 (210 mg, 275.15 umol, 1 eq) in HCl/EtOAc (1 mL) was stirred at 20° C. for 1 hr. LC-MS showed Compound A2BC5R1_1 was consumed completely and one main peak with desired m/z was detected. The mixture reaction was concentrated under reduced pressure to give a residue. Then water (3 mL) was added and the mixture was basified by sat.aq.NaHCO$_3$ to pH=8. Then the mixture was extracted with ethyl acetate (3 mL×2). The combined organic was washed with saturated brine (1 mL) and concentrated under reduce pressure to give product. Compound A2BC5R1_2 (180 mg, 189.20 umol, 68.76% yield, 69.7% purity) was obtained as yellow oil.

To a solution of Compound A2BC5R1_2 (156 mg, 235.25 umol, 1 eq) in pyridine (2 mL) was added EDCI (67.65 mg, 352.88 umol, 1.5 eq) and L1 (70.89 mg, 235.25 umol, 1 eq). The mixture was stirred at 20° C. for 1 hr. LC-MS showed Compound A2BC5R1_2 was consumed completely and one main peak with desired m/z was detected. The mixture was filtered. The filtrate was purified by pre-HPLC (0.04% HCl) to give product. Compound A2BC5R1 (NUCC-0226145) (125 mg, 132.07 umol, 56.14% yield, 100% purity) was obtained as a yellow solid.

$^1$H NMR (ET32240-853-P1400 MHz, chloroform-d)

δ ppm 1.26 (br d, J=4.17 Hz, 3H) 1.66-2.21 (m, 10H) 2.32 (br s, 1H) 2.68-2.80 (m, 2H) 2.80-2.90 (m, 1H) 3.13 (br s, 1H) 3.44 (br s, 3H) 3.59-3.76 (m, 17H) 3.84 (br s, 2H) 4.17 (br s, 2H) 4.86-4.97 (m, 1H) 6.47 (br s, 1H) 6.89 (d, J=8.33 Hz, 1H) 7.07 (t, J=6.58 Hz, 1H) 7.15 (dd, J=8.44, 2.74 Hz, 1H) 7.31 (br d, J=9.87 Hz, 1H) 7.46 (dd, J=8.33, 7.23 Hz, 1H) 7.68-7.79 (m, 2H) 7.89 (br d, J=9.21 Hz, 1H) 8.49 (br s, 1H) 8.66 (br dd, J=9.43, 4.60 Hz, 1H) 8.90 (br d, J=9.65 Hz, 1H) 9.03 (br s, 1H) 9.57-9.75 (m, 1H)

$^{19}$F NMR (ET32240-853-P1 376 MHz, DMSO-d$_6$)

LCMS: Rt=2.208 min, 100% purity, m/z=946.3 (M+H)$^+$

A2BC1R1 (NUCC-0223793):

$^1$H NMR (400 MHz, DMSO-d$_6$) δ=11.10 (s, 1H), 10.11 (s, 1H), 8.98 (br t, J=4.2 Hz, 1H), 8.22-8.05 (m, 2H), 7.85-7.64 (m, 2H), 7.63-7.50 (m, 2H), 7.31 (d, J=8.6 Hz, 1H), 7.22-7.10 (m, 2H), 7.02 (d, J=7.0 Hz, 1H), 6.64 (br s, 1H), 5.04 (dd, J=5.3, 12.7 Hz, 1H), 4.13 (br t, J=4.4 Hz, 2H), 3.88-3.80 (m, 2H), 3.74 (t, J=5.4 Hz, 2H), 3.51 (br d, J=2.8 Hz, 3H), 2.97-2.94 (m, 1H), 2.97-2.80 (m, 1H), 2.63-2.53 (m, 2H), 2.06-1.71 (m, 7H), 1.70-1.54 (m, 3H), 1.14 (d, J=6.6 Hz, 3H)

LCMS: Rt=2.437 min, 98.4% purity, m/z=770.3 (M+H)$^+$

A2BC2R1 (NUCC-0223795):

1H NMR: (400 MHz, CHLOROFORM-d)

δ=8.87 (br s, 1H), 8.82 (t, J=4.0 Hz, 1H), 8.71 (br s, 1H), 8.22-8.12 (m, 1H), 7.88-7.75 (m, 1H), 7.63 (td, J=3.3, 10.6 Hz, 1H), 7.53-7.40 (m, 2H), 7.36-7.29 (m, 1H), 7.26-7.24 (m, 1H), 7.18 (d, J=8.6 Hz, 1H), 7.08-6.94 (m, 2H), 6.87 (dd, J=5.0, 8.5 Hz, 1H), 6.55-6.42 (m, 1H), 5.00-4.84 (m, 1H), 4.23-4.03 (m, 2H), 3.98-3.84 (m, 2H), 3.83-3.66 (m, 6H), 3.42 (quin, J=5.7 Hz, 2H), 3.29 (br s, 1H), 2.90-2.64 (m, 3H), 2.57 (td, J=6.7, 10.7 Hz, 1H), 2.16-2.04 (m, 2H), 1.99-1.60 (m, 8H), 1.26 (dd, J=5.0, 6.4 Hz, 3H)

LCMS: Rt=2.443 min, 100% purity, m/z=814.3 (M+H)$^+$

A2BC3R1 (NUCC-0226140):

$^1$H NMR (ET32240-737-P1, 400 MHz, chloroform-d)

δ ppm 1.27 (br d, J=4.77 Hz, 3H) 1.69-1.86 (m, 5H) 1.87-1.97 (m, 2H) 1.98-2.22 (m, 3H) 2.27 (br d, J=1.22 Hz, 1H) 2.75 (br s, 2H) 2.83-2.90 (m, 1H) 3.09 (br s, 1H) 3.44 (br d, J=4.77 Hz, 2H) 3.66 (br s, 5H) 3.72 (br dd, J=14.00, 4.95 Hz, 3H) 3.85 (br s, 2H) 4.17 (br s, 2H) 4.92 (br s, 1H) 6.45 (br s, 1H) 6.87 (br d, J=8.44 Hz, 1H) 7.03 (dd, J=6.97, 3.30 Hz, 1H) 7.16 (br d, J=8.56 Hz, 1H) 7.43 (t, J=7.89 Hz, 1H) 7.72 (br d, J=9.66 Hz, 2H) 7.89 (br d, J=9.78 Hz, 1H) 8.44 (br s, 1H) 8.62-8.72 (m, 1H) 8.84 (s, 1H) 8.91 (br s, 1H) 8.96 (br d, J=2.81 Hz, 1H) 9.34-9.55 (m, 1H)

$^{19}$F NMR (ET32240-737-P1, 376 MHz, chloroform-d)

LCMS: Rt=2.207 min, 100% purity, m/z=858.3 (M+H)$^+$

A2BC4R1 (NUCC-0226195):

$^1$H NMR (ET32240-924-P1, 400 MHz, methanol-d4)

δ ppm 1.26 (d, J=6.75 Hz, 3H) 1.77-1.85 (m, 2H) 1.85-2.00 (m, 4H) 2.01-2.13 (m, 4H) 2.63-2.76 (m, 2H) 2.79-2.94 (m, 2H) 3.44 (t, J=5.13 Hz, 2H) 3.59-3.73 (m, 15H) 3.79-3.94 (m, 2H) 4.11-4.20 (m, 2H) 4.94-5.06 (m, 1H) 6.99 (dd, J=18.70, 7.82 Hz, 2H) 7.09 (ddd, J=8.63, 4.13, 2.25 Hz, 1H) 7.24 (dd, J=8.63, 1.38 Hz, 1H) 7.48 (t, J=7.48 Hz, 1H) 7.54 (s, 1H) 7.97-8.03 (m, 1H) 8.11 (d, J=5.75 Hz, 1H) 8.26-8.33 (m, 2H) 9.11 (d, J=5.63 Hz, 1H)

$^{19}$F NMR (ET32240-924-P1, 376 MHz, methanol-d4)

LCMS: Rt=2.207 min, 100% purity, m/z=902.2 (M+H)$^+$

Synthetic Scheme:

Scheme 1: Synthesis of A2BC1R2~C5R2, Take A2BC1R2 as an example.

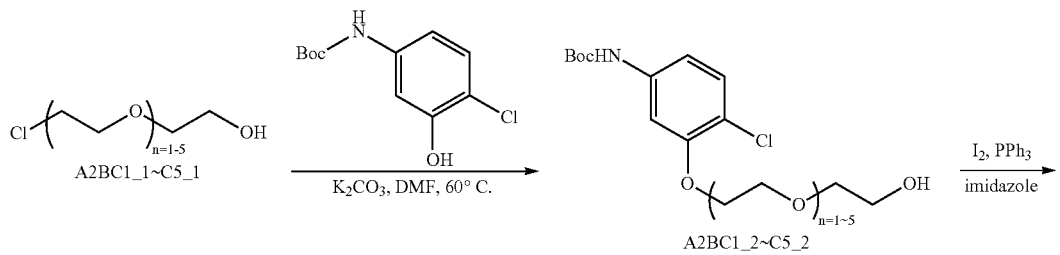

55
-continued
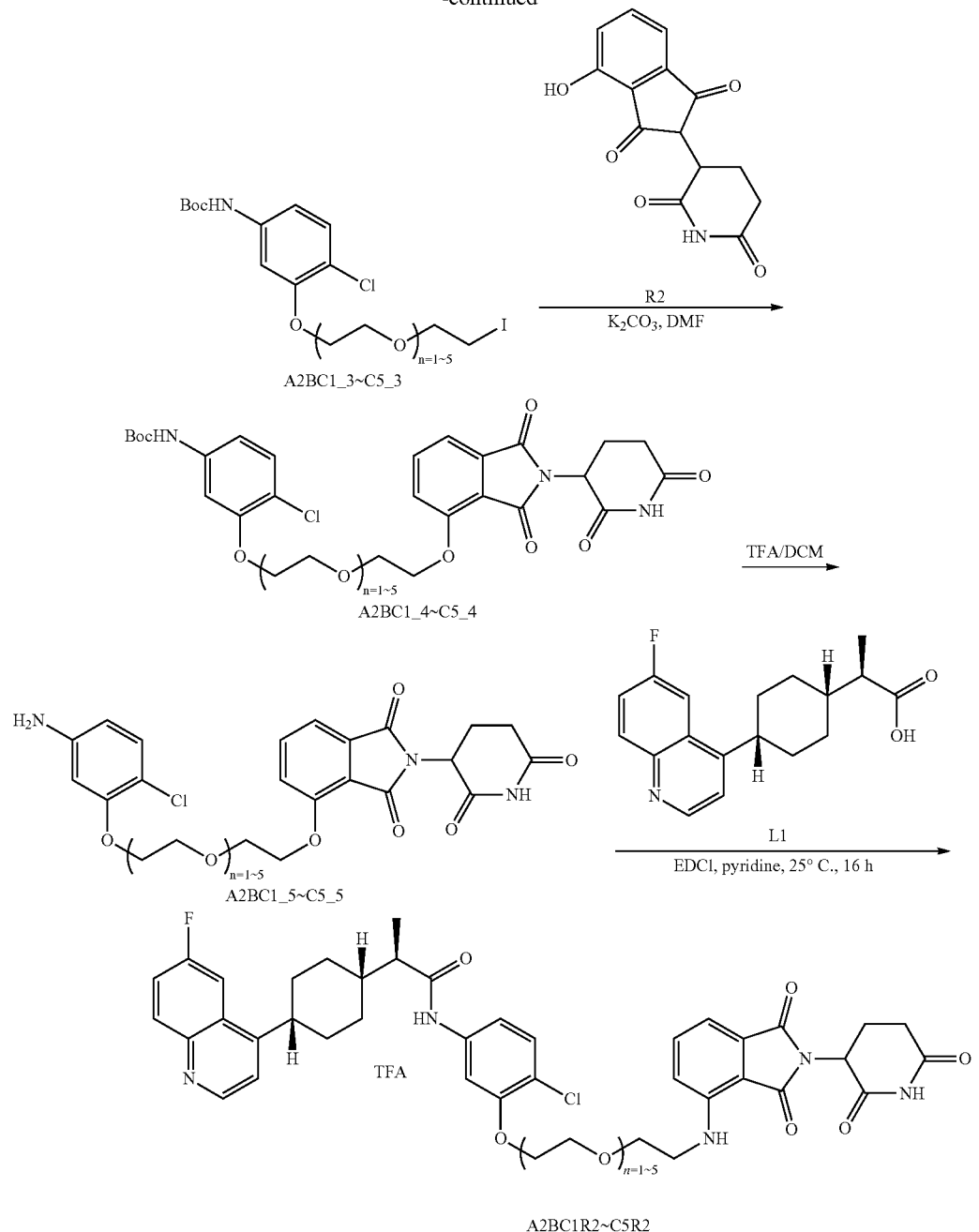
Experimental for Largest Scale Run:
General Procedure for Preparation of A2BC1-2—Notebook Page: ET32240-17
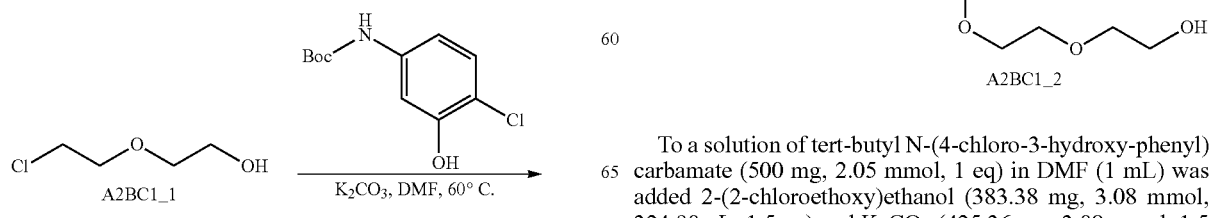
To a solution of tert-butyl N-(4-chloro-3-hydroxy-phenyl) carbamate (500 mg, 2.05 mmol, 1 eq) in DMF (1 mL) was added 2-(2-chloroethoxy)ethanol (383.38 mg, 3.08 mmol, 324.90 uL, 1.5 eq) and $K_2CO_3$ (425.36 mg, 3.08 mmol, 1.5 eq). Then the mixture was stirred at 80° C. for 2 h. LCMS showed the reaction was completed. The mixture was filtered to give the filtrate. The filtrate was purified by reversed-phase HPLC (0.1% TFA condition) to give A2BC1-2 (500 mg, 1.51 mmol, 73.45% yield) was obtained as colorless oil.

LCMS (ESI+): m/z 330.1 [M−1]⁻, Rt: 1.195 min.

General Procedure for Preparation of A2BC1-3—Notebook Page: ET32240-32

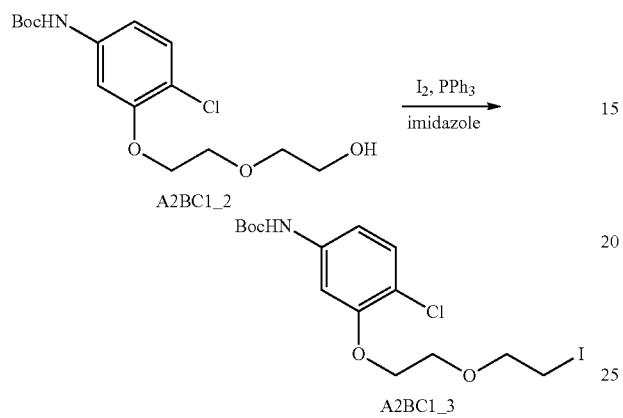

General Procedure for Preparation of A2BC1-4—Notebook Page: ET32240-4.

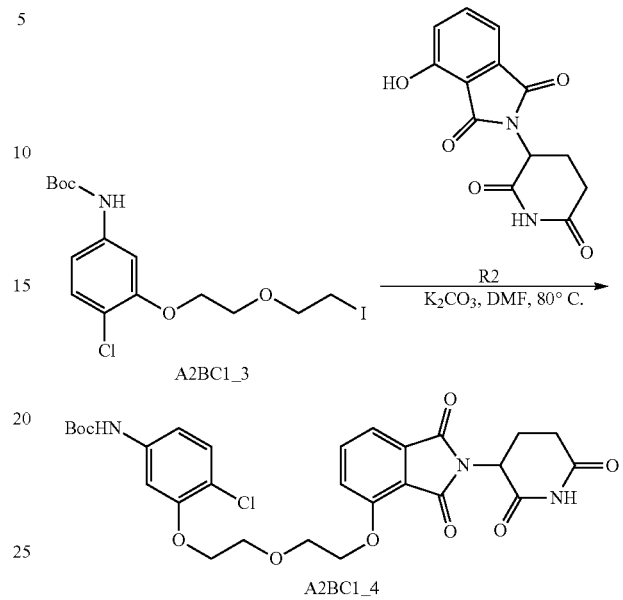

To a solution of A2BC1-2 (500 mg, 1.51 mmol, 1 eq) in DCM (3 mL) was added imidazole (133.37 mg, 1.96 mmol, 1.3 eq) and I2 (497.23 mg, 1.96 mmol, 394.63 uL, 1.3 eq) and PPh3 (513.84 mg, 1.96 mmol, 1.3 eq). Then the mixture was stirred at 25° C. for 1 h. TLC showed the reaction was completed. The residue was diluted with saturated sodium bisulfite solution 100 mL and extracted with ethyl acetate. The combined organic layers was dried over Na2SO4, filtered and concentrated under reduced pressure to give a residue. The residue was purified by column chromatography (SiO2, Petroleum ether/Ethyl acetate=1/0 to 10/1) to give A2BC2-3 (500 mg, 1.13 mmol, 75.12% yield) as a white solid.

To a solution of A2BC1-3 (490 mg, 1.11 mmol, 1.1 eq) in DMF (1 mL) was added 2-(2,6-dioxo-3-piperidyl)-4-hydroxy-isoindoline-1,3-dione (276.57 mg, 1.01 mmol, 1 eq) and K2CO3 (209.08 mg, 1.51 mmol, 1.5 eq). Then the mixture was stirred at 80° C. for 1 h. LCMS showed the reaction was completed. The mixture was filtered to give filtrate. The filtrate was purified by reversed-phase (0.1% FA condition) to give A2BC1-4 (250 mg, 425.17 umol, 42.16% yield) as a white solid LCMS (ESI+): m/z 488.1 [M−100]+, Rt: 0.833 min.

General Procedure for Preparation of A2BC1 S—Notebook Page: ET32240-68

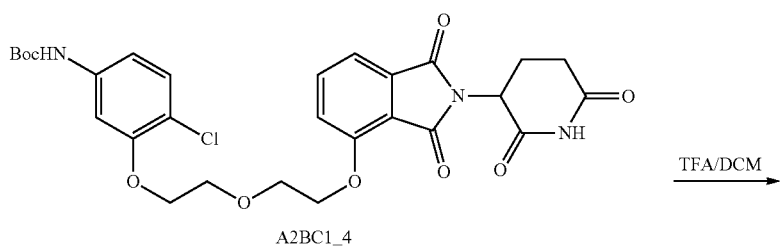

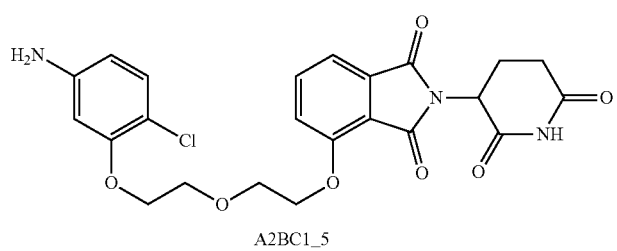

A mixture of A2BC2-4 (250 mg, 425.17 umol, 1 eq) in DCM (1 mL) and TFA (0.3 mL) was stirred at 25° C. for 1 h. LCMS showed the reaction was completed. The mixture was concentrated to give A2BC2-5 (200 mg, 409.93 umol, 96.42% yield) as a white solid.

LCMS (ESI+): m/z 488.1 [M+1]+, Rt: 1.223 min.

To a solution of (2R)-2-[4-(6-fluoro-4-quinolyl)cyclohexyl]propanoic acid (50 mg, 165.92 umol, 1 eq) in Py (1.5 mL) was added A2BC1-5 (89.04 mg, 182.51 umol, 1.1 eq) and EDCI (47.71 mg, 248.88 umol, 1.5 eq) at 25° C. Then the mixture was stirred at 25° C. for 12 h. The mixture was filtered and the filtrate was purified by pre-HPLC (TFA condition) to give A2BC1R2 (NUCC-0223616) (93.0 mg, 120.59 umol, 72.68% yield, 100% purity) as a white solid.

A2BC1R2 (NUCC-0223616):

$^1$H NMR (400 MHz, DMSO-d$_6$) δ=11.11 (s, 1H), 10.10 (s, 1H), 8.99 (br d, J=3.0 Hz, 1H), 8.21-8.07 (m, 2H), 7.78 (t, J=7.9 Hz, 2H), 7.70 (br d, J=2.9 Hz, 1H), 7.61-7.50 (m, 2H), 7.44 (d, J=7.3 Hz, 1H), 7.31 (d, J=8.6 Hz, 1H), 7.17 (dd, J=2.1, 8.7 Hz, 1H), 5.08 (dd, J=5.4, 12.8 Hz, 1H), 4.44-4.31 (m, 2H), 4.13 (br t, J=4.4 Hz, 2H), 4.01-3.85 (m, 4H), 3.48 (br t, J=9.8 Hz, 1H), 2.96-2.78 (m, 2H), 2.62-2.54 (m, 2H), 2.07-1.70 (m, 7H), 1.70-1.55 (m, 3H), 1.13 (d, J=6.6 Hz, 3H)

LCMS: Rt=2.341 min, 100% purity, m/z=771.3 (M+H)+

A2BC2R2 (NUCC-0223617):

$^1$H NMR (400 MHz, DMSO-d$_6$) δ=11.12 (s, 1H), 10.12 (s, 1H), 8.99 (br d, J=4.8 Hz, 1H), 8.24-8.06 (m, 2H), 7.85-7.74 (m, 2H), 7.70 (br d, J=4.9 Hz, 1H), 7.60 (d, J=2.0 Hz, 1H), 7.52 (d, J=8.5 Hz, 1H), 7.45 (d, J=7.3 Hz, 1H), 7.33 (d, J=8.6 Hz, 1H), 7.18 (dd, J=2.1, 8.6 Hz, 1H), 5.09 (dd, J=5.3, 12.8 Hz, 1H), 4.40-4.29 (m, 2H), 4.12 (t, J=4.6 Hz, 2H), 3.82 (td, J=4.5, 8.7 Hz, 4H), 3.73-3.61 (m, 4H), 3.56-3.44 (m, 1H), 2.98-2.80 (m, 2H), 2.63-2.56 (m, 1H), 2.06-1.72 (m, 7H), 1.71-1.57 (m, 3H), 1.15 (d, J=6.6 Hz, 3H)

LCMS: Rt=2.359 min, 99.55% purity, m/z=815.3 (M+H)+

A2BC3R2 (NUCC-0226141):

$^1$H NMR: ET32240-811-P1A1, 400 MHz, DMSO-d$_6$

δ 1.10 (d, J=6.80 Hz, 3H), 1.52-2.02 (m, 10H), 2.51-2.58 (m, 1H), 2.78-2.89 (m, 2H), 3.38-3.61 (m, 9H), 3.72-3.77 (m, 4H), 4.04-4.10 (m, 2H), 4.26-4.32 (m, 2H), 5.04 (dd, J=12.72, 5.26 Hz, 2H), 7.13 (d, J=8.92 Hz, 1H), 7.27 (d, J=8.54 Hz, 1H), 7.40 (d, J=7.19 Hz, 1H), 7.47 (d, J=8.55 Hz, 1H), 7.54 (d, J=2.41 Hz, 1H), 7.66 (d, J=4.60 Hz, 11H), 7.72-7.77 (m, 2H), 8.06-8.15 (m, 2H), 8.95 (d, J=4.82 Hz, 1H), 10.05 (s, 1H), 11.06 (s, 11H)

LCMS (ESI+): m/z 859.2 [M+1]+, Rt: 2.132 min.

A2BC4R2 (NUCC-0226196):

$^1$H NMR (ET32240-894-P1, 400 MHz, methanol-d4)

δ ppm 1.26 (d, J=6.80 Hz, 3H) 1.75-1.98 (m, 6H) 2.01-2.17 (m, 4H) 2.57-2.97 (m, 4H) 3.58-3.68 (m, 8H) 3.68-3.77 (m, 5H) 3.83-3.91 (m, 4H) 4.12-4.20 (m, 2H) 4.33 (t, J=4.38 Hz, 2H) 5.08 (dd, J=12.06, 5.48 Hz, 1H) 7.07-7.13 (m, 1H) 7.25 (dd, J=8.77, 2.19 Hz, 1H) 7.40 (t, J=8.33 Hz, 2H) 7.53 (dd, J=4.06, 2.30 Hz, 1H) 7.67-7.74 (m, 1H) 7.99-8.07 (m, 1H) 8.15 (d, J=5.92 Hz, 1H) 8.27-8.38 (m, 2H) 9.13 (d, J=5.70 Hz, 1H)

$^{19}$F NMR (ET32240-894-P1, 376 MHz, methanol-d4)

LCMS: Rt=2.142 min, 100% purity, m/z=902.2 (M+H)+

A2BC5R2 (NUCC-0226146):

$^1$H NMR (ET32240-815-P1B, 400 MHz, methanol-d4)

δ ppm 1.26 (d, J=6.75 Hz, 3H) 1.76-2.17 (m, 11H) 2.62-2.78 (m, 2H) 2.79-2.94 (m, 2H) 3.59 (br d, J=1.00 Hz, 7H) 3.61-3.66 (m, 5H) 3.72 (dt, J=5.53, 2.67 Hz, 5H) 3.82-3.91 (m, 4H) 4.17 (t, J=4.57 Hz, 2H) 4.27-4.35 (m, 2H) 5.02-5.12 (m, 1H) 7.11 (td, J=8.57, 2.25 Hz, 1H) 7.26 (dd, J=8.63, 1.75 Hz, 1H) 7.40 (dd, J=7.88, 5.00 Hz, 2H) 7.52 (d, J=2.25 Hz, 1H) 7.71 (dd, J=8.44, 7.44 Hz, 1H) 7.97-8.06 (m, 1H) 8.11 (d, J=5.63 Hz, 1H) 8.25-8.37 (m, 2H) 9.12 (d, J=5.82, 1.44 Hz, 1H)

$^{19}$F NMR (ET32240-815-P1B 376 MHz, methanol-d6)

LCMS: Rt=2.141 min, 99% purity, m/z=947.3 (M+H)+

Synthetic Scheme 1: Synthesis of A2BC1R3 as an example.

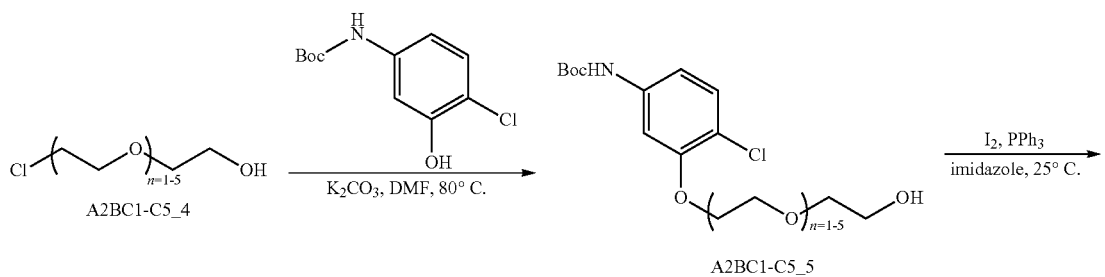

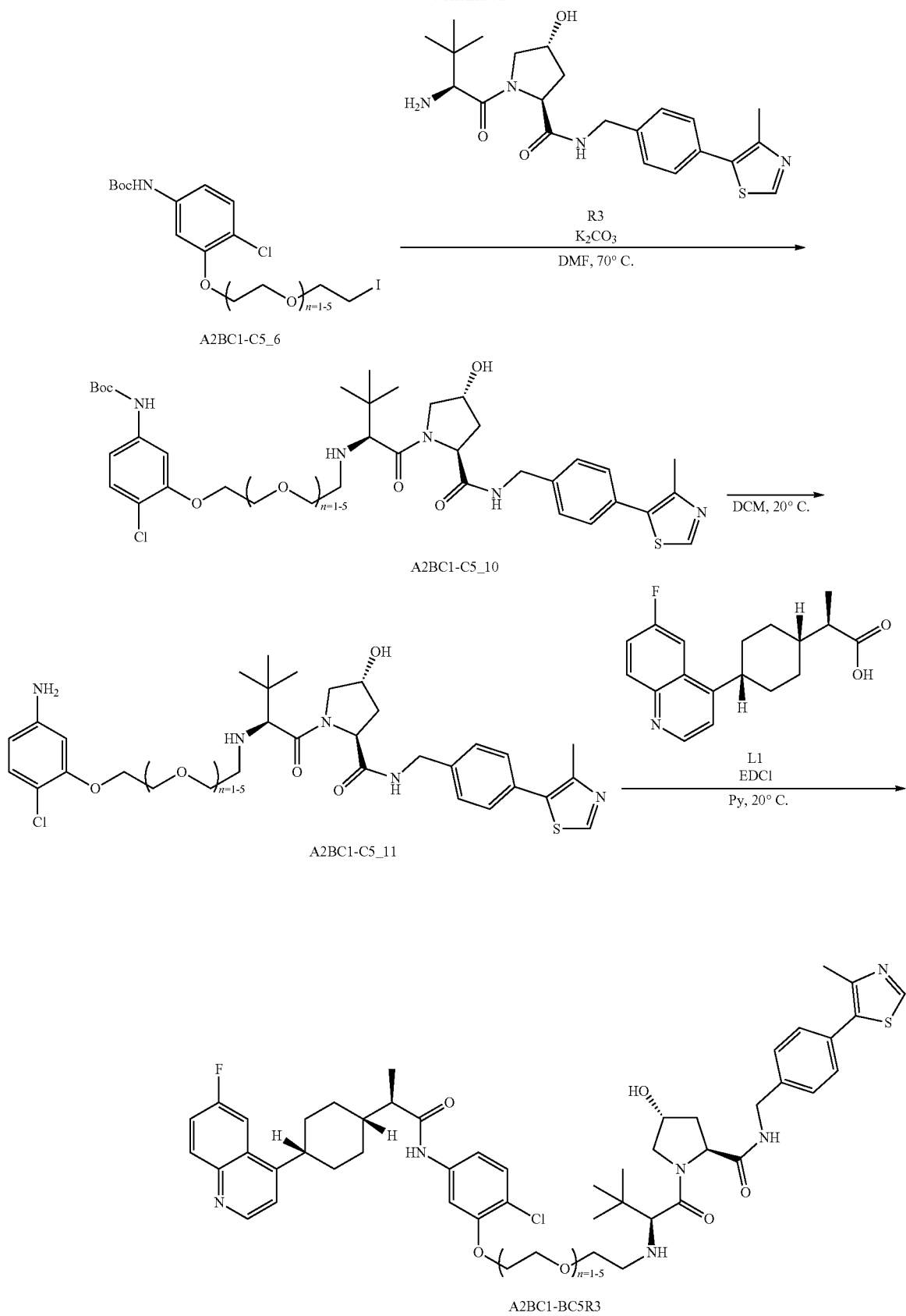

Experimental for Largest Scale Run:

Synthetic Scheme 1: Synthesis of A2BC1R3 (NUCC-0223809) as an Example.

General Procedure for Preparation of Compound A2BC1_S—Notebook Page: ET32240-389.

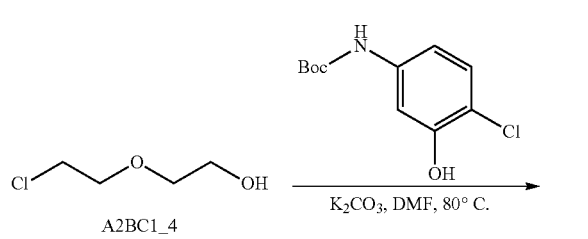

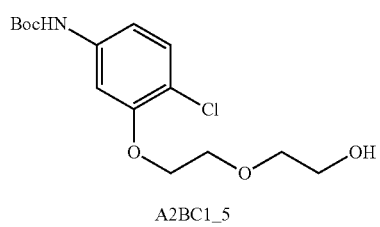

To a solution of tert-butyl N-(4-chloro-3-hydroxy-phenyl) carbamate (1 g, 4.10 mmol, 1 eq) in N,N'-dimethylformamide (5 mL) were added Compound A2BC1-4 (766.76 mg, 6.16 mmol, 649.80 uL, 1.5 eq) and $K_2CO_3$ (850.72 mg, 6.16 mmol, 1.5 eq). The mixture was stirred at 80° C. for 2 hrs. LC-MS showed 0% of Compound A2BC1-4 was remained. Several new peaks were shown on LC-MS and 89% of desired compound was detected. The mixture was filtered. The reaction mixture was diluted with water 20 mL and extracted with methyl tertiary butyl ether 30 mL (10 mL×3). The combined organic layers were washed with brine 20 mL (10 mL×2), dried over anhydrous sodium sulfate, filtered and concentrated under reduced pressure to give Compound A2BC1-5 (1.4 g, 4.00 mmol, 97.46% yield, 94.78% purity) as colorless oil.

General Procedure for Preparation of Compound A2BC1-6—Notebook Page: ET32240-420.

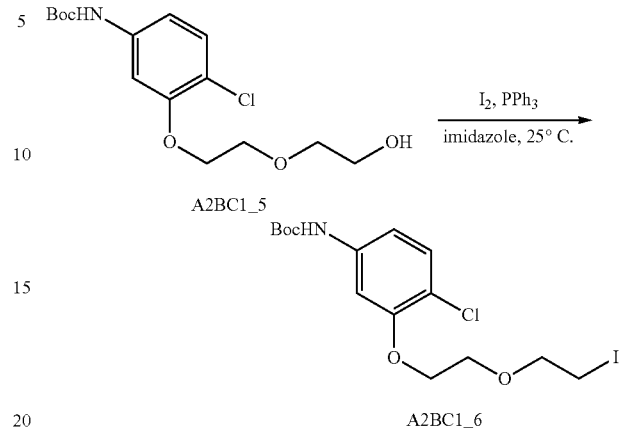

To a solution of Compound A2BC1-5 (1.4 g, 4.22 mmol, 1 eq) in DCM (9 mL) was added imidazole (373.43 mg, 5.49 mmol, 1.3 eq) and $PPh_3$ (1.44 g, 5.49 mmol, 1.3 eq) and I2(1.39 g, 5.49 mmol, 1.10 mL, 1.3 eq). Then the mixture was stirred at 25° C. for 1 hr. TLC (Petroleum ether/Ethyl acetate=3:1) indicated Compound A2BC1-5 was consumed completely and one new spot formed. The reaction was clean according to TLC. The residue was diluted with saturated sodium bisulfite solution 100 mL and extracted with ethyl acetate 90 mL (30 mL×3). The combined organic layers was dried over anhydrous sodium sulfate, filtered and concentrated under reduced pressure to give a residue. The residue was purified by column chromatography (SiO2, Petroleum ether/Ethyl acetate=1/0 to 10/1), filtered and concentrated under reduced pressure to get Compound A2BC1-6 (1.3 g, 2.93 mmol, 69.54% yield, 99.7% purity) as a white solid.

$^1$H NMR (ET32240-P1C1, 400 MHz, chloroform-d) δ ppm 1.52 (s, 9H) 3.31 (t, J=6.78 Hz, 1H) 3.28-3.33 (m, 1H) 3.87-3.95 (m, 3H) 3.87-3.95 (m, 1H) 4.20-4.24 (m, 1H) 4.20-4.24 (m, 1H) 6.49 (br s, 1H) 6.70 (dd, J=8.60, 2.45 Hz, 1H) 7.20-7.28 (m, 1H) 7.23 (d, J=8.66 Hz, 1H) 7.35 (br s, 1H)

General Procedure for Preparation of Compound A2BC1_10—Notebook Page: ET32240-457.

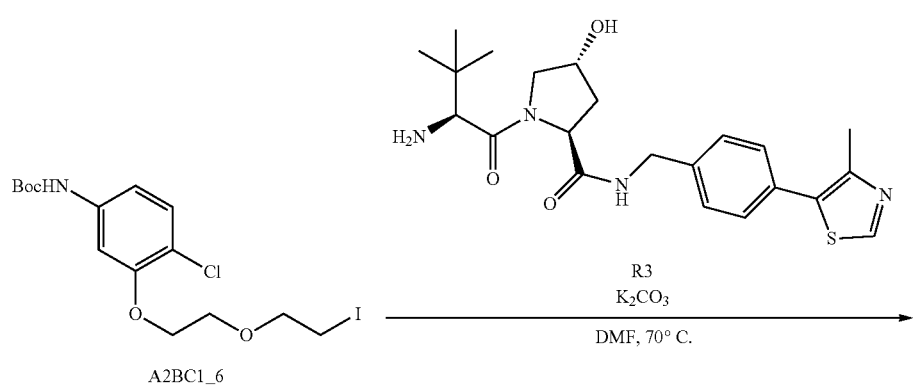

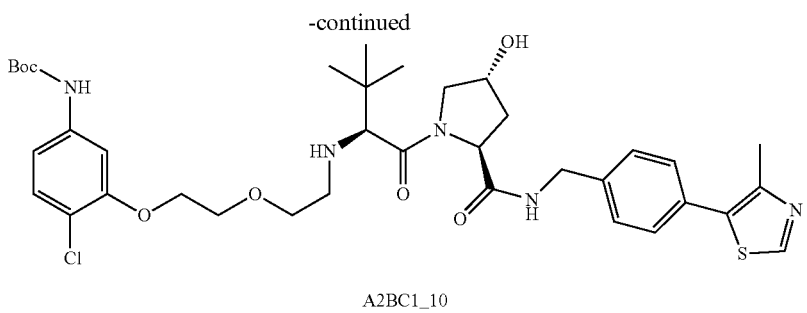

A2BC1_10

To a solution of Compound A2BC1-6 (512.92 mg, 1.16 mmol, 2 eq) in N,N'-dimethylformamide (2 mL) were added K$_2$CO$_3$ (160.50 mg, 1.16 mmol, 2 eq) and R3 (250 mg, 580.64 umol, 1 eq). The mixture was stirred at 70° C. for 12 hrs. LC-MS showed 38.7% of R3 was remained. Several new peaks were shown on LC-MS and 27.0% of desired compound was detected. The reaction mixture was quenched by water 10 mL, and then extracted with ethyl acetate 40 mL (20 mL×2). The combined organic layers were washed with brine 10 mL, dried over anhydrous sodium sulfate, filtered and concentrated under reduced pressure to give a residue. The residue was purified by prep-TLC (Dichloromethane:Methanol=10:1) to get Compound A2BC1-10 (103 mg, 127.72 umol, 22.00% yield, 92.3% purity) as a colorless oil.

General Procedure for Preparation of Compound A2BC1_11—Notebook Page: ET32240-516.

mg, 193.44 umol, 1.5 eq). The mixture was stirred at 20° C. for 15 mins. A solution of L1 (38.86 mg, 128.96 umol, 1 eq) in Py (0.5 mL) was added to above mixture dropwise at 20° C. Then the mixture was stirred at 20° C. for 12 hrs. The residue was purified by prep-HPLC and then lyophilized to afford A2BC1R3 (NUCC-0223809) (48 mg, 51.75 umol, 40.13% yield, 100% purity) as a white solid.

$^1$H NMR (ET32240-535-P1A 400 MHz, DMSO-d$_6$)

δ ppm 1.03-1.07 (m, 9H) 1.12 (d, J=6.65 Hz, 3H) 1.56-1.80 (m, 6H) 1.80-1.99 (m, 3H) 1.80-1.99 (m, 1H) 2.09-2.24 (m, 2H) 2.43 (s, 3H) 2.99 (br s, 1H) 3.10 (br dd, J=10.67, 6.78 Hz, 2H) 3.42 (dd, J=11.04, 3.26 Hz, 1H) 3.59 (br d, J=11.42 Hz, 1H) 3.74-3.91 (m, 5H) 4.12-4.26 (m, 4H) 4.29 (br s, 1H) 4.43 (dd, J=15.69, 6.53 Hz, 1H) 4.60 (br t, J=8.53 Hz, 1 H) 7.25-7.35 (m, 2H) 7.38 (s, 2H) 7.37-7.39 (m, 1H) 7.37-7.39 (m, 1 H) 7.79 (d, J=2.01 Hz, 1H) 7.95-8.02 (m, 1H) 8.22 (br d, J=5.15 Hz, 1H) 8.34 (br d, J=8.41 Hz, 1H)

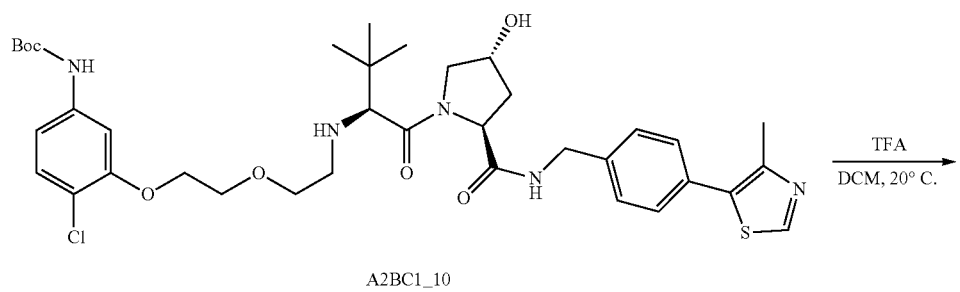

A2BC1_10

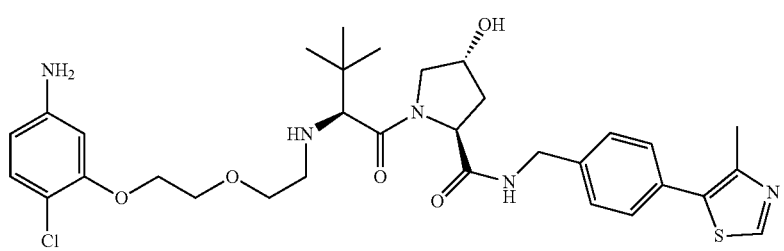

A2BC1_11

To a solution of Compound A2BC1-10 (103 mg, 138.38 umol, 1 eq) in DCM (2 mL) was added TFA (1.54 g, 13.51 mmol, 1 mL, 97.61 eq). The mixture was stirred at 20° C. for 0.5 hr. The reaction mixture was concentrated under reduced pressure to give Compound A2BC1-11 (108 mg, crude) as light yellow oil.

A mixture of Compound A2BC1-11 (108 mg, 167.64 umol, 1.3 eq) in Py (0.5 mL), then was added EDCI (37.08

8.40 (dd, J=9.29, 5.40 Hz, 1 H) 8.48 (br s, 1H) 8.77 (br t, J=5.96 Hz, 2H) 9.00 (s, 1H) 9.17 (d, J=5.40 Hz, 1H) 10.67 (s, 1H)

$^{19}$F NMR (ET32240-535-P1A 400 MHz, DMSO-d$_6$)

LCMS: Rt=2.186 min, 100% purity, m/z=927.4 (M+H)$^+$

A2BC2R3 (NUCC-0223810):

$^1$H NMR (ET32240-536-P1P3 400 MHz, chloroform-d)

δ ppm 0.85 (s, 9H) 1.30 (d, J=6.78 Hz, 4H) 1.56-2.17 (m, 20H) 2.55-2.77 (m, 4H) 3.87-3.96 (m, 2H) 4.03 (br d, J=12.17 Hz, 1H) 4.23 (t, J=4.71 Hz, 2H) 4.33 (dd, J=14.81, 5.02 Hz, 1H) 4.45 (br s, 1H) 4.56 (dd, J=14.87, 6.46 Hz, 1H) 4.87 (s, 1H) 6.83 (br d, J=8.66 Hz, 1H) 7.34 (s, 2H) 7.35-7.36 (m, 2H) 7.37 (s, 1H) 7.40-7.52 (m, 1H) 7.59-7.67 (m, 1H) 7.64 (d, J=2.26 Hz, 1H) 7.78 (br s, 1H) 8.12 (s, 1H) 8.68 (s, 1H) 8.83 (d, J=4.64 Hz, 1H)

$^{19}$F NMR (ET32240-536-P1P3 400 MHz, chloroform-d)

LCMS: Rt=2.206 min, 99.5% purity, m/z=971.4 (M+H)[+]

A2BC3R3 (NUCC-0226142):

$^1$H NMR (ET32240-744-P1, 400 MHz, chloroform-d)

δ ppm 0.80 (br s, 1H) 1.28 (br s, 12H) 1.56-2.86 (m, 20H) 3.38 (br d, J=1.96 Hz, 3H) 3.52-3.80 (m, 10H) 3.88 (br s, 3H) 4.10 (br d, J=10.27 Hz, 1H) 4.15-4.40 (m, 4H) 4.49-4.62 (m, 1H) 4.73-4.92 (m, 1H) 7.02 (br d, J=2.81 Hz, 2H) 7.24 (br d, J=8.44 Hz, 1H) 7.32 (br d, J=5.87 Hz, 2H) 7.76 (br d, J=7.82 Hz, 1H) 7.85-8.01 (m, 1H) 8.70-8.82 (m, 1H) 8.83-8.99 (m, 1H) 9.26 (br s, 1H) 9.31-9.53 (m, 1H) 10.46 (br s, 1H)

$^{19}$F NMR (ET32240-744-P1, 376 MHz, chloroform-d)

LCMS: Rt=1.987 min, 100% purity, m/z=1015.4 (M+H)[+]

A2BC4R3 (NUCC-0226197):

$^1$H NMR (ET32240-895-P1, 400 MHz, methanol-d4)

δ ppm 1.17 (s, 9H) 1.26 (d, J=6.58 Hz, 3H) 1.76-1.99 (m, 6H) 2.09 (ddd, J=13.21, 9.59, 3.95 Hz, 3H) 2.16-2.26 (m, 1H) 2.32 (dd, J=13.15, 7.67 Hz, 1H) 2.59 (s, 3H) 3.03-3.21 (m, 2H) 3.28 (dd, J=6.36, 3.73 Hz, 1H) 3.61-3.83 (m, 16H) 3.86-3.98 (m, 3H) 4.14-4.21 (m, 2H) 4.30-4.44 (m, 2H) 4.51-4.62 (m, 2H) 4.71 (dd, J=9.43, 7.89 Hz, 1H) 7.15-7.28 (m, 2H) 7.47-7.59 (m, 4H) 7.64 (d, J=2.19 Hz, 1H) 7.99-8.08 (m, 1H) 8.31-8.39 (m, 3H) 9.16 (d, J=5.70 Hz, 1H) 9.96 (s, 1H)

$^{19}$F NMR (ET32240-895-P1, 376 MHz, methanol-d4)

LCMS: Rt=2.019 min, 100% purity, m/z=1059.4 (M+H)[+]

A2BC5R3 (NUCC-0226147):

1H NMR (ET32240-801-P1, 400 MHz, chloroform-d)

δ ppm 1.24-1.30 (m, 12H) 1.57-2.09 (m, 8H) 2.10-2.23 (m, 3H) 2.55 (br s, 7H) 3.24-3.99 (m, 24H) 4.08-4.41 (m, 5H) 4.63 (br s, 1H) 4.82 (br d, J=10.58 Hz, 1H) 5.30 (br s, 1H) 7.12 (br s, 1H) 7.22 (br d, J=7.72 Hz, 1H) 7.45 (br s, 2H) 7.54 (br d, J=10.80 Hz, 1H) 7.77 (br s, 2H) 7.94 (br d, J=7.94 Hz, 1H) 8.73 (br s, 1H) 8.91 (br s, 1H) 9.30 (br s, 2H) 10.00 (br s, 1H) 10.45 (br s, 1H)

$^{19}$F NMR (ET32240-801-P1, 376 MHz, chloroform-d)

LCMS: Rt=2.014 min, 99% purity, m/z=1103.4 (M+H)[+]

Synthetic Scheme:

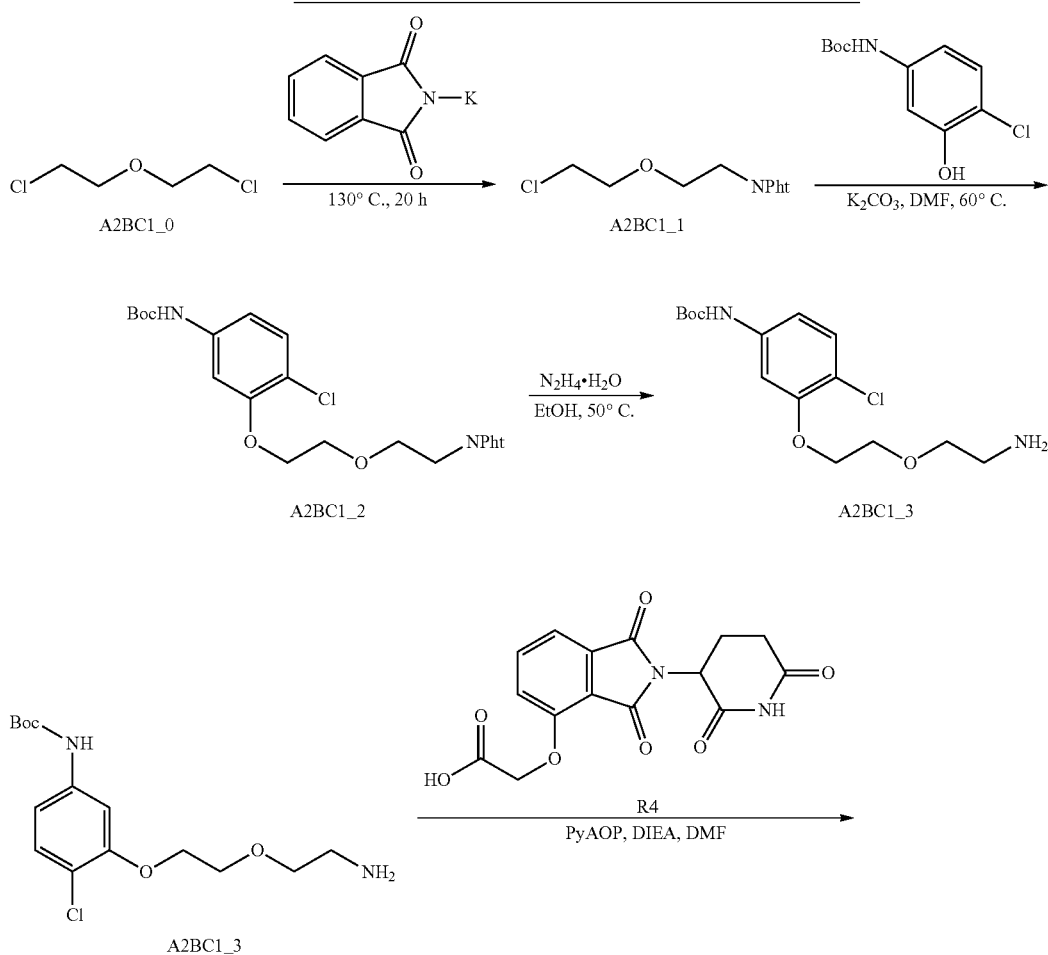

Scheme 1: Synthesis of A2BC1R4-C5R4. Take A2BC1R4 as an example.

-continued
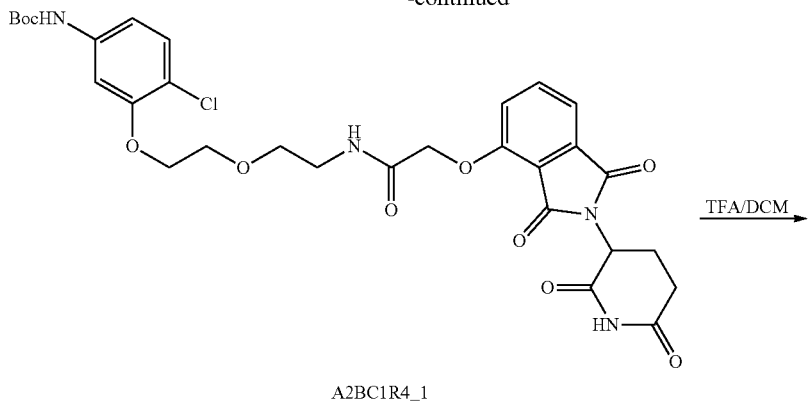
A2BC1R4_1
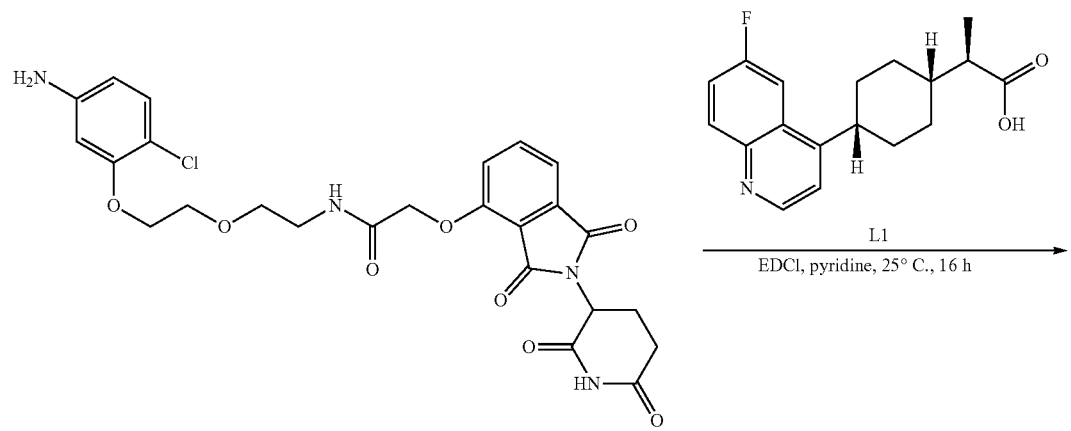
A2BC1R4_2
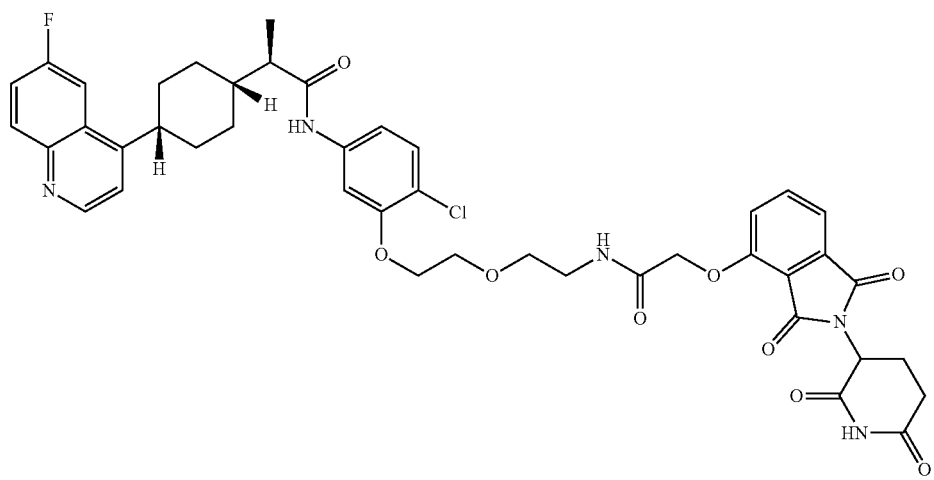
A2BC1R4

Experimental for Largest Scale Run:

General Procedure for Preparation of A2BC1-1—Notebook Page: ET32240-31

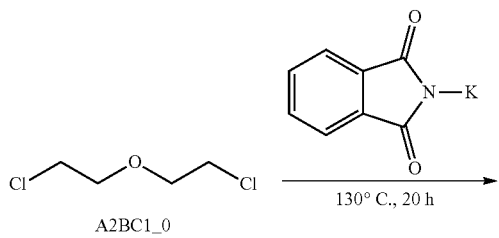

A mixture of (1,3-dioxoisoindolin-2-yl) potassium (3.5 g, 18.90 mmol, 1 eq) and A2BC1-0 (25 g, 174.81 mmol, 20.49 mL, 9.25 eq) was stirred at 130° C. for 20 h. TLC indicated (1,3-dioxoisoindolin-2-yl)potassium was consumed completely and a new spot was found. Then the reaction mixture was concentrated to give the crude product. The crude product was purified by column chromatography (SiO$_2$, Petroleum ether/Ethyl acetate=50/1 to 3/1) to give A2BC1-1 (3.0 g, 11.83 mmol, 62.76% yield) as a white solid.

$^1$H NMR (400 MHz, CHLOROFORM-d)

δ=7.90-7.84 (m, 2H), 7.78-7.70 (m, 2H), 3.94-3.90 (m, 2H), 3.80-3.72 (m, 4H), 3.60-3.55 (m, 2H).

General Procedure for Preparation of A2BC1-2—Notebook Page: ET32240-82

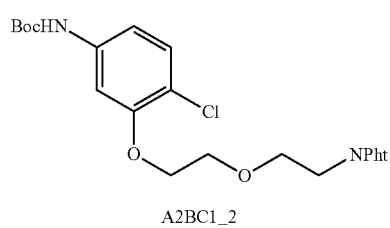

A mixture of tert-butyl N-(4-chloro-3-hydroxy-phenyl) carbamate (2.88 g, 11.83 mmol, 1 eq), A2BC1-1 (3.0 g, 11.83 mmol, 1 eq) and K$_2$CO$_3$ (3.27 g, 23.65 mmol, 2.0 eq) in DMF (30 mL) was stirred at 80° C. for 12 h. LCMS showed one major peak with desired MS. The reaction mixture was filtered, the filtrate was purified by reversed-phase column (eluting with 0%-60% of acetonitrile/water) to give A2BC1-2 (2 g, 4.34 mmol, 36.69% yield) as a white solid.

$^1$H NMR (400 MHz, CHLOROFORM-d)

δ=7.89-7.83 (m, 2H), 7.73-7.69 (m, 2H), 7.21-7.12 (m, 2H), 7.02-6.94 (m, 2H), 4.19-4.14 (m, 2H), 3.98-3.92 (m, 2H), 3.87-3.82 (m, 4H), 1.54 (s, 9H).

General Procedure for Preparation of A2BC1-3—Notebook Page: ET32240-118

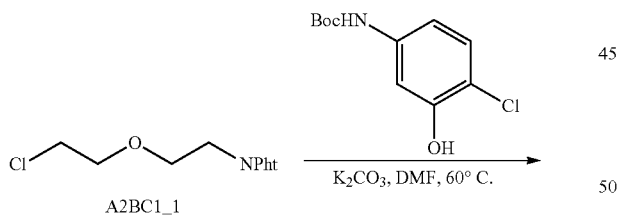

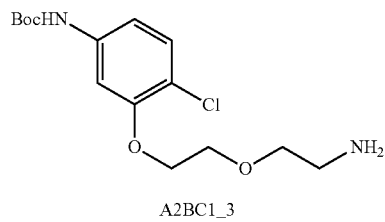

A mixture of A2BC1-2 (2 g, 4.34 mmol, 1 eq) and N$_2$H$_4$·H$_2$O (664.97 mg, 13.02 mmol, 645.61 uL, 98% purity, 3 eq) in EtOH (30 mL) was stirred at 50° C. for 12 h. LCMS showed a major peak with desired MS. Then the reaction mixture was filtered, and the filtrate was concentrated to give the crude product, which was purified by flash SNAP C18 (Eluent with water:acetonitrile gradient from 100-0% @100 mL/min) to give A2BC1-3 (0.7 g, 2.12 mmol, 48.76% yield) as a yellow oil.

$^1$H NMR (400 MHz, CHLOROFORM-d)

δ=7.37 (br s, 1H), 7.22 (d, J=8.6 Hz, 1H), 6.74-6.65 (m, 1H), 6.57 (br s, 1H), 4.30-4.13 (m, 2H), 3.96-3.82 (m, 2H), 3.62 (t, J=5.1 Hz, 2H), 2.89 (br t, J=4.5 Hz, 2H), 1.52 (s, 9H).

General Procedure for Preparation of A2BC1R4_1—Notebook Page: ET32240-224

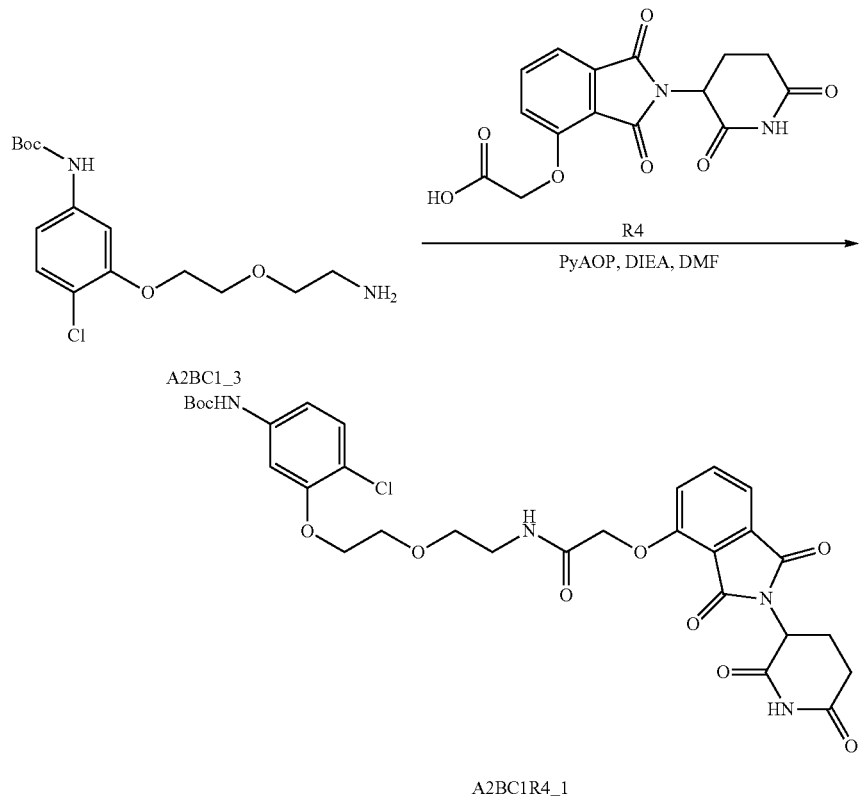

A2BC1R4_1

A mixture of $R^4$ (200 mg, 601.93 umol, 1 eq), A2BC1-3 (219.03 mg, 662.12 umol, 1.1 eq), PyAOP (470.75 mg, 902.90 umol, 1.5 eq) and DIEA (233.39 mg, 1.81 mmol, 314.54 uL, 3 eq) in DMF (3 mL) was stirred at 20° C. for 12 h. TLC showed a new spot. Then the reaction mixture was poured into ice water, stirred for 30 min, many solid was precipitated, the precipitate was collected by filtration, washed with water, dried over in vacuum to give A2BC1R4_1 (150 mg, 232.54 umol, 38.63% yield) as a white solid.

$^1$H NMR (400 MHz, DMSO-$d_6$)

δ=9.85-9.84 (m, 1H), 9.43 (br s, 1H), 9.49-9.39 (m, 1H), 8.04 (br t, J=5.5 Hz, 1H), 7.83-7.74 (m, 1H), 7.47 (d, J=7.2 Hz, 1H), 7.37 (br d, J=8.5 Hz, 1H), 7.22 (d, J=8.7 Hz, 1H), 6.96 (br d, J=7.8 Hz, 1H), 5.16-5.05 (m, 1H), 5.10 (br dd, J=5.5, 13.0 Hz, 1H), 4.77 (s, 1H), 4.14-4.02 (m, 1H), 4.07 (br d, J=3.8 Hz, 1H), 3.85-3.72 (m, 2H), 3.58 (br t, J=5.5 Hz, 1H), 3.54-3.53 (m, 1H), 3.01 (br d, J=3.9 Hz, 1H), 2.89-2.80 (m, 1H), 2.09-1.98 (m, 1H), 1.89 (br s, 1H), 1.73 (br t, J=6.3 Hz, 1H), 1.49-1.42 (m, 1H), 1.46 (s, 7H), 1.55-1.37 (m, 1H).

General Procedure for Preparation of A2BC1R4_2—Notebook Page: ET32240-264

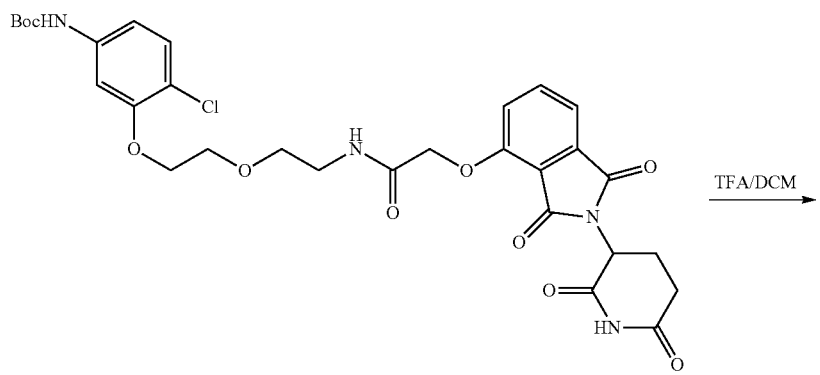

A2BC1R4_1

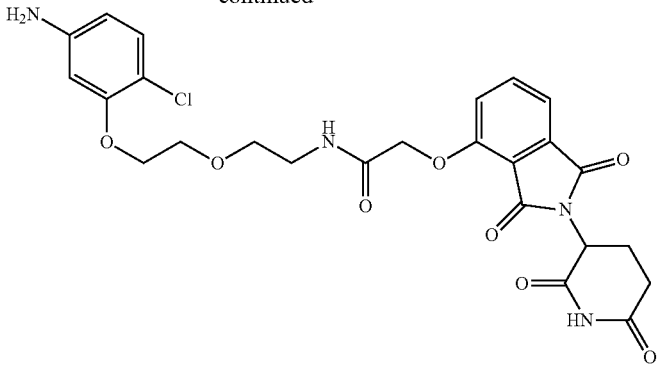

A2BC1R4_2

A mixture of A2BC1R4_1 (150 mg, 232.54 umol, 1 eq) in TFA (825.00 mg, 7.24 mmol, 535.71 uL, 31.11 eq) and DCM (5 mL) was stirred at 20° C. for 2 h. TLC showed the reaction was completed. The mixture was concentrated to give A2BC1R4_2 (70 mg, 128.45 umol, 55.24% yield) as a brown solid.

A mixture of L1 (25.52 mg, 84.70 umol, 1 eq), EDCI (24.35 mg, 127.04 umol, 1.5 eq) in Py (1 mL) was added A2BC1R4_2 (60 mg, 110.10 umol, 1.3 eq). The mixture was stirred at 20° C. for 16 h. LCMS showed the reaction was completed. The residue was purified by prep-HPLC to give A2BC1R4 (NUCC-0223794) (29 mg, 34.66 umol, 40.93% yield, 99.0% purity) as a white solid. $^1$H NMR (400 MHz, DMSO-$d_6$) δ=11.12 (s, 1H), 10.09 (s, 1H), 8.86 (d, J=4.6 Hz, 1H), 8.13-8.03 (m, 2H), 7.98 (dd, J=2.6, 11.0 Hz, 1H), 7.82-7.74 (m, 1H), 7.67 (dt, J=2.8, 8.7 Hz, 1H), 7.61 (s, 1H), 7.55 (d, J=4.6 Hz, 1H), 7.47 (d, J=7.3 Hz, 1H), 7.37 (d, J=8.6 Hz, 1H), 7.29 (dd, J=2.6, 8.6 Hz, 1H), 7.13 (td, J=2.1, 8.6 Hz, 1H), 5.10 (dd, J=5.3, 12.9 Hz, 1H), 4.78 (s, 2H), 4.12 (br t, J=4.4 Hz, 2H), 3.79 (br t, J=4.4 Hz, 2H), 3.58 (t, J=5.6 Hz, 2H), 3.46-3.38 (m, 1H), 2.95-2.77 (m, 2H), 2.63-2.53 (m, 2H), 2.07-1.98 (m, 11H), 1.96-1.70 (m, 6H), 1.68-1.52 (m, 3H), 1.13 (d, J=6.6 Hz, 3H)

A2BC3R4 (NUCC-0226143):
$^1$H NMR (ET32240-745-P1, 400 MHz, chloroform-d)
δ ppm 1.28 (br s, 3H) 1.62-2.35 (m, 12H) 2.68-2.91 (m, 3H) 3.08 (br s, 1H) 3.41 (br s, 1H) 3.55 (br s, 2H) 3.59-3.70 (m, 7H) 3.74 (br s, 2H) 3.87 (br s, 2H) 4.18 (br s, 2H) 4.64 (br s, 2H) 4.90-5.08 (m, 1H) 7.18 (br d, J=8.19 Hz, 2H) 7.33 (br d, J=18.46 Hz, 1H) 7.48-7.60 (m, 1H) 7.60-7.77 (m, 3H) 7.87 (br s, 1H) 8.36 (br s, 1H) 8.64 (br s, 1H) 9.00 (br d, J=14.06 Hz, 1H) 9.29 (br d, J=10.27 Hz, 1H) 9.36-9.54 (m, 1H)

$^{19}$F NMR (ET32240-745-P1, 376 MHz, chloroform-d)
LCMS: Rt=2.067 min, 100% purity, m/z=916.3 (M+H)$^+$ A2BC4R4 (NUCC-0226198):
$^1$H NMR (ET32240-935-P1, 400 MHz, methanol-d4)
δ ppm 1.24 (d, J=6.50 Hz, 3H) 1.77-1.97 (m, 6H) 1.98-2.17 (m, 4H) 2.64-2.79 (m, 2H) 2.80-3.03 (m, 2H) 3.39-3.65 (m, 14H) 3.66-3.74 (m, 3H) 3.84 (br t, J=4.13 Hz, 2H) 4.13 (br s, 2H) 4.73 (s, 2H) 4.99-5.19 (m, 1H) 7.09-7.23 (m, 2H) 7.37 (d, J=8.38 Hz, 1H) 7.45 (d, J=7.25 Hz, 1H) 7.52 (d, J=1.75 Hz, 1H) 7.75 (t, J=7.88 Hz, 1H) 8.02 (t, J=8.66 Hz, 1H) 8.24 (br d, J=5.75 Hz, 1H) 8.32 (dt, J=9.16, 4.49 Hz, 2H) 9.15 (d, J=5.84 Hz, 1H)

$^{19}$F NMR (ET32240-935-P1, 376 MHz, methanol-d4)
LCMS: Rt=2.088 min, 100% purity, m/z=960.2 (M+H)$^+$ A2BC5R4 (NUCC-0226148):
$^1$H NMR (ET32240-854-P1, 400 MHz, chloroform-d)
δ ppm 1.26 (br s, 3H) 1.67 (br s, 6H) 1.82 (br s, 3H) 1.92 (br s, 2H) 2.15 (br d, J=3.95 Hz, 2H) 2.30 (br s, 1H) 2.77 (br d, J=10.08 Hz, 2H) 3.10 (br s, 1H) 3.39-3.49 (m, 1H) 3.56 (br s, 2H) 3.60-3.68 (m, 13H) 3.73 (br d, J=4.17 Hz, 2H) 3.85 (br s, 2H) 4.18 (br s, 1H) 4.67 (s, 1H) 4.97 (br s, 1H) 7.16-7.23 (m, 2H) 7.33 (br s, 1H) 7.53 (d, J=6.92 Hz, 1H) 7.62-7.79 (m, 3H) 7.89-7.93 (m, 1H) 8.47 (br s, 1H) 8.73 (dd, J=8.99, 5.04 Hz, 1H) 8.98 (br s, 1H) 9.17 (br s, 1H) 9.53 (br s, 1H)

$^{19}$F NMR (ET32240-854-P1 376 MHz, DMSO-$d_6$)
LCMS: Rt=2.090 min, 100% purity, m/z=1004.2 (M+H)$^+$ Synthetic Scheme 2: Synthesis of A2BC1R5 as an example.

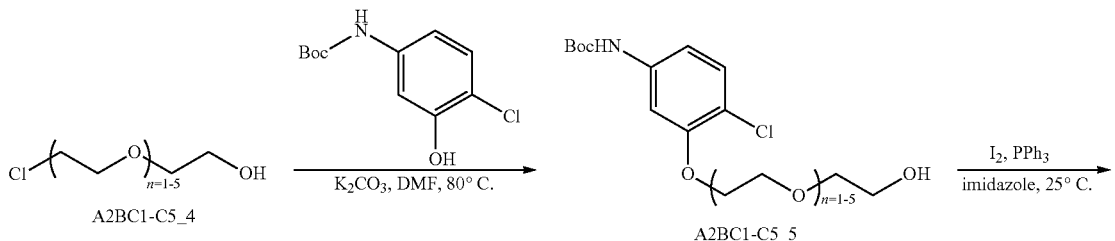

-continued
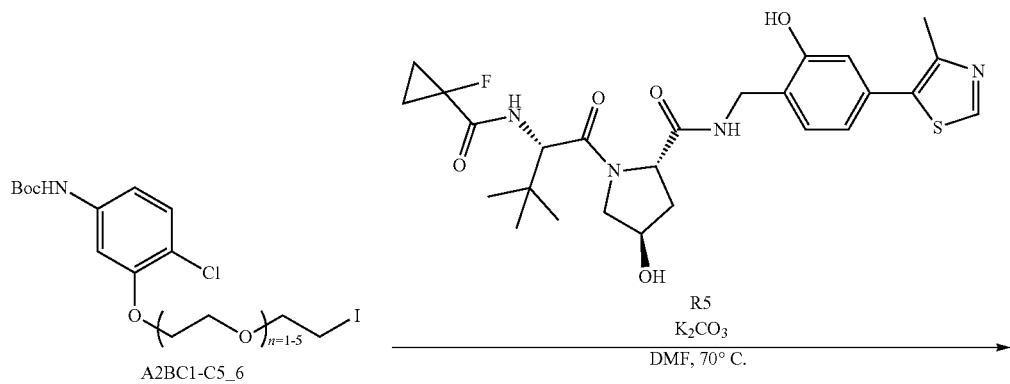
R5
K$_2$CO$_3$
DMF, 70° C.
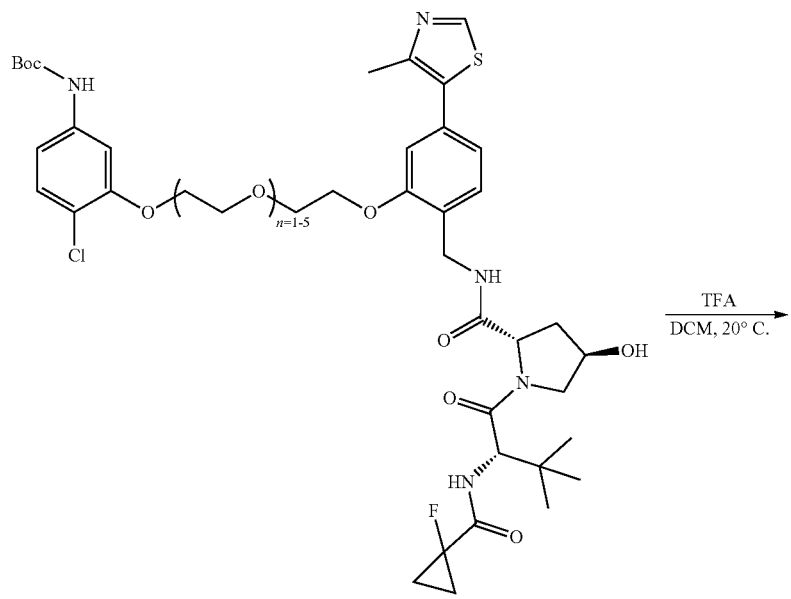
A2BC1-C5_7
TFA
DCM, 20° C.
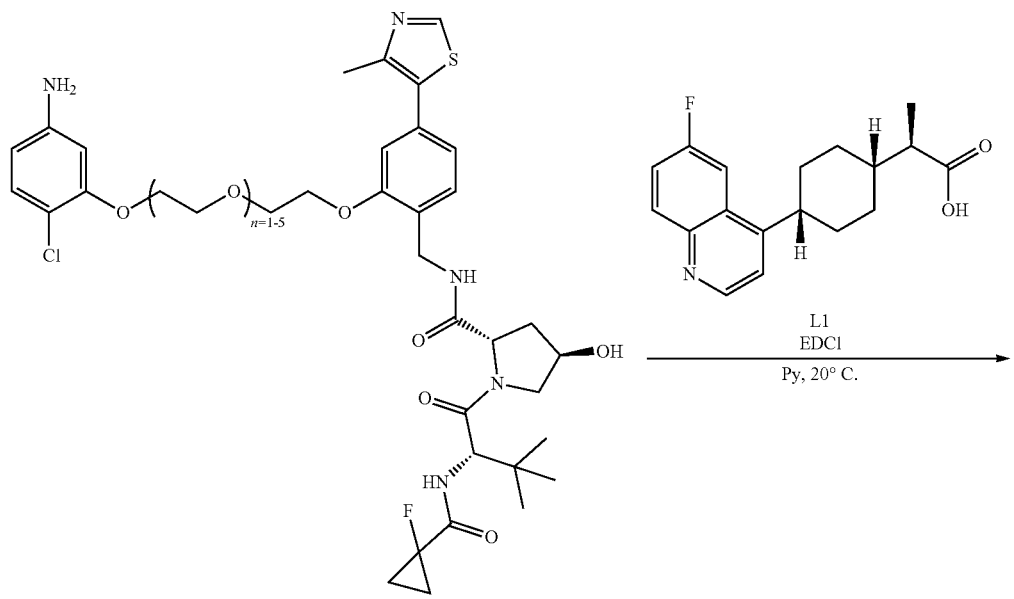
A2BC1-C5_8
L1
EDCl
Py, 20° C.

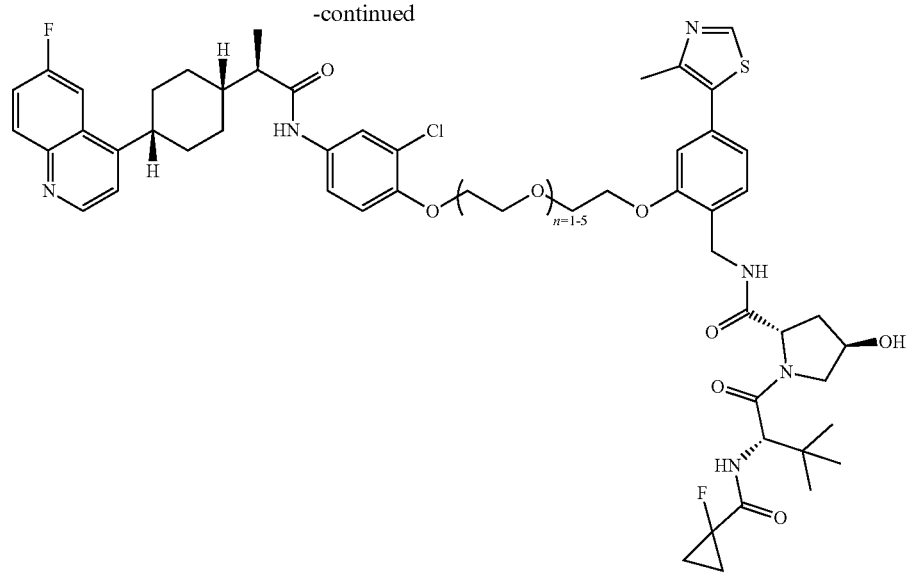
A2BC1R5~C5R5
Synthetic Scheme 2: Synthesis of A2BC1R5 (NUCC-0223811) as an Example.
General Procedure for Preparation of Compound A2BC1-7—Notebook Page: ET32240-458.
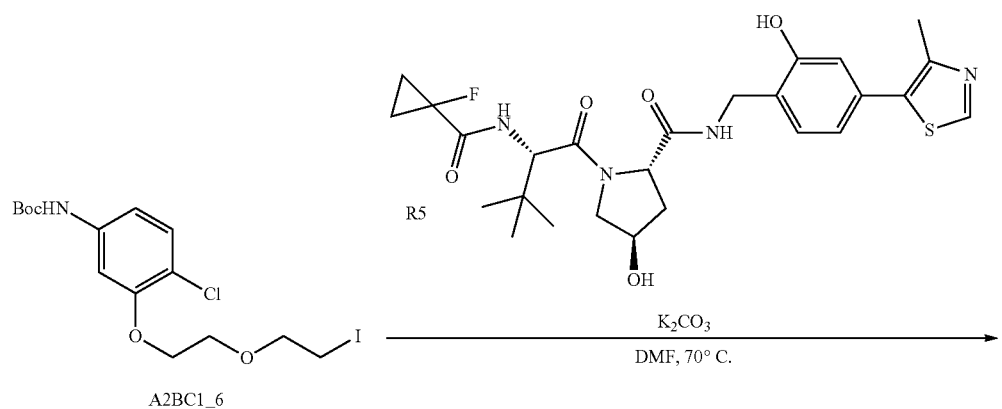

-continued

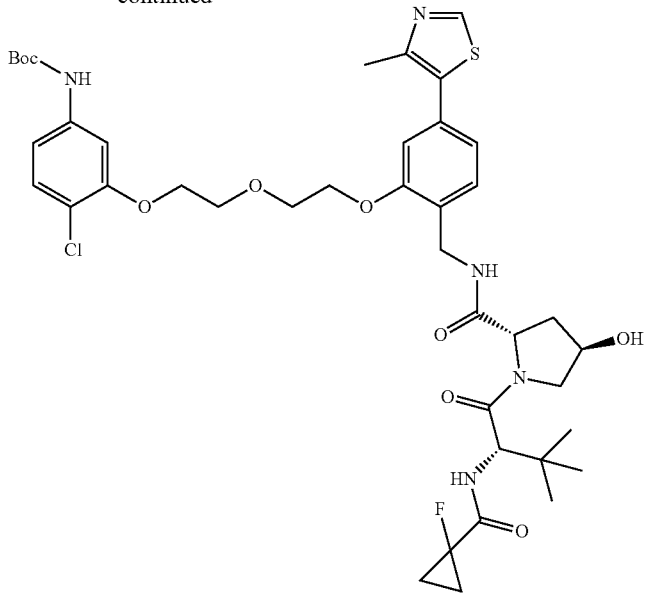

A2BC1_7

To a solution of R5 (100 mg, 187.75 umol, 1 eq) in N,N'-dimethylformamide (2 mL) was added K$_2$CO$_3$ (51.90 mg, 375.50 umol, 2 eq). The mixture was stirred at 20° C. for 10 mins under N$_2$ protection. Then a solution of Compound A2BC1-6 (165.85 mg, 375.50 umol, 2 eq) in N,N'-dimethylformamide (2 mL) was added under N$_2$ protection. The mixture was stirred for 15 hrs at 70° C. under N$_2$ protection. LCMS showed the R5 was consumed and desired product was detected. The mixture was quenched with water (20 mL) and extracted with ethyl acetate (3×50) mL, dried over anhydrous sodium sulfate, filtered and the filtrate was concentrated by reduce pressure to get a crude. The crude was purified by Prep-TLC (Dichloromethane: Methanol=10:1) to give Compound A2BC1-7 (100 mg, 100.43 umol, 53.49% yield, 85% purity) as light yellow oil.

General Procedure for Preparation of Compound A2BC1-8—Notebook Page: ET32240-520.

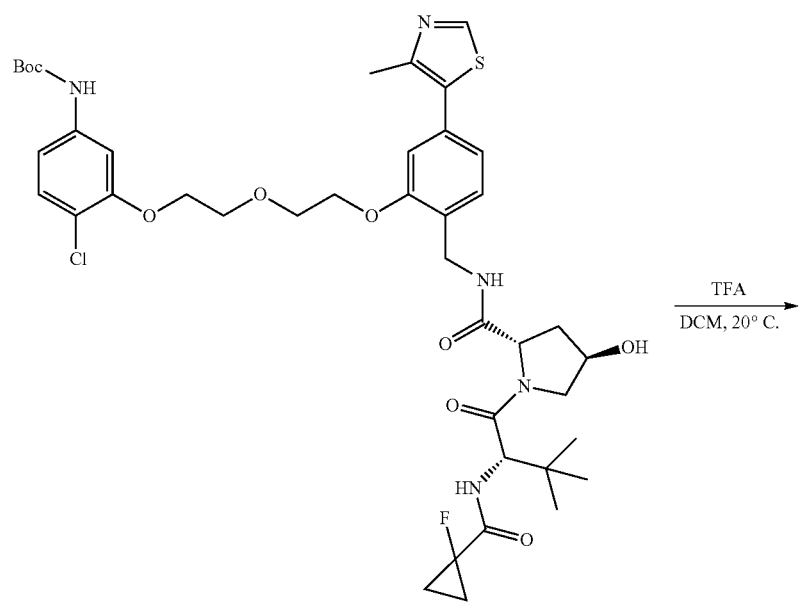

A2BC1_7

$\xrightarrow{\text{TFA}}$ DCM, 20° C.

-continued

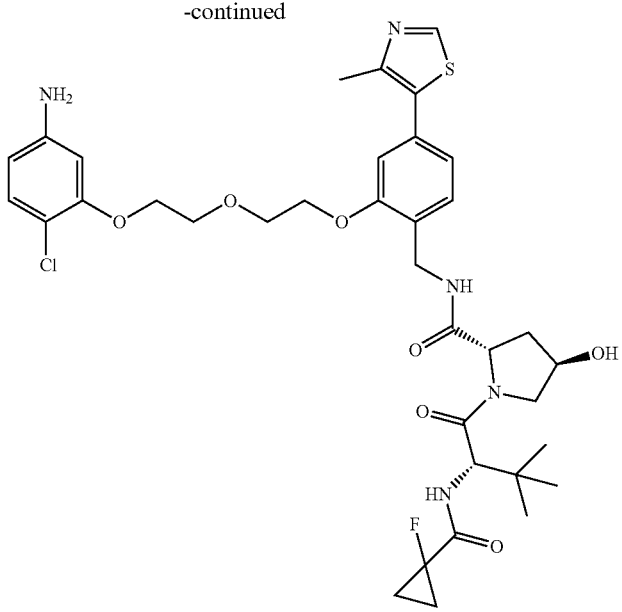

A2BC1_8

To a solution of Compound A2BC1-7 (104 mg, 122.87 umol, 1 eq) in DCM (2 mL) was added TFA (760.39 mg, 6.67 mmol, 493.76 uL, 54.27 eq). The mixture was stirred at 20° C. for 0.5 hr. LC-MS showed Compound A2BC1-7 was consumed completely and one main peak with desired m/z was detected. The reaction mixture was concentrated under reduced pressure to give Compound A2BC1-8 (143 mg, crude) as light colorless oil.

A mixture of L1 (44.42 mg, 147.40 umol, 1 eq),EDCI (42.38 mg, 221.09 umol, 1.5 eq) in Py (1 mL), then was added Compound A2BC1-8 (143 mg, 191.62 umol, 1.3 eq) was stirred at 20° C. for 12 hrs. The residue was purified by prep-HPLC and then lyophilized to afford A2BC1R5 (NUCC-0223811) (70 mg, 65.27 umol, 44.28% yield, 96% purity) as a white solid.

$^1$H NMR (ET32240-539-P1P2, 400 MHz, chloroform-d)

δ ppm 0.99 (s, 9H) 1.27 (br d, J=5.65 Hz, 5H) 1.73-1.97 (m, 9H) 2.04 (br d, J=13.55 Hz, 1H) 2.10-2.22 (m, 2H) 2.28 (br s, 2H) 2.54 (s, 3H) 3.10 (br s, 1H) 3.47 (br s, 1H) 3.65 (d, J=3.51 Hz, 1H) 3.68 (d, J=3.89 Hz, 1H) 3.92 (s, 1H) 3.96 (br d, J=8.91 Hz, 3H) 4.02 (br d, J=2.01 Hz, 2H) 4.22-4.28 (m, 3H) 4.38 (d, J=5.77 Hz, 1H) 4.43 (d, J=5.77 Hz, 1H) 4.51 (br s, 1H) 4.55-4.61 (m, 2H) 6.91 (s, 1H) 6.93 (s, 1H) 6.96 (s, 1H) 7.01 (s, 1H) 7.07 (br d, J=5.14 Hz, 1H) 7.19 (s, 1H) 7.21 (s, 1H) 7.57 (br s, 1H) 7.78 (br d, J=2.01 Hz, 1H) 7.92 (dd, J=9.35, 2.70 Hz, 1H) 8.44 (br s, 1H) 8.73 (dd, J=9.29, 4.64 Hz, 1H) 8.89 (br s, 1H) 8.97 (br s, 1H) 9.50 (br s, 1H)

$^{19}$F NMR (ET32240-539-P1P2, 400 MHz, chloroform-d)

LCMS: Rt=2.514 min, 95.7% purity, m/z=515.3 (M/2+H)$^+$

A2BC2R5 (NUCC-0223812):

$^1$H NMR (ET32240-537-P1, 400 MHz, chloroform-d)

δ ppm 1.02 (s, 11H) 1.19-1.40 (m, 10H) 1.74-2.02 (m, 9H) 2.07 (br d, J=11.54 Hz, 2H) 2.13-2.34 (m, 5H) 2.13-2.34 (m, 1H) 2.44 (br s, 5H) 3.20 (br d, J=3.26 Hz, 1H) 3.48 (br d, J=12.55 Hz, 2H) 3.69-4.24 (m, 20H) 4.42 (br d, J=5.65 Hz, 1H) 4.48 (br d, J=6.27 Hz, 2H) 4.56-4.62 (m, 3H) 4.71 (t, J=8.03 Hz, 1H) 6.75-6.83 (m, 2H) 7.03-7.12 (m, 3H) 7.42 (br d, J=7.65 Hz, 2H) 7.50 (br s, 1H) 7.57 (br t, J=5.65 Hz, 1H) 7.79 (br t, J=8.16 Hz, 1H) 7.94 (dd, J=9.10, 1.82 Hz, 1H) 8.67 (br s, 1H) 8.81 (br dd, J=9.41, 5.02 Hz, 1H) 9.08 (br s, 1H) 9.61 (br s, 1H) 9.88 (br s, 1H)

$^{19}$F NMR (ET32240-537-P1, 400 MHz, chloroform-d)

LCMS: Rt=2.520 min, 100% purity, m/z=537.3 (M/2+H)$^+$

A2BC3R5 (NUCC-0226144):

$^1$H NMR (ET32240-746-P1, 400 MHz, chloroform-d)

δ ppm 1.01 (s, 9H) 1.27 (br d, J=5.87 Hz, 7H) 1.67-2.57 (m, 17H) 3.18 (br s, 1H) 3.45 (br s, 1H) 3.58-3.79 (m, 9H) 3.80-4.01 (m, 5H) 4.04-4.24 (m, 3H) 4.41 (br d, J=5.38 Hz, 2H) 4.54 (br s, 1H) 4.60 (br d, J=8.44 Hz, 1H) 4.68 (br t, J=7.89 Hz, 1H) 6.76-6.89 (m, 2H) 7.06 (br d, J=5.75 Hz, 1H) 7.11 (br d, J=8.56 Hz, 1H) 7.31 (br d, J=7.82 Hz, 2H) 7.58 (br s, 2H) 7.76 (br t, J=7.27 Hz, 1H) 7.92 (br d, J=10.39 Hz, 1H) 8.54 (br s, 1H) 8.75 (br dd, J=9.17, 4.77 Hz, 1H) 9.01-9.20 (m, 2H) 9.78 (br s, 1H)

$^{19}$F NMR (ET32240-746-P1, 376 MHz, chloroform-d)

LCMS: Rt=2.286 min, 100% purity, m/z=1117.4 (M+H)$^+$

A2BC4R5 (NUCC-0226199):

$^1$H NMR (ET32240-897-P1A, 400 MHz, methanol-d$_4$)

δ ppm 1.03 (s, 9H) 1.23-1.40 (m, 7H) 1.78-1.97 (m, 6H) 1.97-2.29 (m, 5H) 2.59 (s, 3H) 2.98-3.08 (m, 1H) 3.61-3.81 (m, 14H) 3.83-3.91 (m, 5H) 4.10-4.19 (m, 2H) 4.24 (br d, J=2.88 Hz, 2H) 4.34-4.43 (m, 1H) 4.46-4.56 (m, 2H) 4.63 (t, J=8.38 Hz, 1H) 4.74 (s, 1H) 7.07-7.16 (m, 3H) 7.23 (d, J=8.63 Hz, 1H) 7.58 (d, J=7.44 Hz, 2H) 7.59 (s, 1H) 8.01-8.07 (m, 1H) 8.27-8.39 (m, 3H) 9.16 (d, J=5.88 Hz, 1H) 9.89 (s, 1H)

$^{19}$F NMR (ET32240-897-P1A, 376 MHz, methanol-d4)

LCMS: Rt=2.285 min, 100% purity, m/z=1161.3 (M+H)$^+$

A2BC5R5 (NUCC-0226149):

$^1$H NMR (ET32240-802-P1, 400 MHz, chloroform-d)

δ ppm 1.02 (s, 9H) 1.25-1.34 (m, 8H) 1.78-2.12 (m, 11H) 2.19 (br s, 2H) 2.32-2.43 (m, 1H) 2.60 (s, 3H) 3.22 (br s, 1H) 3.51-3.76 (m, 1H) 3.51-3.76 (m, 17H) 3.82 (br s, 2H) 3.89 (br s, 2H) 4.02 (br d, J=10.96 Hz, 1H) 4.11 (br s, 2H) 4.30 (br s, 2H) 4.47 (br t, J=5.81 Hz, 2H) 4.52-4.62 (m, 2H) 4.70

(t, J=8.00 Hz, 1H) 6.88 (br d, J=7.23 Hz, 1H) 6.99-7.07 (m, 1H) 7.10 (br s, 1H) 7.16 (d, J=8.33 Hz, 1H) 7.41 (br d, J=7.89 Hz, 2H) 7.49 (br s, 1H) 7.63 (br d, J=8.55 Hz, 1H) 7.75-7.83 (m, 1H) 7.90-7.99 (m, 1H) 8.75 (br s, 1H) 8.91 (dd, J=9.10, 4.93 Hz, 1H) 9.02 (br s, 1H) 9.80 (br s, 1H) 9.97-10.13 (m, 1H)

$^{19}$F NMR (ET32240-802-P1, 376 MHz, chloroform-d)

LCMS: Rt=2.229 min, 99% purity, m/z=1205.4 (M+H)$^+$

Example 2—Exemplary IDO-PROTAC Compounds

Figure 50:
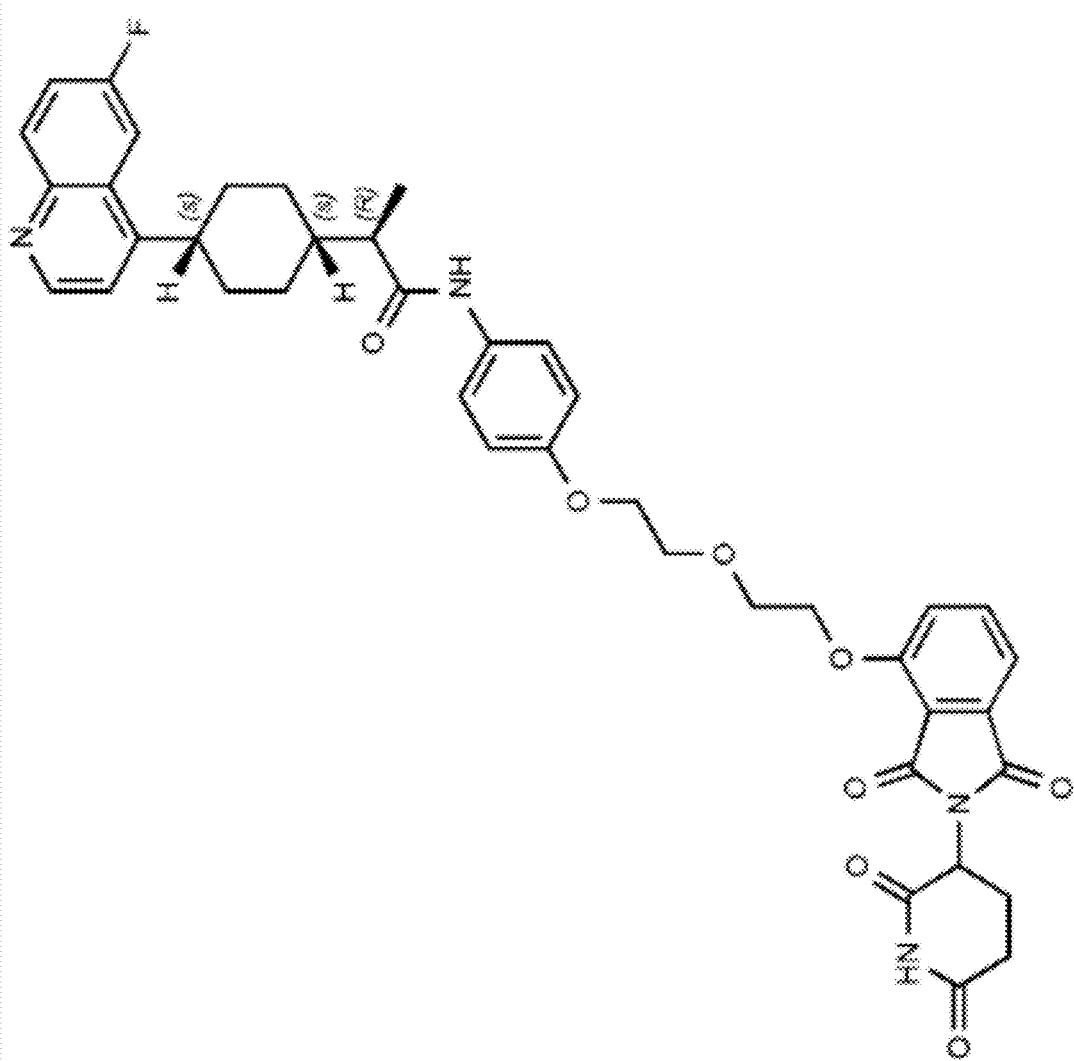
FIG. 50 shows the exemplary IDO-PROTAC compounds as disclosed herein.
Figure 50:
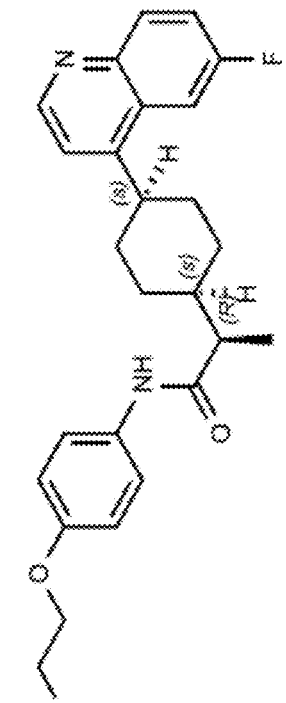
Figure 50:
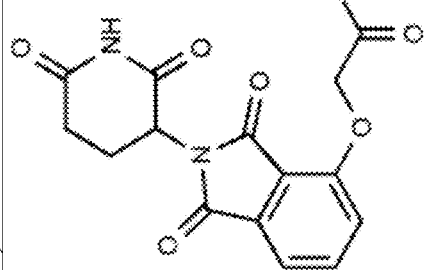
Figure 50:
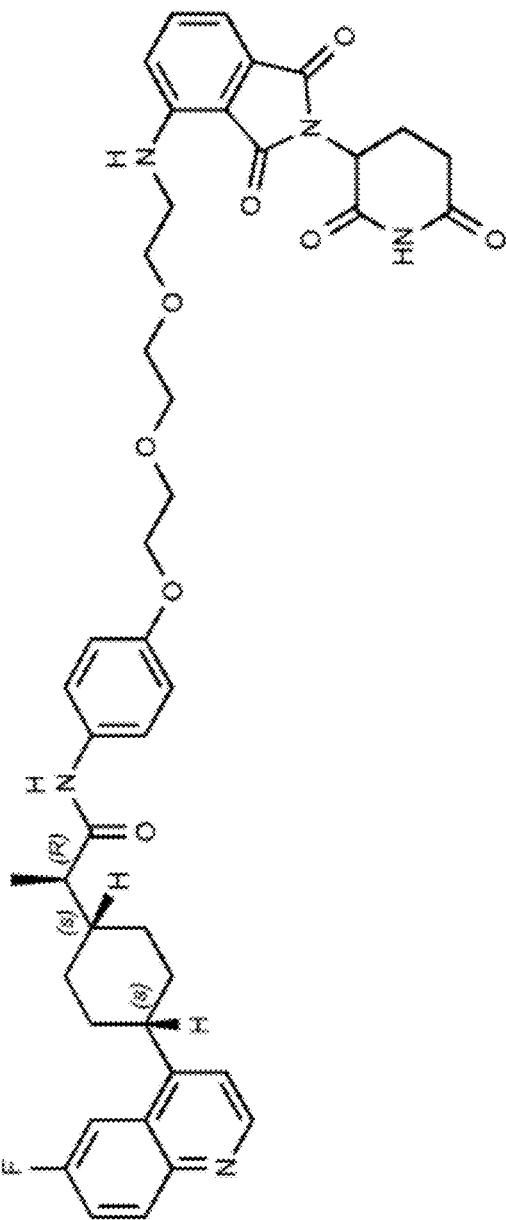
Figure 50:
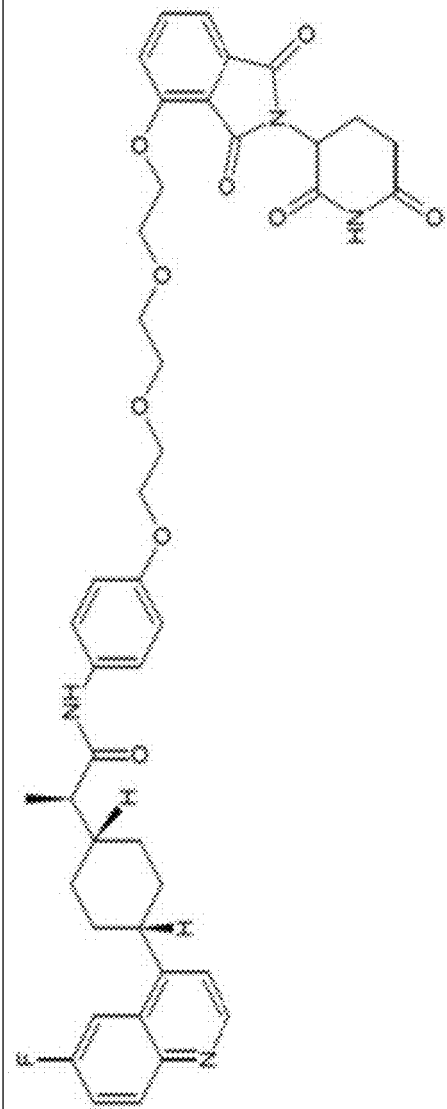
Figure 50:
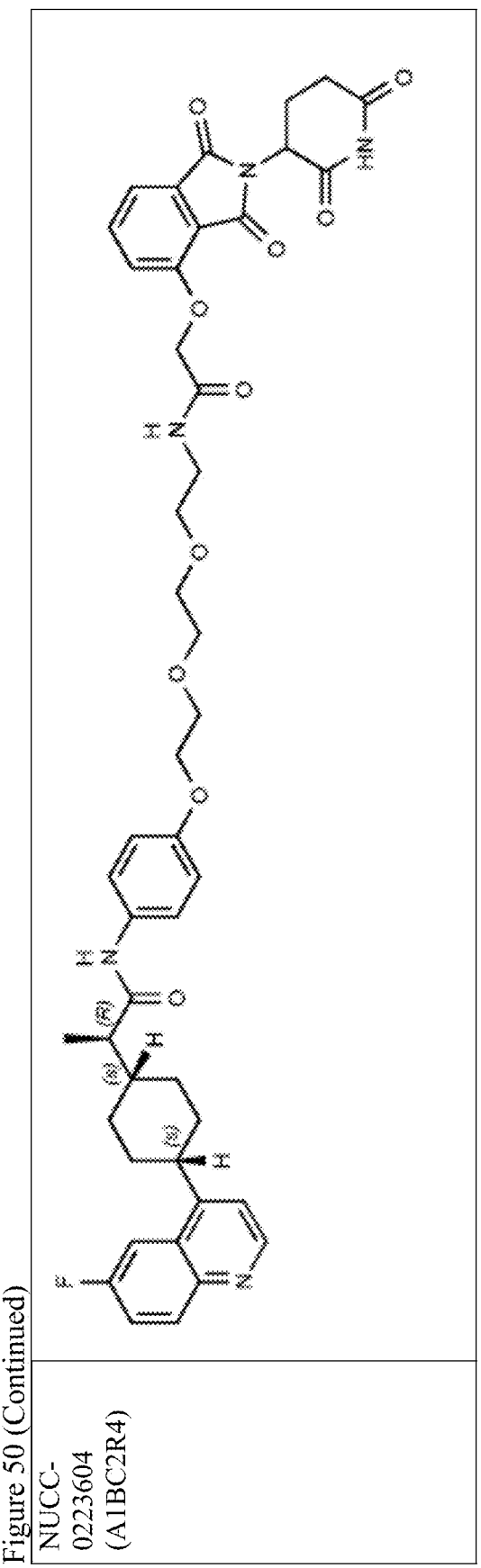
Figure 50:
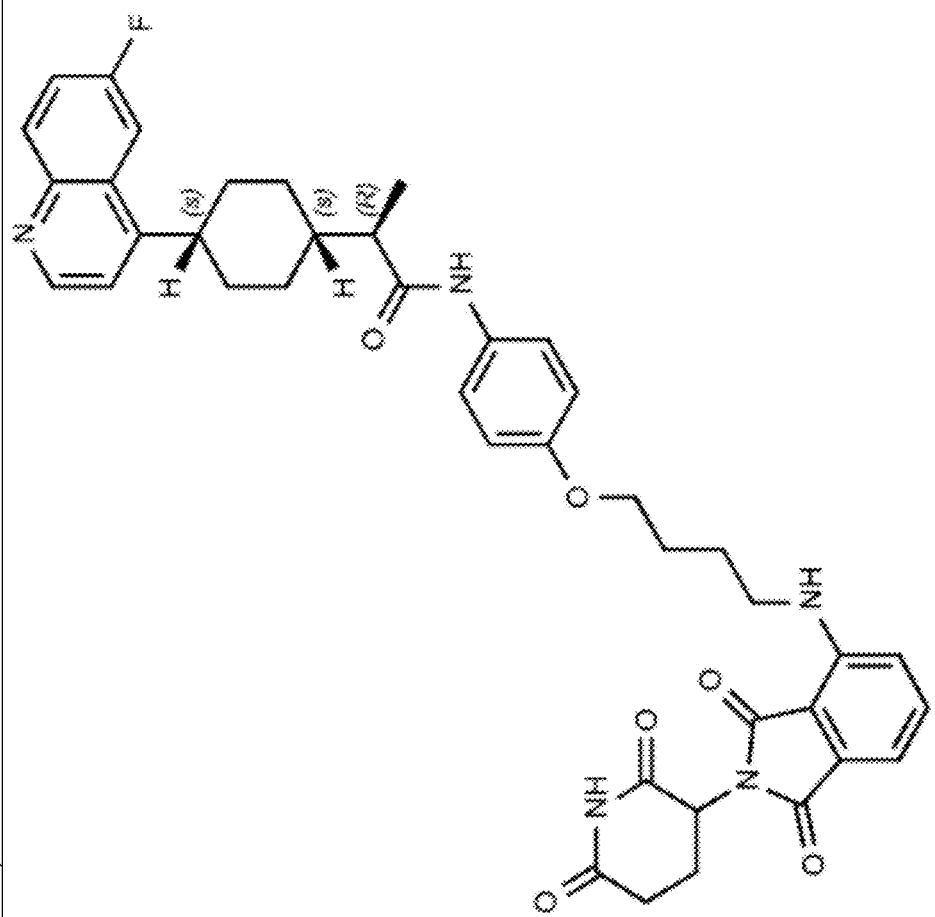
Figure 50:
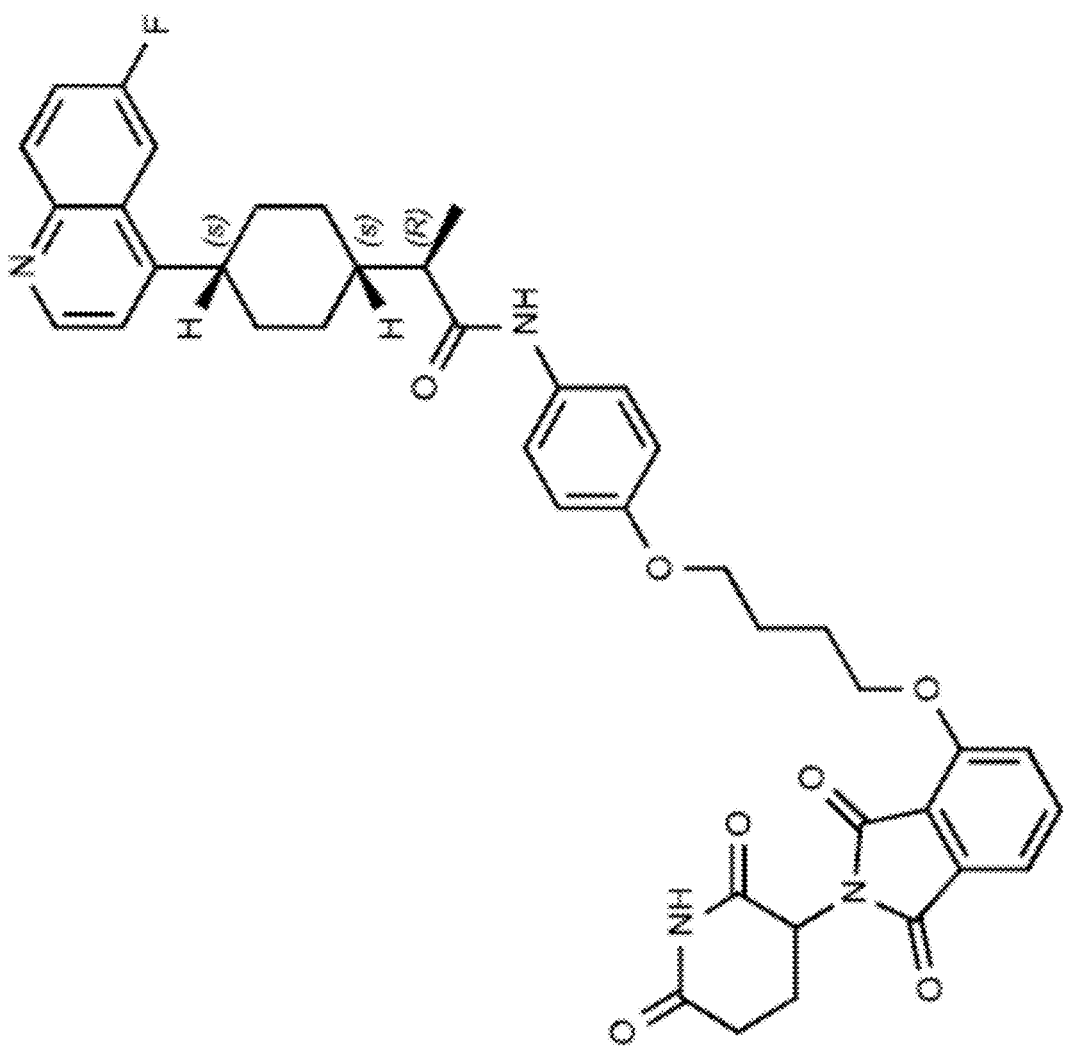
Figure 50:
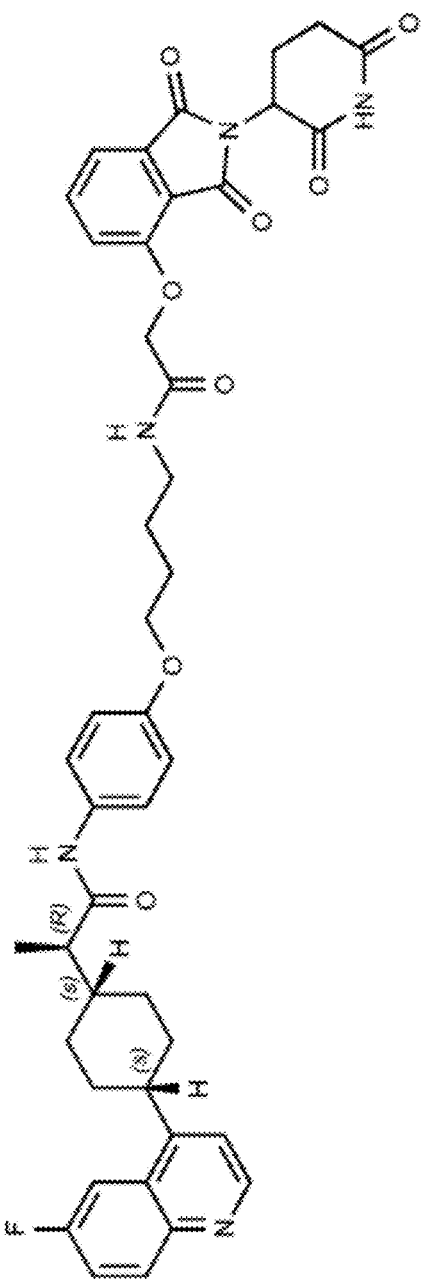
Figure 50:
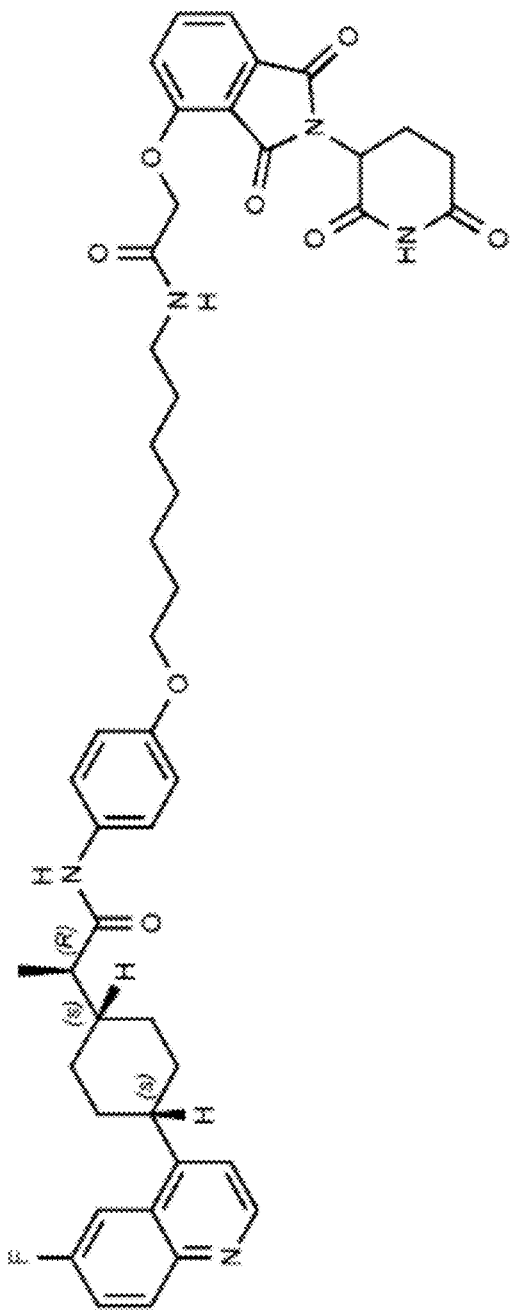
Figure 50:
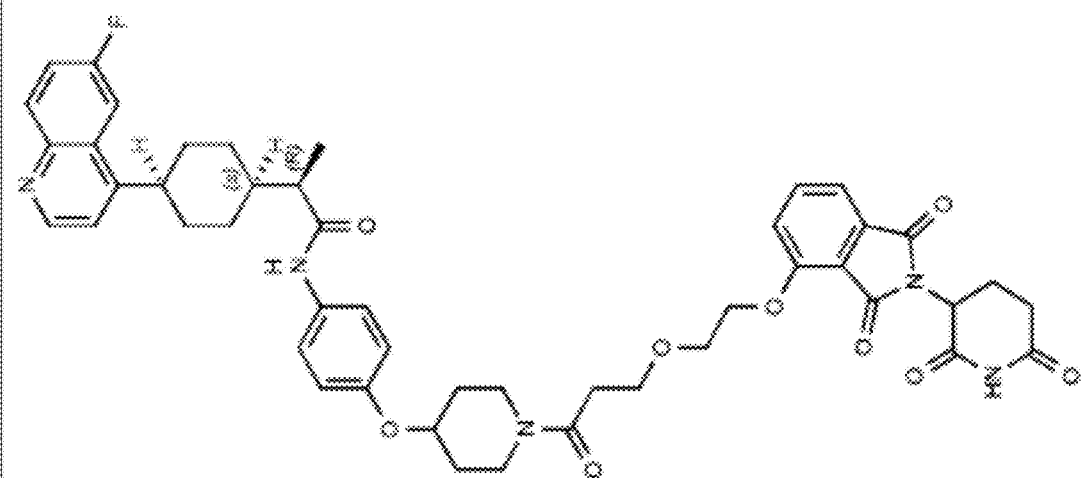
Figure 50:
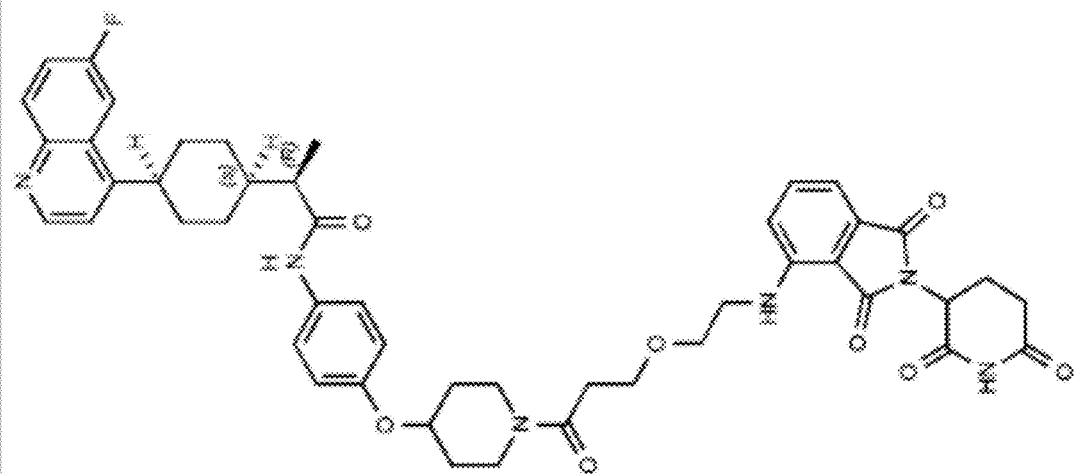
Figure 50:
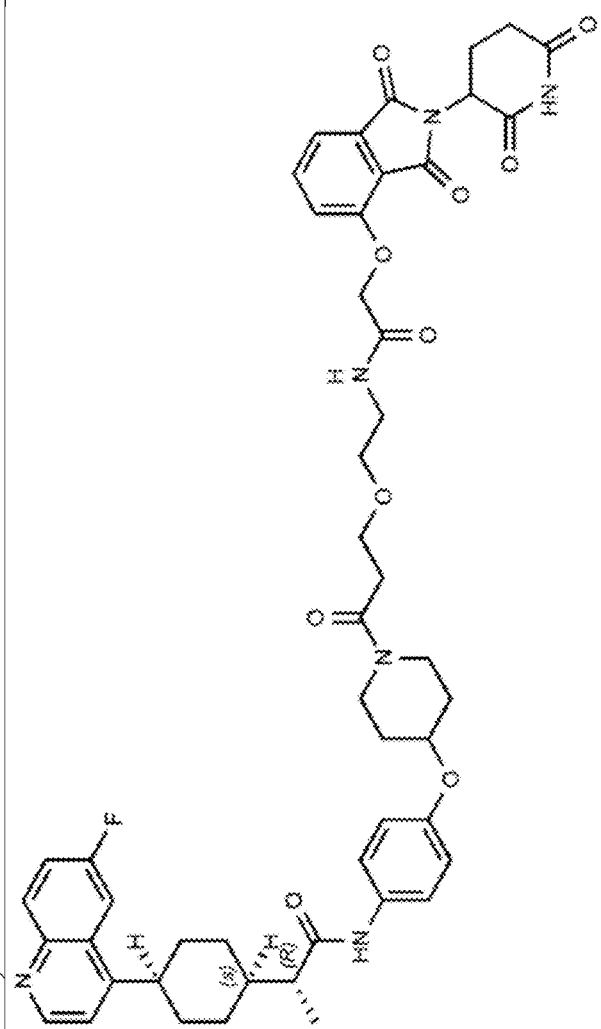
Figure 50:
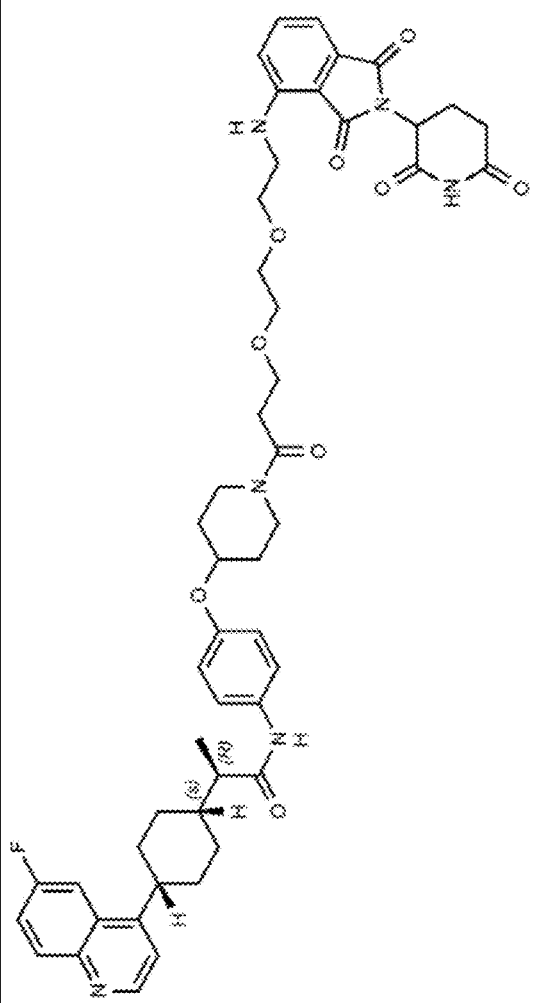
Figure 50:
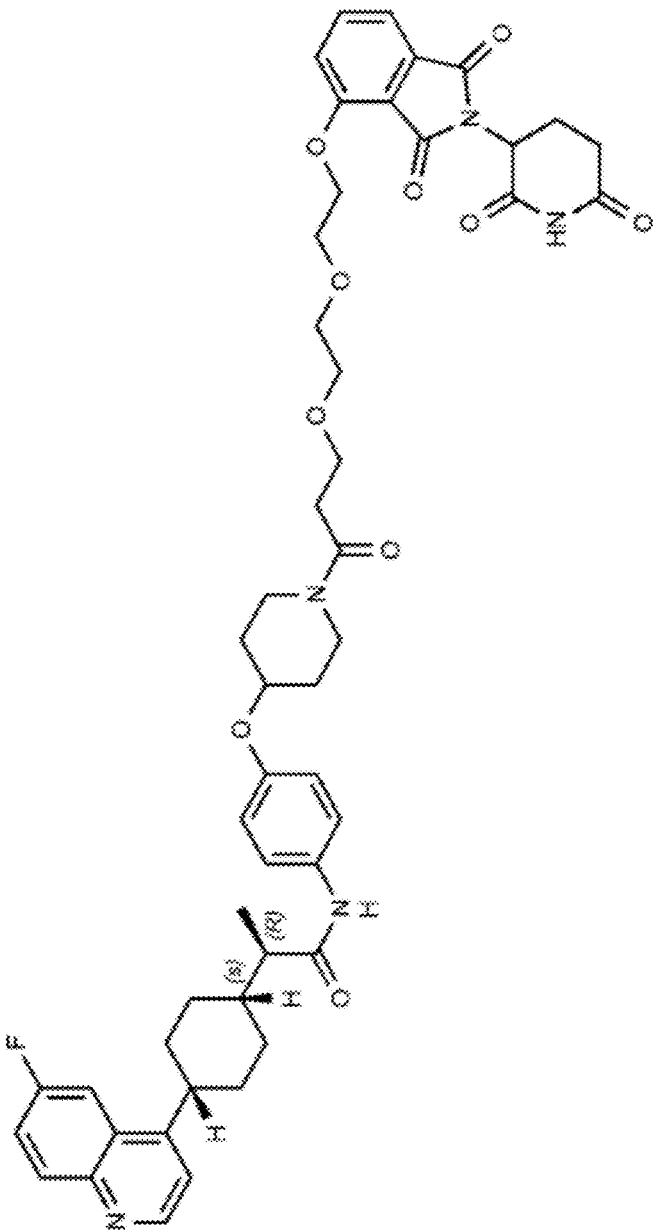
Figure 50:
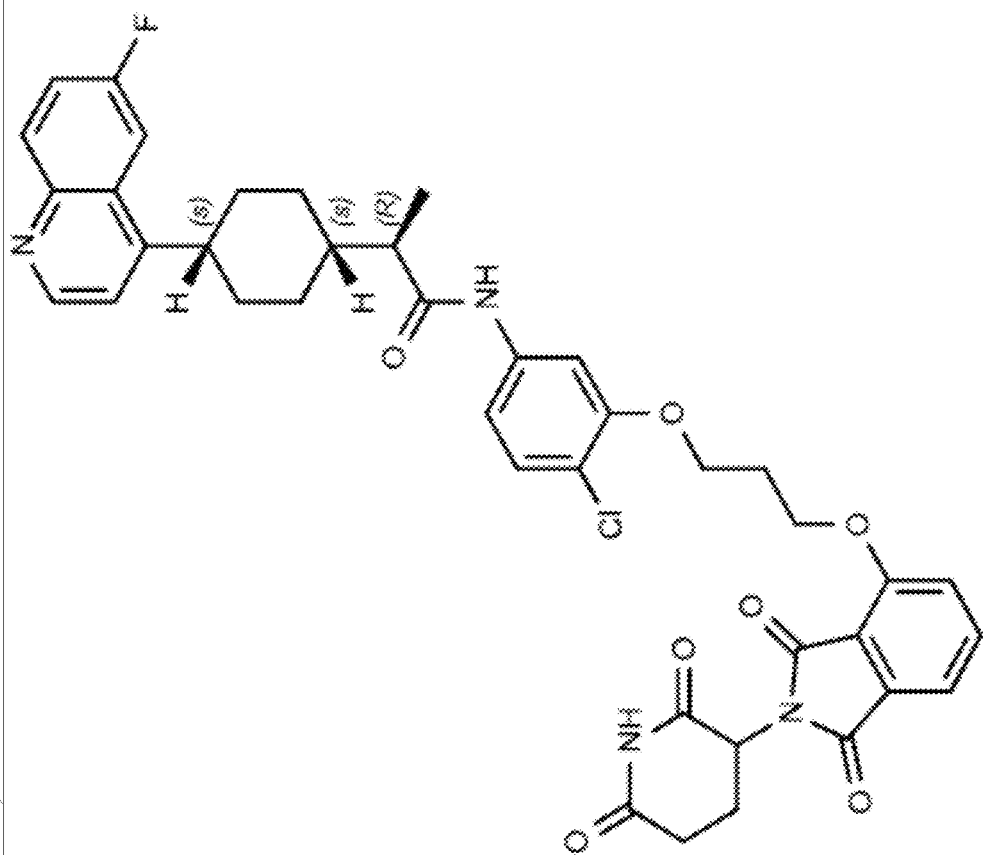
Figure 50:
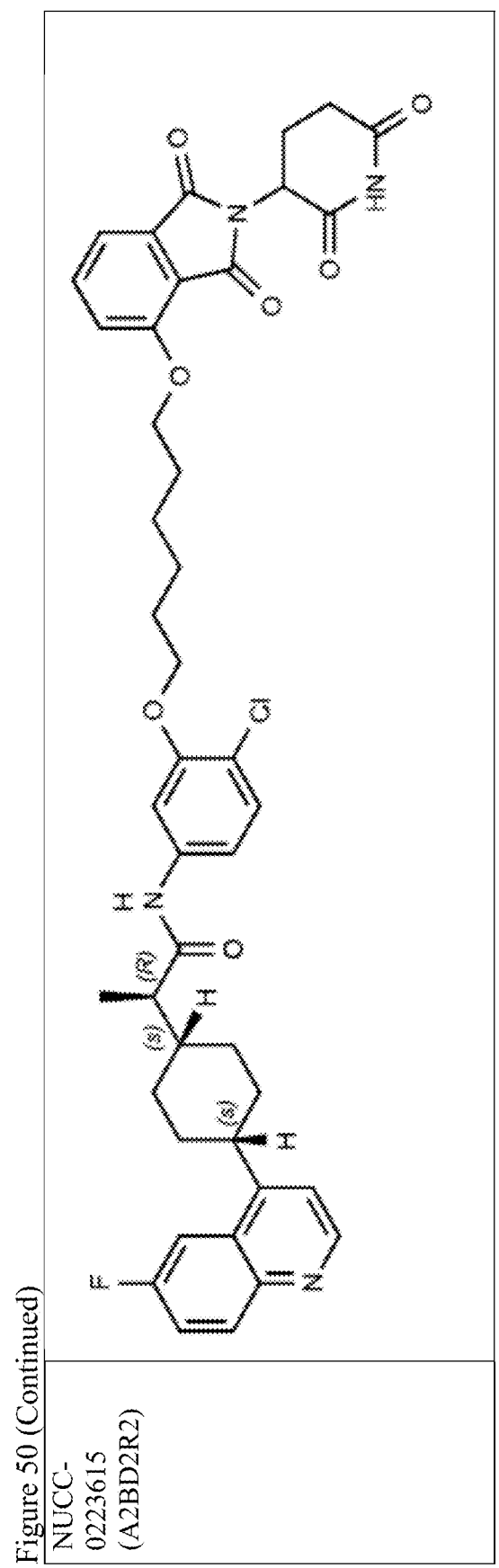
Figure 50:
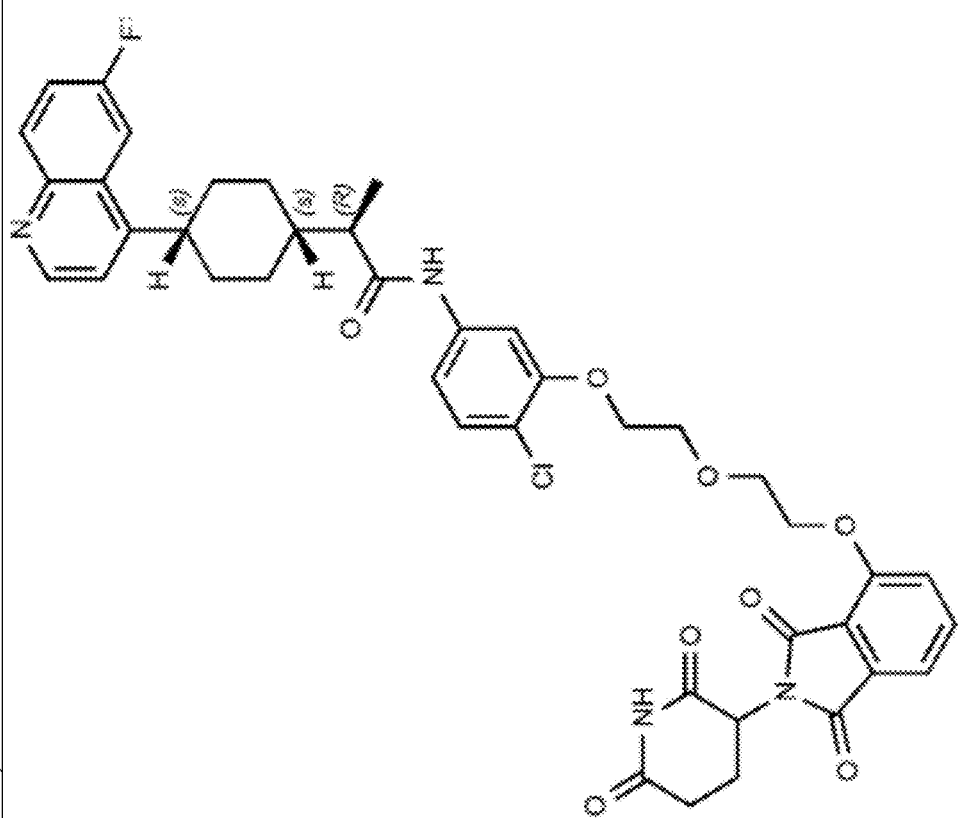
Figure 50:
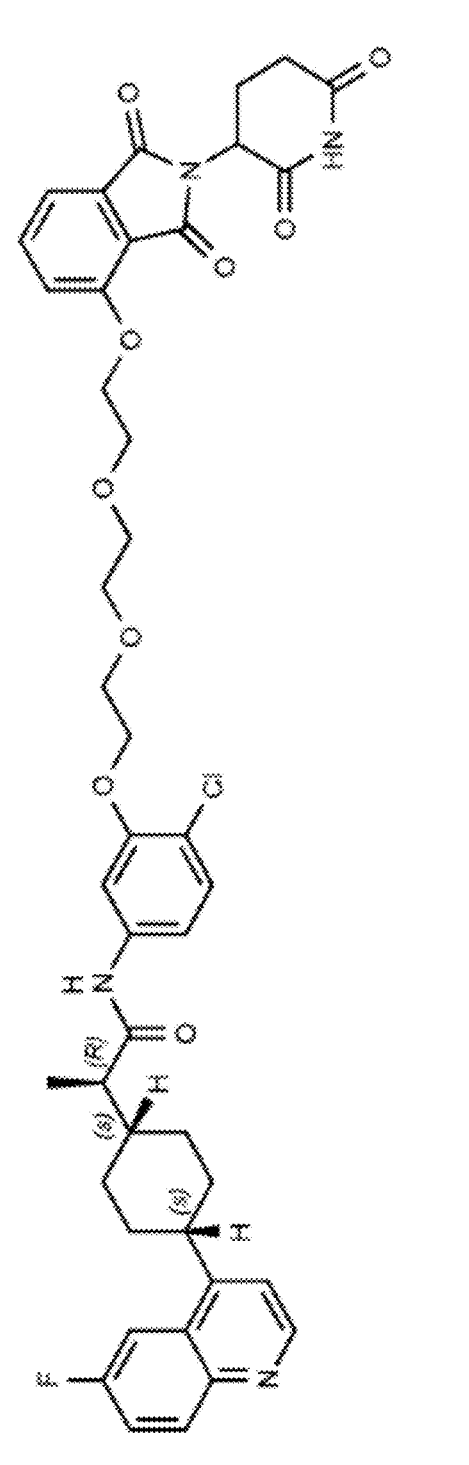
Figure 50:
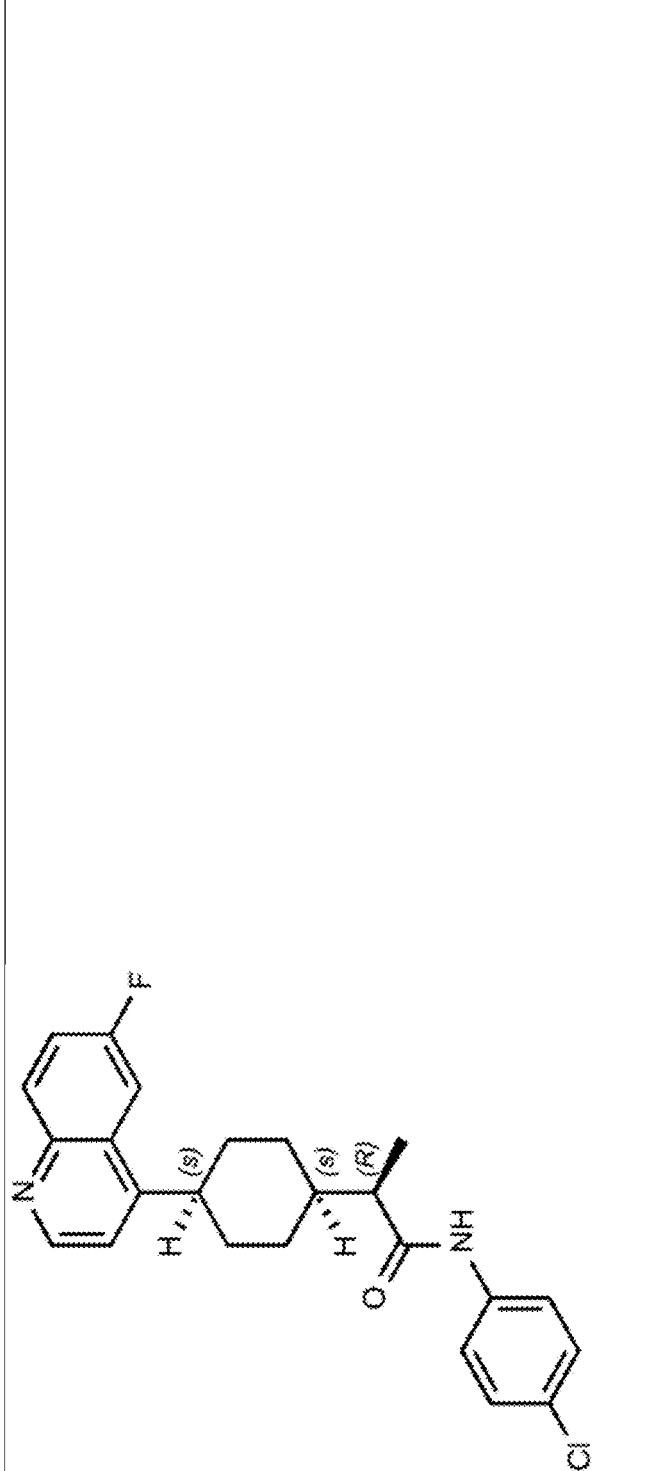
Figure 50:
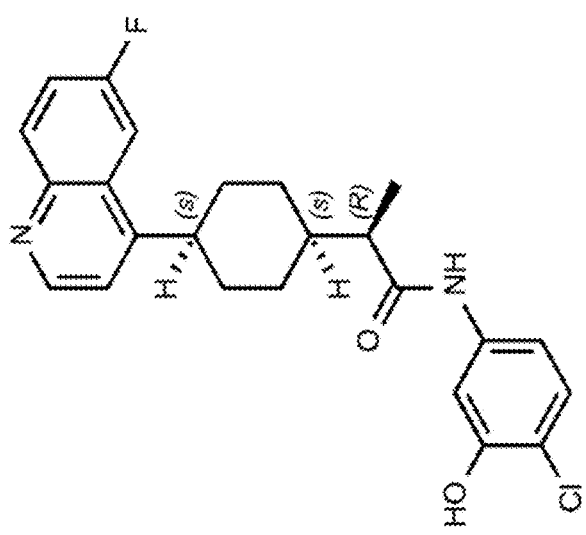
Figure 50:
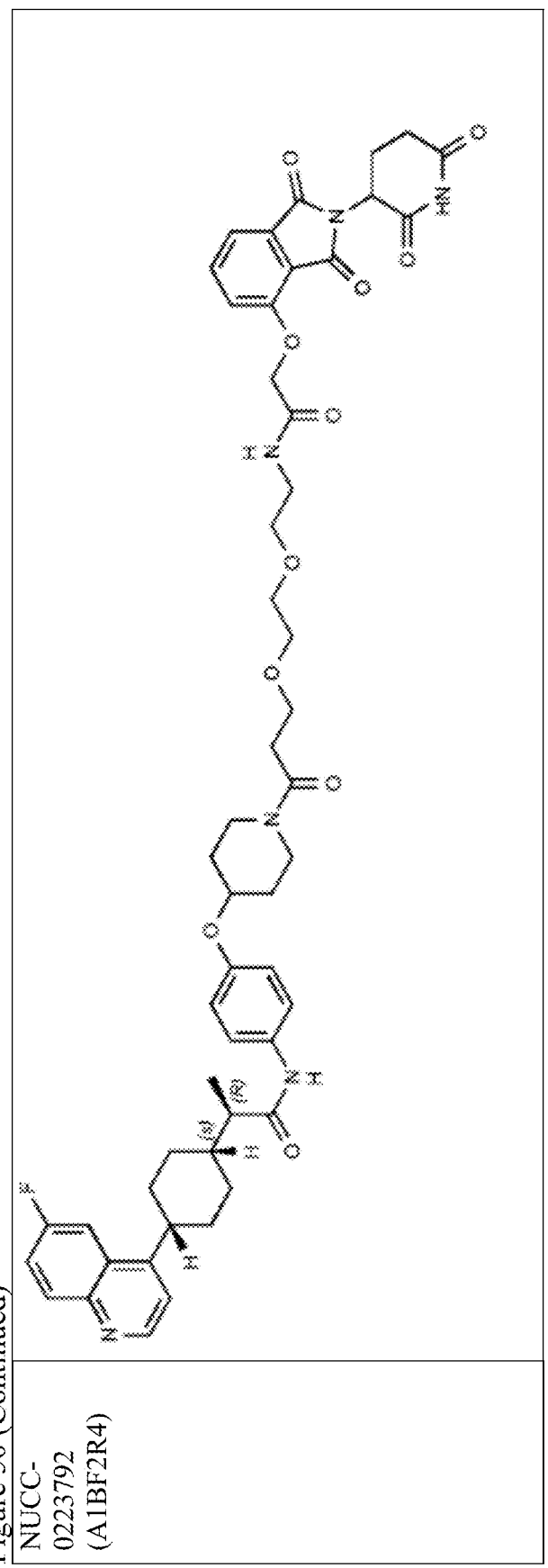
Figure 50:
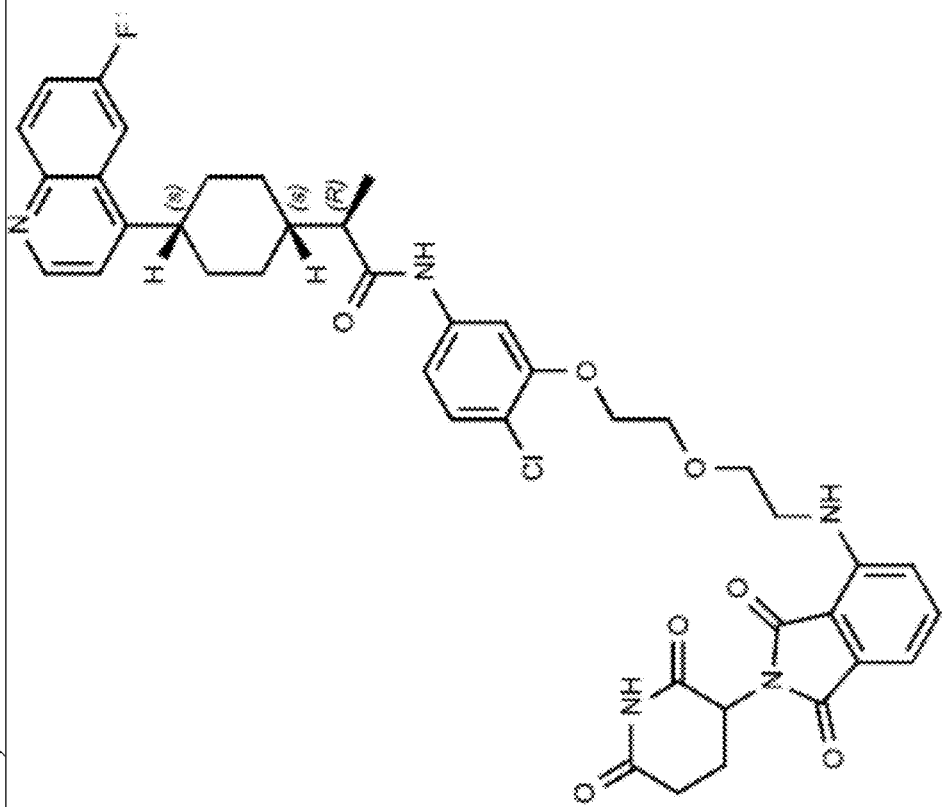
Figure 50:
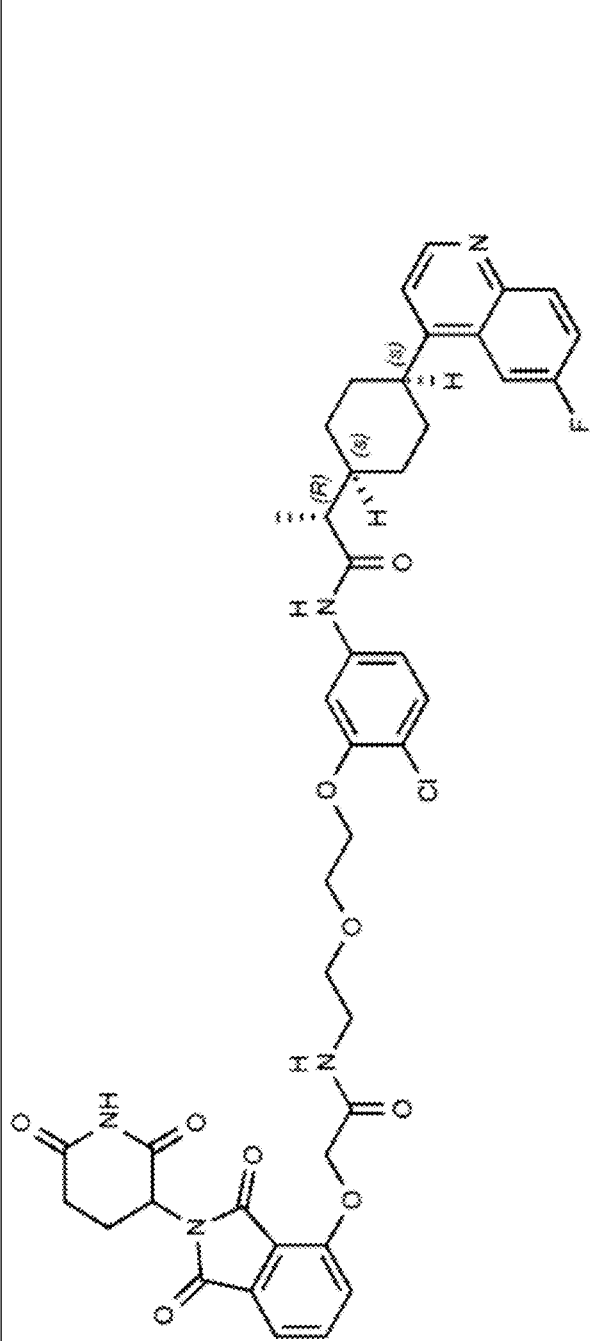
Figure 50:
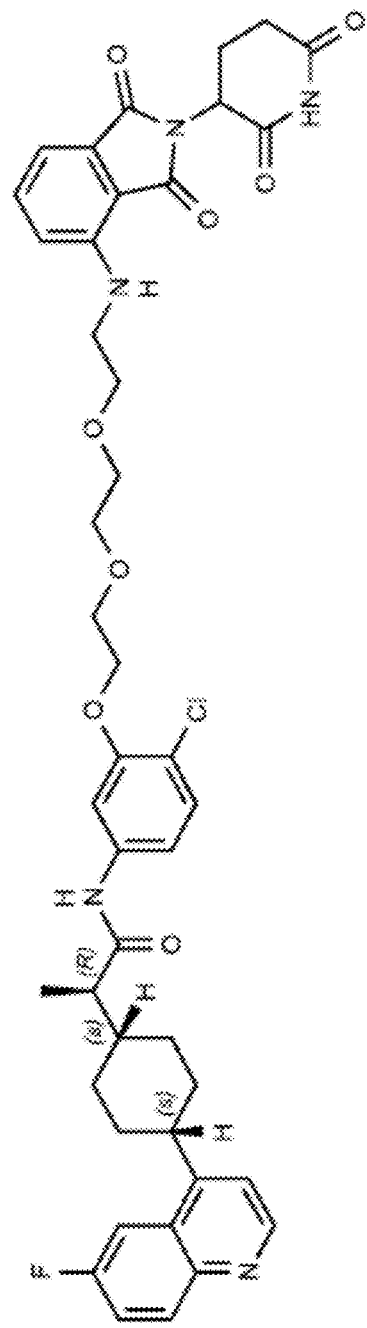
Figure 50:
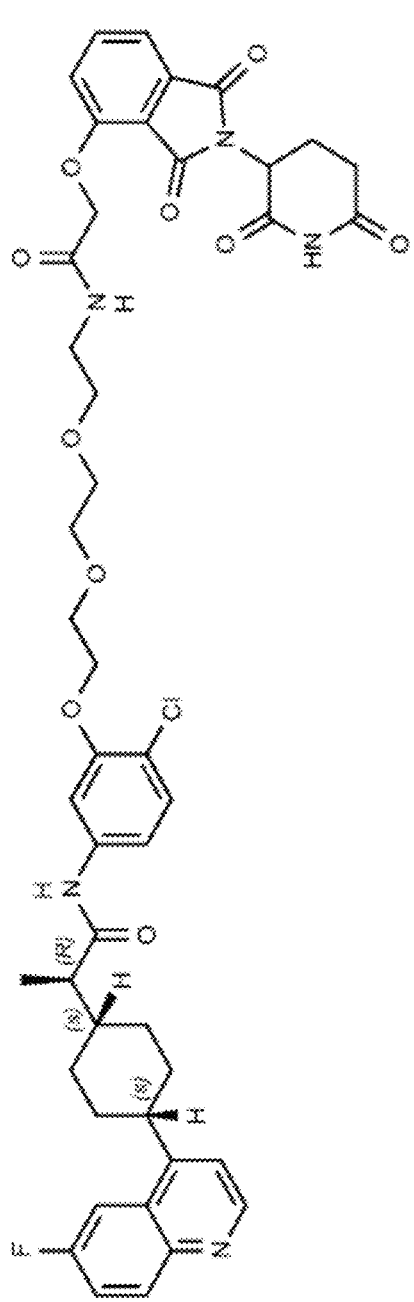
Figure 50:
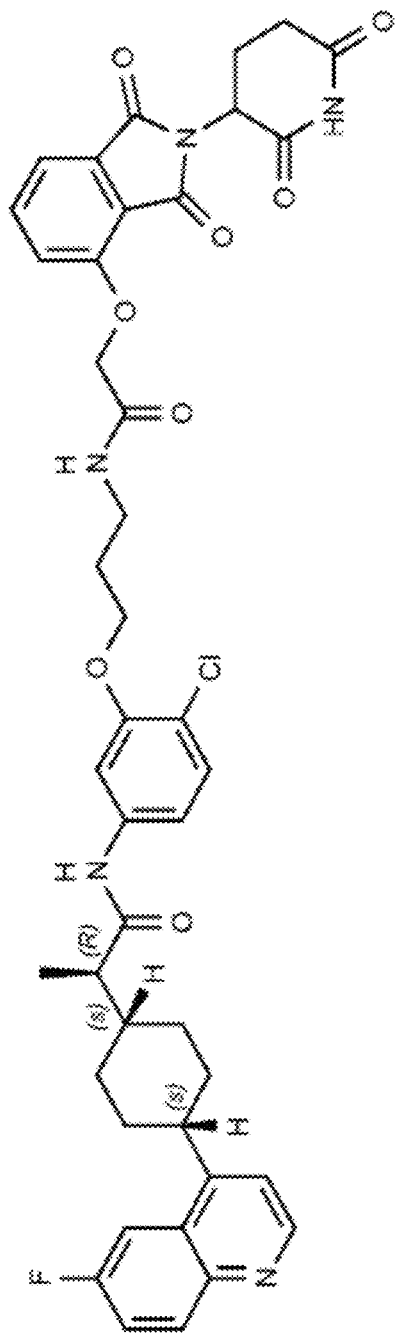
Figure 50:
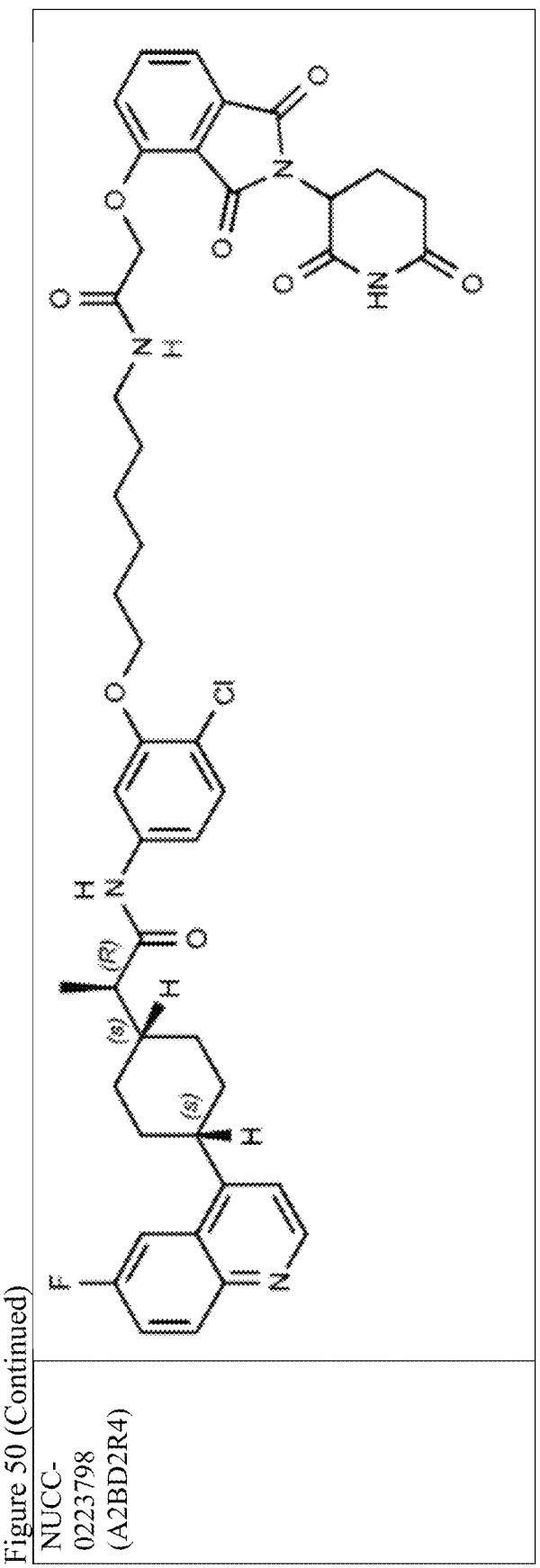
Figure 50:
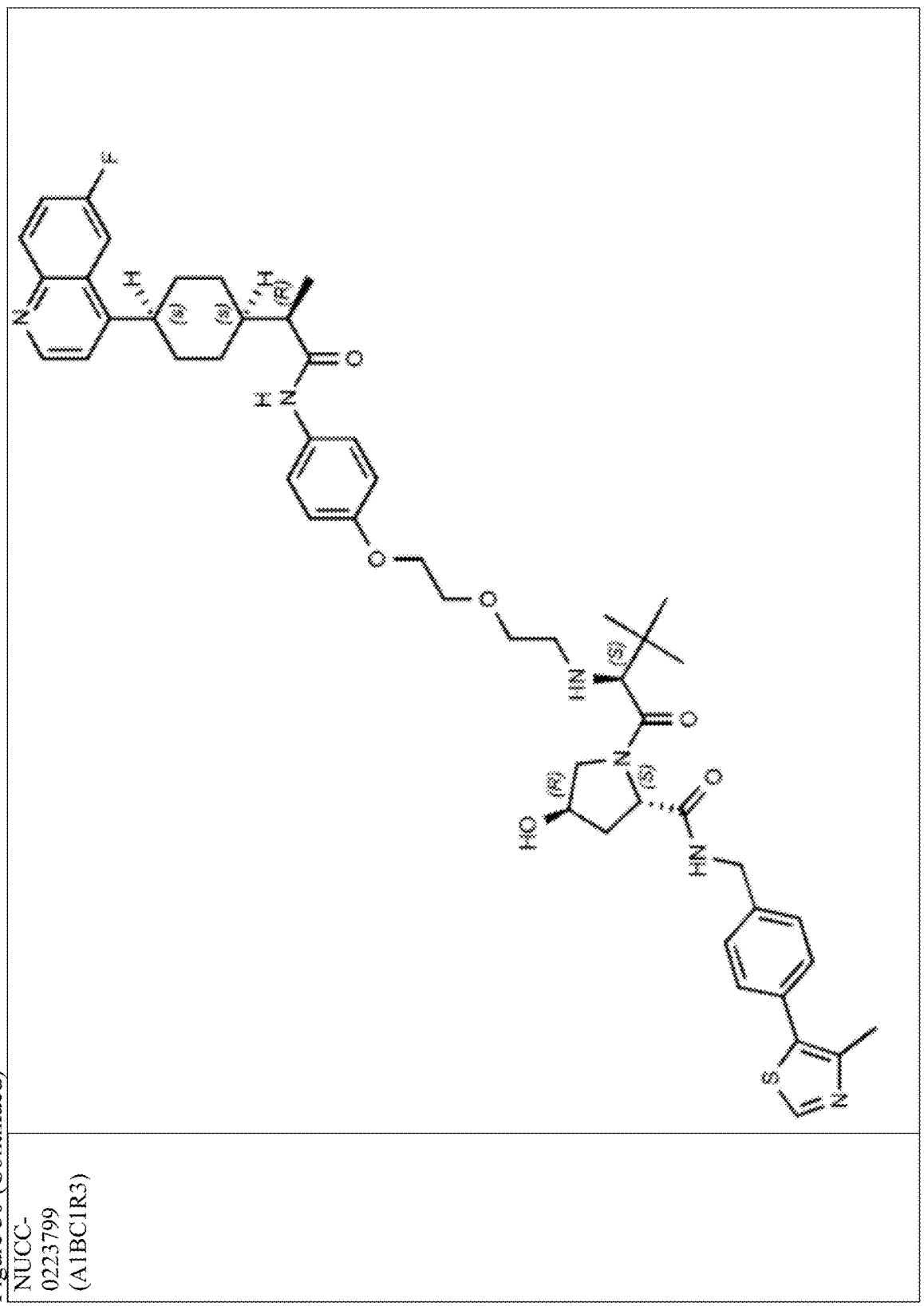
Figure 50:
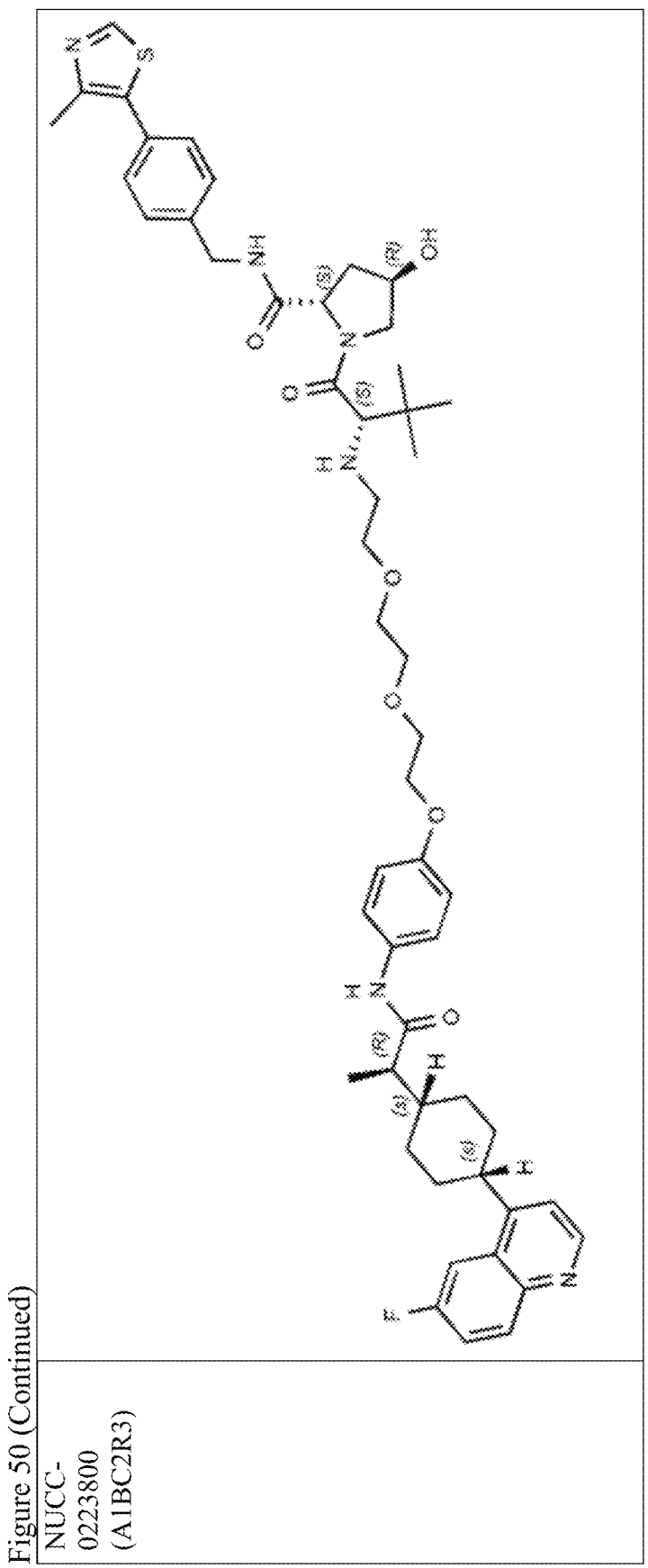
Figure 50:
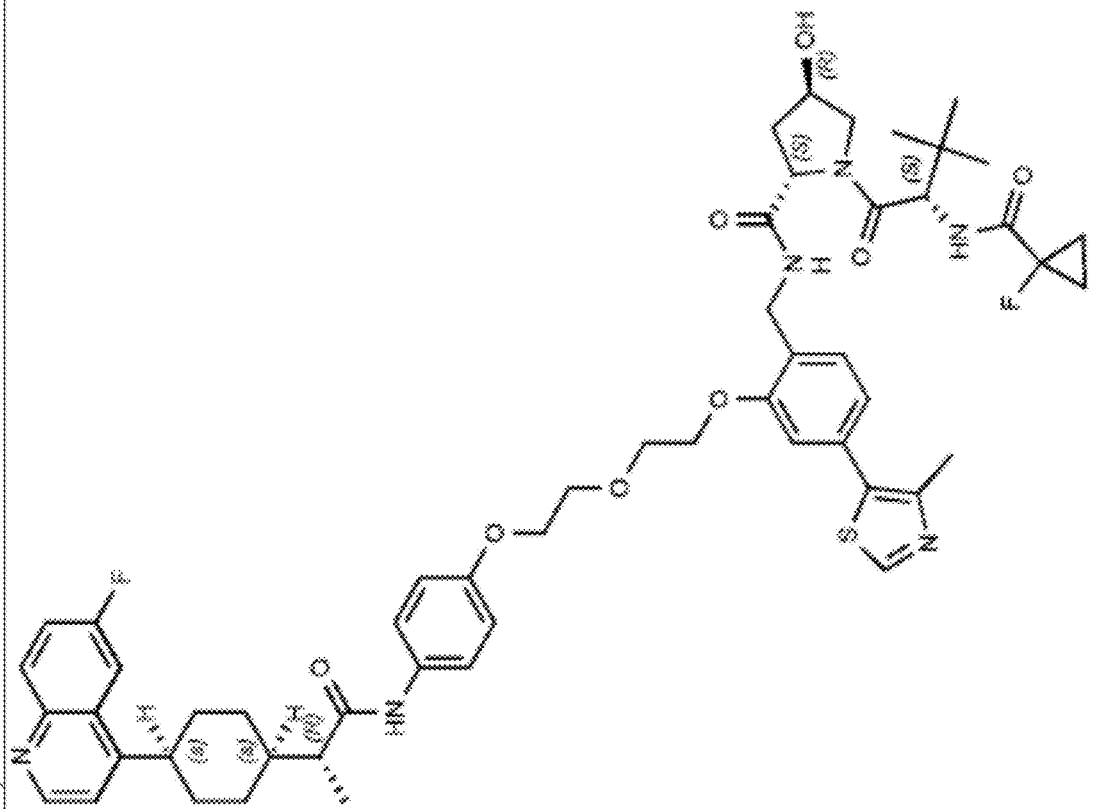
Figure 50:
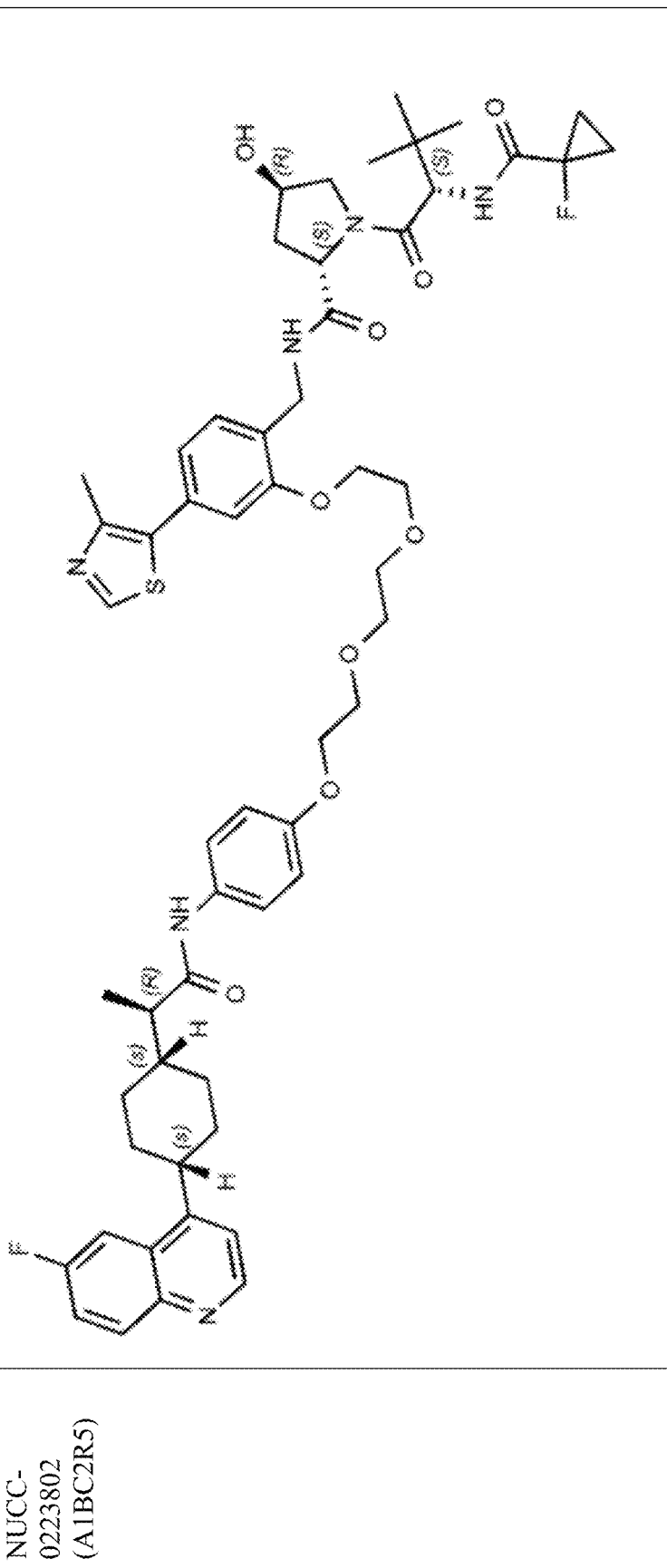
Figure 50:
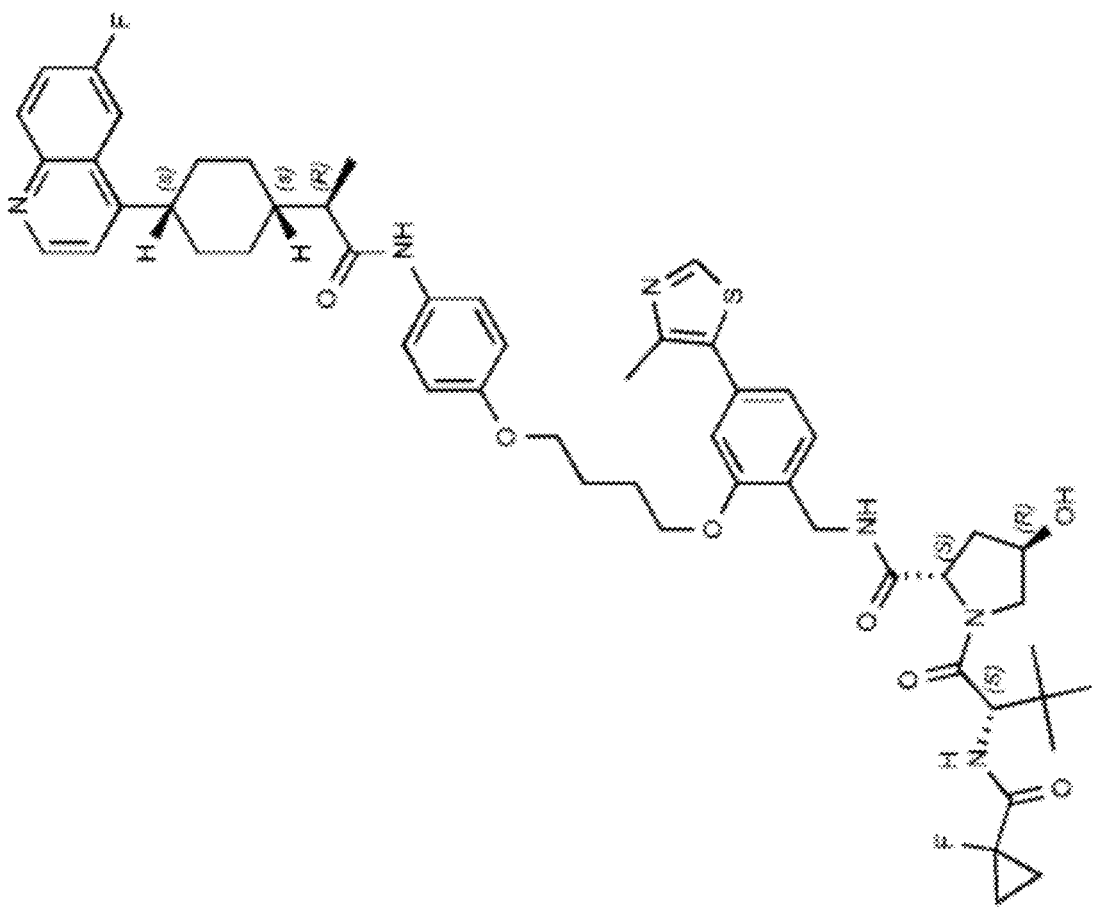
Figure 50:
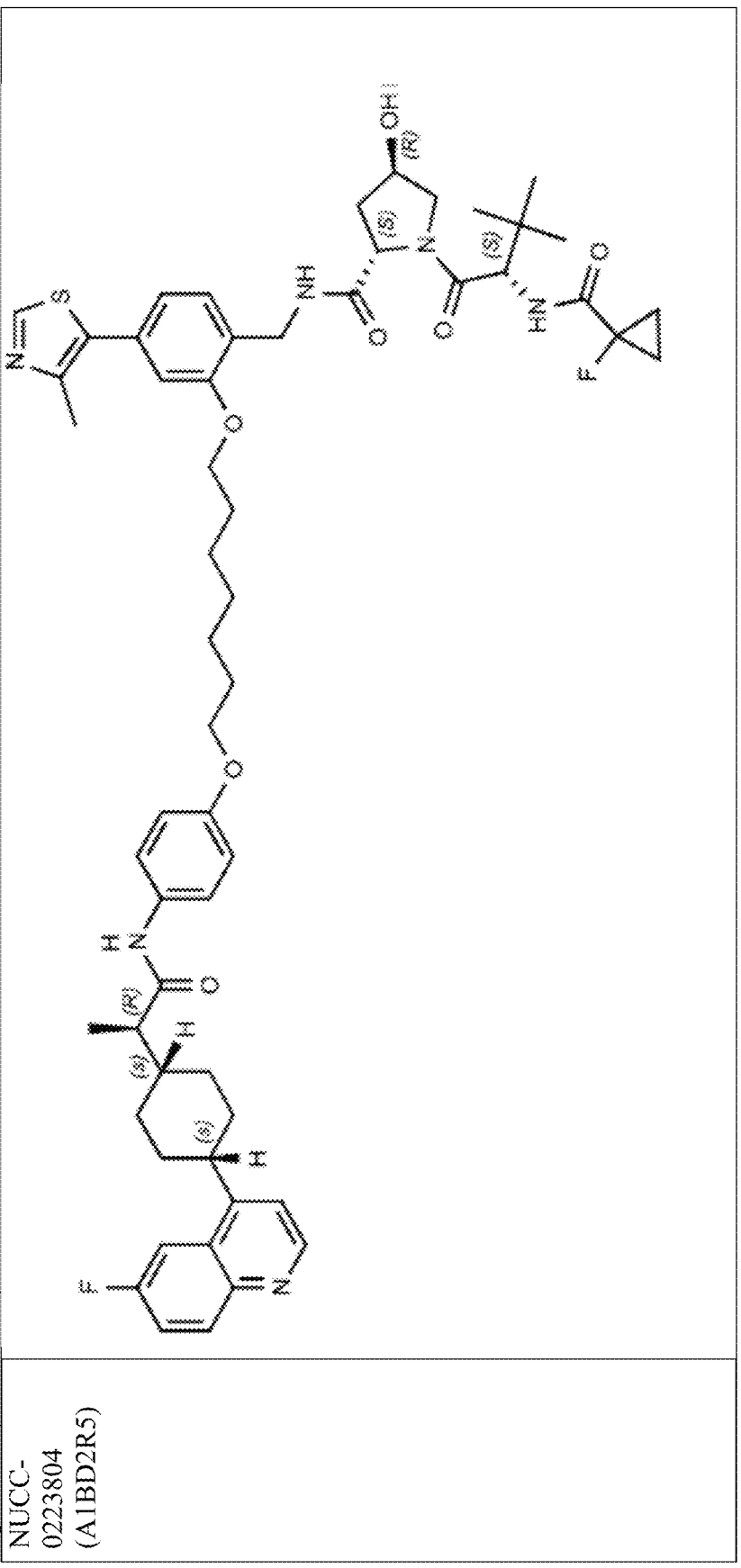
Figure 50:
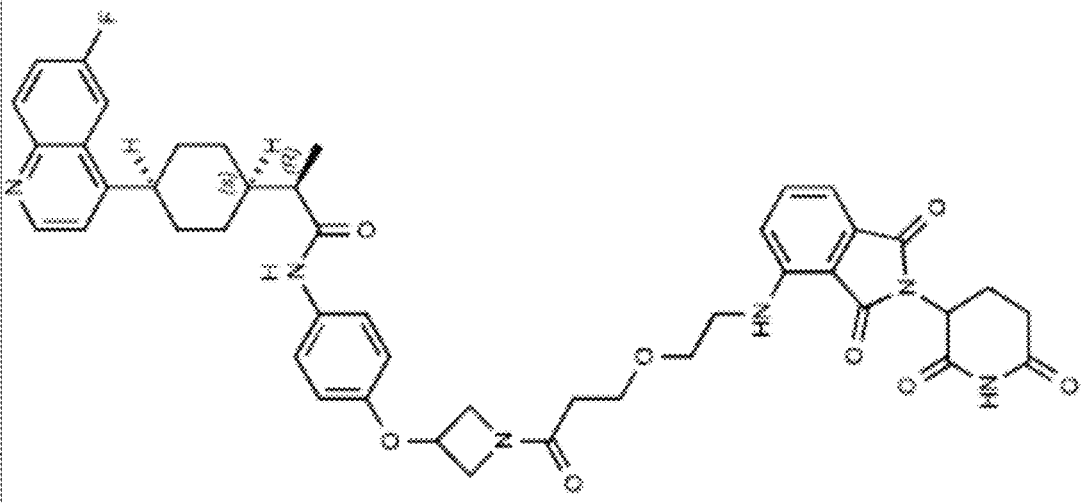
Figure 50:
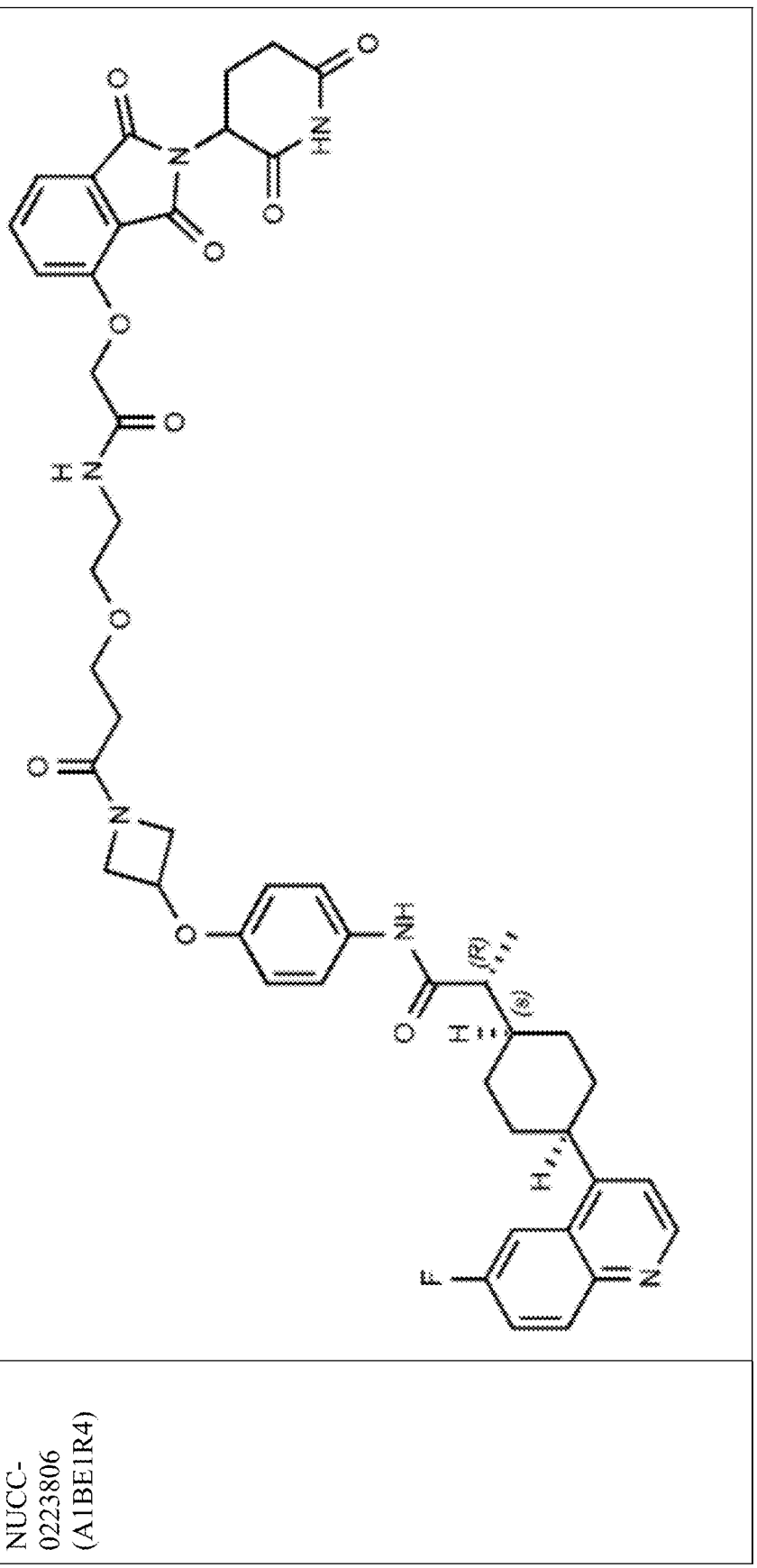
Figure 50:
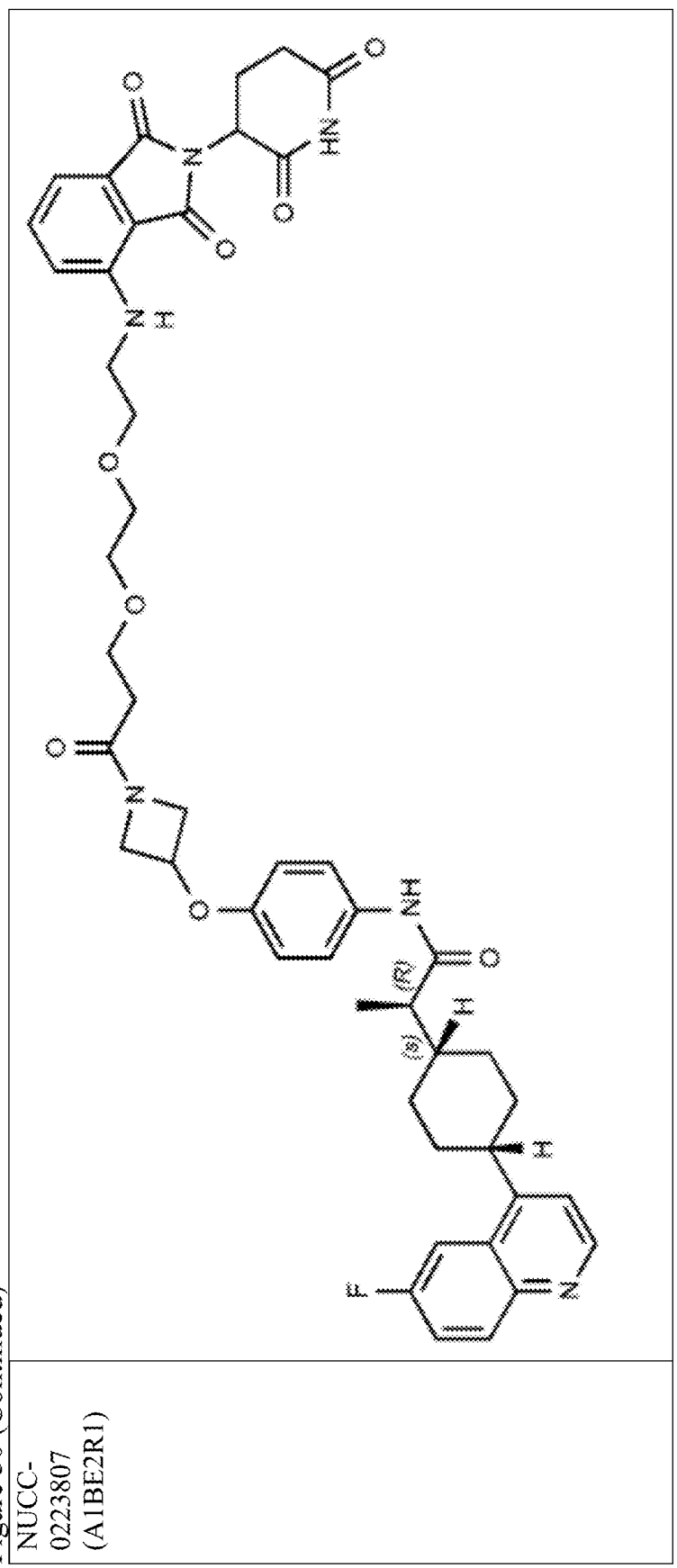
Figure 50:
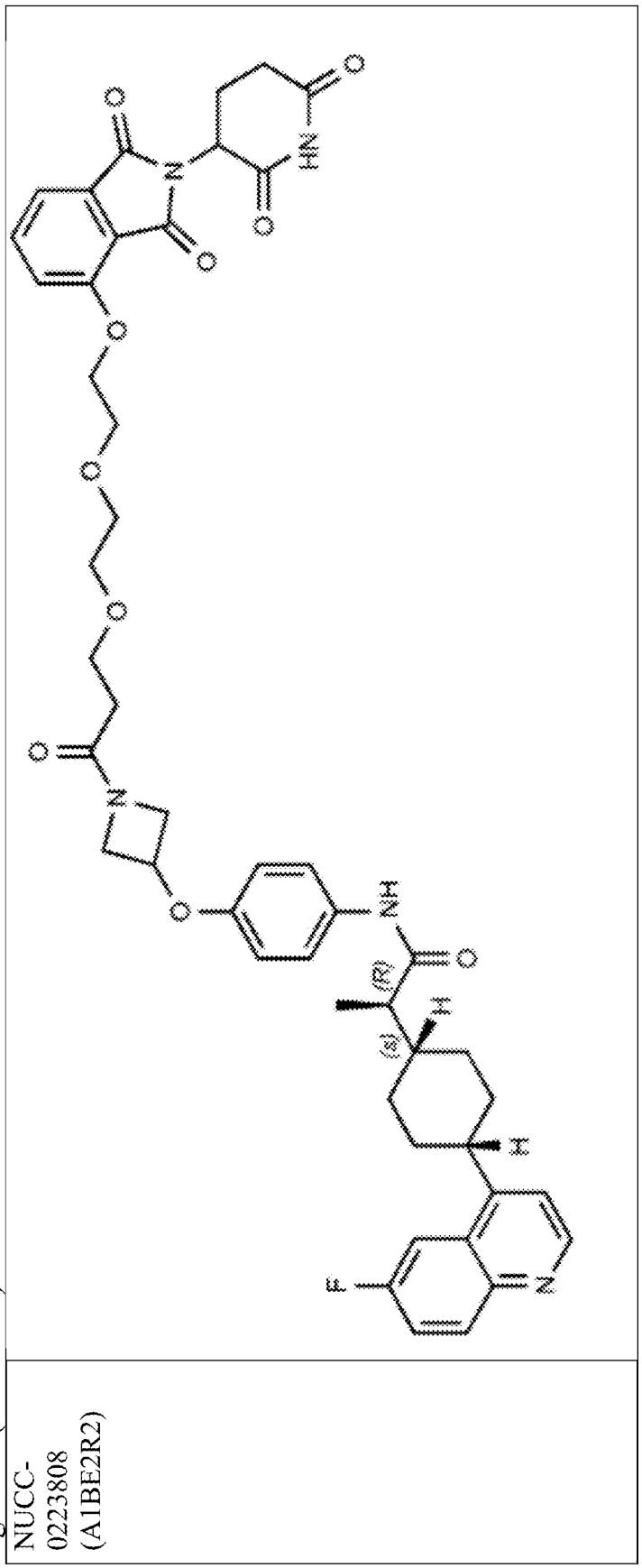
Figure 50:
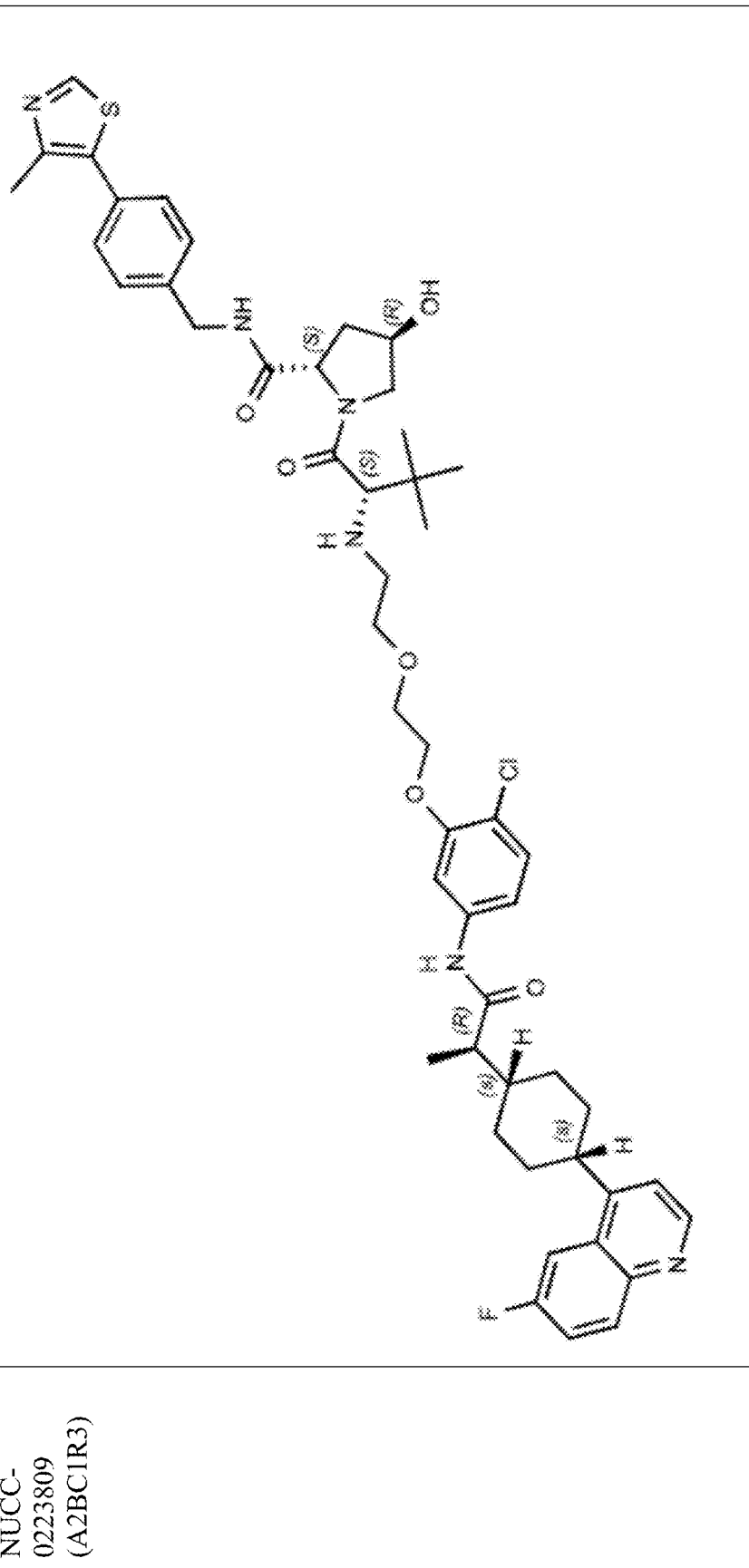
Figure 50:
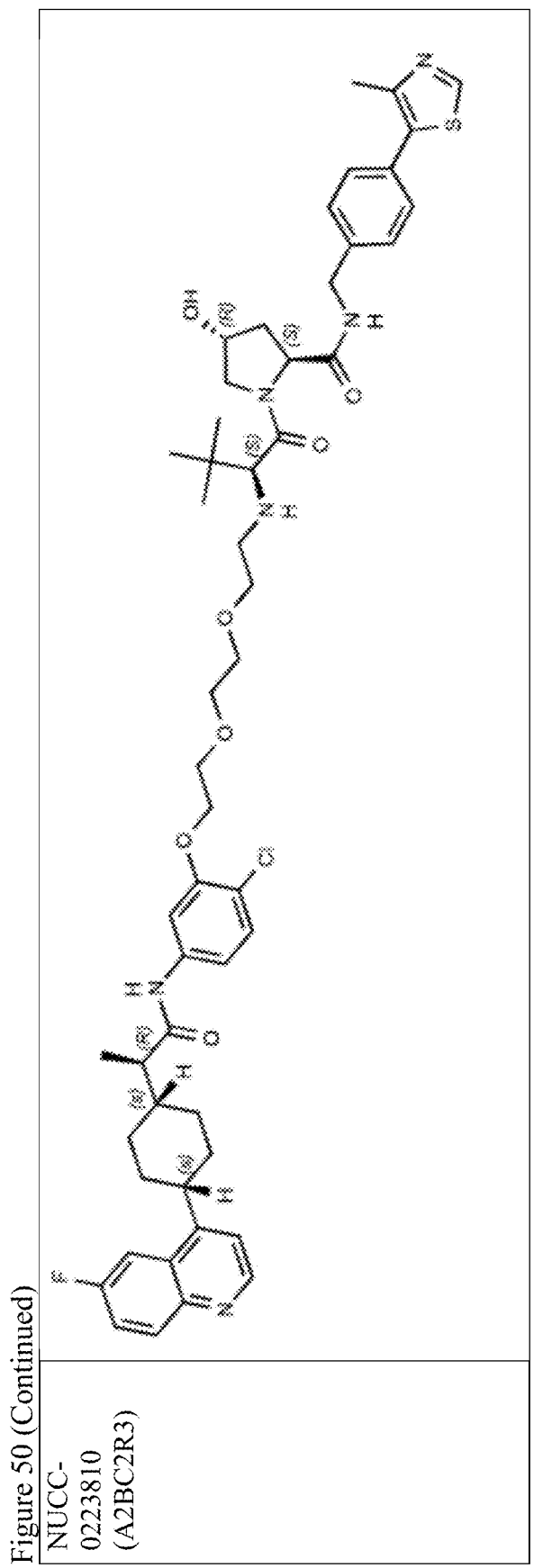
Figure 50:
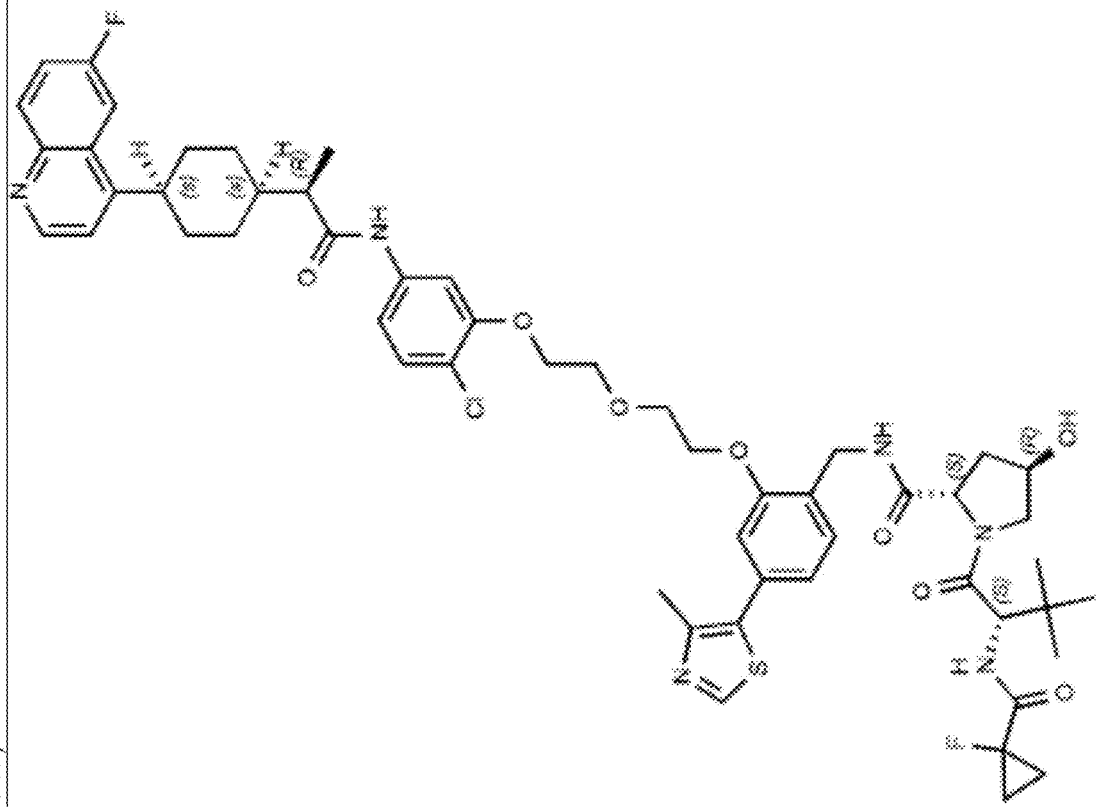
Figure 50:
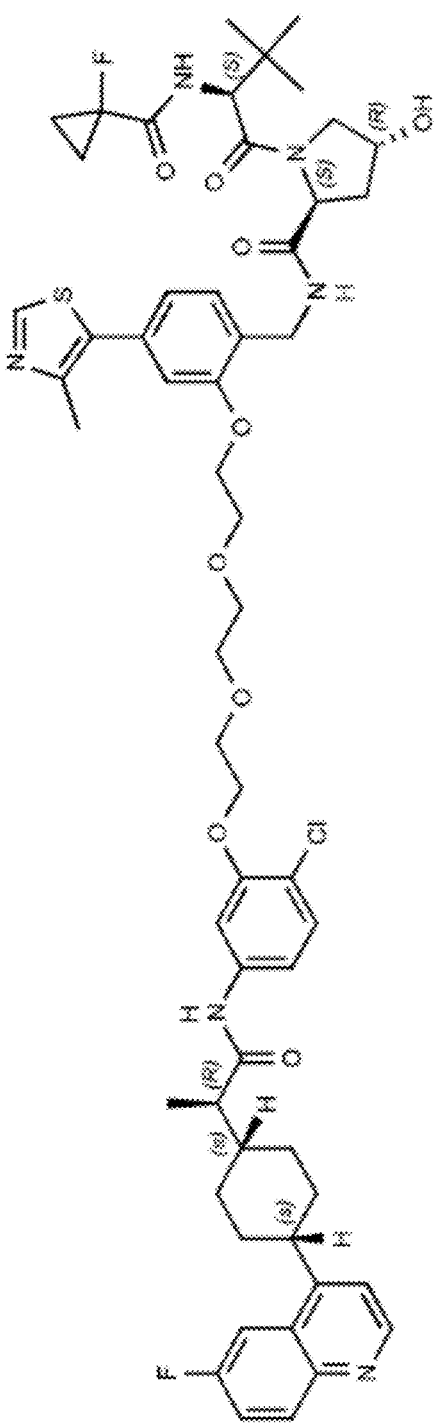
Figure 50:
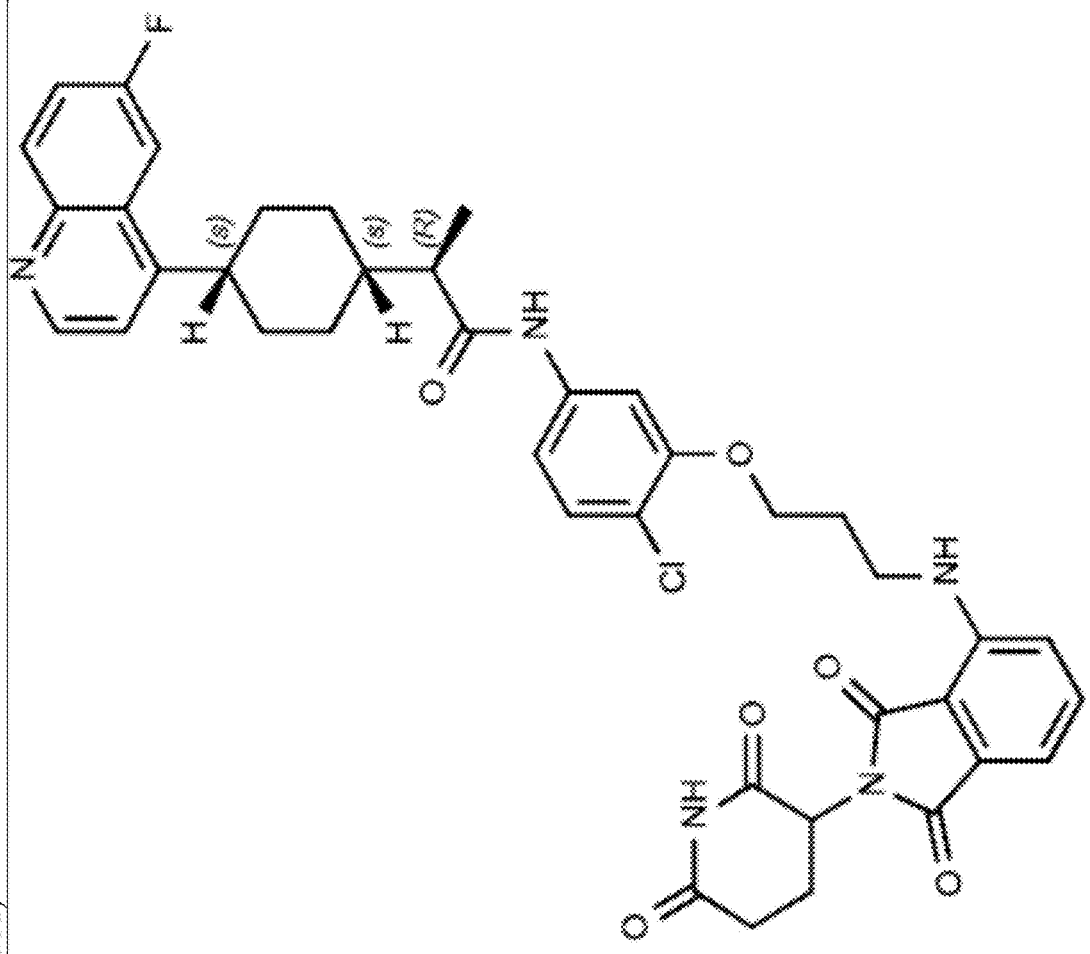
Figure 50:
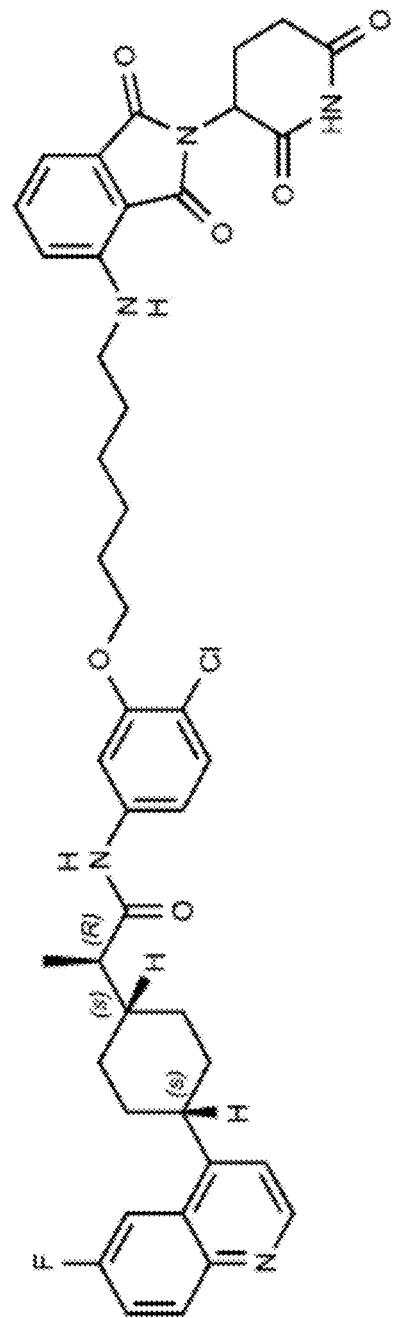
Figure 50:
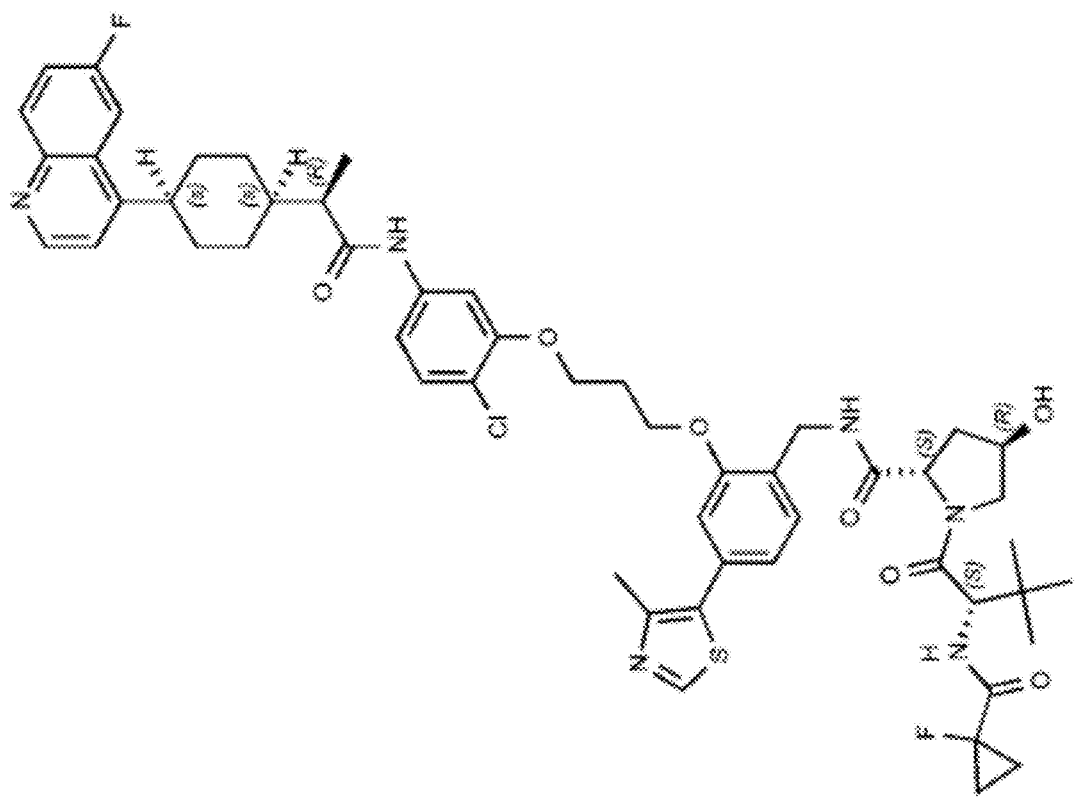
Figure 50:
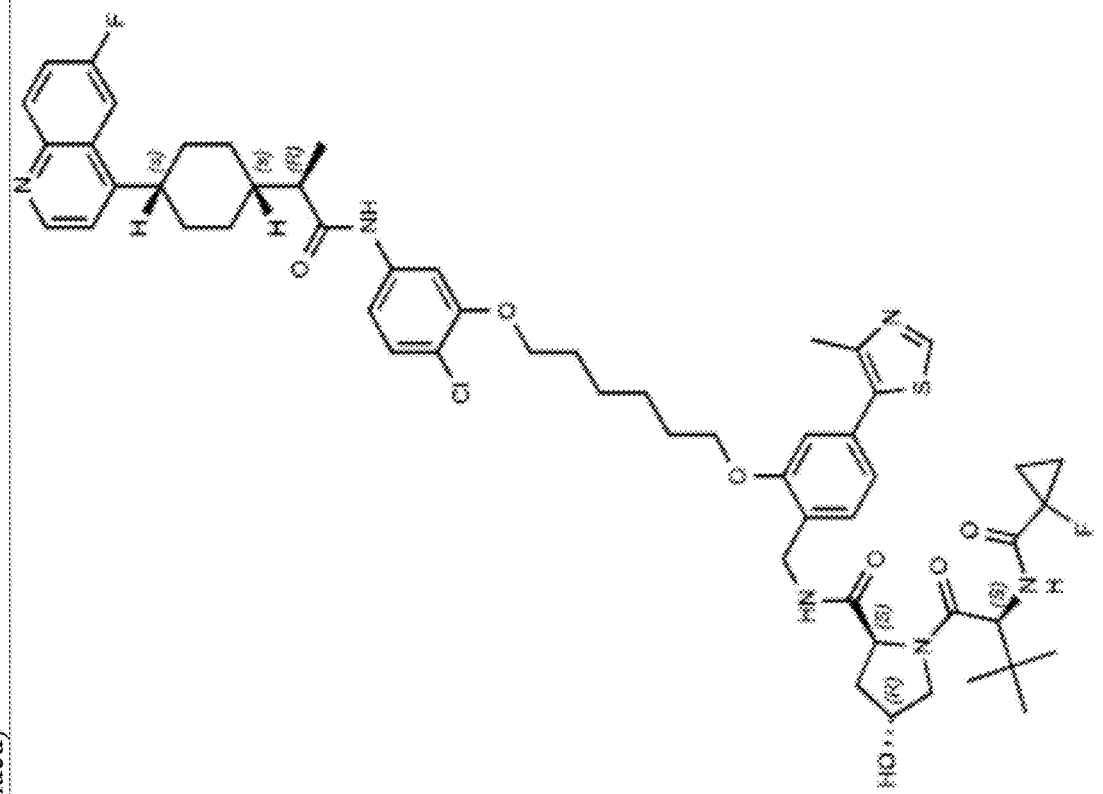
Figure 50:
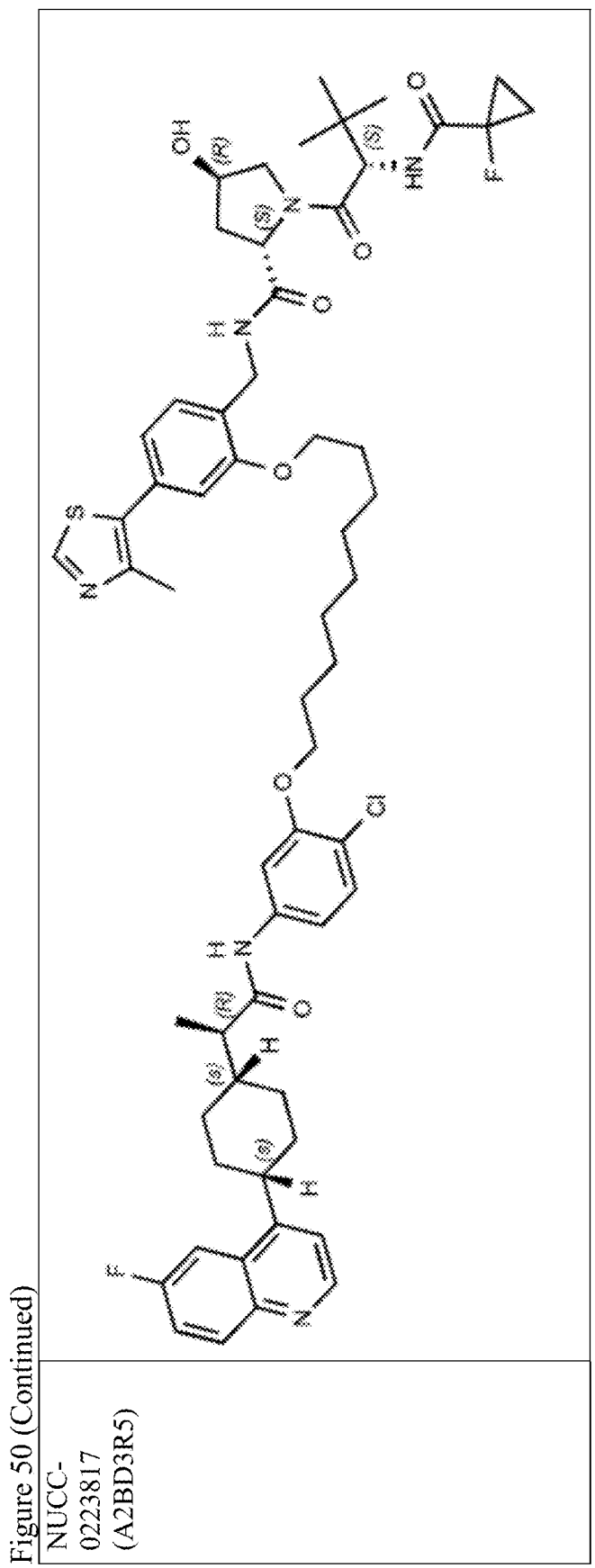
Figure 50:
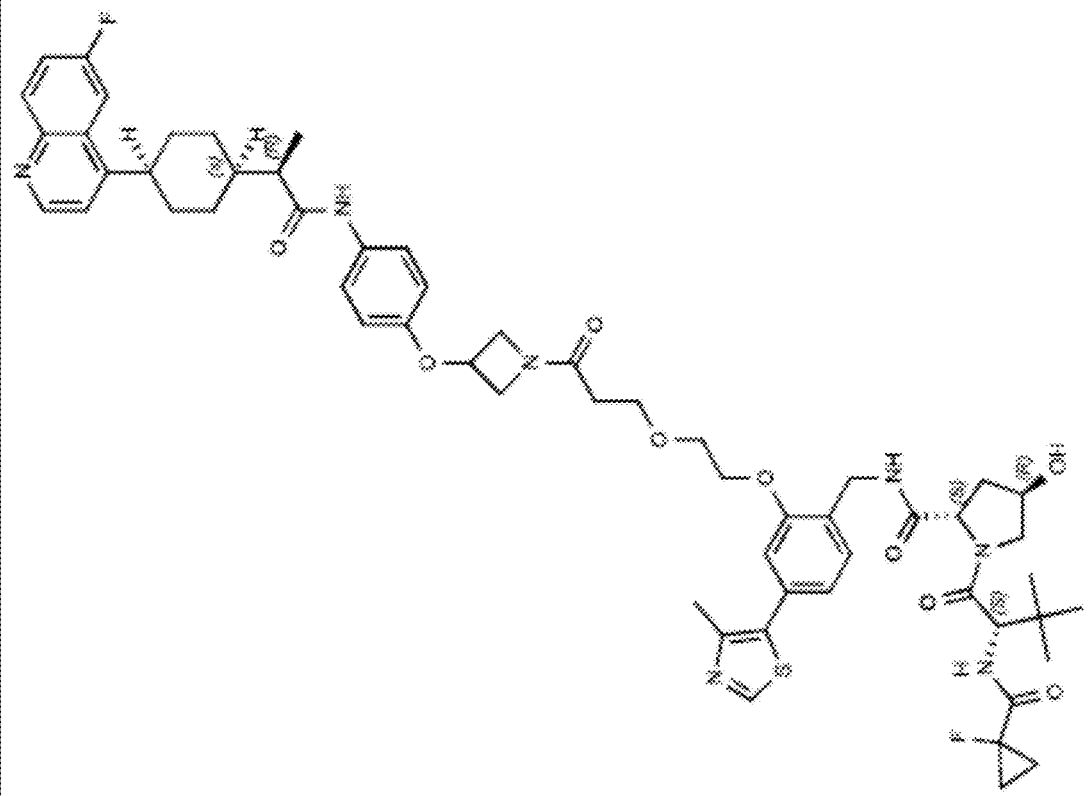
Figure 50:
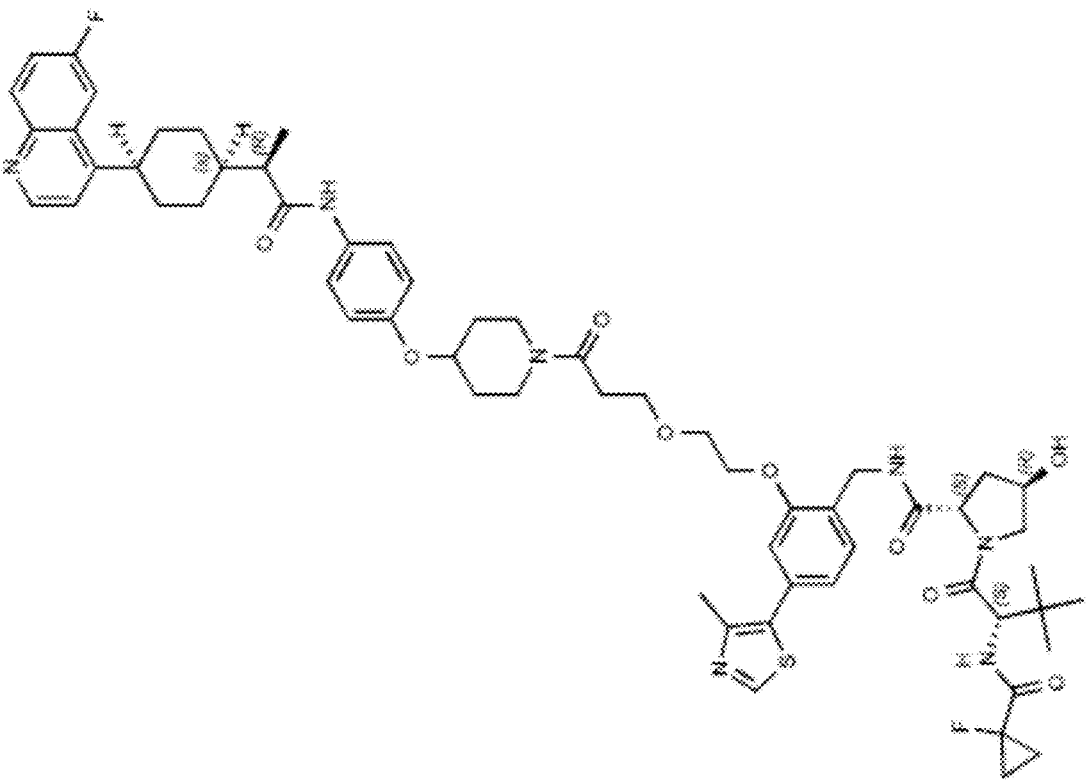
Figure 50:
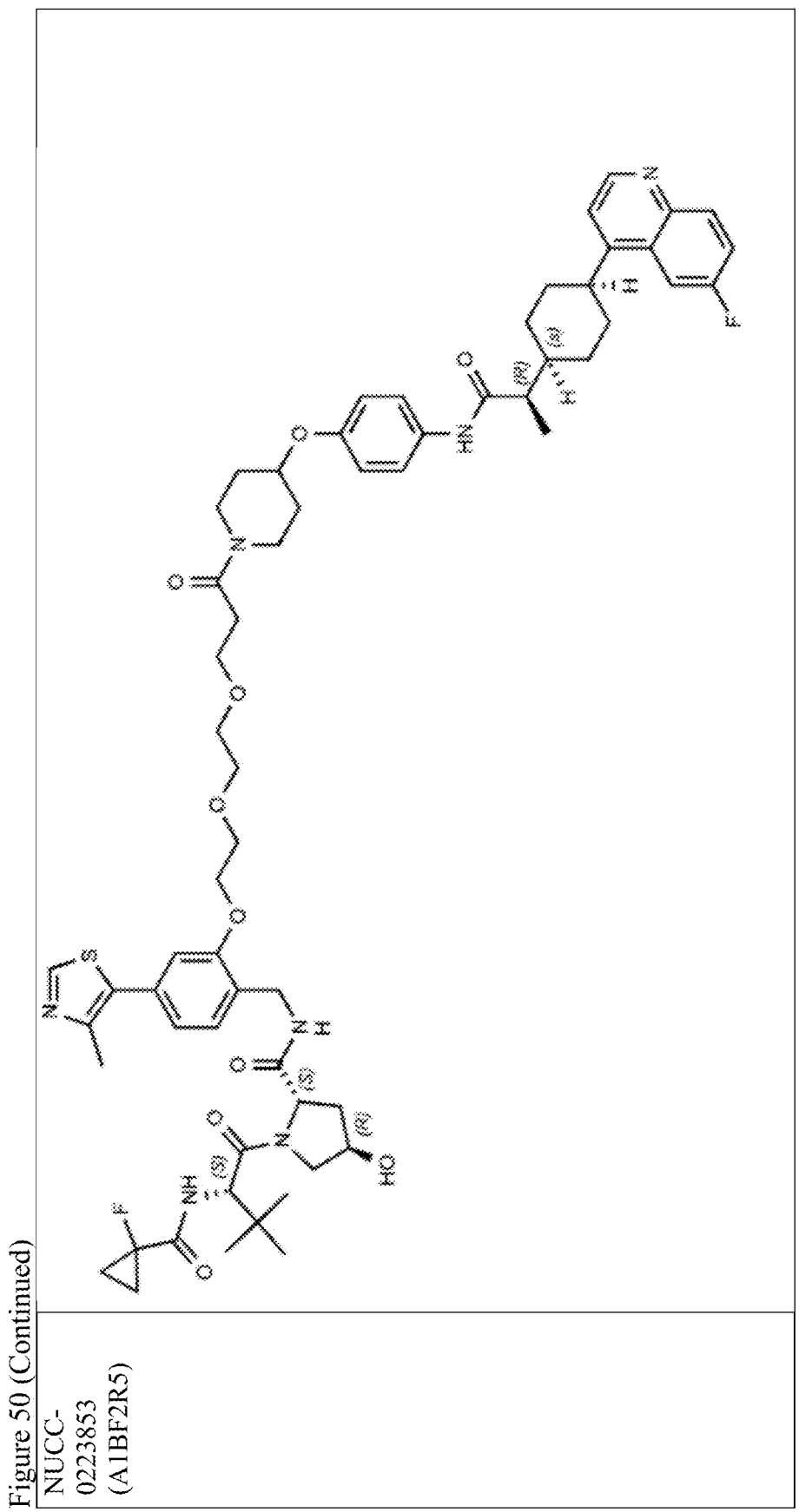
Figure 50:
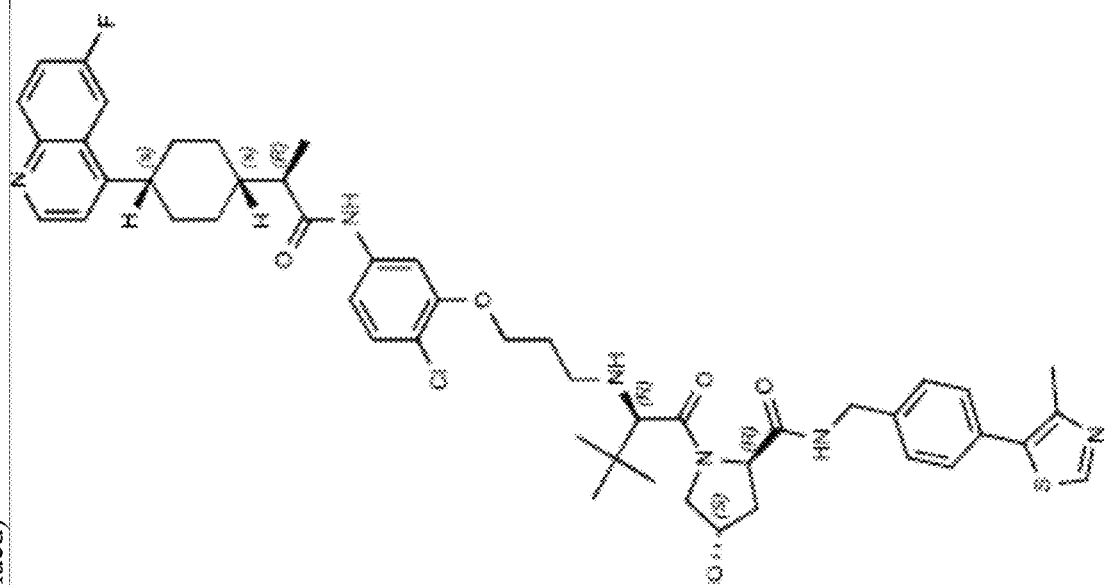
Figure 50:
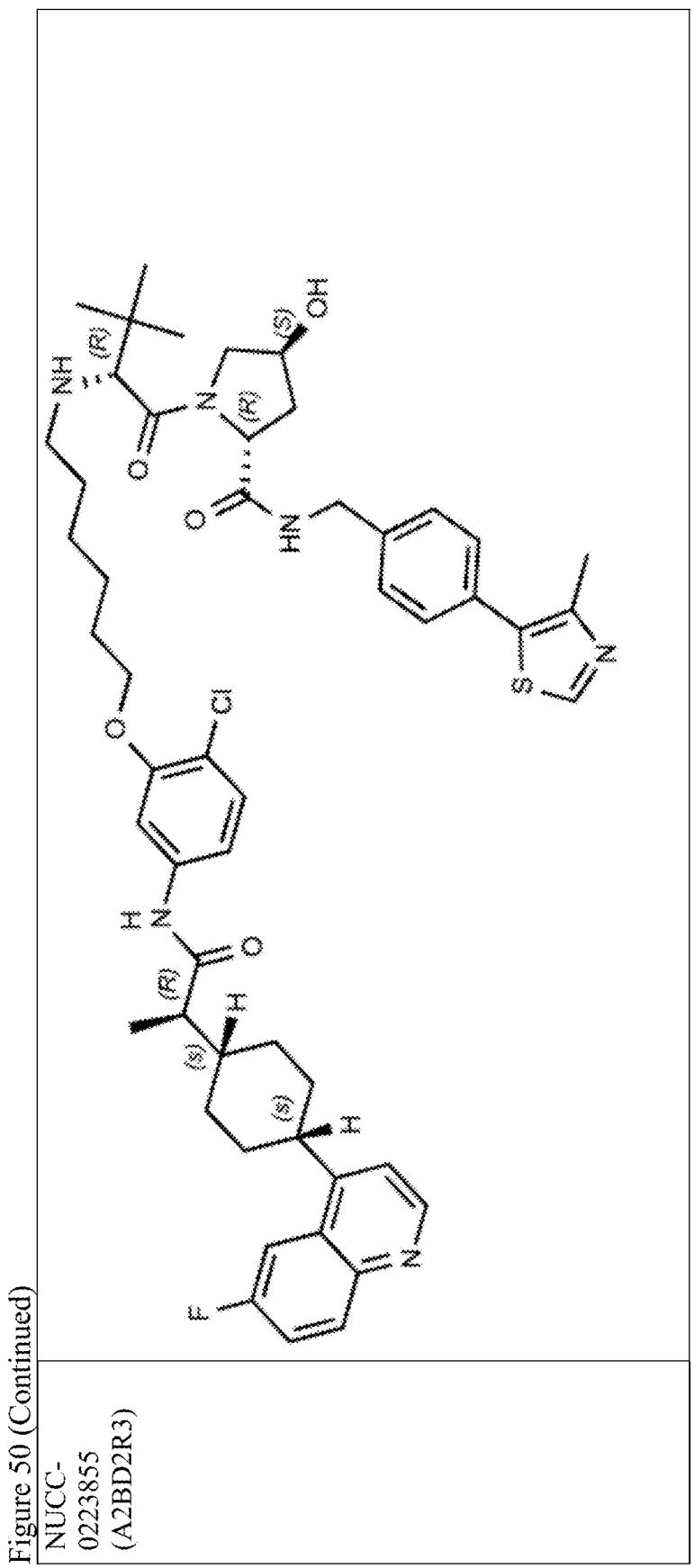
Figure 50:
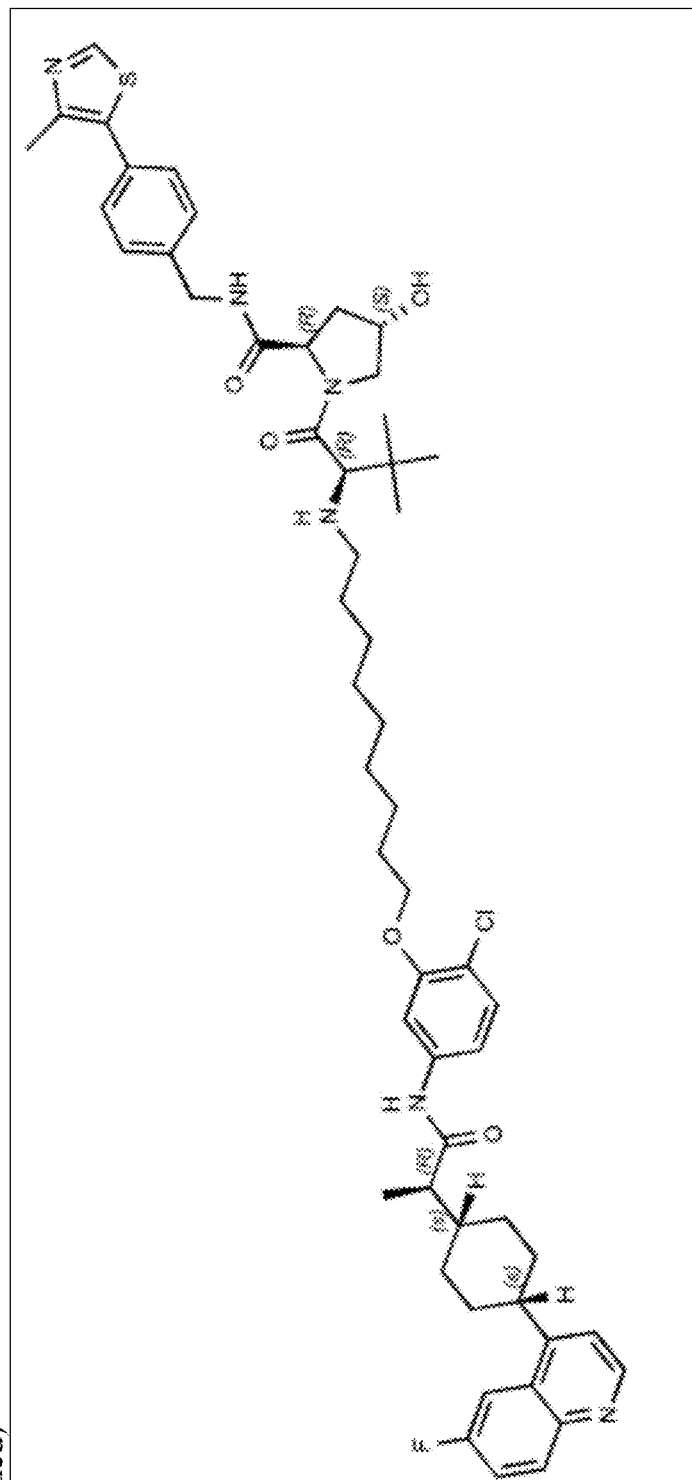
Figure 50:
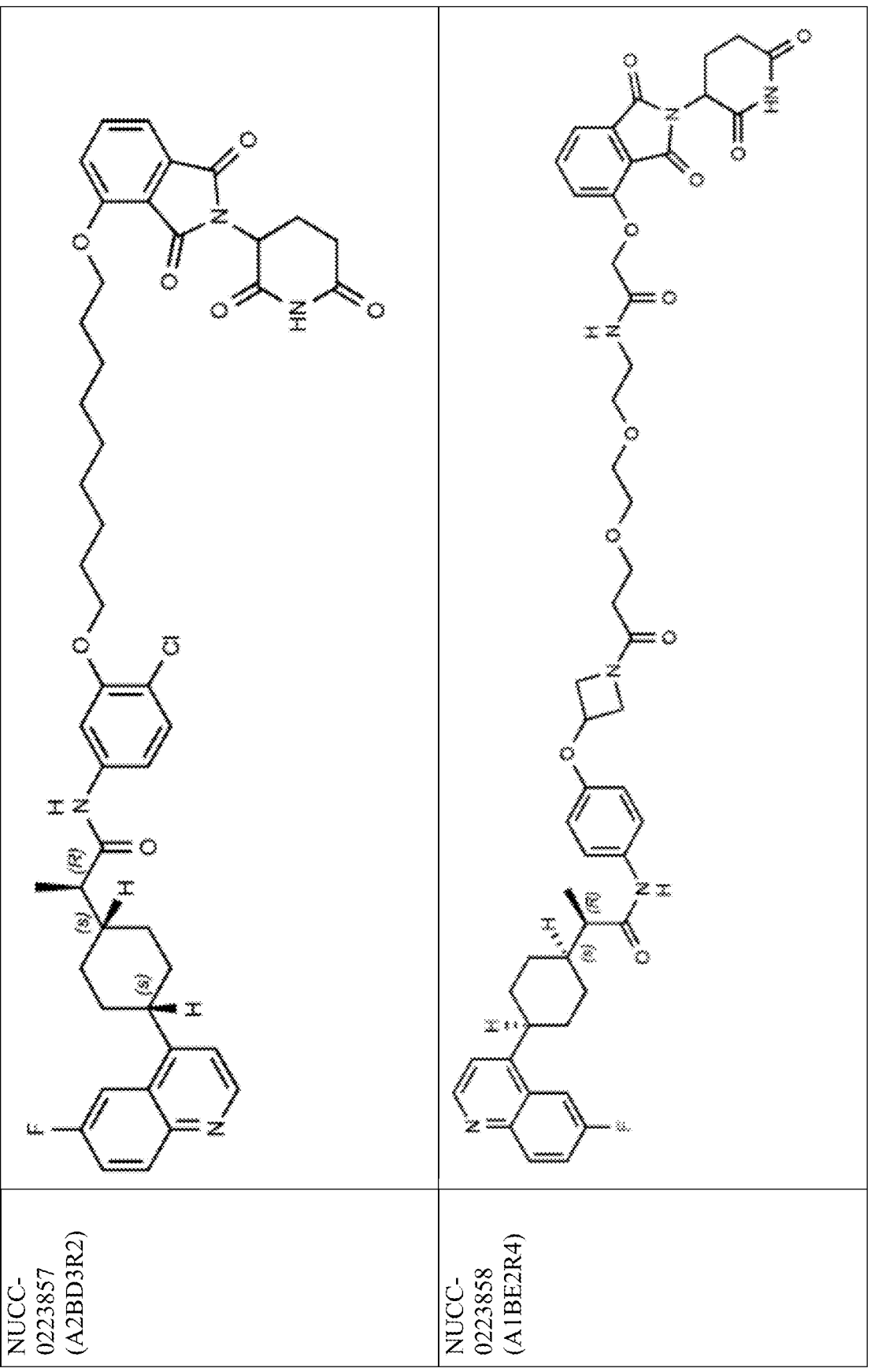
Figure 50:
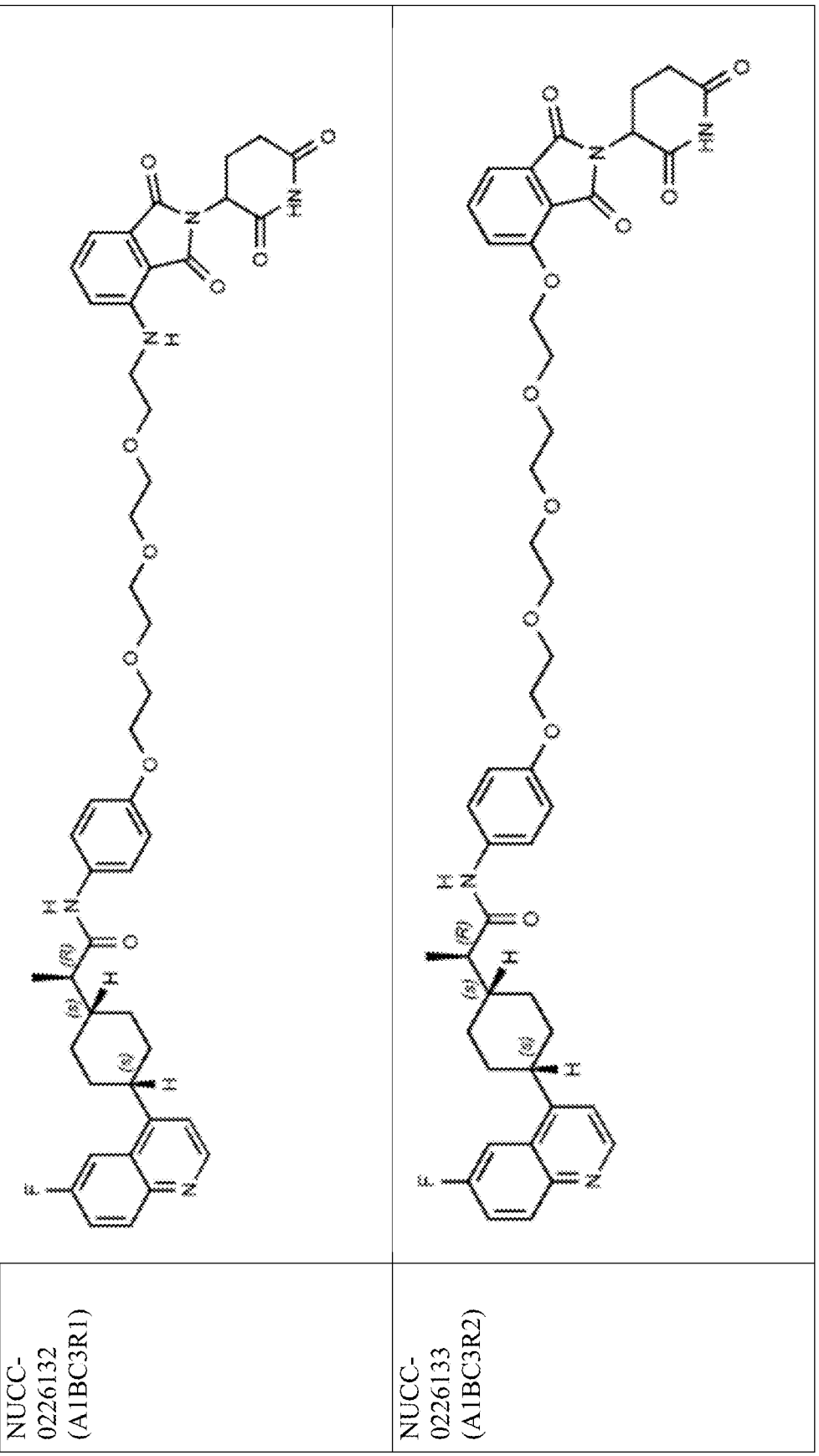
Figure 50:
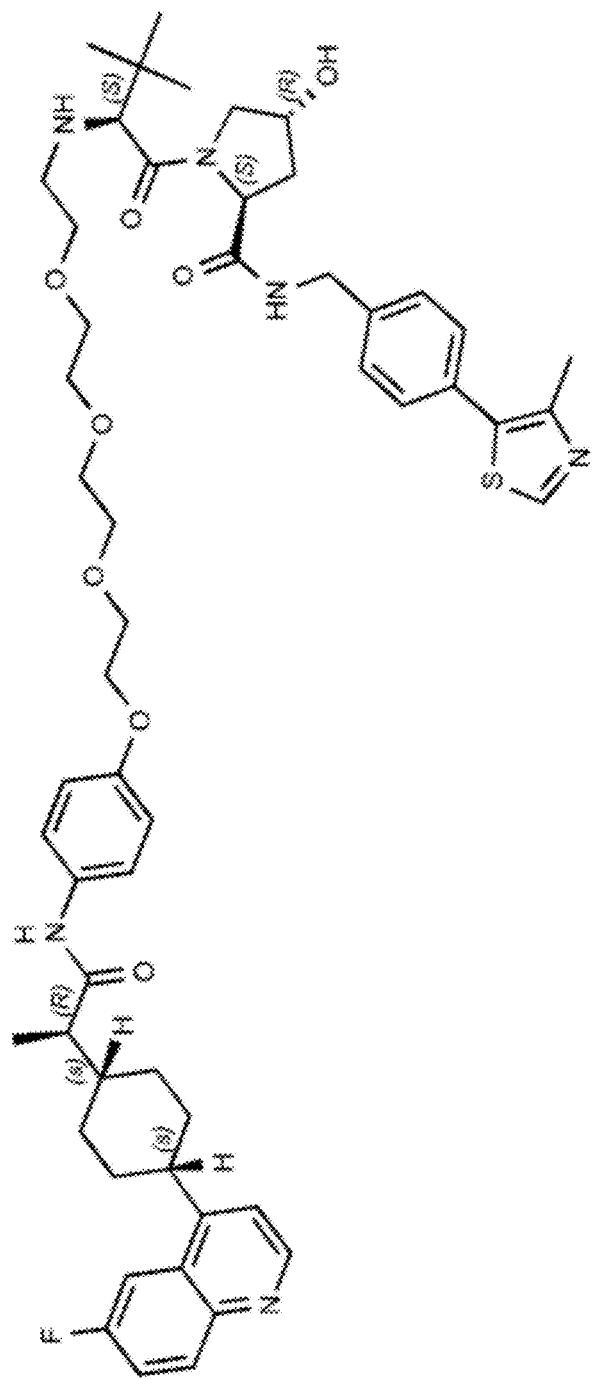
Figure 50:
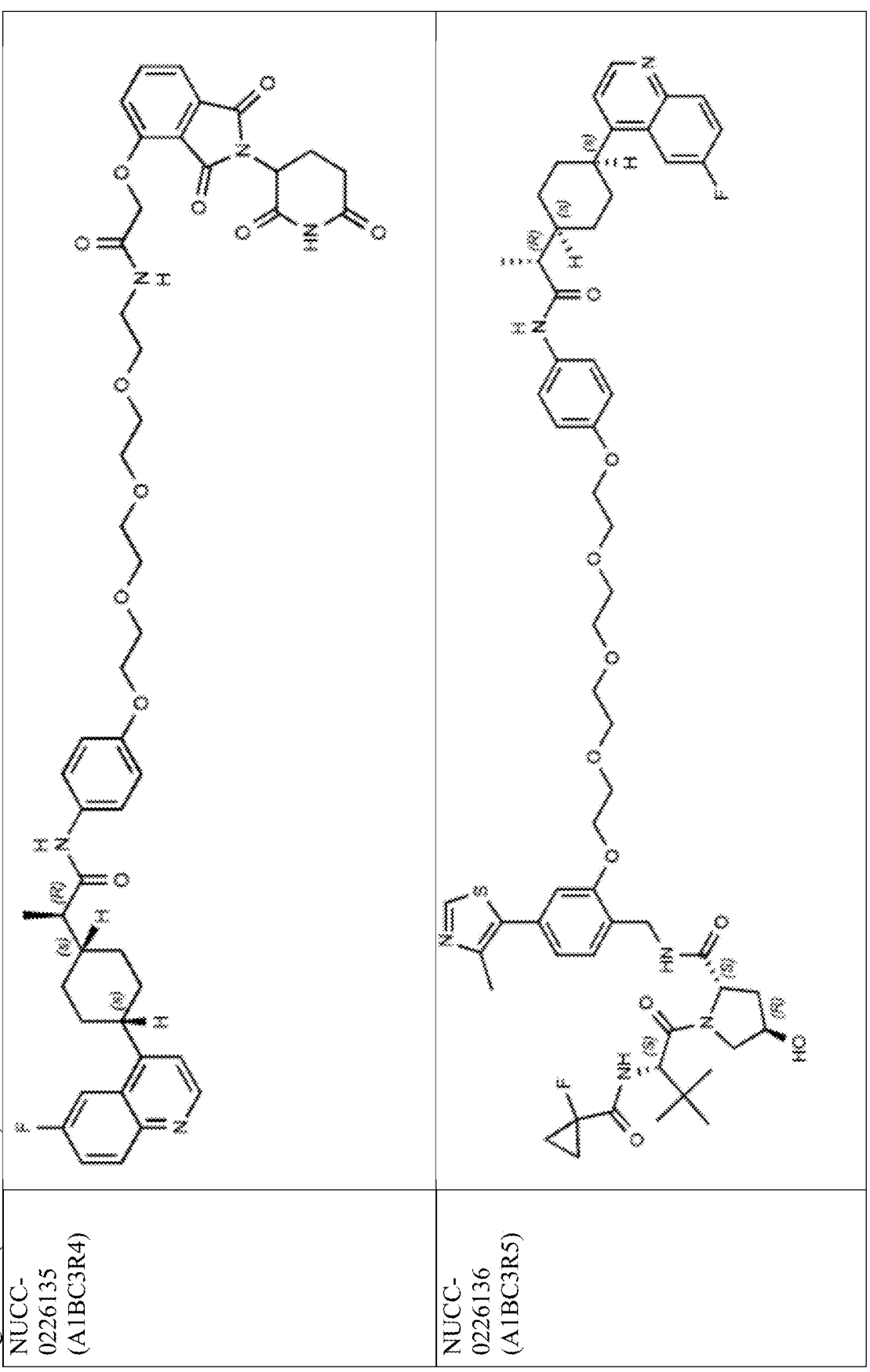
Figure 50:
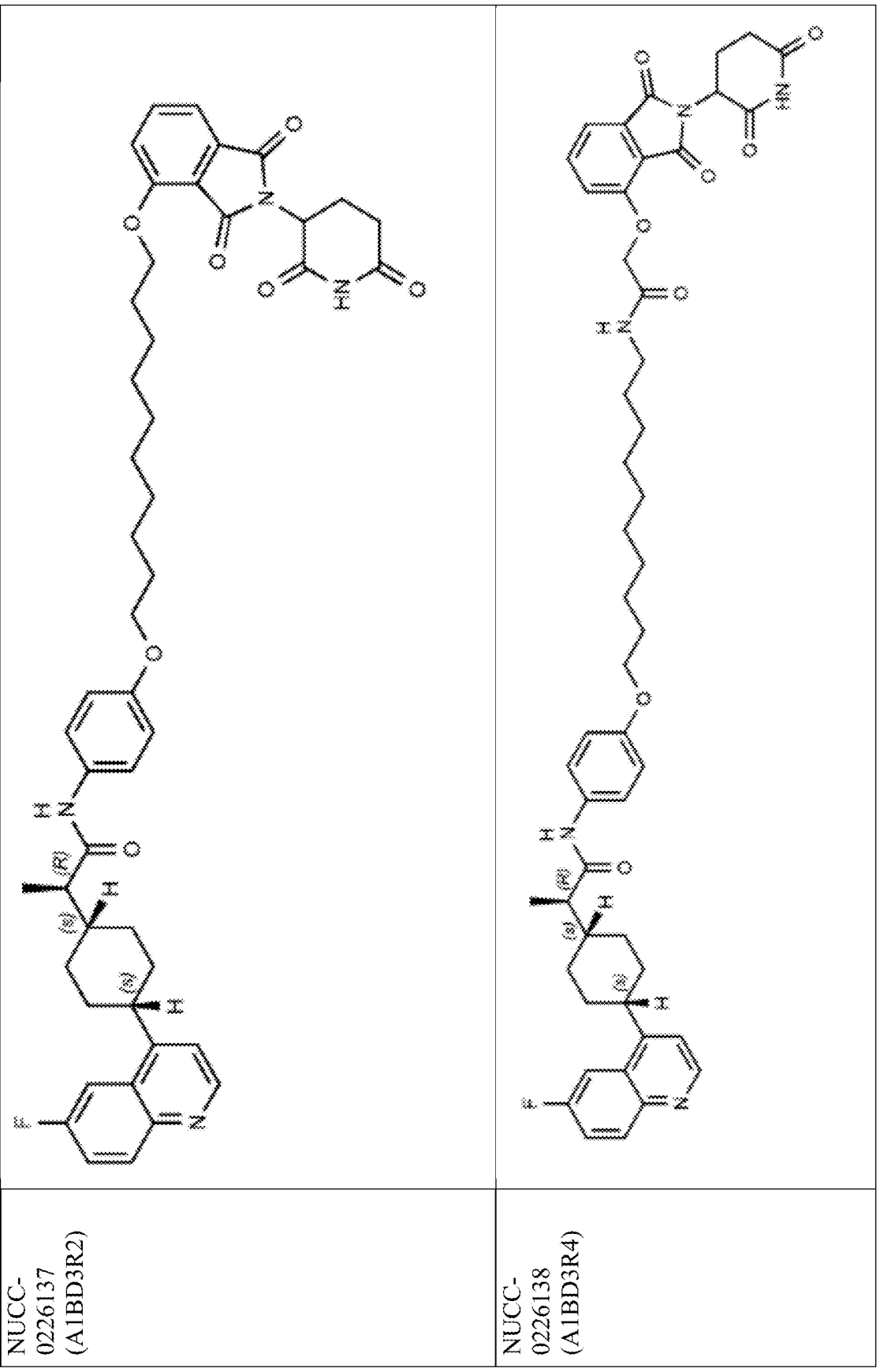
Figure 50:
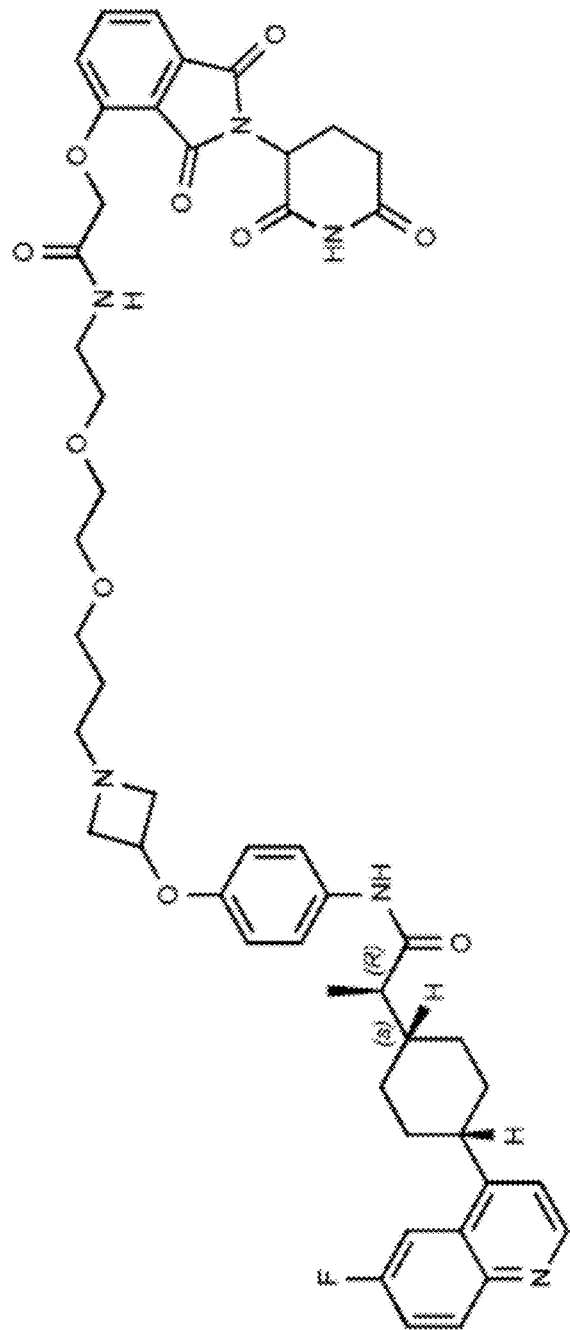
Figure 50:
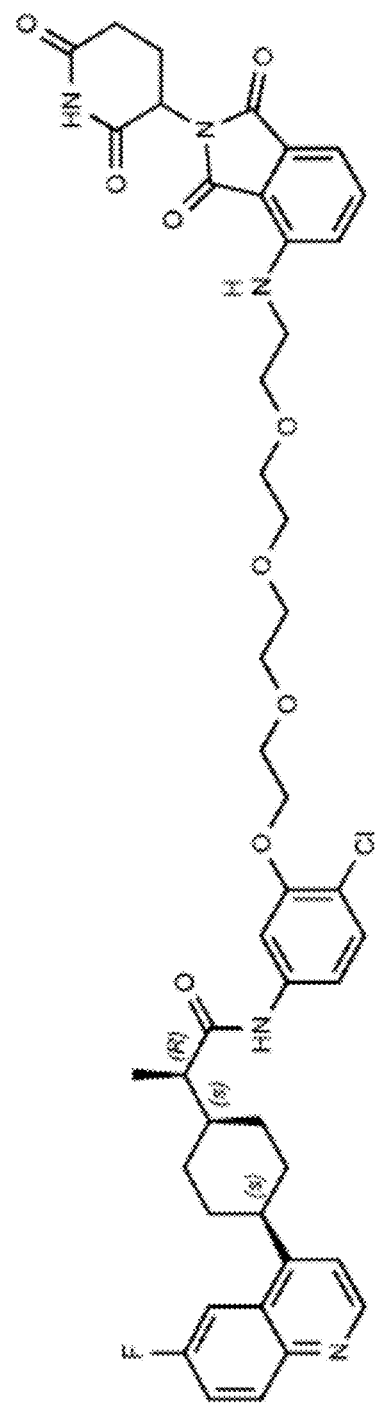
Figure 50:
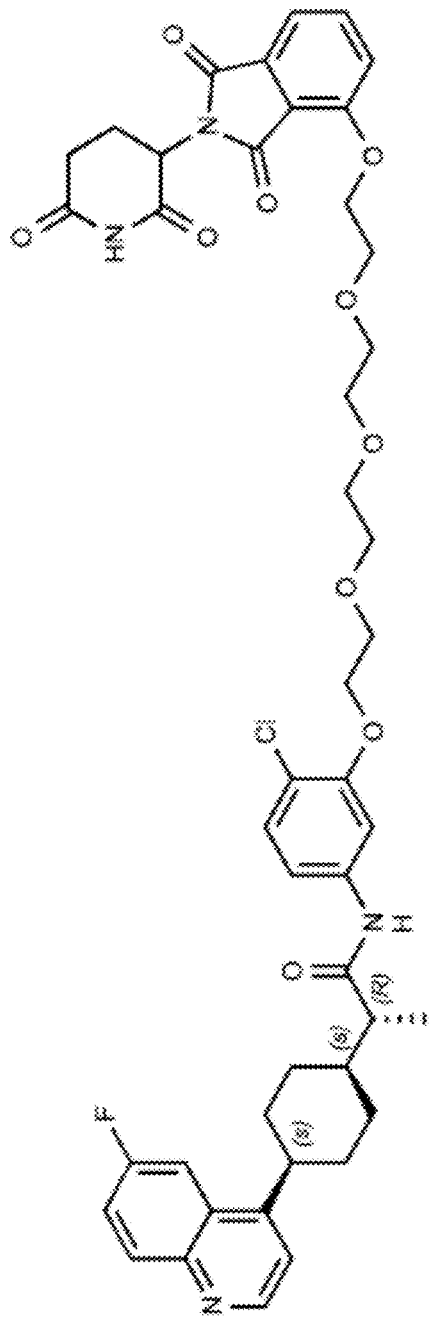
Figure 50:
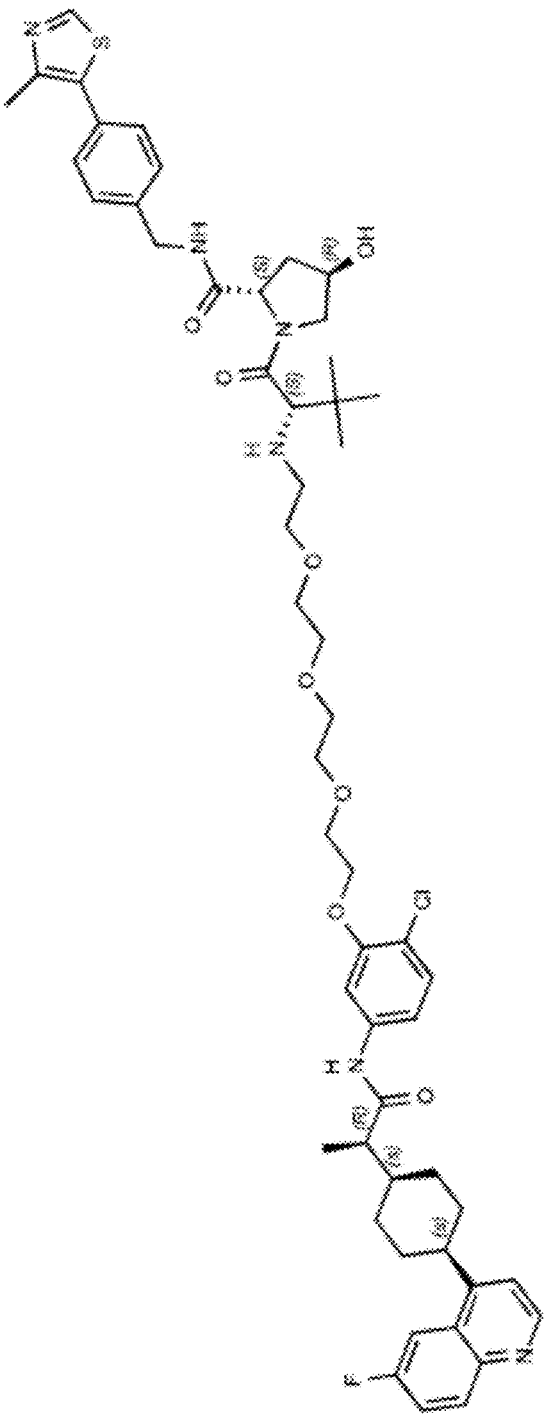
Figure 50:
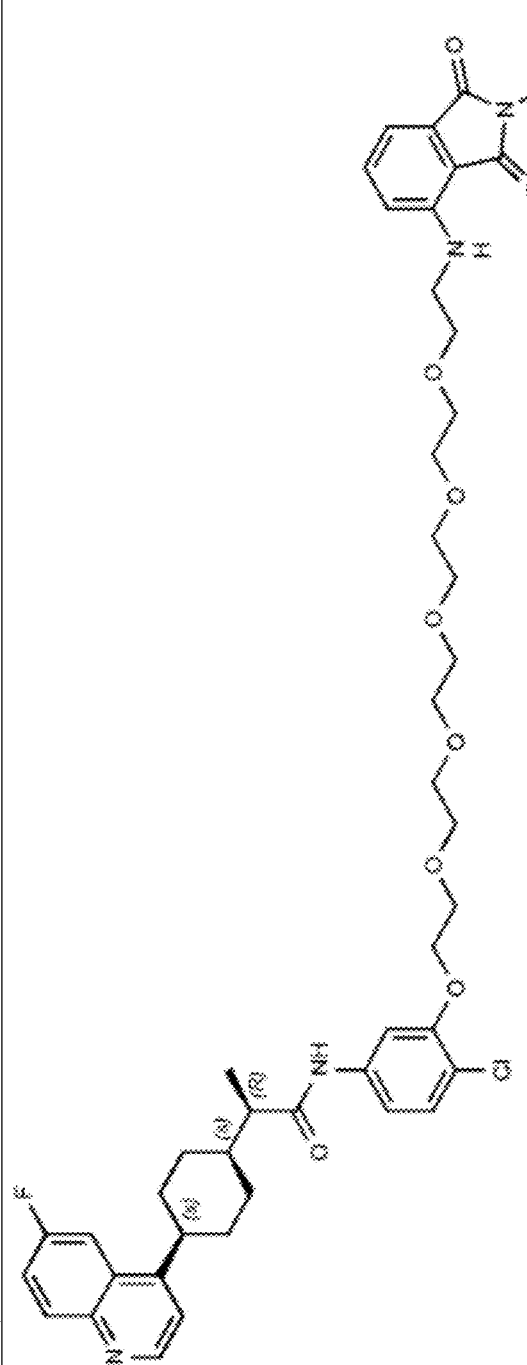
Figure 50:
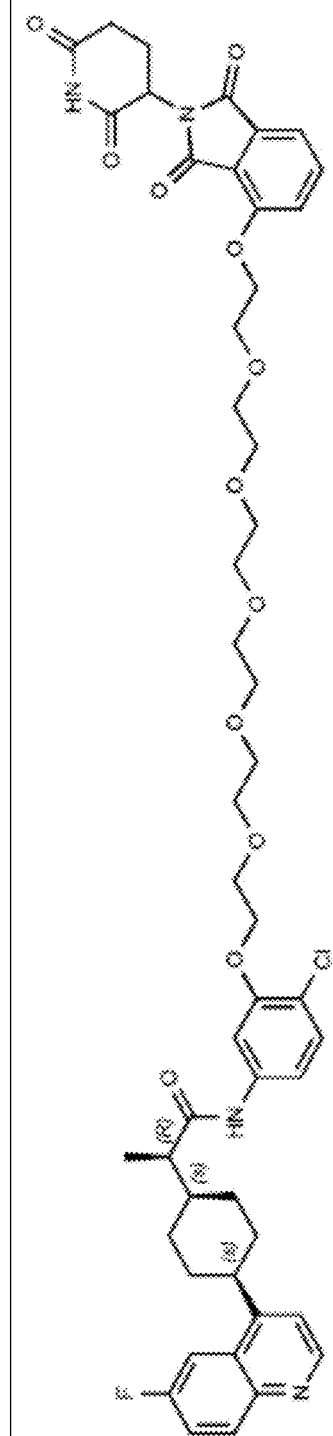
Figure 50:
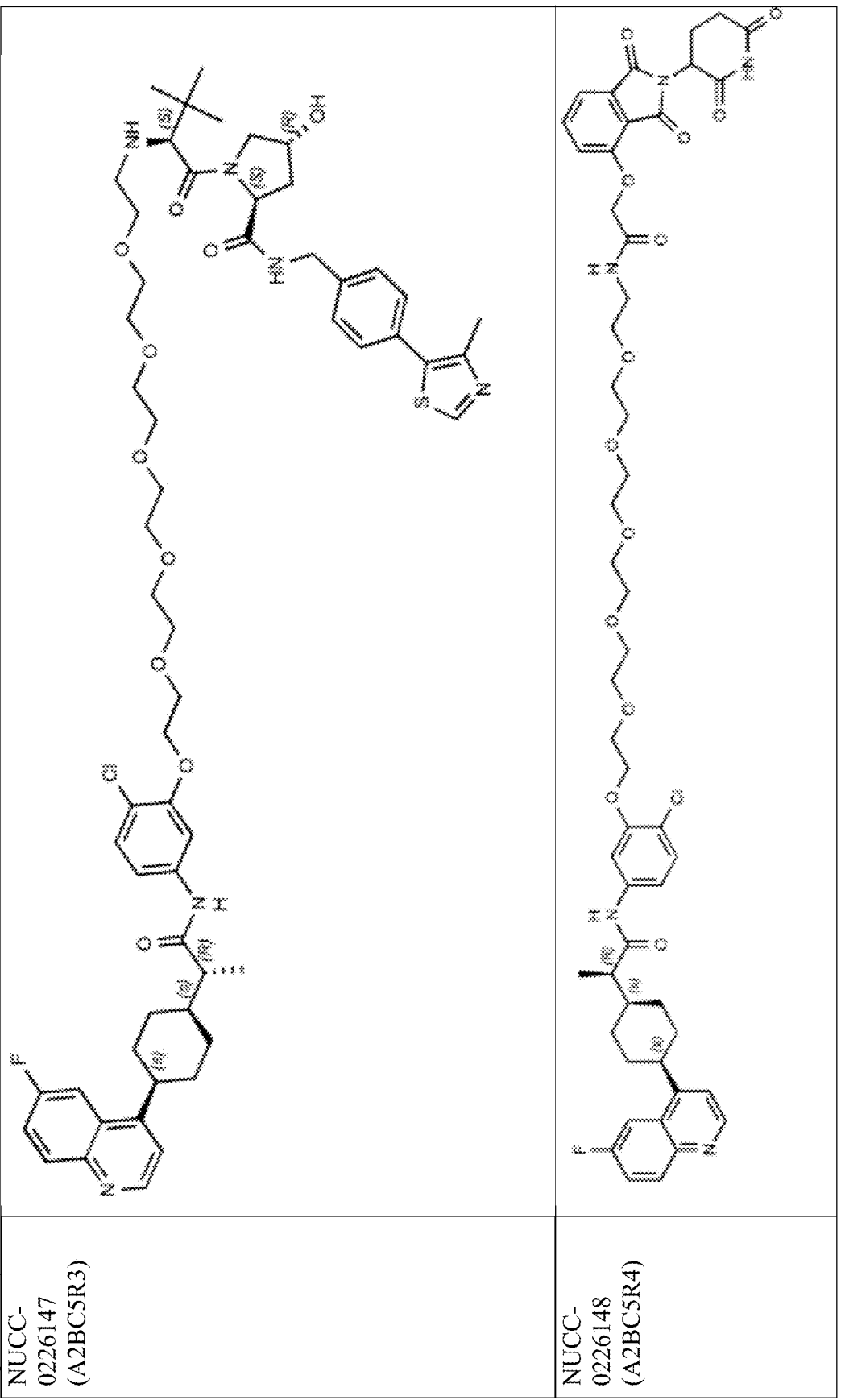
Figure 50:
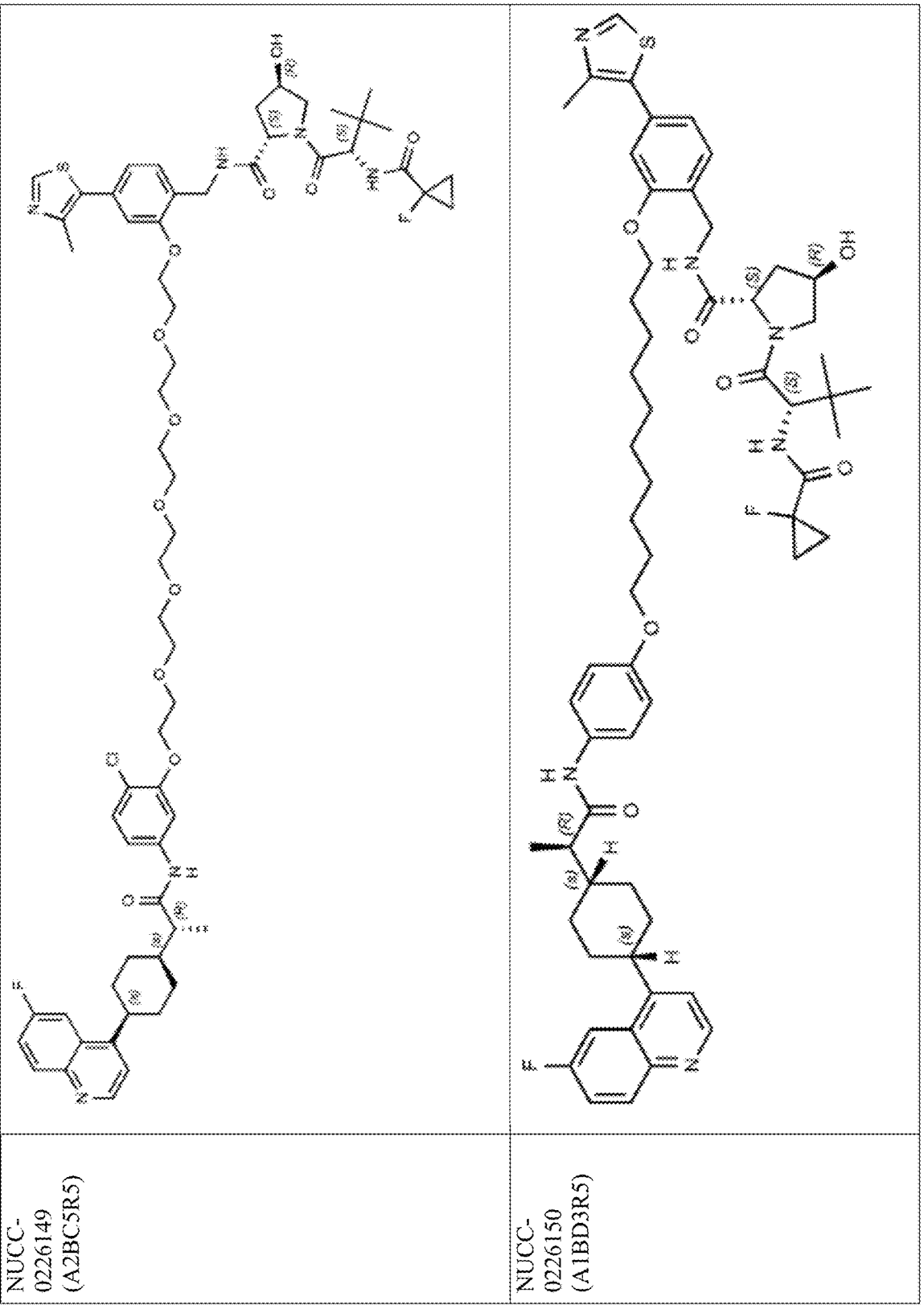
Figure 50:
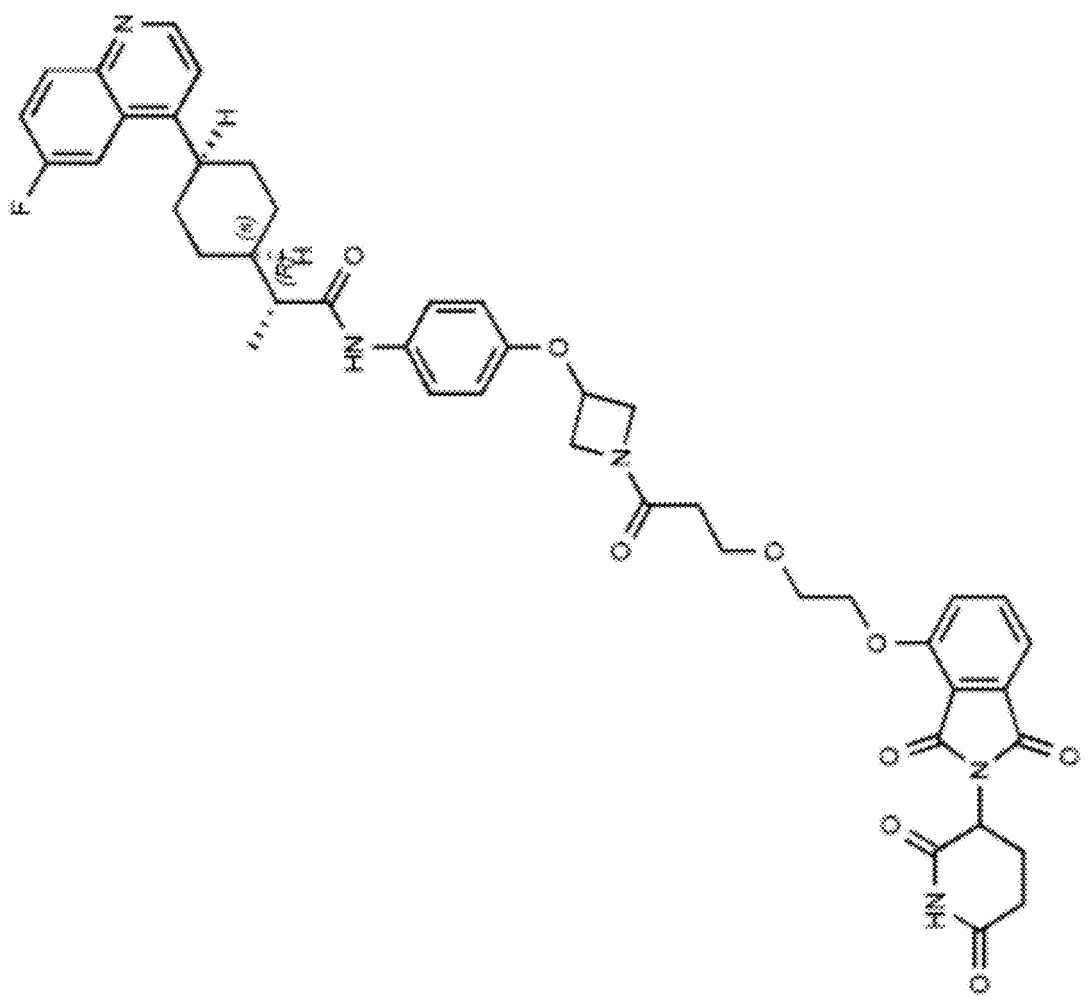
Figure 50:
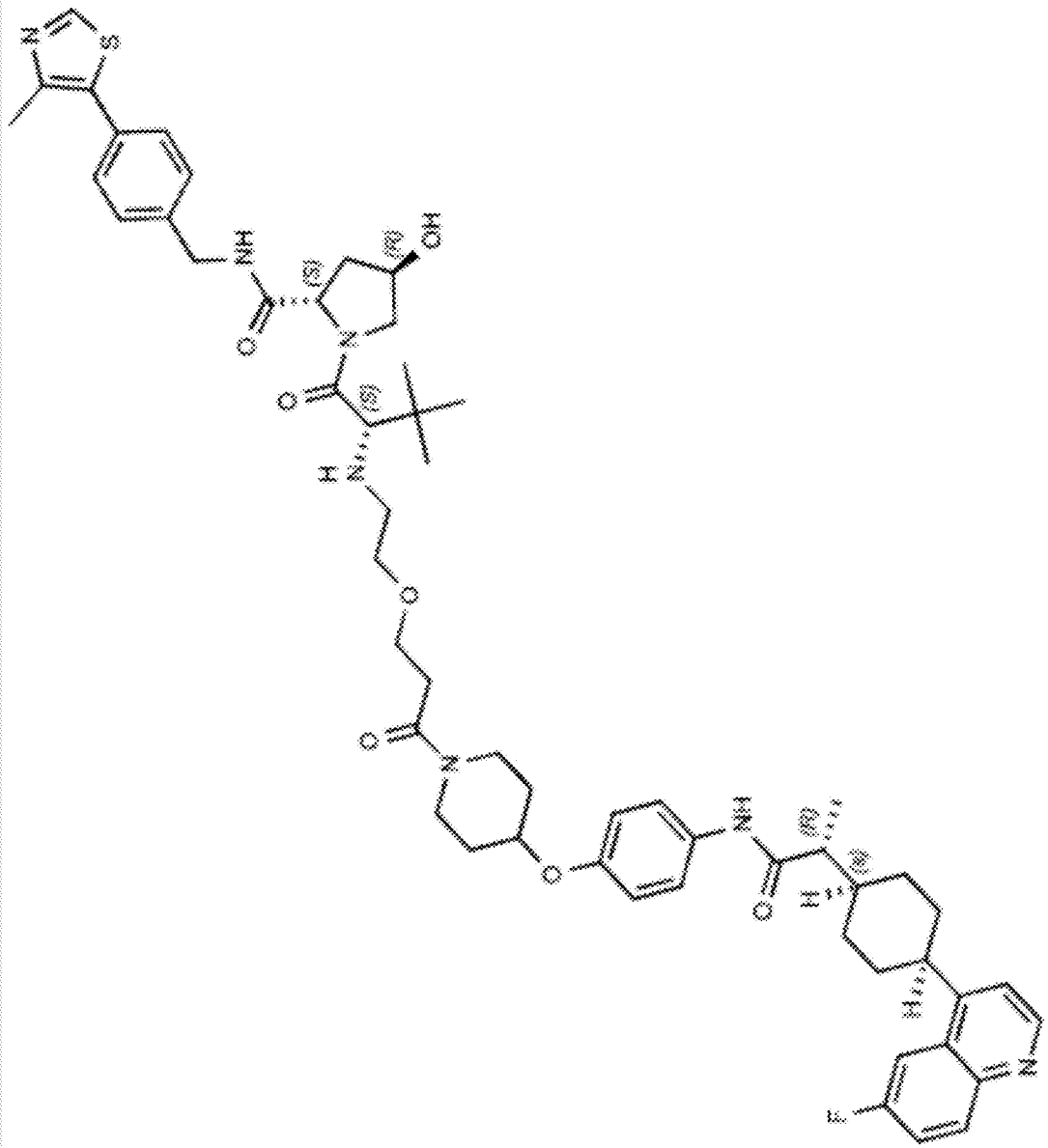
Figure 50:
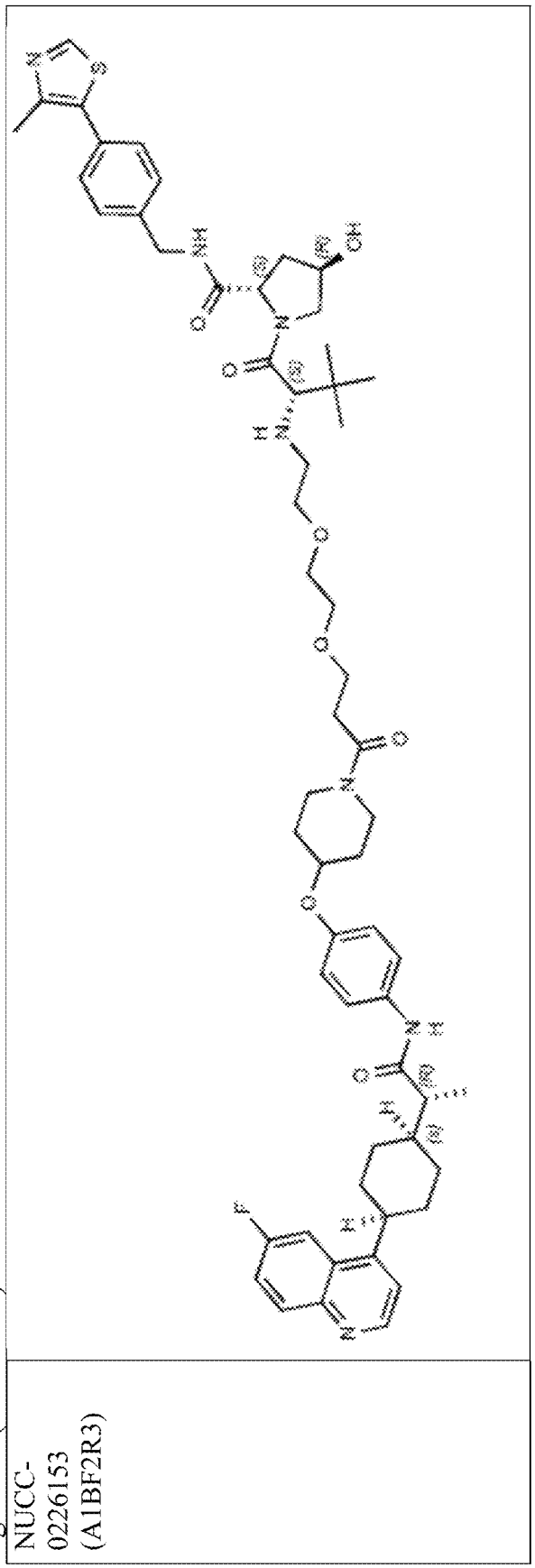
Figure 50:
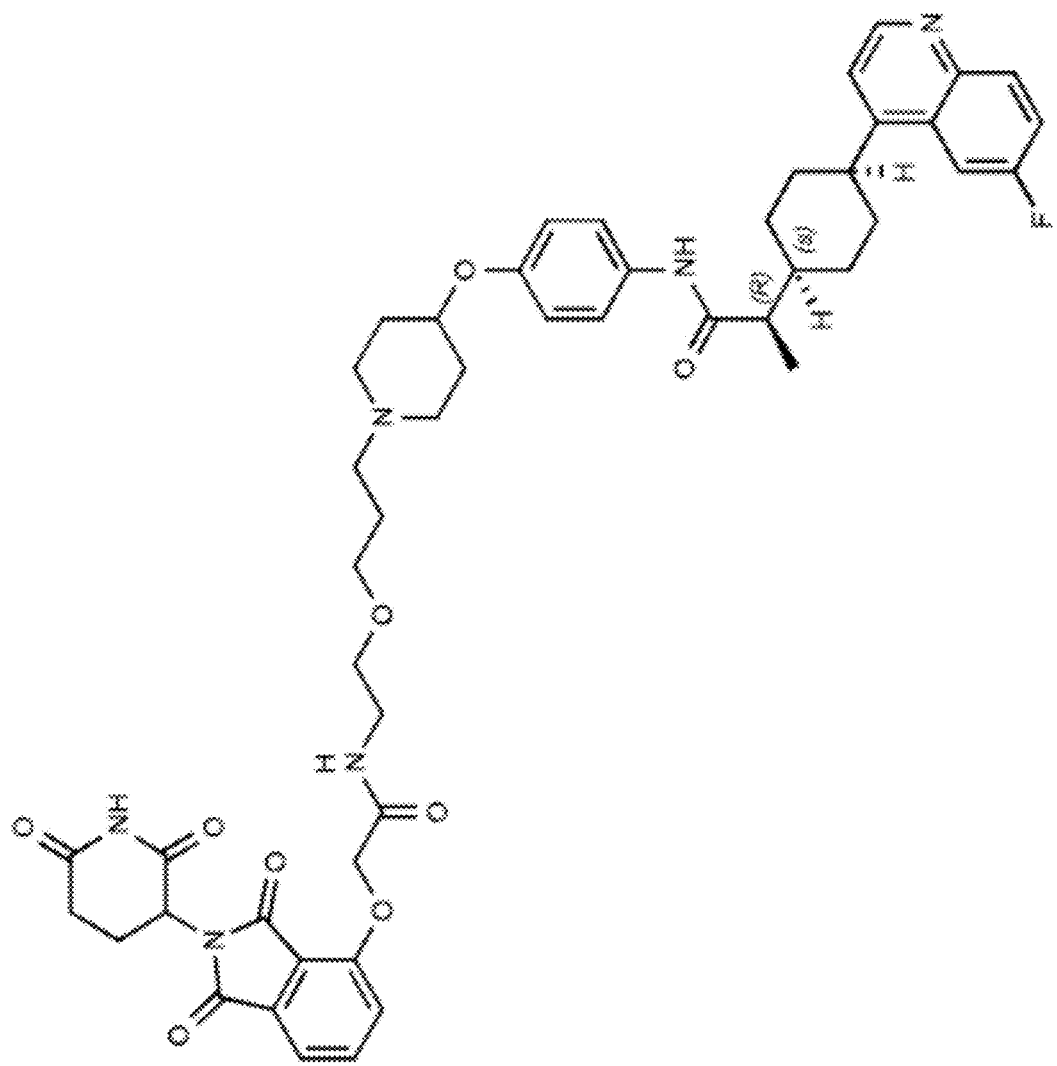
Figure 50:
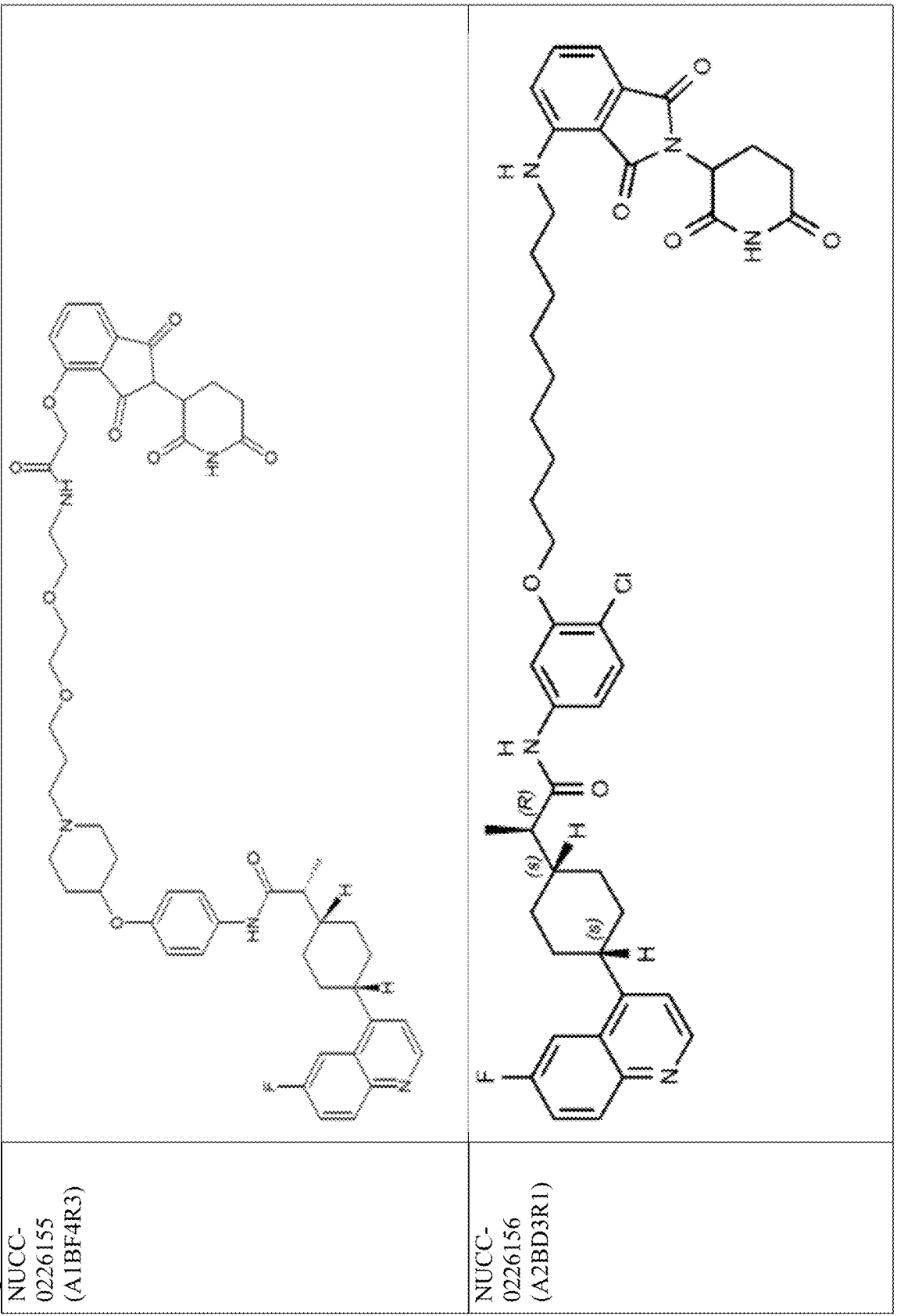
Figure 50:
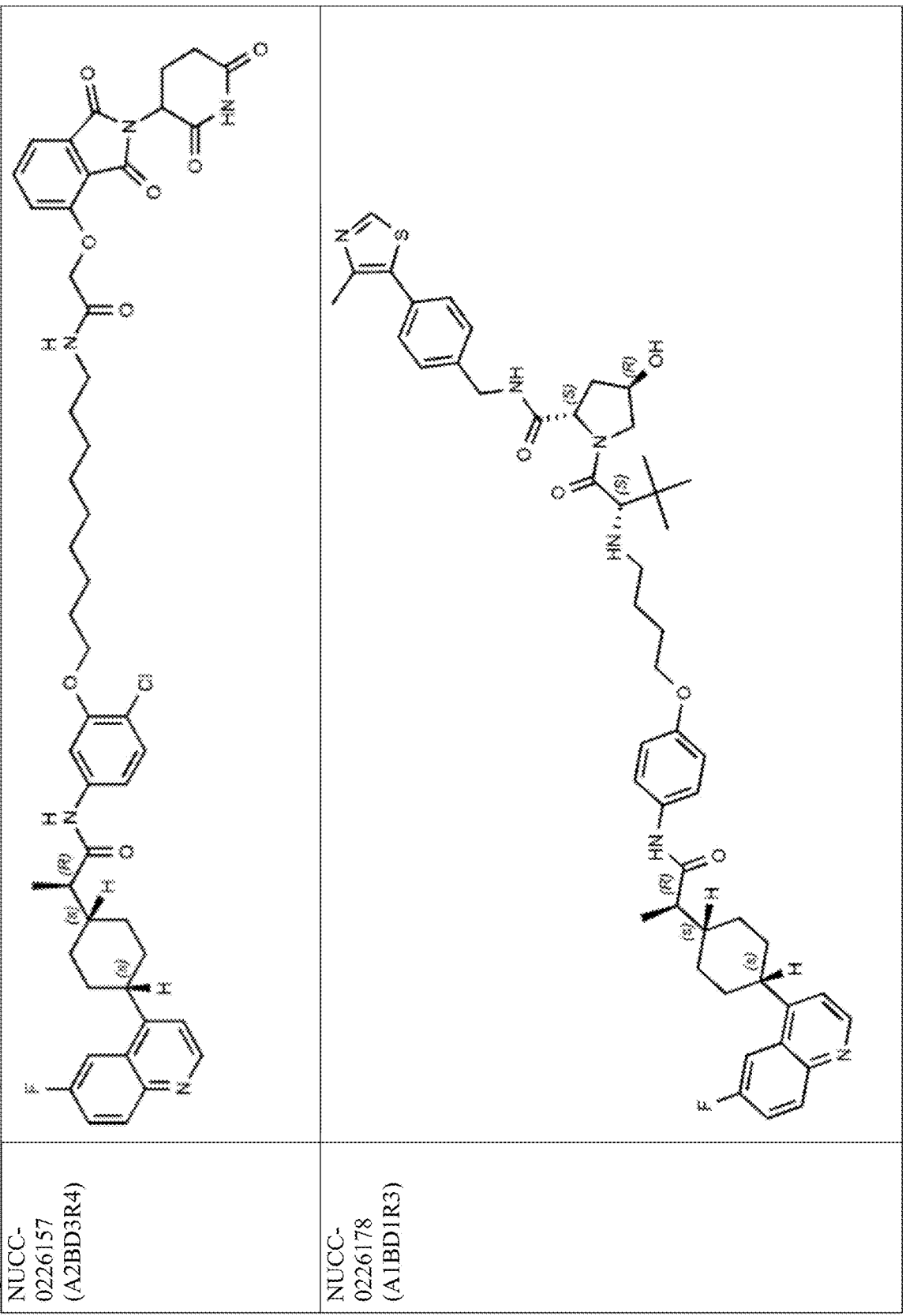
Figure 50:
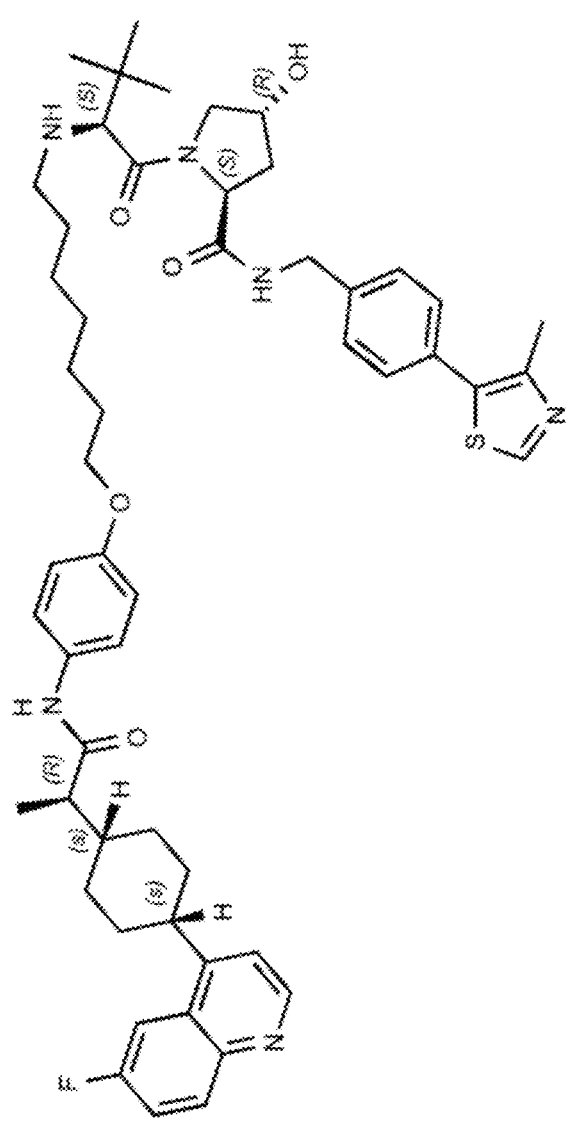
Figure 50:
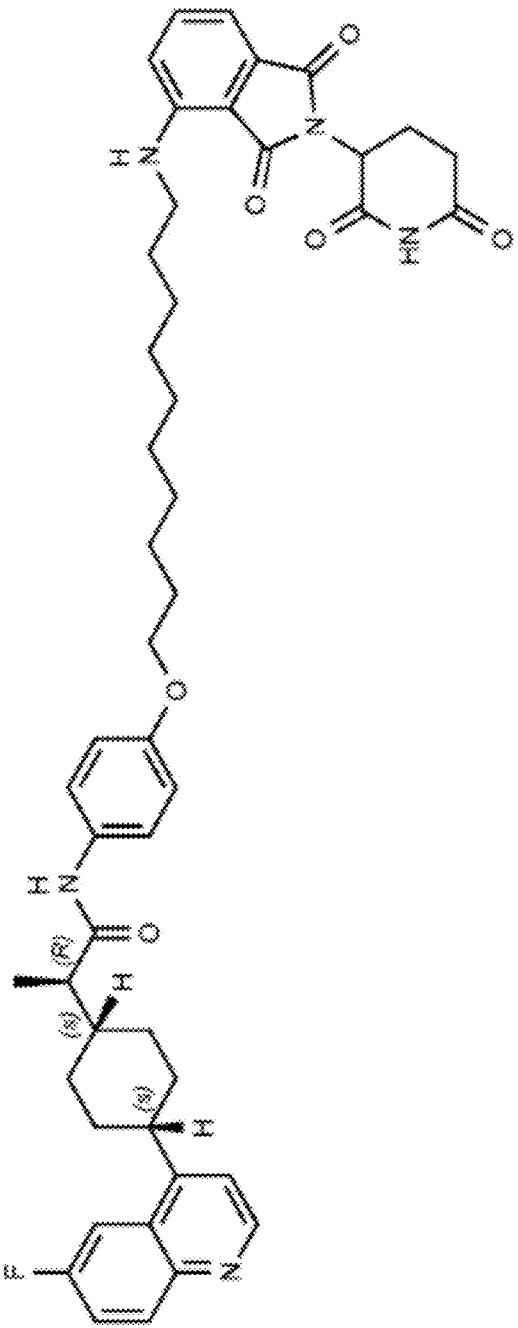
Figure 50:
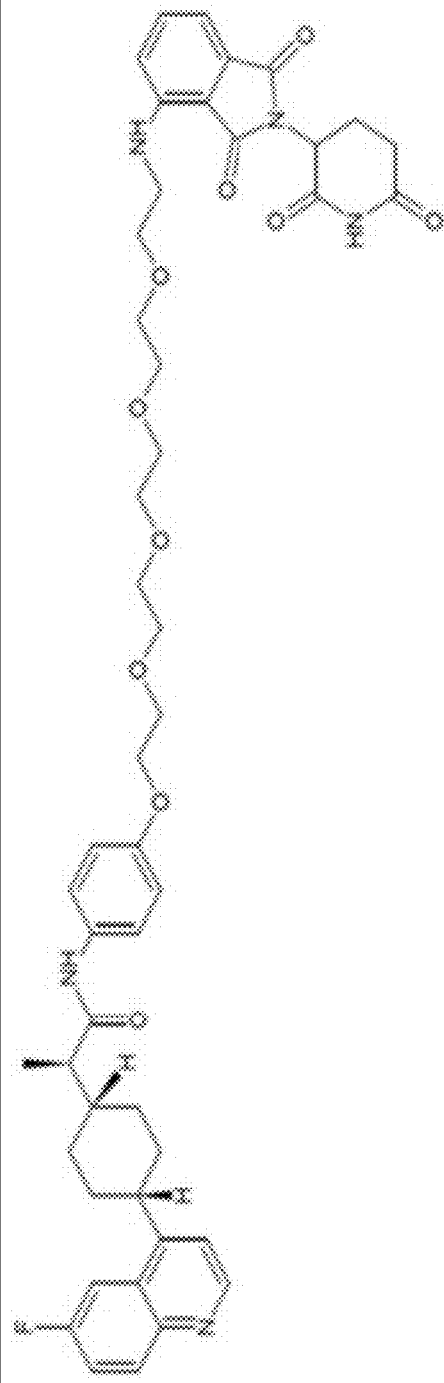
Figure 50:
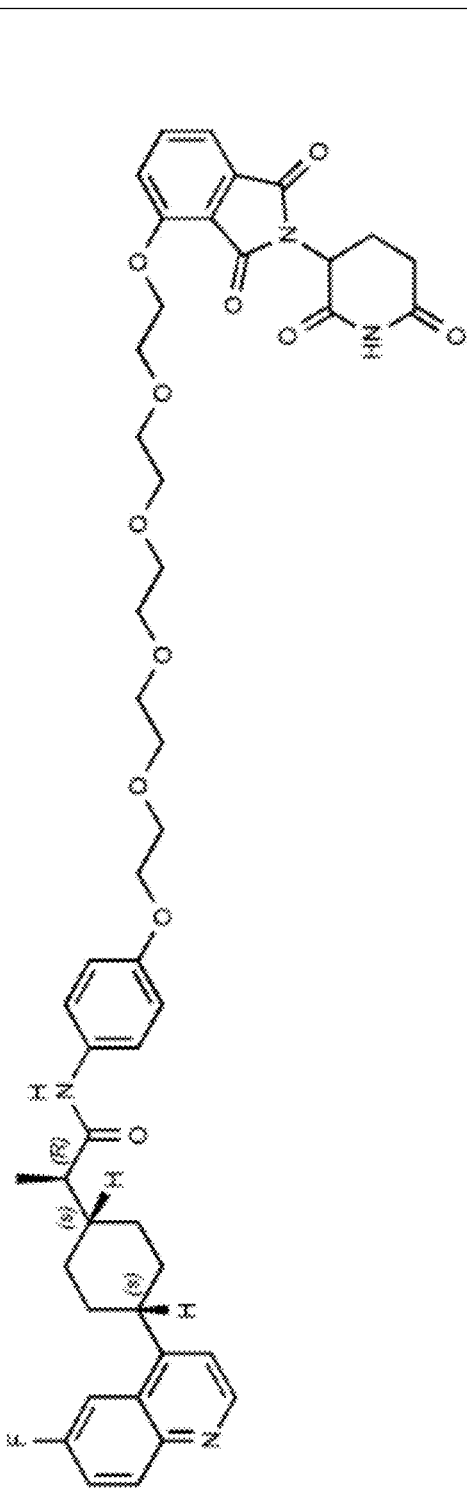
Figure 50:
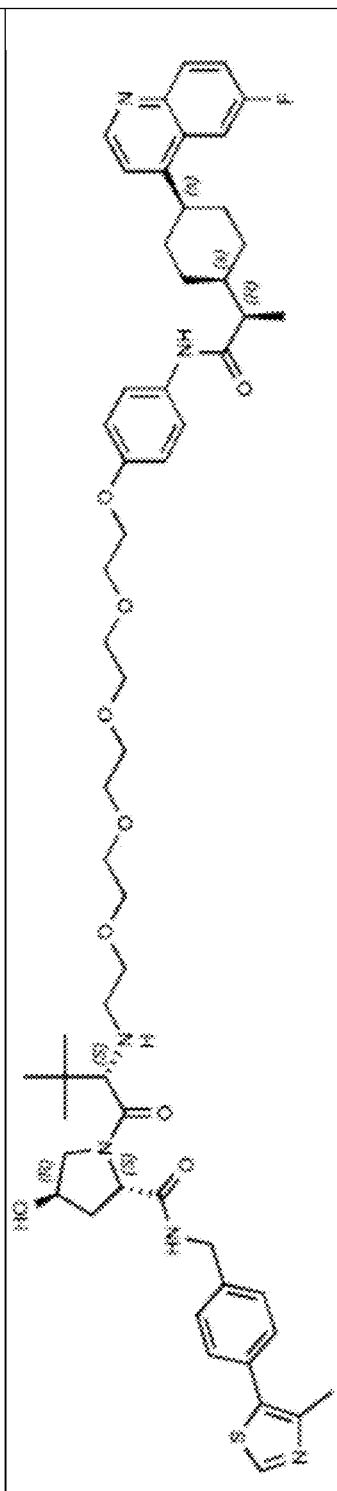
Figure 50:
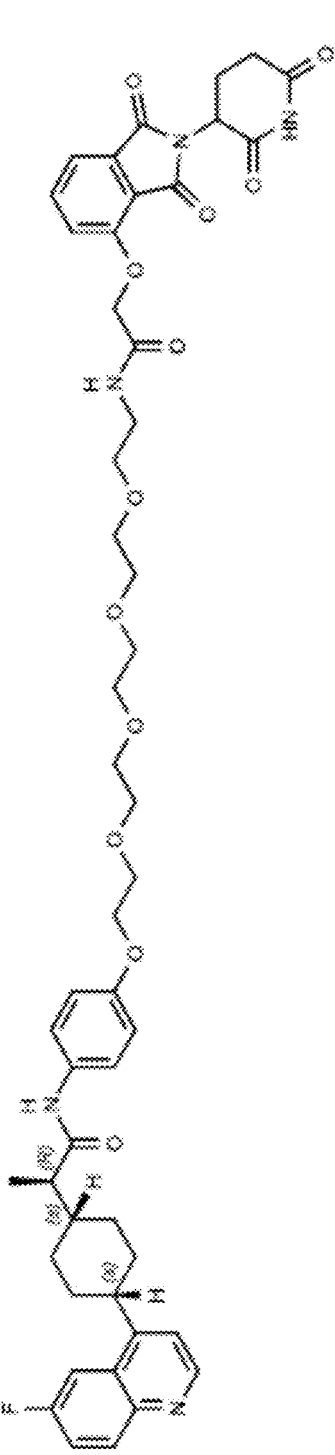
Figure 50:
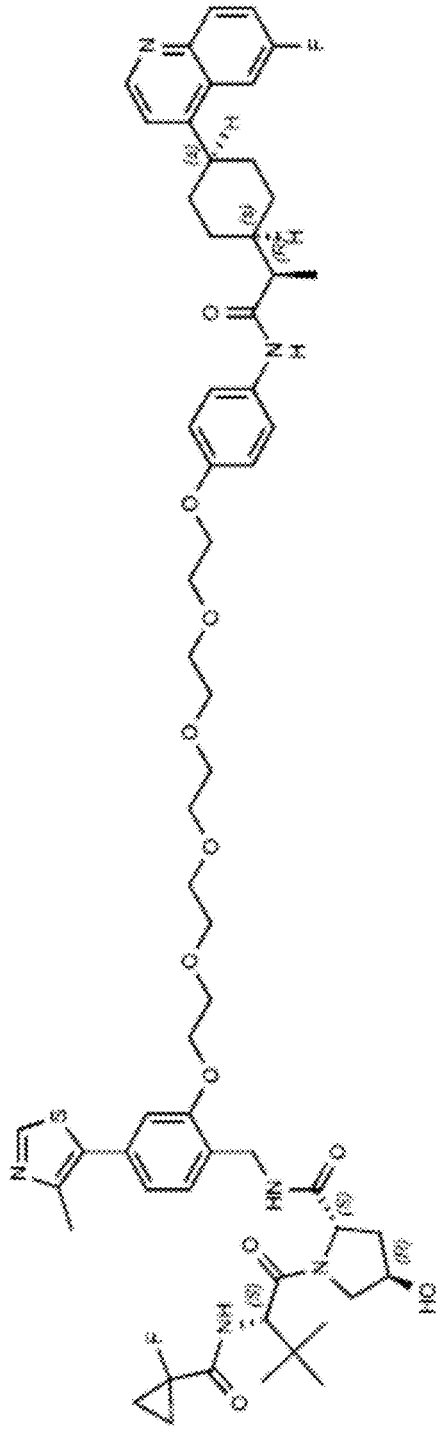
Figure 50:
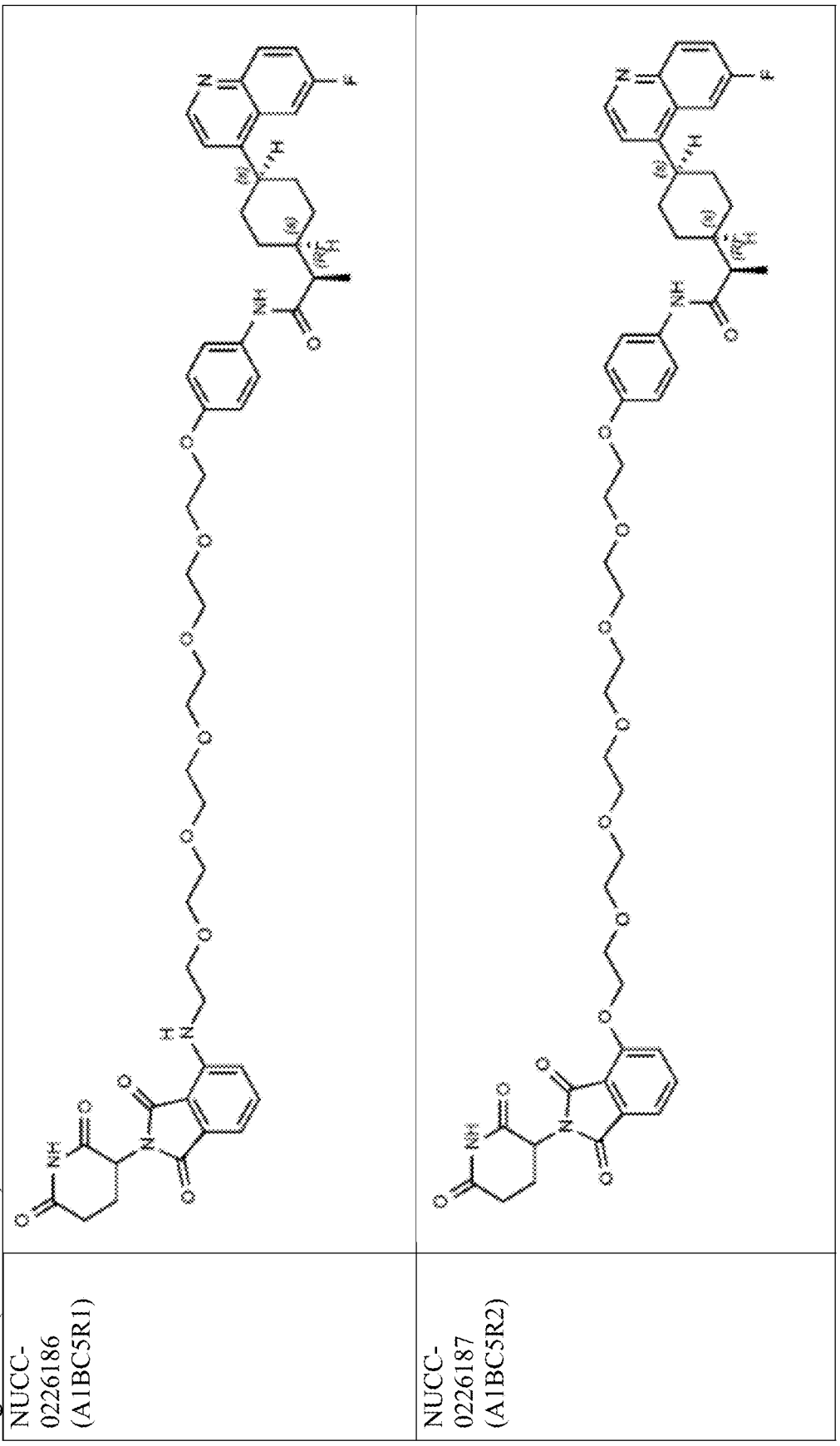
Figure 50:
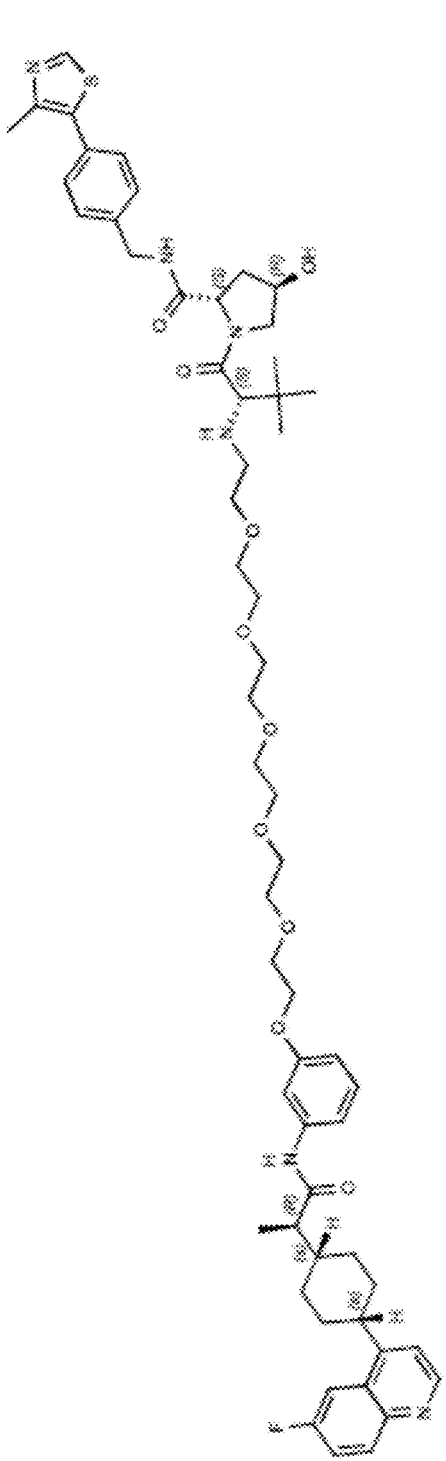
Figure 50:
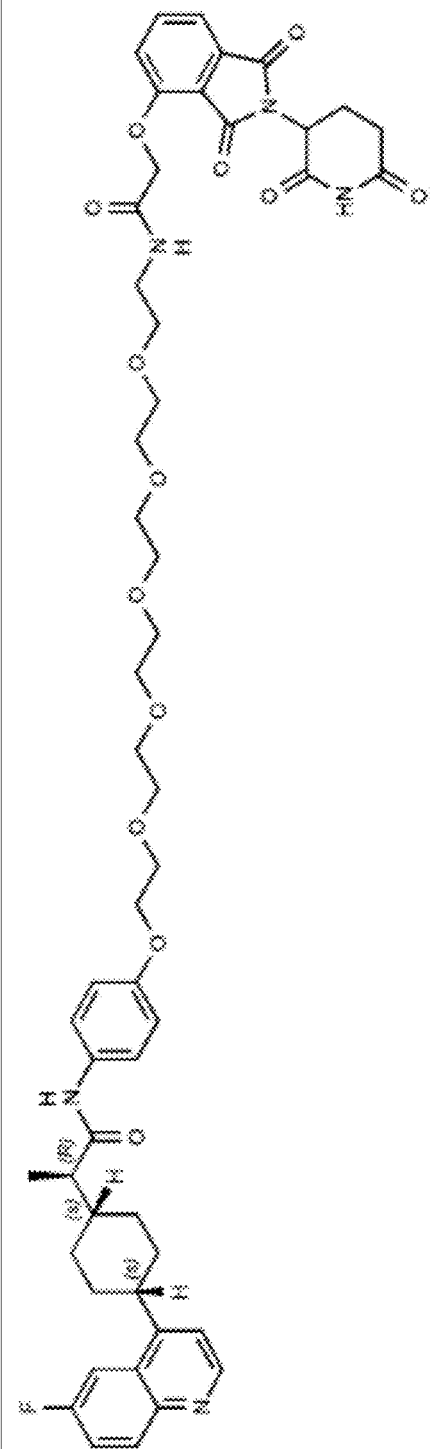
Figure 50:
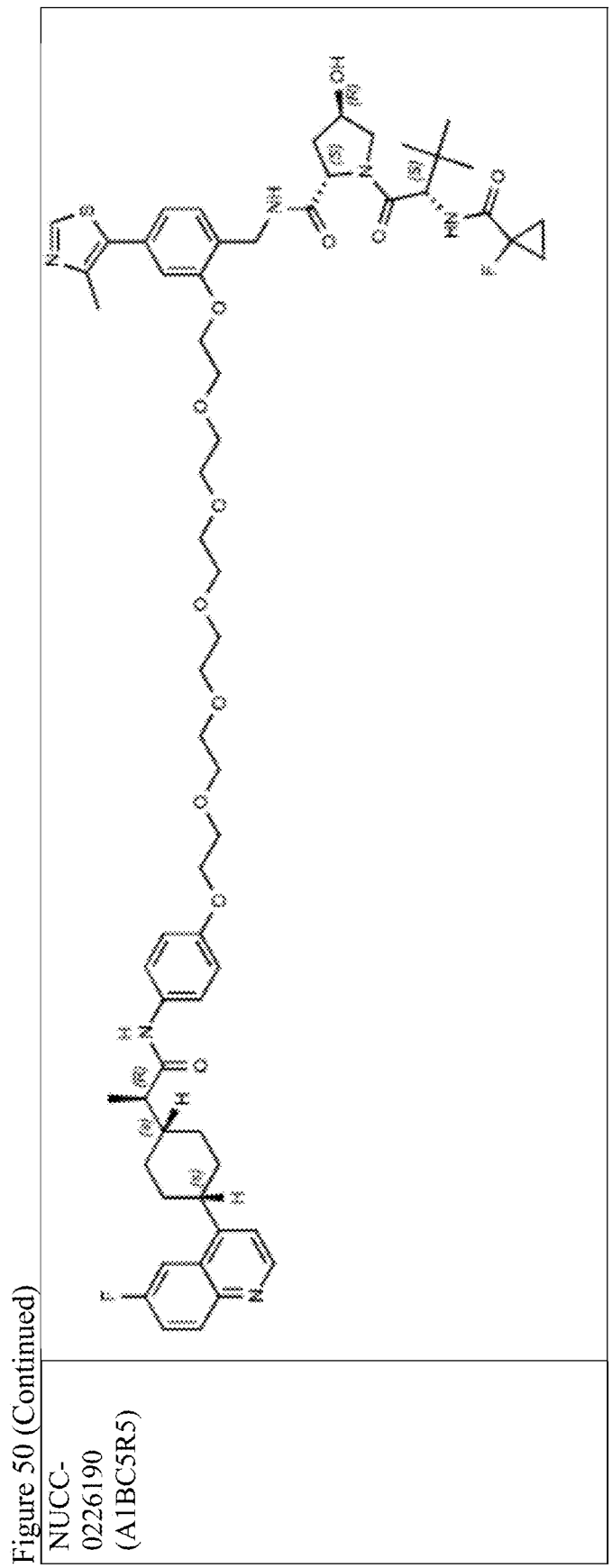
Figure 50:
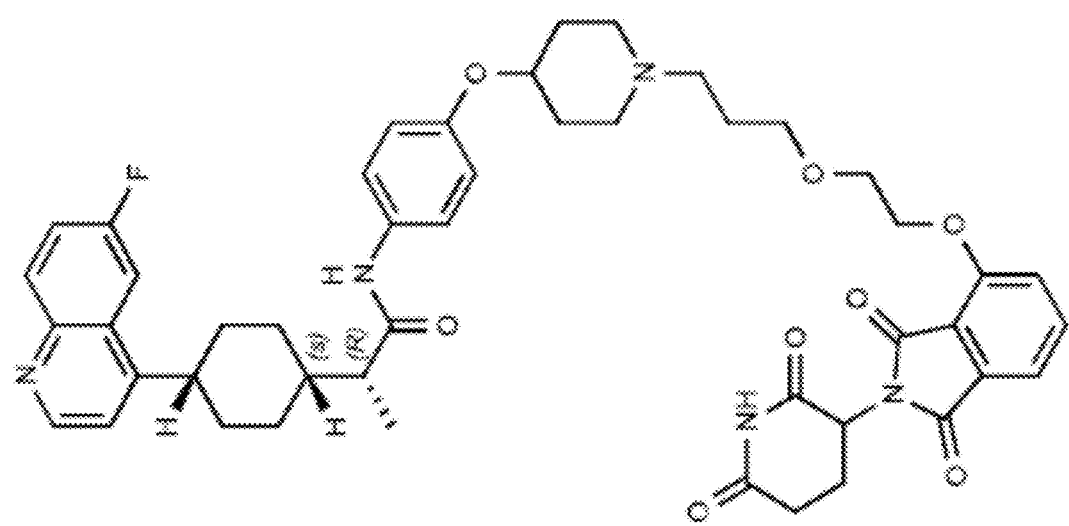
Figure 50:
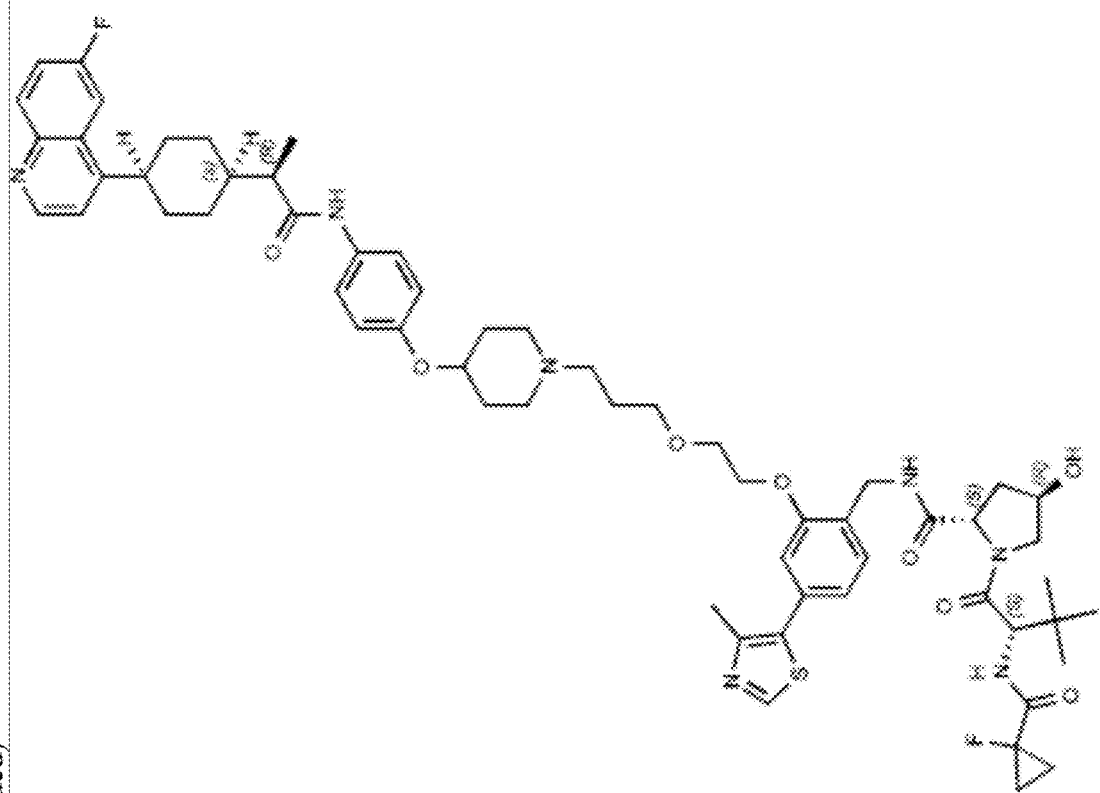
Figure 50:
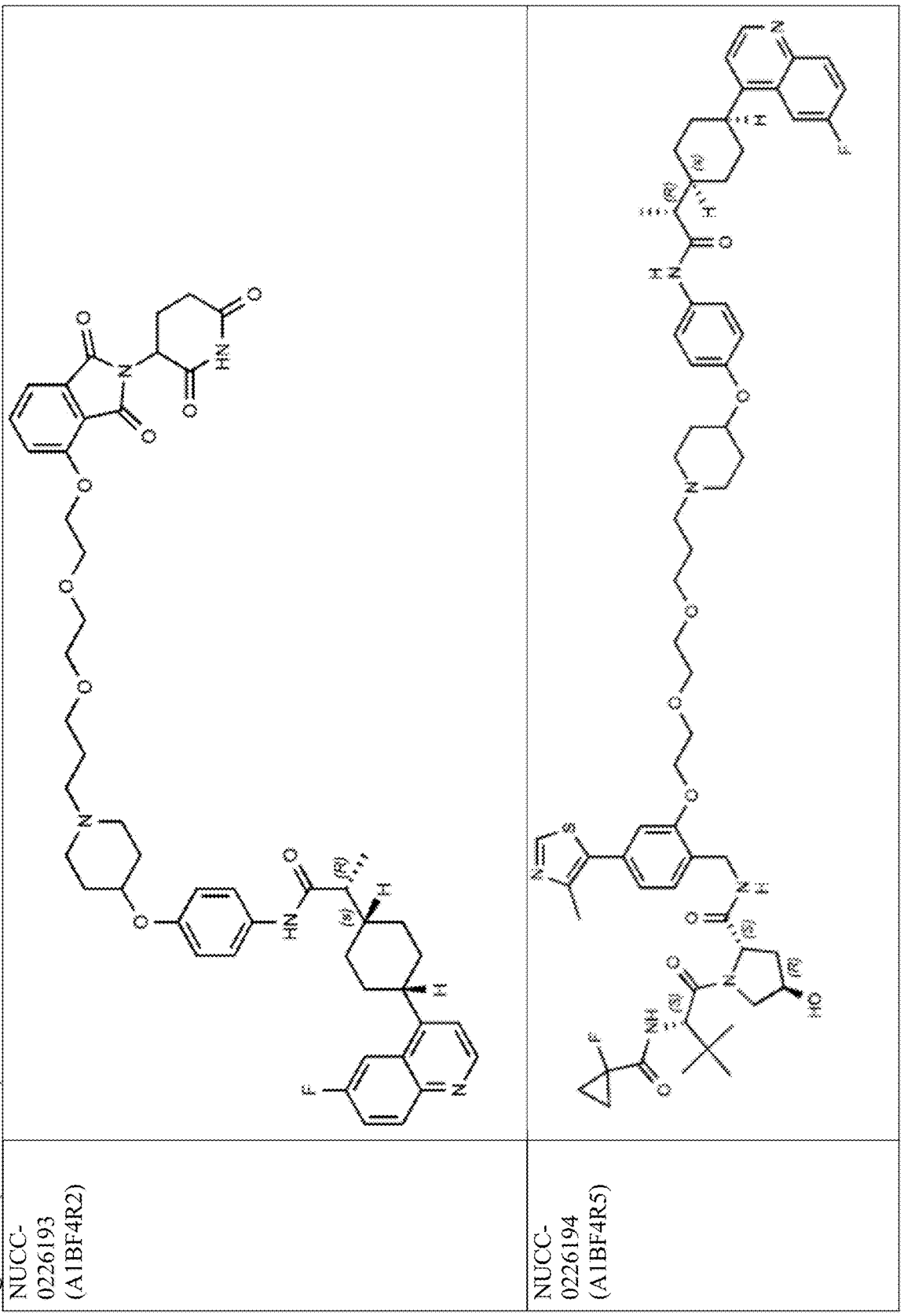
Figure 50:
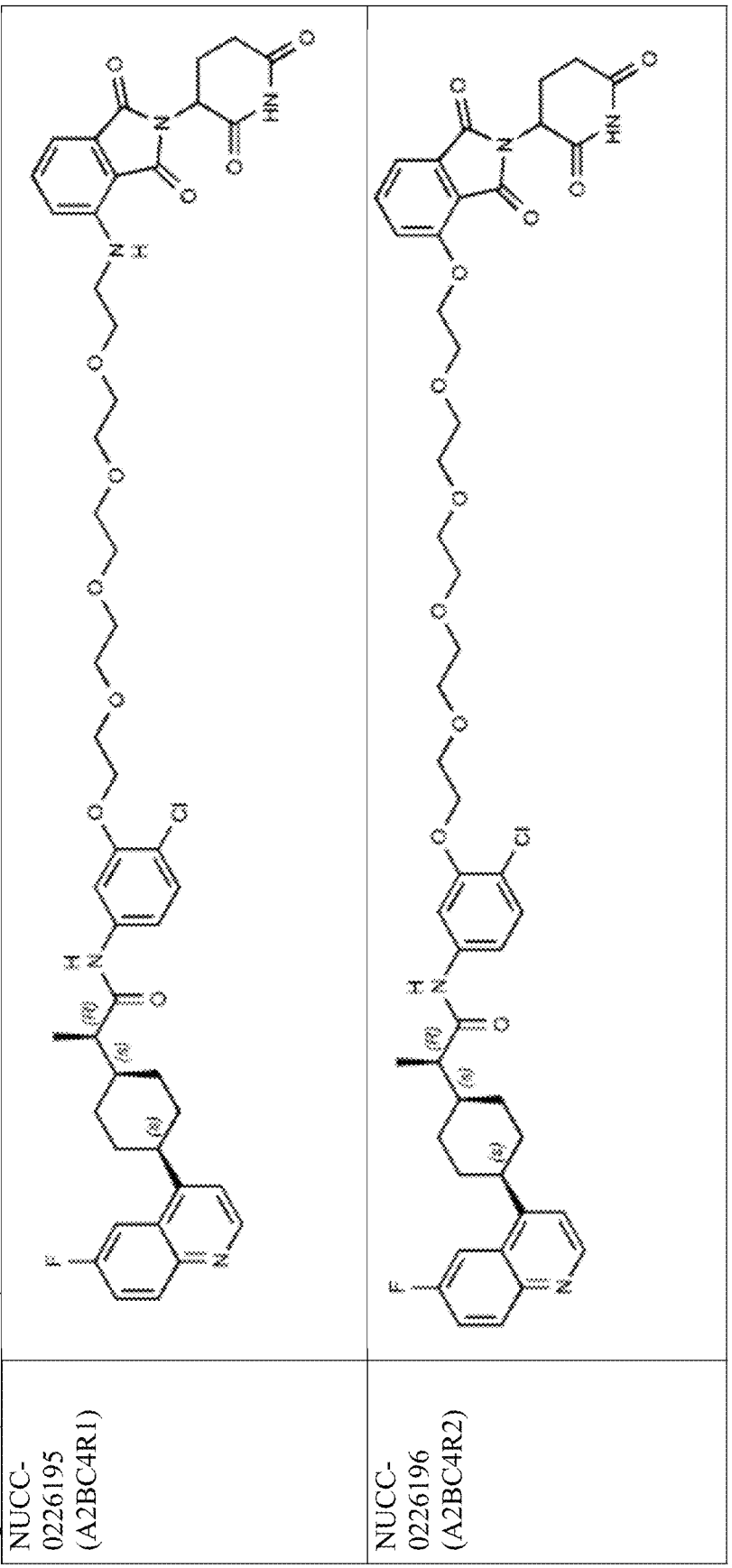
Figure 50:
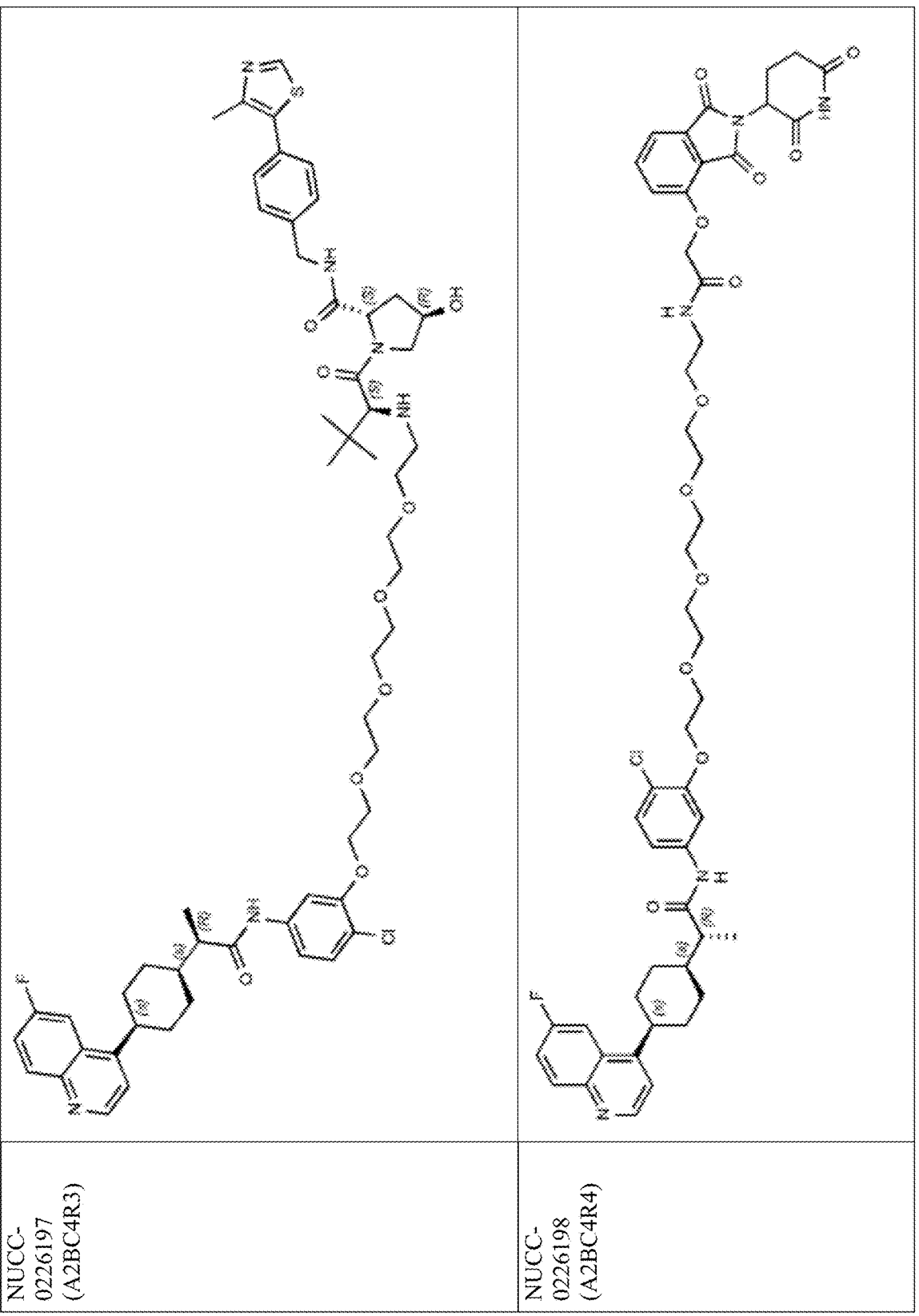
Figure 50:
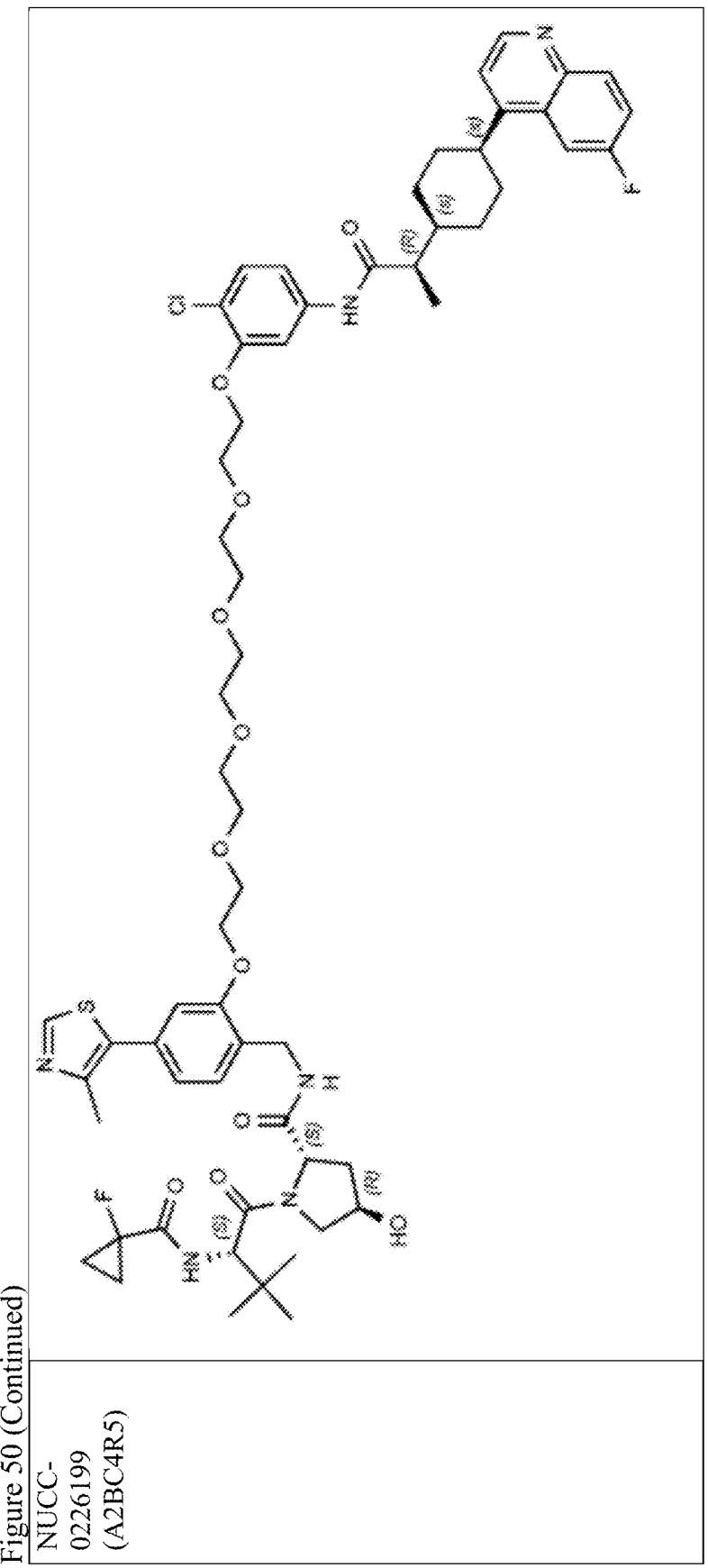

The exemplary IDO-PROTAC compounds as disclosed herein are shown in FIG. 50.

Example 3—Degradation of Indoleamine 2,3-Dioxygenase (IDO) by IDO-PROTACs

Reference is made to the experiments and results provided in FIGS. 20-32 which demonstrate that the disclosed compounds induce degradation of IDO.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

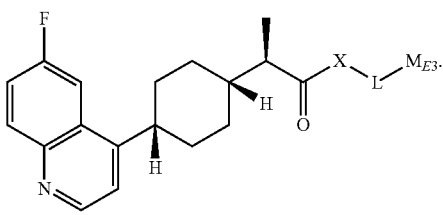

9. The method of claim 1, wherein $M_{IDO}$-L-$M_{E3}$ has a formula:
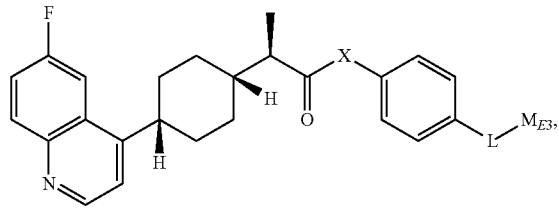
and
L is *—$(CH_2)_m$—$(CH_2CH_2O)_n$—* or *—$CH_2$—C(O)—NH—$(CH_2)_m$—$(CH_2CH_2O)_n$—*; or
$M_{IDO}$-L-$M_{E3}$ has a formula:
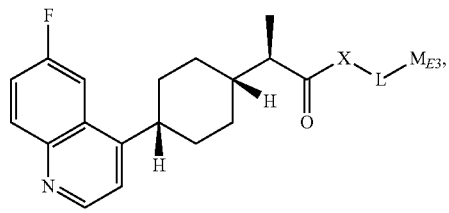
and
L is selected from the group consisting of
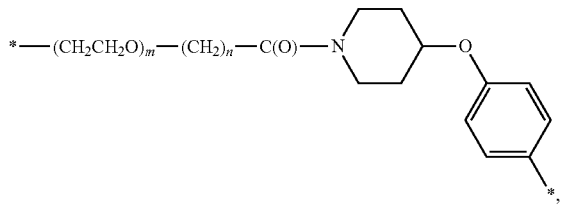
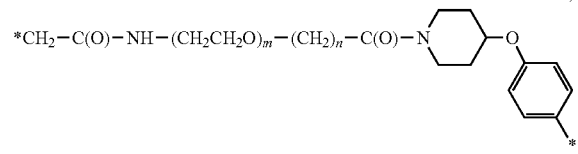
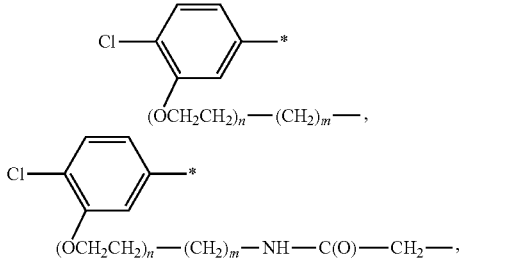
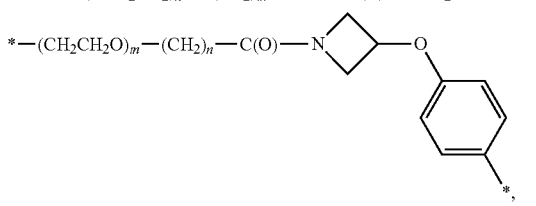
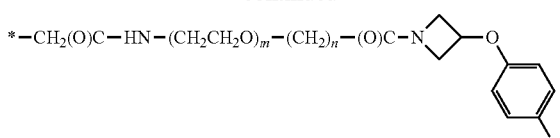
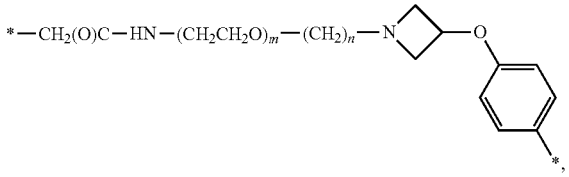
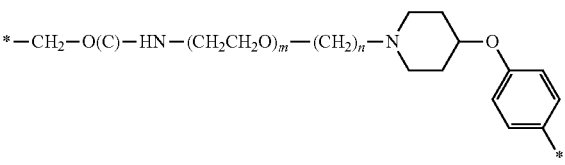
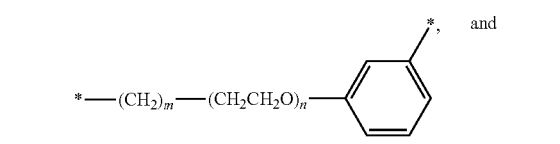
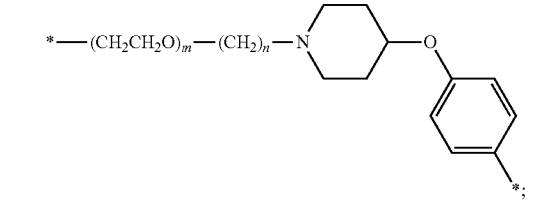
X is O or NH;
m is 0-20 and n is 0-20; and
$M_{E3}$ has a formula selected from
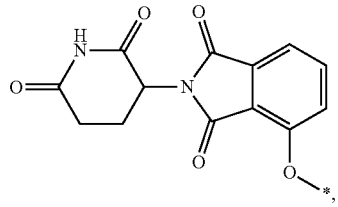
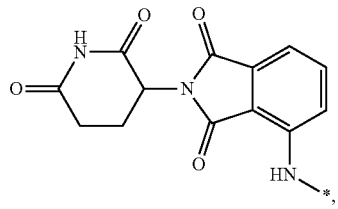
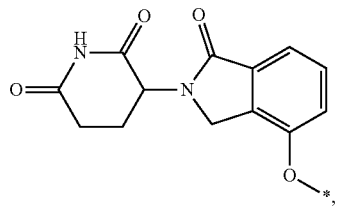

89
-continued
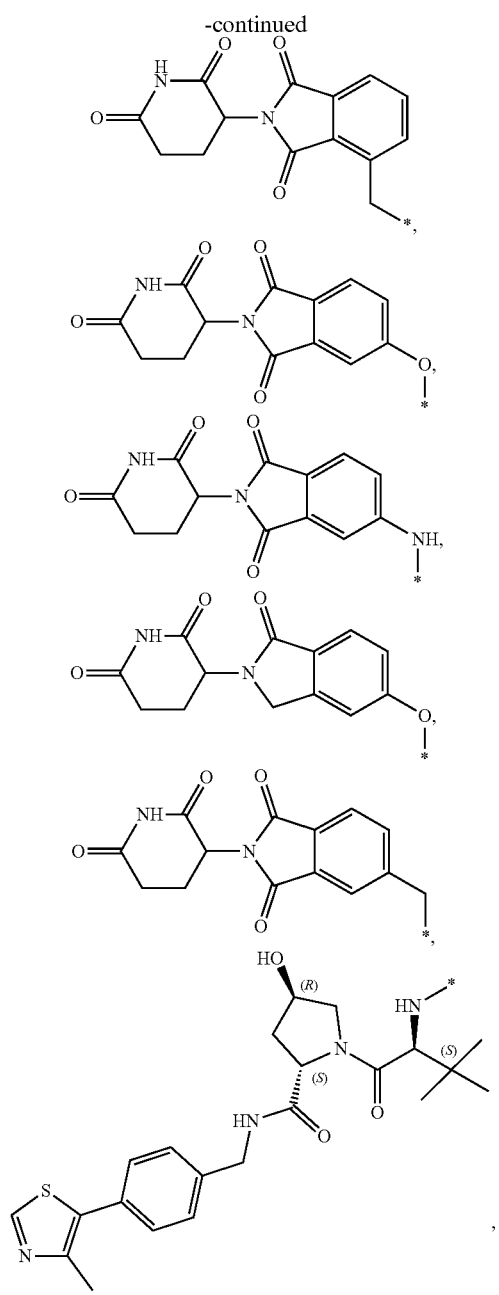
90
-continued
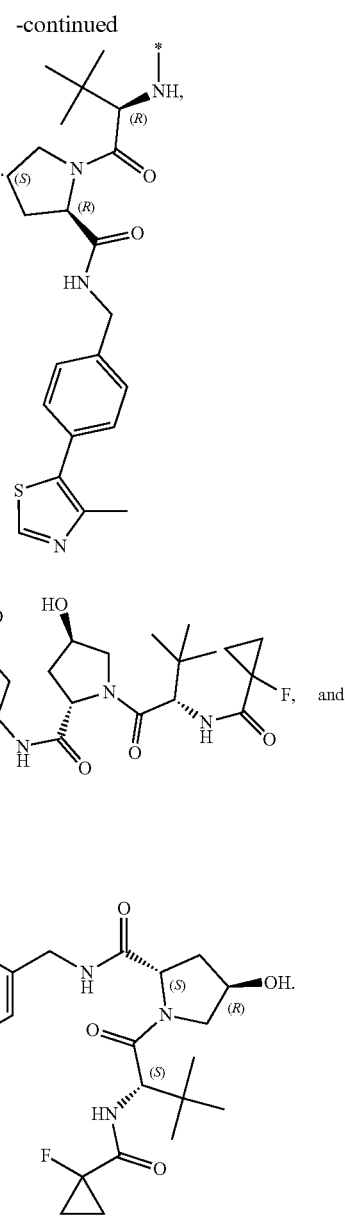
10. The method of claim 1, wherein the molecule has a formula:
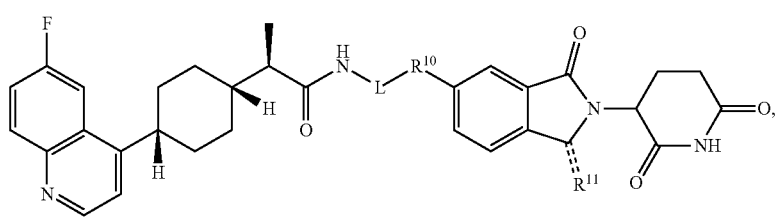

wherein $R^{10}$ is O or NH;
$R^{11}$ is absent or present and when present $R^{11}$ is O.
11. The method of claim 1 wherein the molecule has a formula:
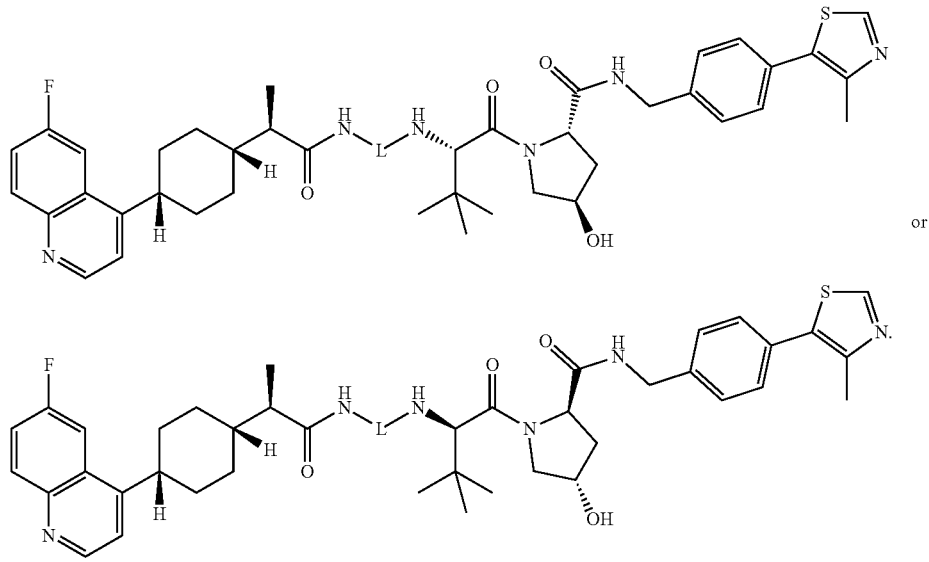
or
12. The method of claim 1, wherein the molecule has a formula:
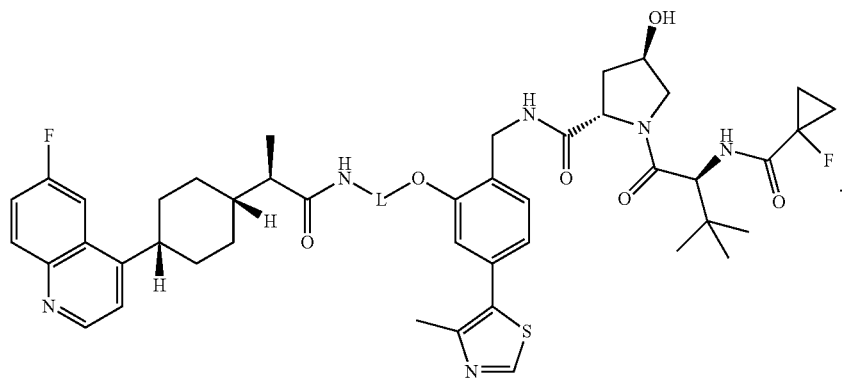
13. The method of claim 1, wherein the molecule has a formula selected from:
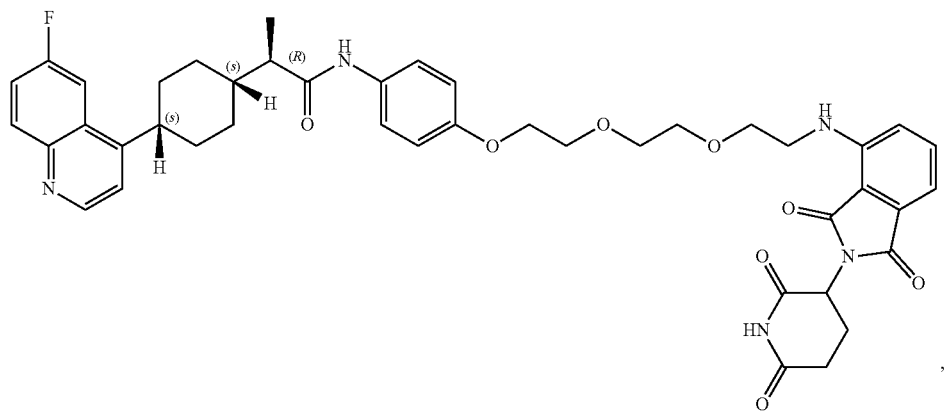

-continued
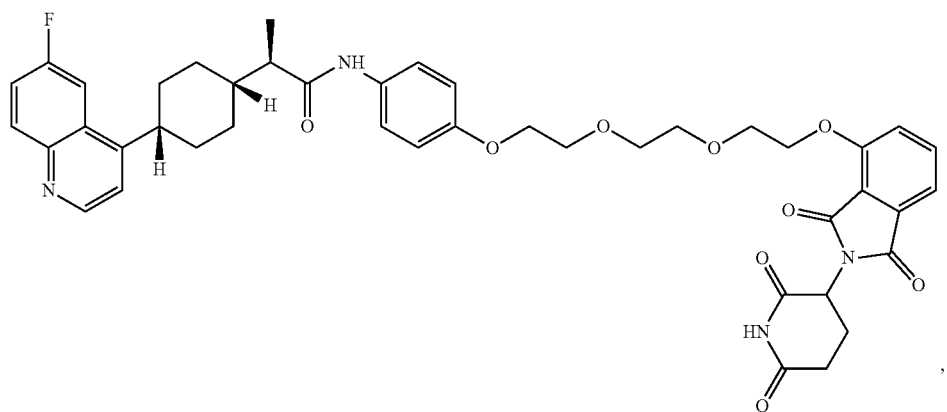
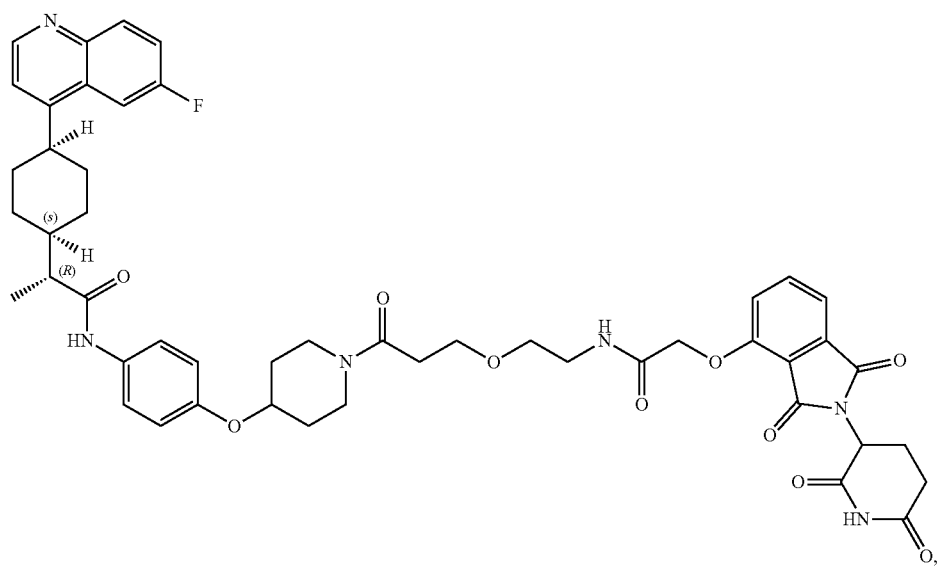
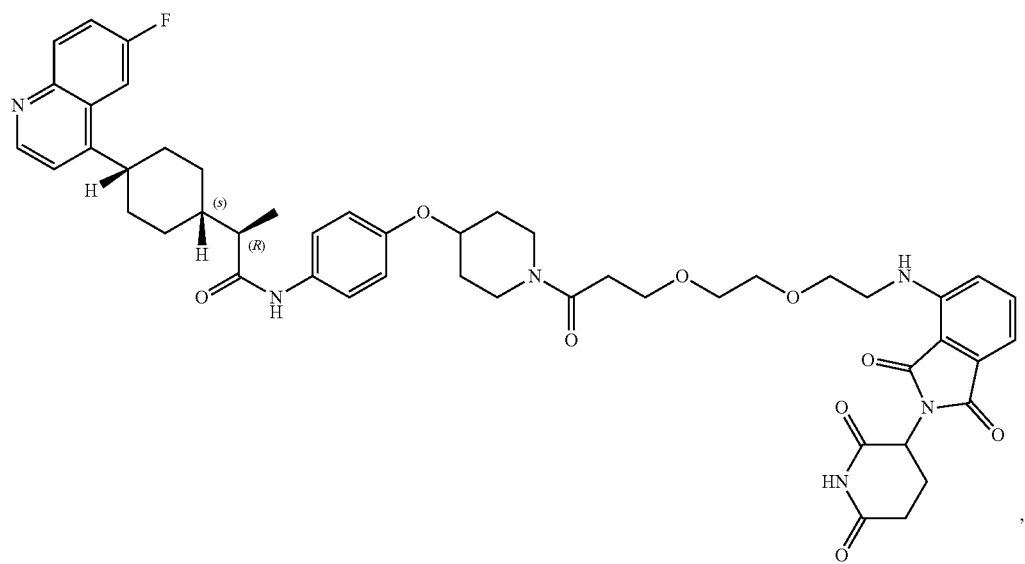

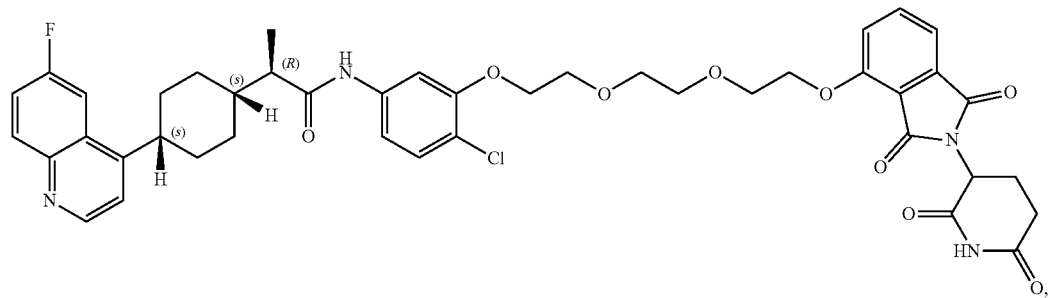
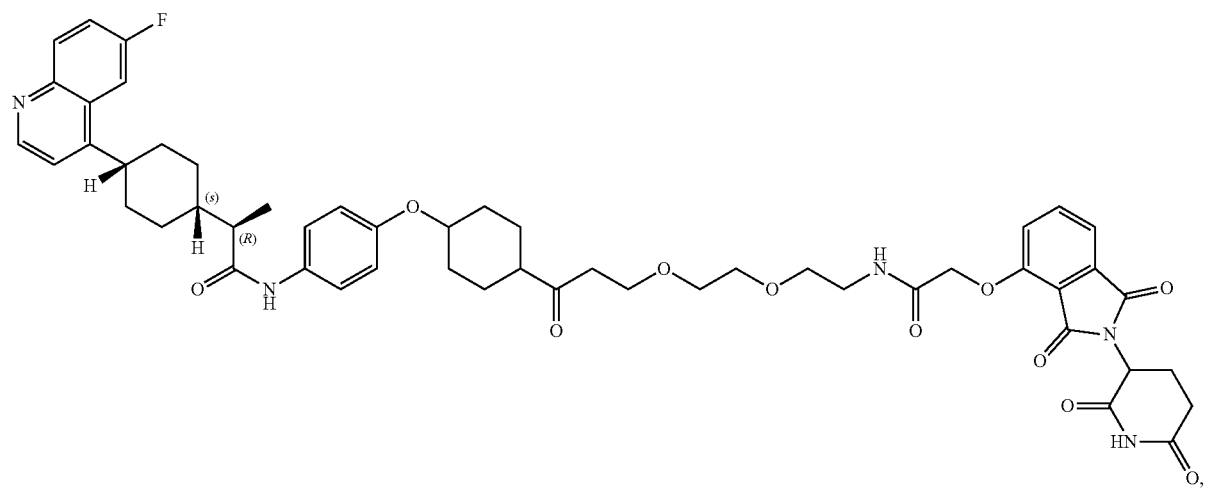
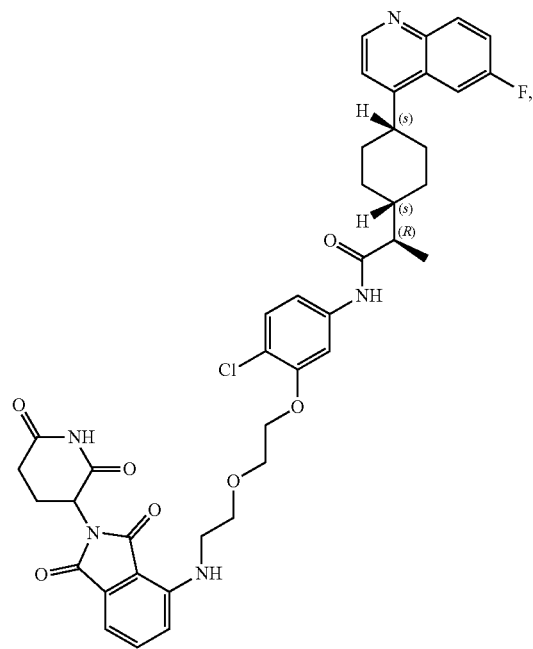

-continued
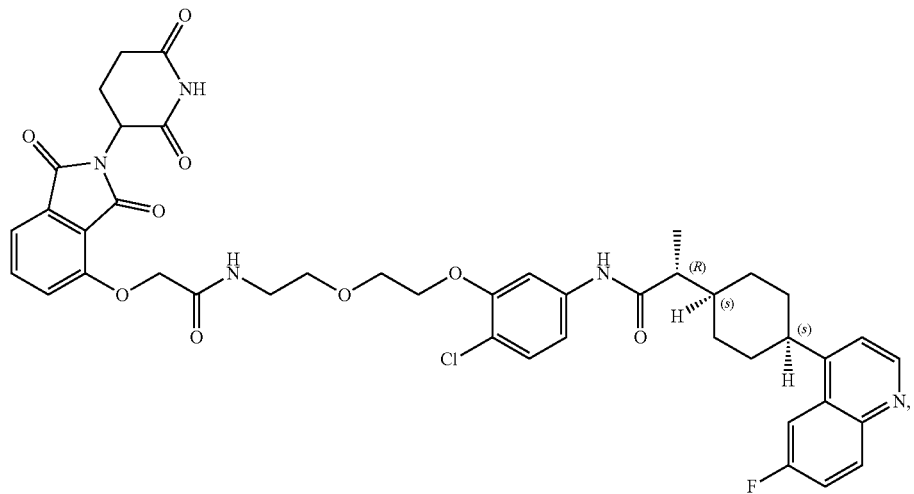
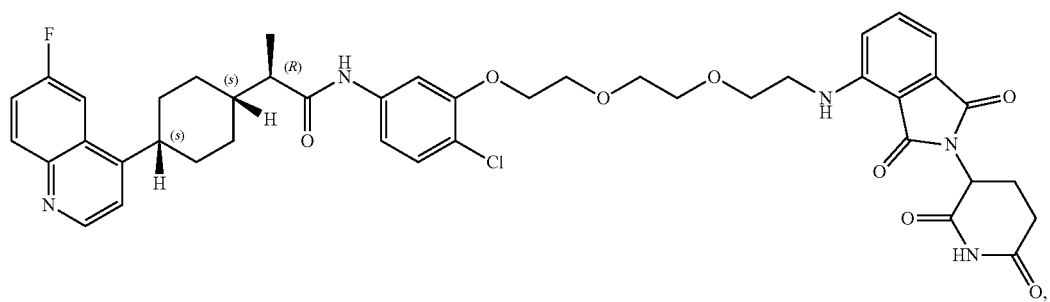
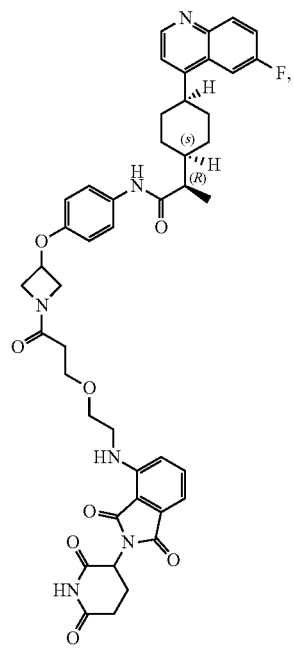

-continued
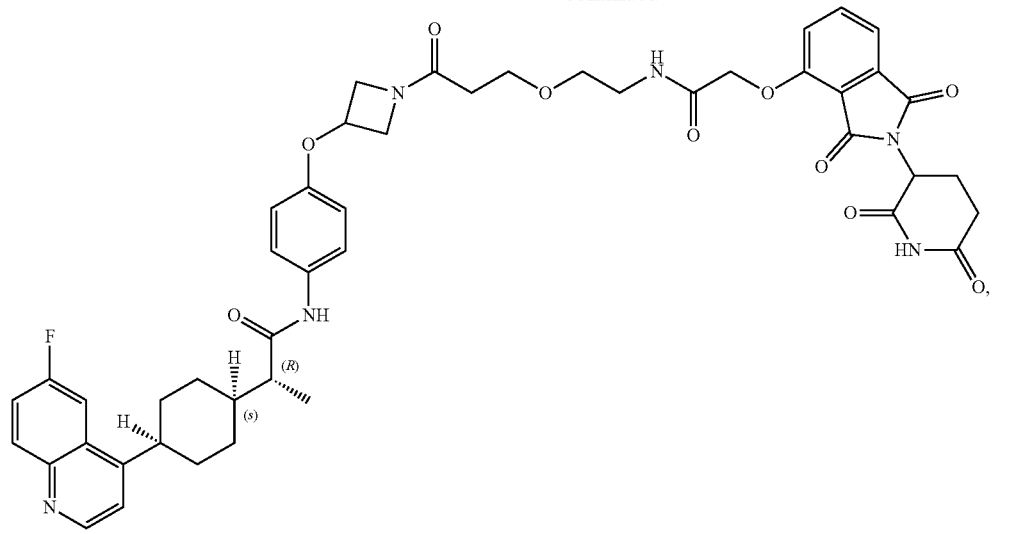
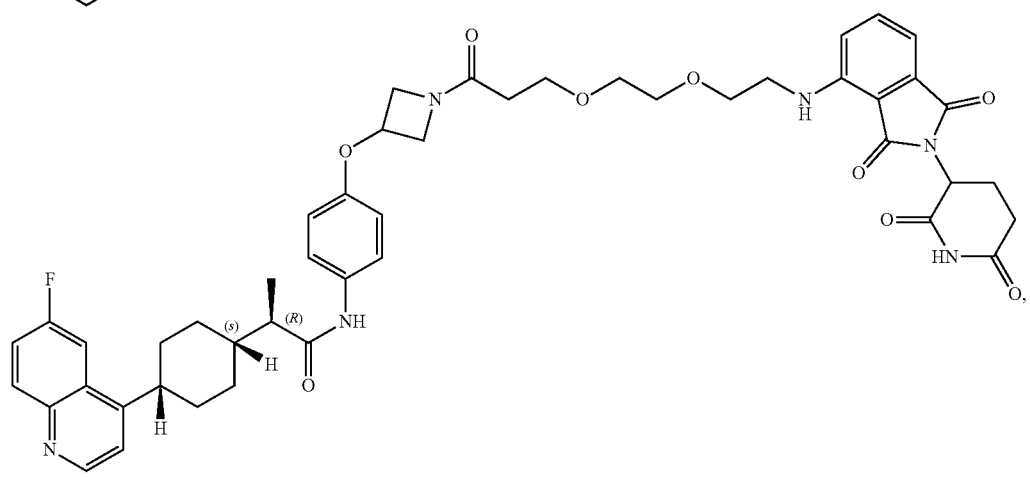
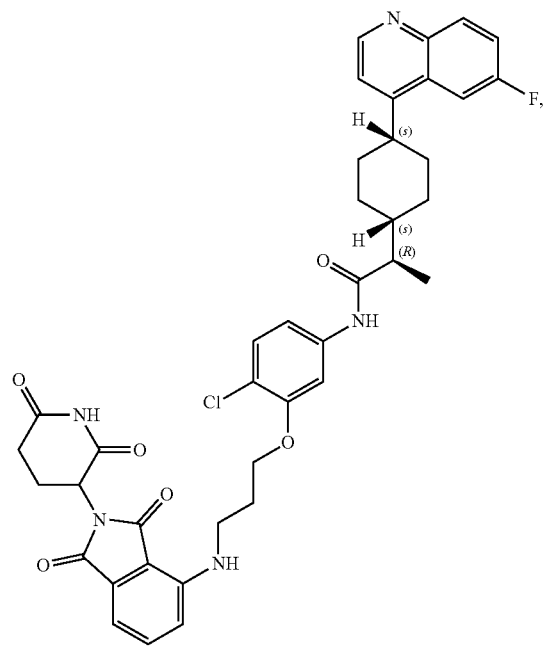

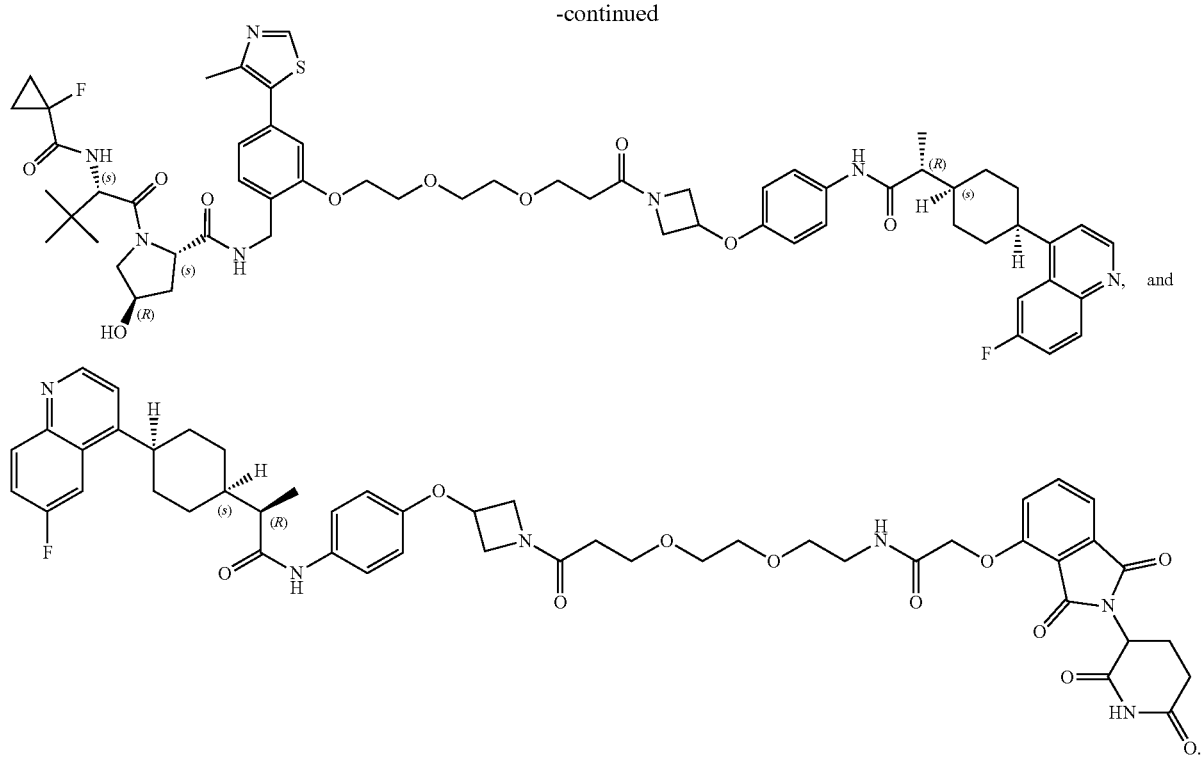
14. The method of claim 1, wherein $M_{IDO}$-L-$M_{E3}$ has the formula
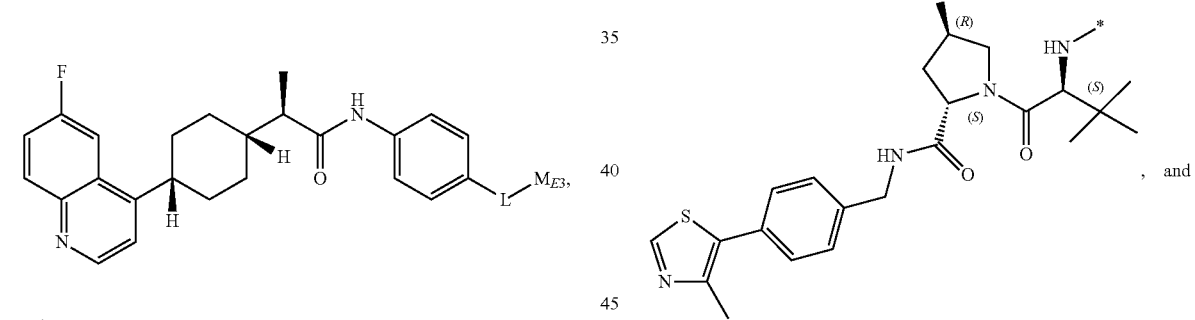
and
$M_{E3}$ is selected from the group consisting of
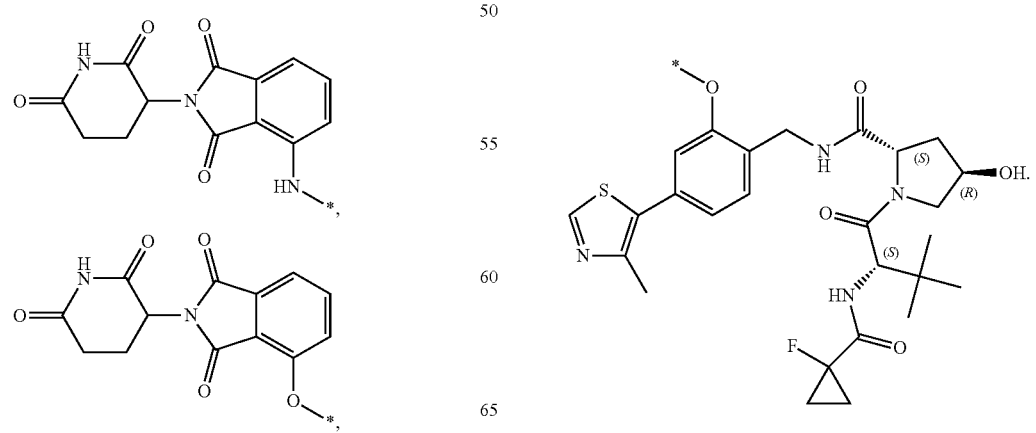

15. The method of claim 14, wherein the molecule is selected from the group consisting of
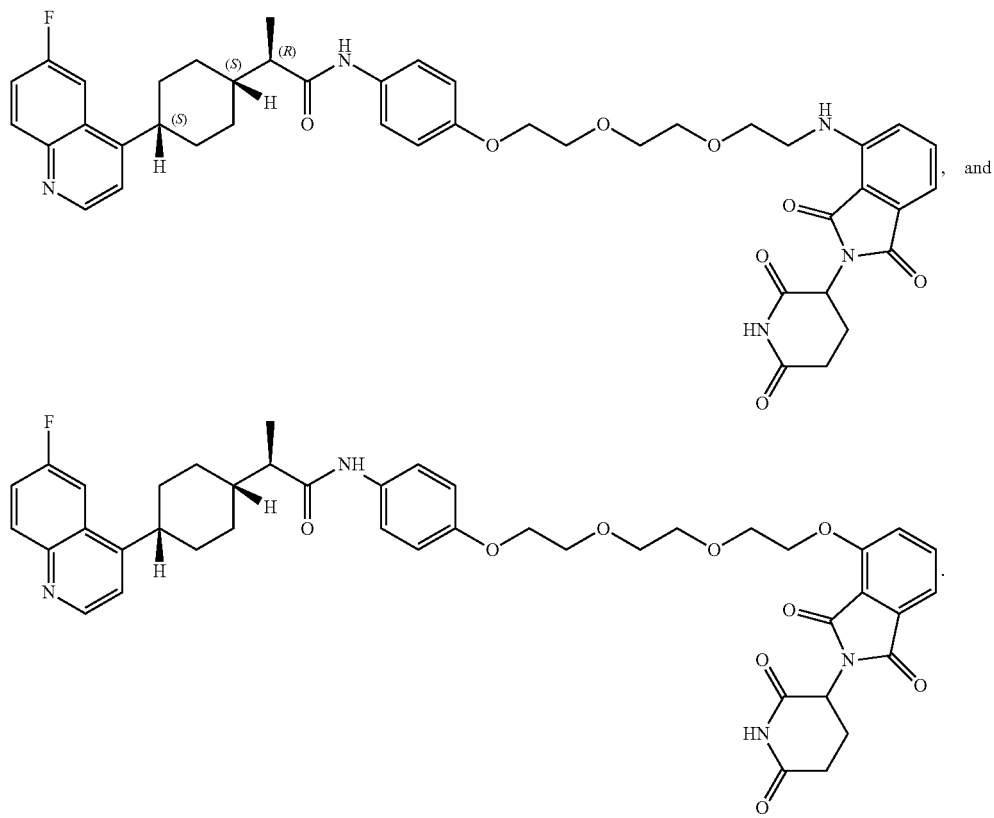
, and
16. The method of claim 1, wherein $M_{IDO}$-L-$M_{E3}$ has the formula
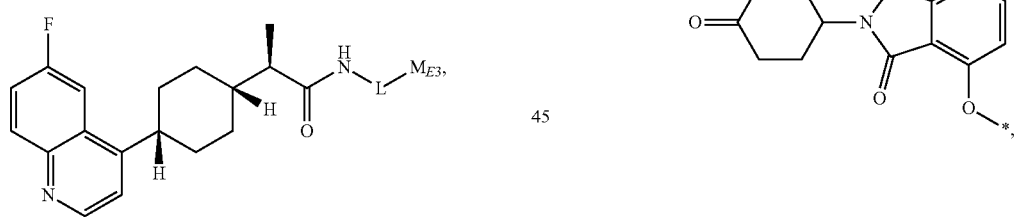
and
$M_{E3}$ is selected from the group consisting of
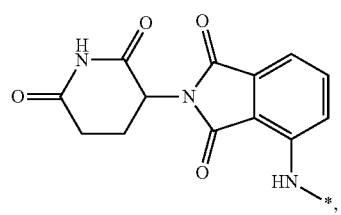
-continued
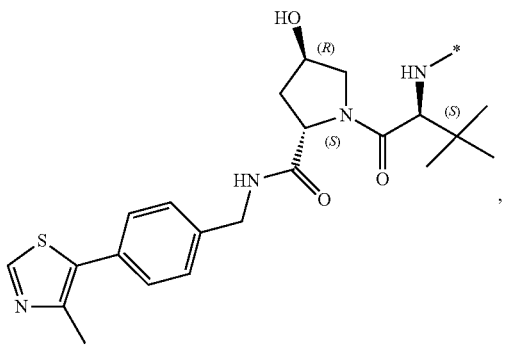

105
-continued
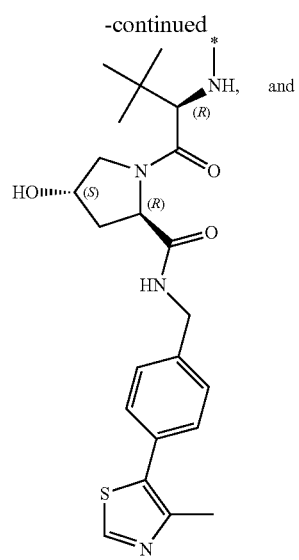
and
106
-continued
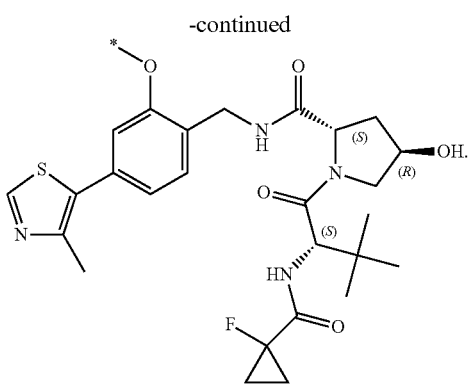
17. The method of claim 16, wherein the molecule is selected from the group consisting of
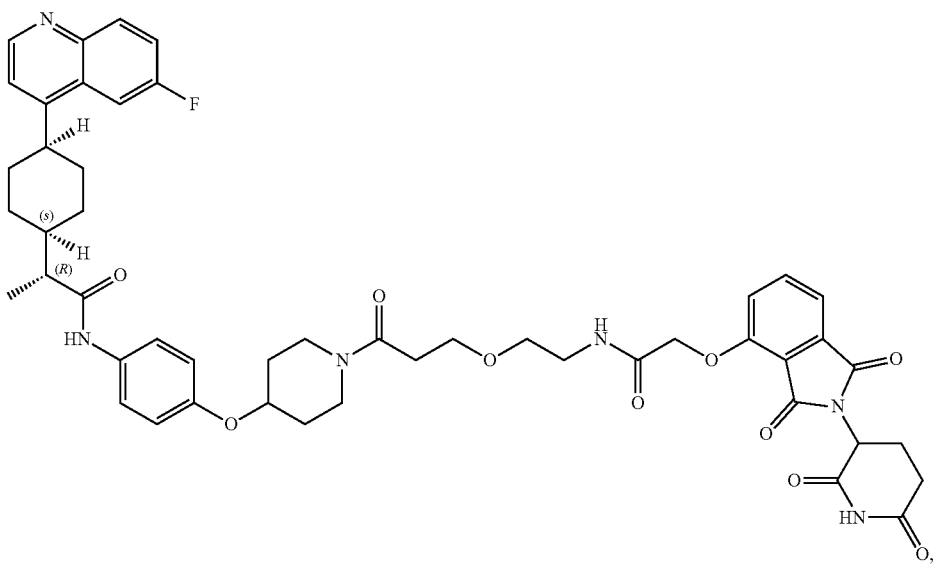
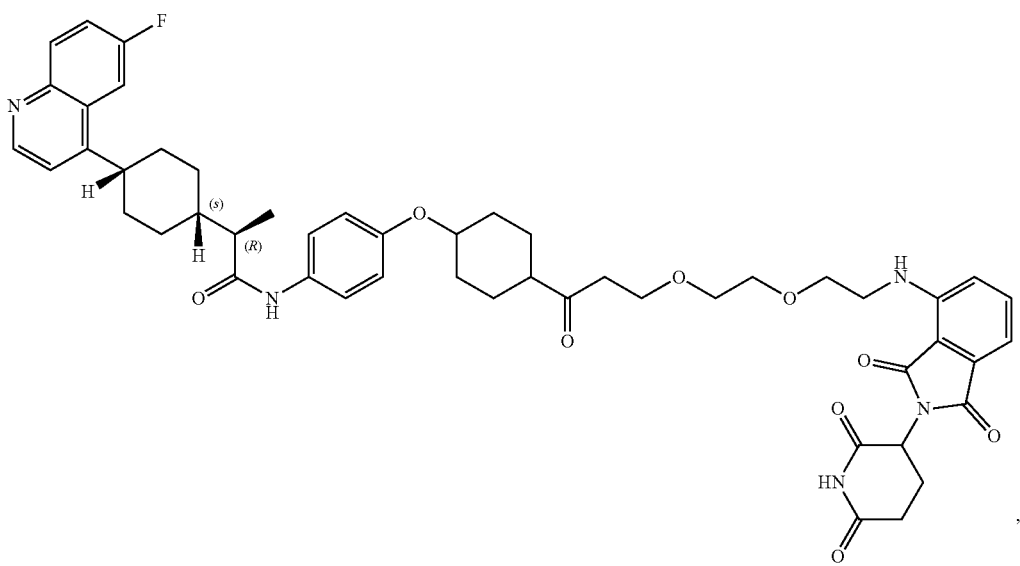

107
-continued
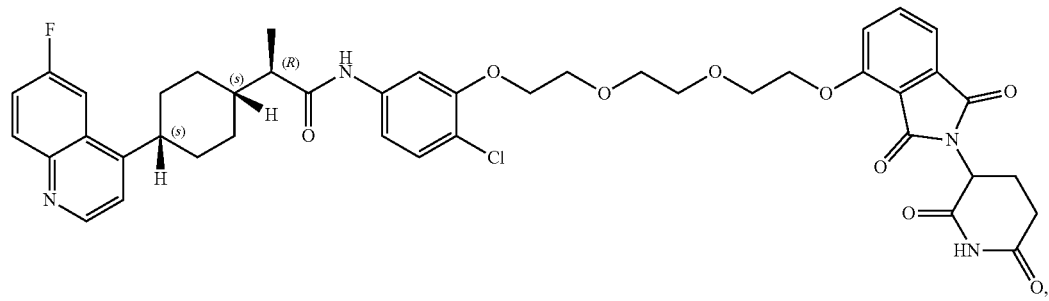
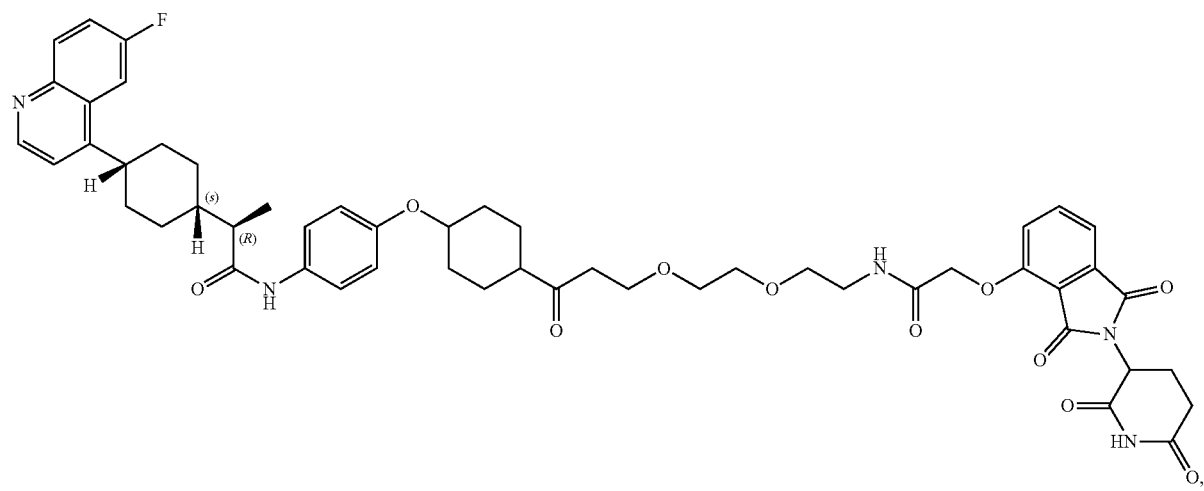
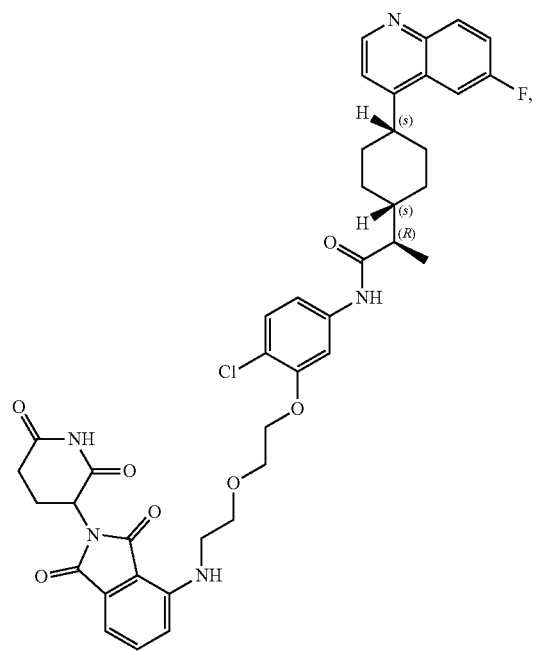

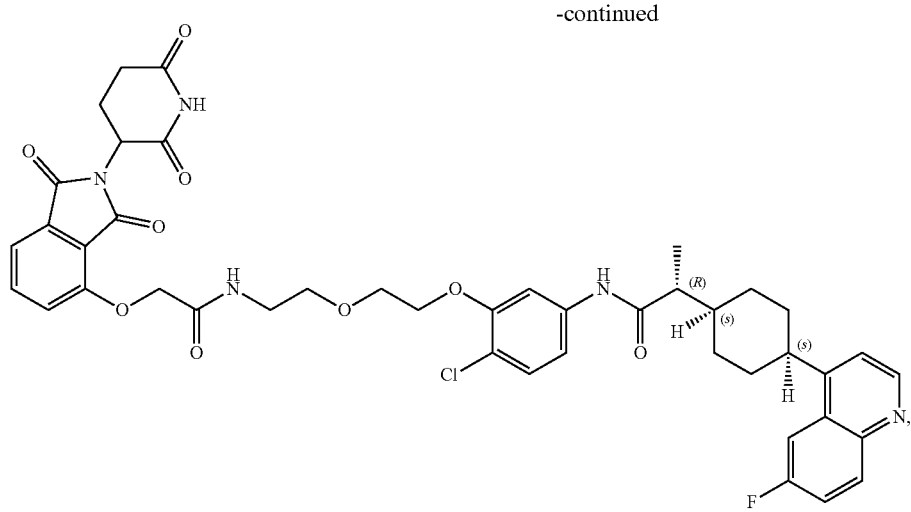
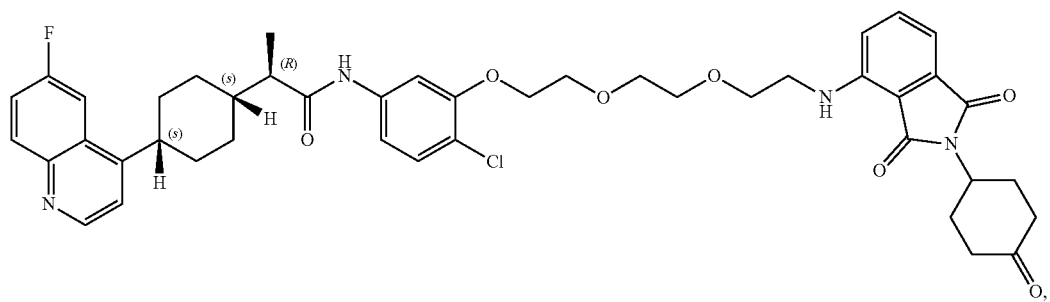
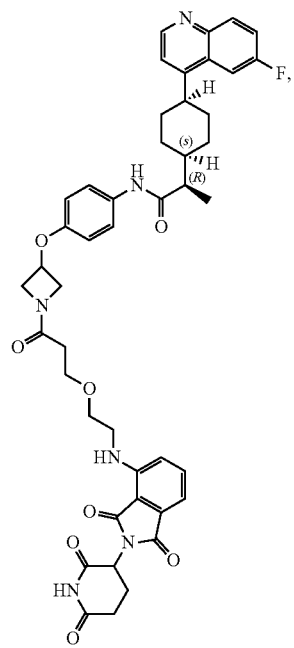

-continued
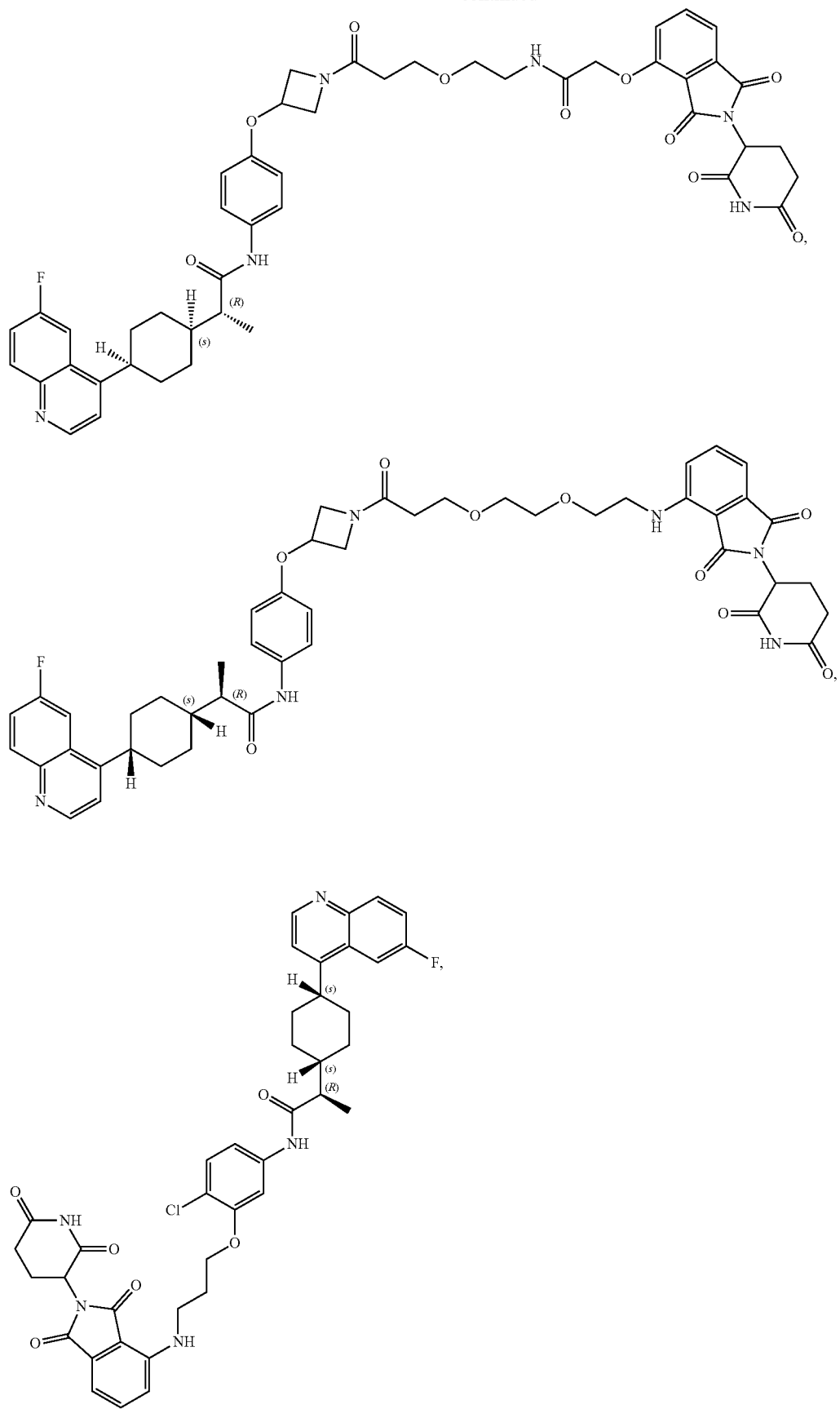

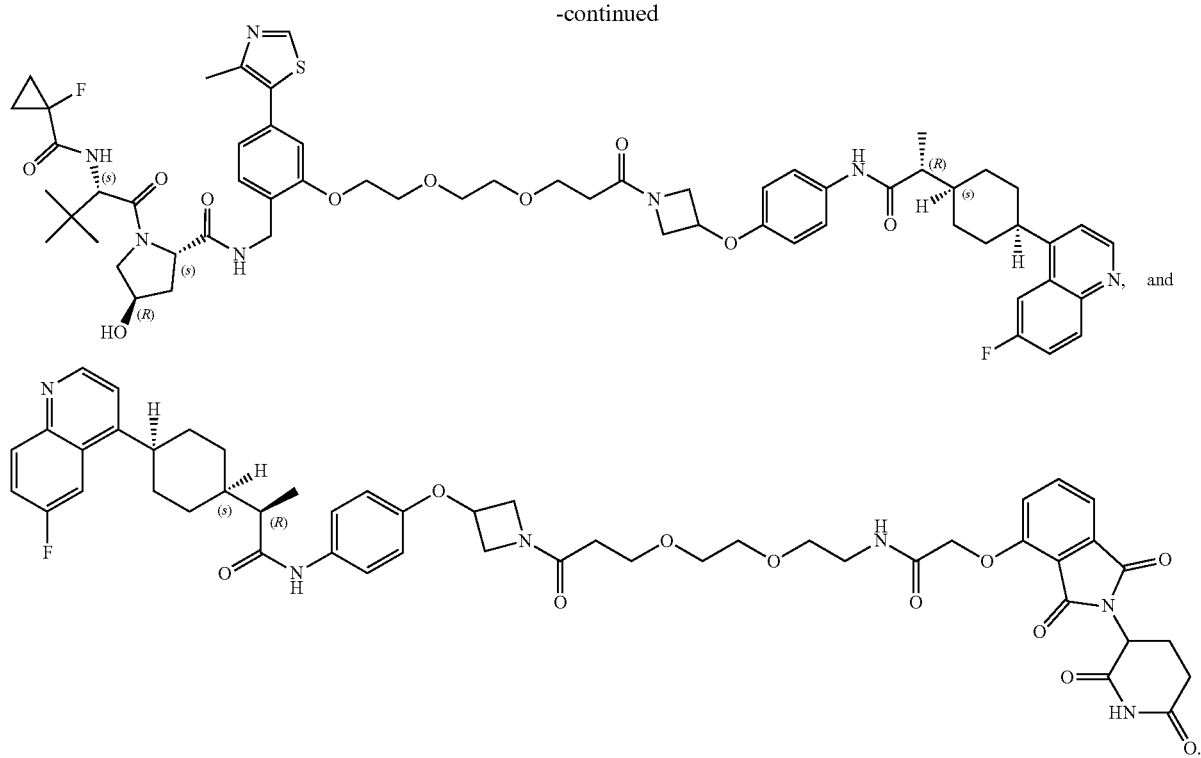

We claim:

1. A method of treating cancer, the method comprising administering a pharmaceutical composition to a subject having the cancer,
   wherein the pharmaceutical composition comprises
   (a) a molecule having a formula $M_{IDO}$-L-$M_{E3}$, wherein $M_{IDO}$ is a moiety that binds to indoleamine 2,3-dioxygenase (IDO), L is a bond or a linker covalently attaching $M_{IDO}$ and $M_{E3}$, and $M_{E3}$ is a moiety that binds to an E3 ubiquitin ligase; and
   (b) a suitable pharmaceutical carrier, excipient, or diluent, wherein $M_{IDO}$-L-$M_{E3}$ has a formula wherein X is O or NH, L comprises a polyethylene glycol moiety, an alkylalkyne moiety, and/or an aminoalkyl alkyne moiety, and $M_{E3}$ is a moiety that binds to an E3 ubiquitin ligase selected from Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

2. The method of claim 1, wherein the cancer is selected from multiple glioblastoma, colorectal cancer, myeloma, leukemia, non-small cell lung cancer, colon cancer, cancer of the central nervous system, melanoma, ovarian cancer, renal cancer, prostate cancer, uterine cancer, pancreatic cancer, and breast cancer.

3. The method of claim 1, wherein the cancer is glioblastoma.

4. The method of claim 1 further comprising administering immunotherapy to the subject, wherein the immunotherapy is administered before, concurrently with, or after administering the composition of claim 1.

5. The method of claim 1 further comprising administering an anti-PD1 agent to the subject, before, concurrently with, or after administering the composition of claim 1.

6. The method of claim 1 further comprising administering an anti-PD-L1 agent to the subject, before, concurrently with, or after administering the composition of claim 1.

7. The method of claim 1, wherein $M_{IDO}$-L-$M_{E3}$ has the formula:

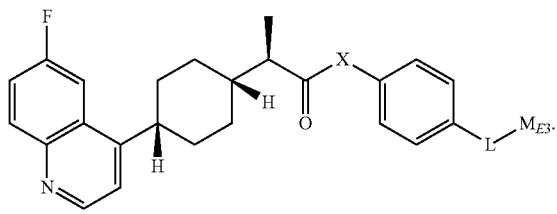

8. The method of claim 1, wherein $M_{IDO}$-L-$M_{E3}$ has the formula: